(12) United States Patent
Bodie et al.

(10) Patent No.: US 11,976,266 B2
(45) Date of Patent: May 7, 2024

(54) FILAMENTOUS FUNGAL STRAINS COMPRISING REDUCED VISCOSITY PHENOTYPES

(71) Applicant: DANISCO US INC., Palo Alto, CA (US)

(72) Inventors: Elizabeth A. Bodie, Belmont, CA (US); Robert James Pratt, II, San Jose, CA (US); Michael Ward, San Francisco, CA (US); Jonathan M. Palmer, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 704 days.

(21) Appl. No.: 17/042,308

(22) PCT Filed: Apr. 16, 2019

(86) PCT No.: PCT/US2019/027590
§ 371 (c)(1),
(2) Date: Sep. 28, 2020

(87) PCT Pub. No.: WO2019/209576
PCT Pub. Date: Oct. 31, 2019

(65) Prior Publication Data
US 2021/0017487 A1 Jan. 21, 2021

Related U.S. Application Data

(60) Provisional application No. 62/661,658, filed on Apr. 24, 2018.

(51) Int. Cl.
C12N 1/14 (2006.01)
C07K 14/37 (2006.01)

(52) U.S. Cl.
CPC ............. C12N 1/14 (2013.01); C07K 14/37 (2013.01)

(58) Field of Classification Search
CPC ........................................ C12N 1/14
See application file for complete search history.

(56) References Cited

FOREIGN PATENT DOCUMENTS

| WO | 200179558 A1 | 10/2001 |
| WO | 2012027580 A1 | 3/2012 |
| WO | 2012145584 A1 | 10/2012 |
| WO | 2012145592 A1 | 10/2012 |
| WO | 2012145595 A1 | 10/2012 |
| WO | 2012145596 A1 | 10/2012 |
| WO | 2016130523 A1 | 8/2016 |

OTHER PUBLICATIONS

International Search Report from PCT Application No. PCT/US2019/027590 dated Aug. 5, 2019, 4 pages.
Written Opinion from PCT Application No. PCT/US2019/027590 dated Aug. 5, 2019, 5 pages.
Ward, "Production of Recombinant proteins by filamentous fungi", Biotechnology Advances, vol. 30, No. 5, 1119-1139, 2012.

*Primary Examiner* — Suzanne M Noakes

(57) ABSTRACT

The present strains and methods of the disclosure relate to genetic modifications in filamentous fungi that give rise to variant strains having altered phenotypes, altered morphologies, altered growth characteristics, and the like. More specifically, as presented and described herein, such variant strains of filamentous fungi comprising reduced viscosity phenotypes are well-suited for growth in submerged cultures (e.g., for the large-scale production of enzymes and other proteins or metabolites for commercial applications).

9 Claims, 25 Drawing Sheets

Specification includes a Sequence Listing.

FIG. 3A

MQQPPSLVGDRSITGLGDAASRPNLSSSSPTVTSAPSAPTSPPPRPPISLNPPSREPPGVEPVLRITPVPRSVFASVHQPRKSSLVQTSHVLPSPRTAAAHHHHPV
SHSASGSSGSNGSGSGSGSGNLLRQTHRDTVHPPVKRPSTPSSHPTRGASTGASPQQGASSRNRSSTSPVSSPASRTPPYASRQASVSHSRQQHNHHQHQHQHY
HSHTSTTSRASIEAVVGAVPDPSGHRAPPKPRRPDRNHFGASDRSATPTLSHFMRAESSMSMRHYESGPLRSMSPNPYGTPAATTSSTARMPHEQSHDPYAPRGH
SRDHSGKSSRDMGKPRAQKNPSQKAMLSRALQKANTAVQLDNAQNFEGAREAYAEACDLLQQVLDRTPGDEDKRKLEAIHQTYTSRIDELDQLGPWQVETVKALPAR
PESEEYSASIFIPQDYDMGDEAPRIETARVVSYIAGDNASPFAAAPNQWQQSGGHTASERLQPNRGLEPGLLQSSFSRAPRSPRRLQSTDDLRAQHQEGQYAPPPLS
PRSQSPVKTHDHDDDMFAELPPHEPYQYQQEHDHQDYHQHHRHHNHHHHERQPSETVLSSYELQGHVDGGIQNSWLDPIDESGGSTASSVHSRTSSLGYRRH
IRAVSGNTEAEFDTALDAAIEAAYDDGYEPMDSVDYGTIDAGGDNSMAGVLHKVEMARERARQTEQEAYDELANLRQAHSQNPQHQQEEDRYTAEGFYEDDSSEEE
RLLDEITRDFAIEDFTMENPNGTQVSARQQDAWNEDETRPDEISGVRSFSALSQRPPIPQAYAANASQPAAPPTSALPDLPPGRPGQNPKQLKIETANIVQTQKSV
YDDDEISPSTQEPPPETLVRTASAQPVRPPIPTESFPSELSAPASPTAKKRLIEGENVLNASPSIHRLRKNFSSSSLRSMKNRNMSVSHLDDSSDASPGTPLNDPFN
KAPAVPVPALPTPLLASFKDHMEAAAGVGFHLFDDEFHAAAAAGPQSPQSPRSPVVVSMDVPVPLEPCPNDFMLRPFWLMRCLYQTLVHPKGGYISTKLFVPRDVWR
VKGVKIKNVEDKIANCDFLTAALLKLSKVDTLDADAVLEEMQALEGILEQIQPVLARKLGNEVGVQGSGLLFKDASMMEGDPGSAVPRSGVSVSGKASAFSWRRLRPK
TSGVGLGGSYSSRNASAEFKEASTLATVPEMTPKPTSRSAKRDVSQVQFIGPNASYMGSLARLFDAAQAVDDPGILRLADKTQVGLELCTRHAAEFFGFYIC
RFVLADLGLLLDKFLKRGSEWVMT

*FIG. 3B*

```
ATGCAGCCAACCGCCCTCCTTAGTTGGCGACCGGCATCACCGGCCTGGGAGACGCAGCCAGCCGACCAAATCTCTCTTCATCCTCGCCTACCGTCACCAGCGCGCC
CTCGGCACCGACATCGCCACCGGCGCGGCCAATATGCTGTCTGCCGGCCTCCTGGCGTCGAGAGCCTCTGGCGTCGAGCCCGTGCTCCGCCATCACGCCAGTCCCGCT
CCGTCTTTGCCTCTGTCTGGCCTCTGGCAGCAGCGGCAAGTCGTCGCTGGCCAGACGTCGCACGTGCGCACGTCCTCGCCAGGACCCGCCTCGCCCAGTTCACCATCCCGTC
TCGCATTCCGCCTCTGGCAGCAGCCCCCGTCGTCTGCCGAAGCGCAGTGGACAGCGGCCAGCCTGCGCAAACTGCTGCGTCAAACGCATCGCGACACCGTGCACCCCG
CGTCAAGCGGCCATCCACCCCGTCGCGAGTGCGACGCCTCCATCCCGCCCAGCCCTCGTCAGCCCTCAGCCTCGTCGAGGGCGCCAGCAGCATCAGCAACCACCAGTTAC
TTTCGTCCCGGCGAGTGCGACGCCTCCATCCCGCCAGCCCGTCAGCCCTCAGCCCTGGTTCGGTGCCGTAGTCGGAGGGCCGTAGTCGCCAGCATCCGAGCGCCGCGAAACCCCGTCGACCGGA
CACTCCCACACCACTTTGGCGCTCAGATCGCGCTCGAGATCGCAGCTCGCGCCAGCATCCGCGCCAGCATCGCGAGCCGCCGTAGTCGGAGGGCCGTAGTCATTCCCCACTTGGCGCCTCAGTGGAGAGCAGCATGTCATGAGACATTACGAGAGCGCCCTTAC
TCGCAACCACTTTGGCGCTGCGTCAGATCGCGCAGATCGCGAGCGCAACTCCCACCCTGTGCCACTTCATGAGGGCAGAGTCGAGCATGTCATGAGACATTACGAGAGCGCCCTTAC
GCTCCATGTCGCCGAACCCCTACGGCAAGCTGCGCGAAATGCCGCAGCCCTCCACTGCGTCGCTCCACTGCGTCAAGGCTGTCGAGAATGCCCTCACAGAGCCCACGATCCCTCACGGCCCTCCGGCCAC
TCGCGATCACTCGGGAAGAGCAGCAGACATGGGCAAGCCAGAGACATTCCCGAGCTCAGAAGAATCCCTCACAGAAGGCAAGCTGCTCCCGTGCCCTGACCGAACACCGGAGATGAGG
CGCAGTTCAGCTCGACAATGCTCAGAACTTCGAAGGCGCTCGAGAAGCGTACGCCGAGAAGCGTCGAGAAGCCGCTTGTTGCCAGCAGGTGCTTGACCGAACACCGGAGATGAGG
ACAAGCGGAAGCTCGAAGCCATTgtaagtcacggcggcggcaaccgaatgtcgagcccgttgtcgtcattgaactgacaatttcaatctgtagCA
CCAAACTTACACCAGCCGCATCGATGAGCTCAGTTGGGCCCTTGAGACCCGTCAAGGCTTGAGCTCGCCCAGAGACGCAGAGCGAGGAGTACAGCGCGT
CCATATTCATACCCCAGATTACGACATGGGCGATGAAGCTCCCAGAGCTGAGACGGCACATCGTCAGCAACCGGGTCGTCCTCTCGGGCCC
GCGCCCAACAGTGGCAGCAGTCGGGAGGTCACACGCGATGATCTTCGCACACAGCATGAGCCCTATCAGTACAGCAAGACCAAGAACTCAAGAAGACCACCACCATCAACAT
GAGGTGCCCAGCATGACGACGACATGTTTGCCAACGACAGCAGCGACAACGACAGCCCAGGCGCGAGACTCAGTACCTCATACGAGACTGCTTGGCTACACTCATCAAGAGTCAGTGATGGAGGAGAATCCAAAACTCATGCT
CACCGCCATCACAACCACCAGCCCCAGGAGGCTCAACAGCGCTCGTCTGTACACTCCCTCTCCTTCGCTTGGCTACGTCCGCCATATCCGGGCCGTGAGCGGGAACACCG
AGATCCAATTGACGAGTCGGGAGGCTCGACGCTGACGCTGCTATCGCGCTCGAAGGTGCACAGGTGGAGATGGCGCGGAACAGCCTATGACGAGCTGGCCAACCTCCGACAGCGCACTCA
AGGCCGAGTTTGACACGCGTATTGCACAGGTGGAGATGGCGCGGAACAGCCTATGACGAGCTGGCCAACCTCCGACAGCGCACTCA
ATAGCATGGCAGCCGTATTGCACAGGTGGAGATGGCGCGGAACAGCCTATGACGAGCTGGCCAACCTCCGACAGCGCACTCGA
CAGAATCCGCAGCACCAGCTTTACCATGGAGGAGGACAGTGTACTGCCGAGGATTCTACGAGGAGGATTCTACGAGGACTCGTCTGAAGAGGAGGAGACTCGTCTGAAGAGGAGACGACTATTGGACGAGATTACACGGA
CTTTGCCATTGAGGACCTTTTCTGCCCTGTCGCAGAAATGGAAAATCCGAAGCACACAGGTGTCAGCCTAGGCGACCCGCCAGGCCGGATTTCATCTCGG
GCGTCCGATCCTTCTGCCCTGTCGCAGAAATGGAAAATCCGAAGCACAGGTGCAGGCCAGGCCGGATTTCATCTCGG
CTGCCACCAGGACGCCCTGGTCAAGCAACTCAAGATCGAGATCGAGATCAAGCCAACTCAAGATCGAGATCGGTCTATGACGACGAAATCTCCCAAG
CACGACAAGAGCCGCCGCCGCTCGTCCGAGACGCTCGTTCCGGACGGGCGAGCCCGCCAGCCTGTAA
```

*FIG. 3C*

Exon 1 (SEQ ID NO: 19)

```
ATGCAGCAACCGCCCCTCCTTAGTTGGCGACCGCTGGGAGACGCAGCCAGCCGACCAGCATCACCGGCCTGGGAGAGACGCAGCCAGCCGACCAAATCTCTCTTCATCCTCGCCTACCGTCACCAGCGCGCC
CTCGGCACCGACATCGCCACCGGCGCGGCCGCCAATATCGCTGAATCCCCCGTCGCCGGCCTTCCTGGCGTGAGAGCGCCTCCTGGCGTCCGCATCACGCCAGTCCCGCGCT
CCGTCTTTGCCTCGTCCACCAGCCGCGGCCAAGTCGTGCTGGTCGTCCAGACGTCGGCAGCCCAGGACCGCTGCTCCGGCGCAGTCCACCATCACCGCGTC
TCGCATTCCGCCTCTGGCAGCAGCGGCCAGTGGCAAGCGGCCAGTGGCCAGCGGCCAATCTGCTGCGTCAAACGCATCGGCGACACCGTGCACCCCCG
CGTCAAGCGGCCATCCACCCCGTCGTGCCACCGGAGCATCGCCGAGCACCCAGAGCACCAGCACAACCACCATCATCAGCACCAACCAGCATTAC
TTTCGTCCCCGGAGTCGCACGCTACCAGTCGCGCCAGCATCGAGGCCGTAGTCGGTGCGCTCCCCGATCCCTCAGGTCACCGAGCGCCCGCAAACCCCGTCGACCGGA
CACTCCCACACCAGCTCGACTAGCGCAGCCAACTCGCCGCCACCAGGCAGCCATGTCGAGCACTTCATGAGGGCAGATGTCGAGCCCACGATCCCTACGCCCTGGCCAC
TCGCAACCACTTTGGCGCGTCAGATGCCGGAACCCCTACGGAAGGGCCAAGCCACATGGGCAAGCAGACAGAGAATCCCTCACAGAAGGCCGATGCTCTCCCGTGCCCTGCAAAAGGCCAACAC
GCTCCATGTGCCGGAACCCCTACGGAAGAGCAGAGAGAATCCCTCACAGAAGGCCGATGCTCTCCCGTGCCCTGCAAAAGGCCAACAC
TCTCGGCGATCACTCGGGGACAATGCTCAGAACTTCGAAGGCGCTTGCGAAGCCGGCTTGTTGCAGCAGGTTGACCGACCACCCGGGAGATGAGG
ACAAGGCGAAGCTCGAAGCCATT
```

FIG. 4A

Exon 2 (SEQ ID NO: 20)

CACCAAACTTACACCAGCCCATCGATGAGCTGGATCAGTTGGGCCCTTGGCAGGTTGAGACCTCAAGGCTCTCTGCCGGCCGCGGCGAGGCGAGGAGTACAGCGC
GTCCATATTCATACGCCAGGATTACGACATGGGCGATGAAGCTCCCAGGATTGAGACGGCACGGCTACATCGCTGGAGACGCAACGCGTCTCCCTTTGCAG
CAGCGCCAACCAGTGGCAGCAGTCGGGAGGTCACACGGCATTCGGAAACGGCTGAACGGCGGTCTGCTACAGTCGTCTGCTCAGTCGCCGTCCTTCTCGGGCC
CCGAGGTCGCCAGGCGGCGCTGCAGTCCAGTCGACATCAGGAGGGCCAGTACCAGCCCTATCAGTCAGTACCAGACCACCATCAAGACTACCATCAAC
GACCCATGACCATGACAACAACCACCACACCAGCAGGACCCAGCTGTCCAGCACTGTCCATCCCTCATACGAGCTTGGCTACGCACCCTTCGACGCCCATATCCGAGCGGGAACAC
ATCACCGCCATCAATTGACAGTCGGGAGGCTCAACAGCCAGCCTGCTCGTGTACACAGCGTCGGGCGCTAATCCGACGACTGAAGTAAGCGTCGGGGGG
CTAGGCCCAGAGTTTGACACGGCCGCTGCTATCGAGGCTGCGCCCATGCGGAGACCAGAAGCCCCATGACTAGCAACCTGCACAGCGCAC
ACAATAGCATGCCAGGCGTATTGCACAAGGTGGAAGCAGGTATACTGCCGAGGGATTCTACGAGGACGACGCGCAGGATCAGGAGACTCGTCAGCAGGATTACACG
TCACAGAATCCGCAGCACCAGCAGCAGCTTTTACCATGGAAAATCCGAATGGCACACAGGTGTGTCAGGATAGGCGCCAACTCCCAAGAACCAAGACCCGATTTCATCT
CGACTTTGCCATTGAGGACTTTACCGCCCCTGTGTCGCAGAGGCCAATTCCTCAGGCTCAACGCGCCAACATTCCTCAGGCTCAAGCGCCAACCAGCCAAACCTGCACAGGATTCGGACGAGATCCTAGGCATTGCCA
CGGGCGTCCGATCCTTTCTGCCGCCCTGGTCAAAATCCAGAGGACCCTGGTCAAAATCGAGACGCGAGCCTGTCCGGAAGGAGCAAGGCCTCTATGACGAGCAAGCGTCGGTCTATGACGACGACGAAATCTCCCG
AAGCACGCAAGAGGCGCGCCAAGAGAGCGCGCCAAGAGAATGTGCTGACAGTGCTGACAGCCTGCTCGGCTCTCCAGGAATGTGCTGACAGCAGTCGGAGAGAATGTGCTGACAGCAGTCGGAGAGAACTTCGTCTTCGTCTTTCGTCTTCGCCGTCCCGTGCC
CATCGCCAACCGCAGGAACACATGTCCGTCTCGGGTCGCCAGCGGATCCATTCACCGCGAAGCACACTGCCCATATCTGCCCCCATATCTGCCCCCGAATCAGTCGAATGACCCCTTCAACAAGCACCTGCCCGTGCCC
ATGAAGAACAGGAACATGTCCGTCTGGACAGCAGCAATTGGACGAGAGAGAACATCATATGAGAGGCAGCCGCGCCTGCCCGGTGTTGGCTTCCACCTGTTTGACGAGTTTCATGCAGCGGCCGCTGCCG
CGGCTGCCGACCCCCCTGCTCGCGCGACCGTTGCTTCAGCAAAGCTCCAGAGTCCCGTTGTGTGTCCTGCGCGGTCTTGGTCTTGGTCCTGGCCAGTTGCCAAGACGAGTTTCATGCCTCAAAGCAGCCGTTCAAAGCGTCTGCGGCCGTGCTGACCGTTTTGGCTG
GCCCCCAAAGCCTACAGCCCTATCCATCGCTAGAGACACTTGTGTCACCCAAGGTGCATCATCCAGGGAGTGCCATAGGCCAAGCCCATGGCTATACTTGTTGCCCCAAGCCTCTGGCCGATGCCATGGCTAAGAGTGTCAAGATCAAGAA
CGTGGAGGACCAACCACAAATTGCCAACTGCGACTTTTGACTGCAGTCCCGCTGAAGTGCGCGAGACTTGGATGCGGATGCCGATGCGGATGCCTGTTCAAAGAACTTGGGCGTTCAAGTGGGCGTTCAAAGAACGGCCTCGATGATGGAA
GAGACCCCGGTTCAGCGTTCAGCGTTCAGCCGGCCAGATACAGCCGCGATCAGCGCAAGGGCTCAGCAAGGCCCTCCTGGCTTCGGCCAAGACGCCAGACGCCAAGCACGTCGGCGGCGACTTGGAGG
GTCGTACAGACGCCAACGCCAGTGCTGAGACGCCAGTGCTGAGACGCCGCCATGACCCAACGGTGCCCAATGACCTGGCAACGGCCCATGACGCCGAAACGCCCATGACCCGTTGCGGCCAAGCCTTCGGCCAAGCCGTTCGGGCCAAGCCGAGACGTGA
GCCAGTTCAGTTCATCGGGGCCCAATGCCGAGCTACATGGGCTCTCTCGCCGCTTGTTTGACGCTGCCGCAGTTG

*FIG. 4B*

Exon 3 (SEQ ID NO: 21)

ATCAAATTGCAAGGCAGGTCGACAGTCGACGACCCCGGTTTGCGACGTTGCGGACAAGACTCAGGTCGGCTTGGAGCTCTGCACCCGGCACGCCGCTGAGTTCTTTGGCTTTAC
ATTTGCCGATTCGTCTTGGCCGACCTCGGCCTGTTGCTGGACAAGTTCCTCAAACGAGGAAGCGAATGGGTCATGACATGA

*FIG. 4C*

SEQ ID NO: 5 ctagtgcatgcgcaaatttaaagcgctgatgaggtcgcccaggcgctgcagtccacgatgatcttcgcgcacagc
atcagagggcagtatgcgcctccccactctcgctcgtcgccgtaaagacgcatgacgaccatgacgac
gacatgtttgccgaactgccaccacacgagcccatcagtaccagcaagcacgaccatcaagaccaccatcaaga
ctaccatcaacatcaccgccatcacacaaccacaccaccaaaactcatggctagatccaaattgacgagtcgggaggctcaacagcg
agctccagggtcatgtgtggatggaggaatccaaaactcatggctagatccgacgccatatcccggctacgacggctgcctacgacgcggctacgagctctgtagact
tcgtctgtacactcacgacgccgctggacgctgctatcgaggctgcctacgacgcggctacgagctctgtagact
cgagtttgacacgggcgctggacgctgctatcgaggctgcctacgacgcggctacgagctctgtagact
atggaccattgatgctggggggacaatagcatgcaggcgtattgcacaagtCgagatggcgcgaacgagcga
gacagaCgaggaagctatgacgagctggccaactccgacaggcgcactcacagaatccgcagcaccagcag
gaggagacaggtatactgccgagggattctacgaggacgactcgtcgaagaggaggagactattggacgagat
tacacgcgacttgccattgaggactttaccatggaaaaccgaatggcacacaggtgtcagctaggcagcagatg
catggaacgaggacgagagcgaggccggattcatctcgggcttcatcctttctgccctgtcgcagaggccacc
attcctcaggcctacgcgcaacgctcaaagcaactcaagatcgagacggcaaacattgtacaaccagaagtcggtctatg
acgacgaaatctcccaagcacgcaagagcgccccgagacgctcatcgatcgcgcgcagatccatatag
ggc

*FIG. 6A*

SEQ ID NO: 6

GACCGGCCGCTAGTCTCCCGTTATCTCACTAGTGGGCCCACGTGGCCAATTCCTAAAGAAACAGCATGAAATGGTATT
ATGTAAGAGCTATAGTCTAAAGGCACTCTGCTGGATAAAATAGTGGCTATAAGTCTGCTGCAAAACTACCCCCAAC
CTCGTAGGTATATAAGTACTGTTTGATGGTAGTCTATCgcaggcgtattgcacaaggGTTTTAGAGCTAGAGTTCG
TTTCGGCTTTTCCTCGGAACCCCCAGAGGTCATCAGTTCGAATACGTAACAGAATAGCAAGTTAAAATAAGGCTAGT
CCGTTATCAACTTGAAAAAGTGGCACCGAGTCGGTGCTTTTTTTTCTCTTAAGCTTGGCACTGGCCGTCGTTTT
ACAACGTCGTGACTGGGAAAACC

FIG. 6B

SEQ ID NO: 7

GACCGGCCGCTAGTCTCCCGTTATCTCACTAGTGGGCCCACGTGGCCAATTCCTAAAGAAACAGCATGAAATGGTATT
ATGTAAGAGCTATAGTCTAAAGGCACTCTGCTGGATAAAATAGTGGCTATAAGTCTGCTGCAAAACTACCCCCAAC
CTCGTAGGTATATAAGTACTGTTTGATGGTAGTCTATCgcgcgaacgagcgagacagaGTTTTAGAGCTAGAGTTCG
TTTCGGCTTTTCCTCGGAACCCCCAGAGGTCATCAGTTCGAATGCTAACAGAATAGCAAGTTAAAATAAGGCTAGT
CCGTTATCAACTTGAAAAAGTGGCACCGAGTCGGTGCTTTTTTTTCTCTTAAGCTTGGCACTGGCCGTCGTTTT
ACAACGTCGTGACTGGGAAAACC

FIG. 6C

PEPSTATS T. *reesei* SSB7 protein (residues 1 through 1,308)

Molecular weight = 142539.41　　Residues = 1,308
Average Residue Weight = 108.975　　Charge = 10.0
Isoelectric Point = 6.7992

| Residue | Number | Mole% | DayhoffStat |
|---|---|---|---|
| A = Ala | 126 | 9.633 | 1.120 |
| B = Asx | 0 | 0.000 | 0.000 |
| C = Cys | 6 | 0.459 | 0.158 |
| D = Asp | 79 | 6.040 | 1.098 |
| E = Glu | 73 | 5.581 | 0.930 |
| F = Phe | 34 | 2.599 | 0.722 |
| G = Gly | 78 | 5.963 | 0.710 |
| H = His | 60 | 4.587 | 2.294 |
| I = Ile | 32 | 2.446 | 0.544 |
| J = --- | 0 | 0.000 | 0.000 |
| K = Lys | 40 | 3.058 | 0.463 |
| L = Leu | 89 | 6.804 | 0.919 |
| M = Met | 26 | 1.988 | 1.169 |
| N = Asn | 40 | 3.058 | 0.711 |
| O = --- | 0 | 0.000 | 0.000 |
| P = Pro | 126 | 9.633 | 1.853 |
| Q = Gln | 76 | 5.810 | 1.490 |
| R = Arg | 92 | 7.034 | 1.435 |
| S = Ser | 157 | 12.003 | 1.715 |
| T = Thr | 68 | 5.199 | 0.852 |
| U = --- | 0 | 0.000 | 0.000 |
| V = Val | 69 | 5.275 | 0.799 |
| W = Trp | 8 | 0.612 | 0.470 |
| X = Xaa | 0 | 0.000 | 0.000 |
| Y = Tyr | 29 | 2.217 | 0.652 |
| Z = Glx | 0 | 0.000 | 0.000 |

| Property | Residues | Number | Mole% |
|---|---|---|---|
| Tiny | (A+C+G+S+T) | 435 | 33.257 |
| Small | (A+B+C+D+G+N+P+S+T+V) | 749 | 57.263 |
| Aliphatic | (A+I+L+V) | 316 | 24.159 |
| Aromatic | (F+H+W+Y) | 131 | 10.015 |
| Non-polar | (A+C+F+G+I+L+M+P+V+W+Y) | 623 | 47.630 |
| Polar | (D+E+H+K+N+Q+R+S+T+Z) | 685 | 52.370 |
| Charged | (B+D+E+H+K+R+Z) | 344 | 26.300 |
| Basic | (H+K+R) | 192 | 14.679 |
| Acidic | (B+D+E+Z) | 152 | 1.621 |

*FIG. 8A*

MQQPPSLVGDRSITGLGDAASRPNLSSSSPTVTSAPSAPTSPPPRPPISLNPPSREPPGVEPVLRITPVPRSVFASVHQPRKSSLVQTSHVLPSPRTAAAAHHHHPV
SHSASGSGSSNGSGSGSGNLLRQTHRDTVHPPVKRPSTPSSHPTRGASTGASPQQGASSRNRSSTSPVSSPASRTPPYASRQASVSHSRQQHNHHHQHQHQHY
HSHTSSTTSRASIEAVVGAVPDPSGHRAPPKPRRPDRNHFGASDRSATPTLSHFMRAESSMSMRHYESGPLRSMSPNPYGTPAATTTSSTARMPHEQSHDPYAPRG

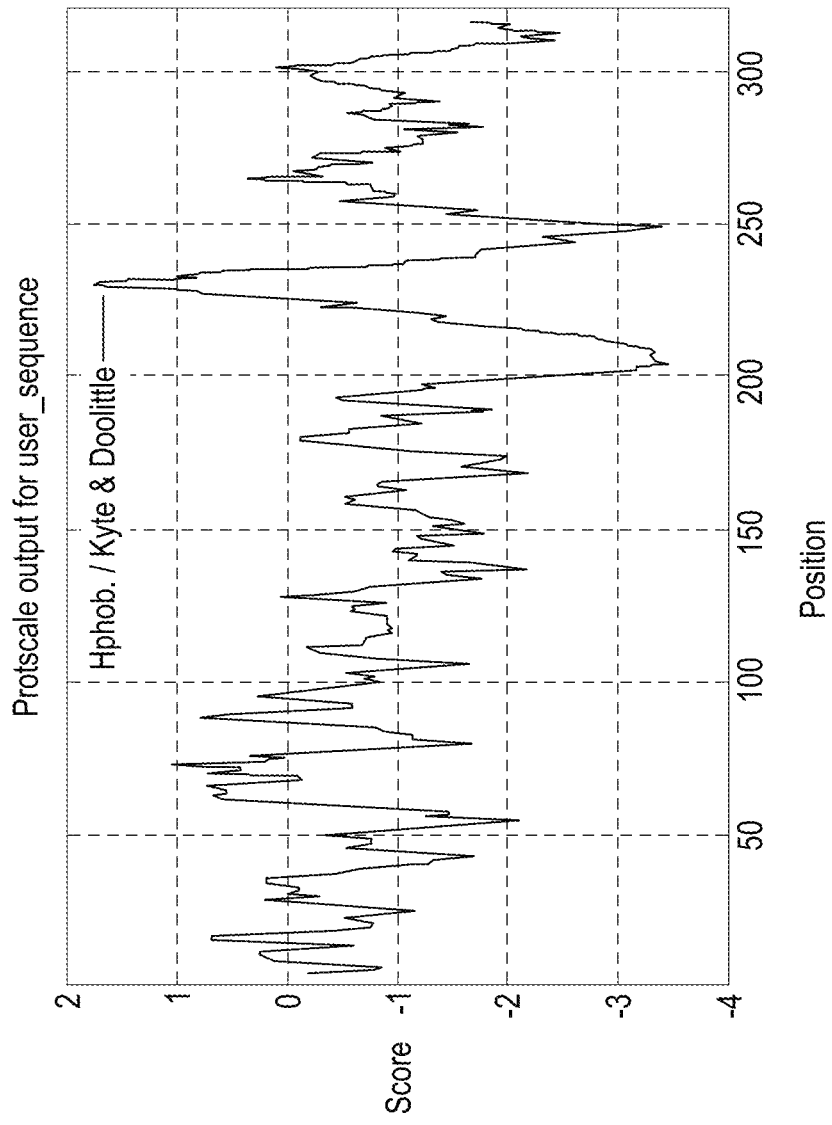

FIG. 8C

HSRDHSGKSSRDMGKPRAQKNPSQKAMLSRALQKANTAVQLDNAQNFEGAREAYAEACDLLQQVLDRTPGDEDKRKLEAIHQTYTSRIDELDQLGPWQVETVKALPA
RPESEYSASIFIPQDYDMGDEAPRIETARVVSYIAGDNASPFAAAPNQWQSGGHTASERLQPNRGLEPGLLQSSFSRAPRSPRRLQSTDDLRAQHQEGQYAPPPL
SPRSQSPVKTHDHDDDMFAELPPHEPYQYQQEHDHQDYHQHRHNHHHERQPSETVLSSYELQGHVDGGIQNSWLDPIDESGGSTASSVHSRTSSLGYRR

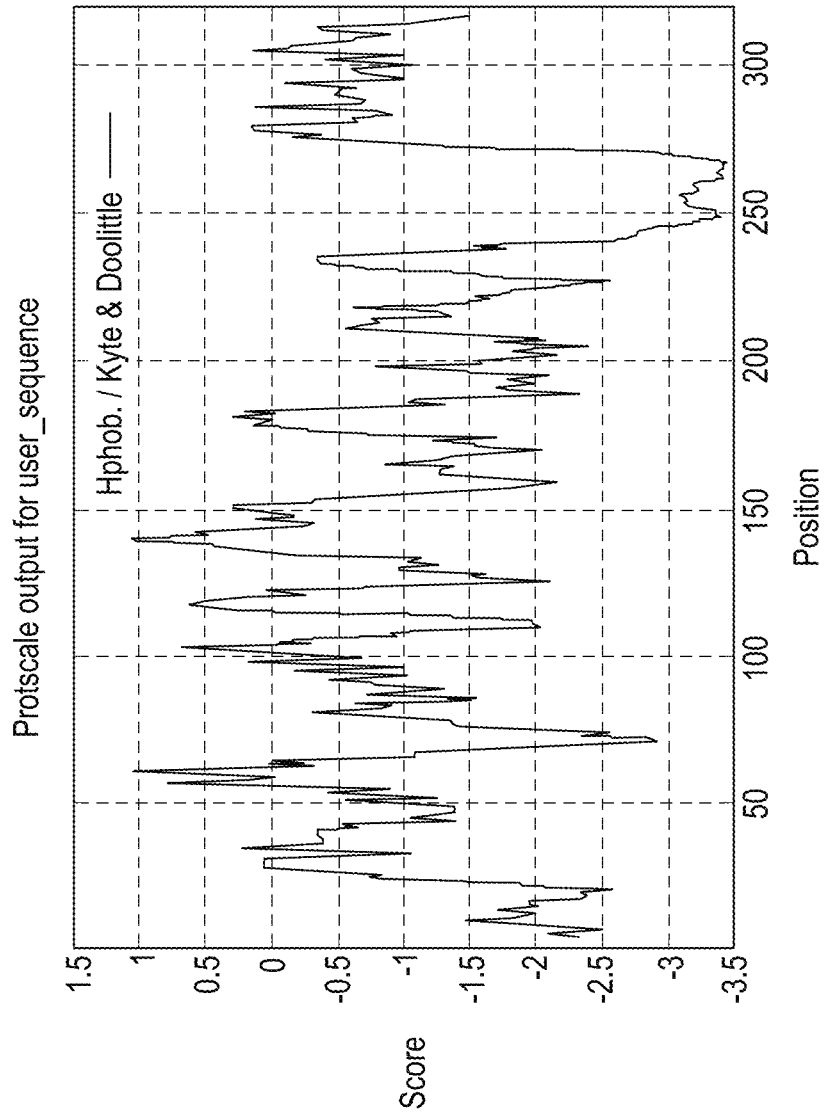

FIG. 8D

RHIRAVSGNTEAEFDTALDAAIEAAYDDGIEPMDSVDYGTIDAGGDNSMAGVLHKVEMARERARQTEQEAYDELANLRQAHSQNPQHQQEEDRYTAEGFYEDDSSEE
EERLLDEITRDFAIEDFTMENPNGTQVSARQQDAWNEDETRPDFISGVRSFSALSQRPPIPQAYAANASQPAAPPTSALPDLPPGRPGQNPKQLKIETANIVQTQK
SVYDDDEISPSTQEPPPETLVRTASAQPVRPPIPTESFPSELSAPASPTAKKRLLEGENVLNASPSIHRLRKNFSSSSLRSMKNRNMSVSHLDDSSDASPGTPLNDP

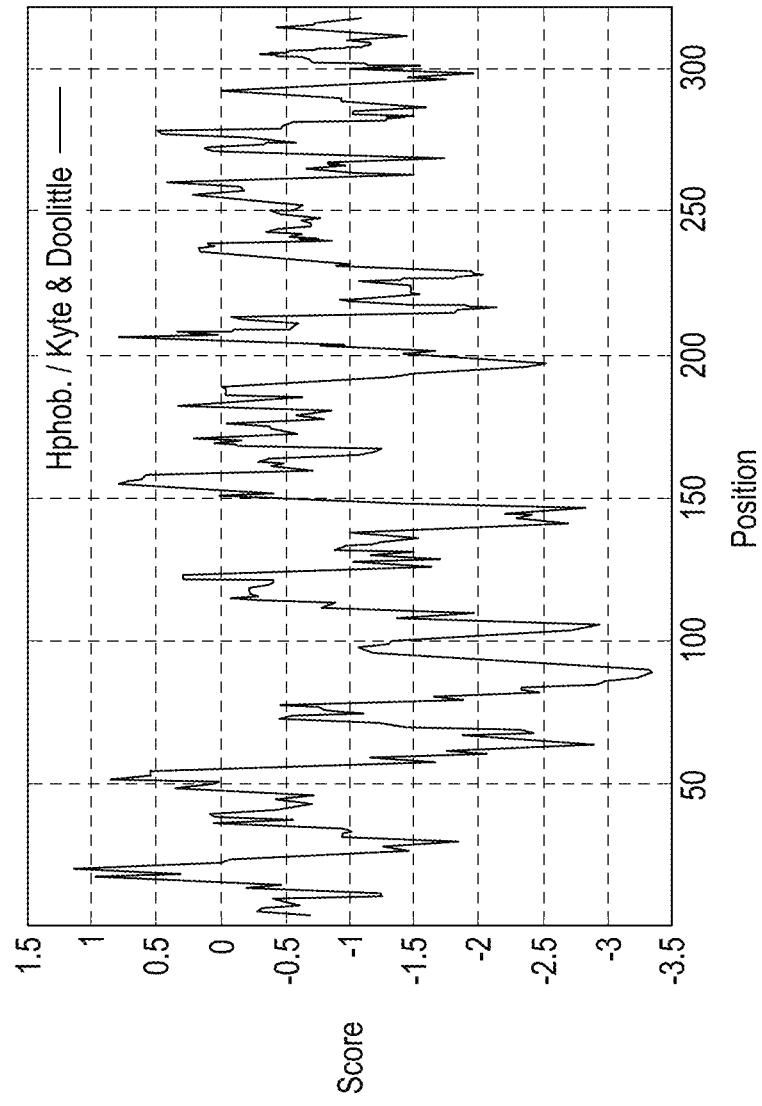

FIG. 8E

FNKAPAVPVPALPTPLLASFKDHMEAAAGPQSPQSPSPRSPVVVSMDVPVPLEPCPNDEMLRPFWLMRCLYQTLVHPKGGYISTKLFVPRDV
WRVKGVKIKNVEDKIANCDFLTAALLKLSKVDTLDADAVLEEMQALEGILEQIQPVLARKLGNEVGQSGLLFKDASMEGDPGSAVPRSGSVSGKASAFSWRRLR
PKTSGVGLGGSYSSRNASAETKEASTLAFVPMTPKPTSRSAKRDVSQVQFIGPNASYMGSLARLFDAAQAVDQIARQVDDPGLRLADKTQVGLELCTRHAAEFFGFY
ICRFVLADLGLLLDKFLKRGSEWVMT

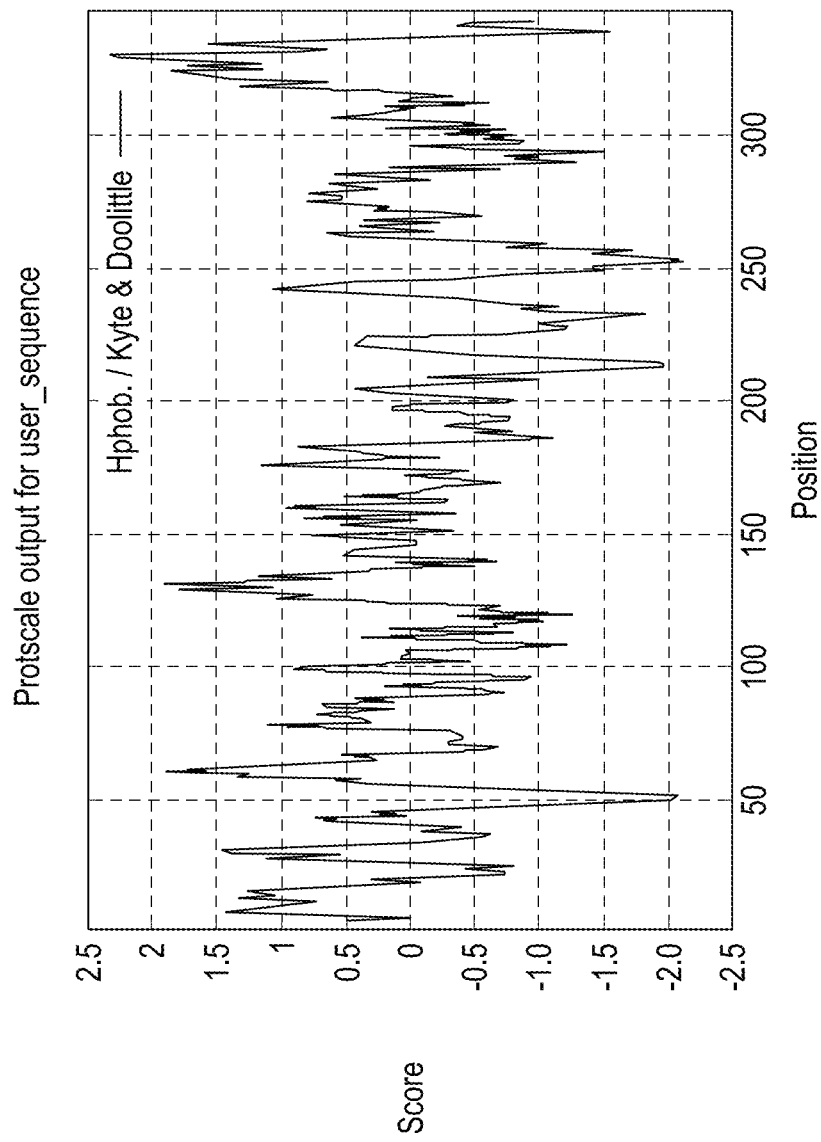

FIG. 8F

Amino Acid Hydropathy Scores

| Amino Acid | One Letter Code | Hydropathy Score |
|---|---|---|
| Isoleucine | I | 4.5 |
| Valine | V | 4.2 |
| Leucine | L | 3.8 |
| Phenylalanine | F | 2.8 |
| Cysteine | C | 2.5 |
| Methionine | M | 1.9 |
| Alanine | A | 1.8 |
| Glycine | G | -0.4 |
| Threonine | T | -0.7 |
| Serine | S | -0.8 |
| Tryptophan | W | -0.9 |
| Tyrosine | Y | -1.3 |
| Proline | P | -1.6 |
| Histidine | H | -3.2 |
| Glutamic Acid | E | -3.5 |
| Glutamine | Q | -3.5 |
| Aspartic Acid | D | -3.5 |
| Asparagine | N | -3.5 |
| Lysine | K | -3.9 |
| Arginine | R | -4.5 |

*FIG. 8G*

CLUSTAL W (1.83) Multiple Sequence Alignment of Ascomycota SSB7 orthologues

```
SID_12    ------------------------------------------------------------
SID_13    ------------------------------------------------------------
SID_11    ------------------------------------------------------------
SID_2     -----MQQPPSLVGDRSITGLGDAASRPNLSSSSPTVTSAPSAP---TSPPPRPPISLNP
SID_31    -----MQQSHPFDDN---------------IISRRATRAPIEP---SSPPPPPPQ---A
SID_8     -----MHDGQISSSPRQFLNHNHNHHHNQRPSASPSSAVTATVPPPWALPAYASSASVST
SID_9     MPLPHFTIAPPPPAPPAPATSTSTSSKIPTSSNNPGSSASATDLSS-ARTPPATVTTFAG
SID_10    ------------------------------------------------------------

SID_12    ------------------------------------------------------------
SID_13    ------------------------------------------------------------
SID_11    ------------------------------------------------------------
SID_2     PSREPPGVEPVLR--ITPVPRSVFAS----------------VHQPRKSSLVQTSHVLPS
SID_31    SSREAPGIEAVLSSPKTPVLRSVFSS----------------ARLPRSSSLIPPLHGSPP
SID_8     DSRPATATGRSHYYPHRDPSRSALSPSASPSLNTHPHHKGPGPRLPRTSSLLPPPHIEPS
SID_9     SASYASSPSPRTRLPDRDFISPGLRNPYPQGQQRPSRPPPPPPRQRQQQQQQPQQHSERF
SID_10    ------------------------------------------------------------

SID_12    -------------------MAHNLTSEGHGRSSRPMSPEYPFTADTAAPRLSRANSWNRF
SID_13    -------------------MLYRAAVEDEPRSFHPRRPSGPLTEPPSGPLPHRPSSRISR
SID_11    ------------------------------------------------------------
SID_2     PRTAAAAHH-------HHPVSHSASGSSGSNGSGSGSGSGSGNLLRQTHRDTVHPPV--K
SID_31    SASTAAAIN-------TNSPPHHANAS------------------QHTHRGPVHPPVSLK
SID_8     PRAVTFQRSDRLSPTPTPTPGSSSNGNGNGNGNGIPHNAAESSWLLNRLSSSTVSTNFSR
SID_9     GTVTVPTAAEHNQSTFSPFPPDRLPPKVPTDSRPSQDLLESFNEPLLHGPATPDSTKGLK
SID_10    ------------------------------------------------------------

SID_12    KKKGSDSTELASRFGAVTPTRPELVSELITGSPSTSPGDHIQEGLGSLNRWSQSTSSSKG
SID_13    SASRNRLAHPAGGGARIASTSPDPLADLTPSSP--------IKEGLGNLNRCPSRTPARAE
SID_11    ------------------------------------------------------------
SID_2     RPSTPSSHPTRGASTGASPQQGASSRNRSSTSPVSSPASRTPPY----ASRQASVSHSRQ
SID_31    RPSTPSSQLNRGASSGASPQEASRTRNRWSTSSISSASSRTSPY----ASRQASISNSRI
SID_8     VSALPPRANHTSSRLGKSPSIDATTFIDNSPPPSKPSPRKLQKN----HRPSTSVSNPDT
SID_9     PPSHKRGHSRSGSSSSIGDRLRNFNRWSVSSASSKGSNGGGSSWRIGWDSGKEREDSPGQ
SID_10    ------------------------------------------------------------

SID_12    SPKYDSYHKGIPFKASVDHDYTSPKARASPERNAISGLSPLVAAPTNNESPLQGHHSSDS
SID_13    LP----------------EVSVPELRAS--EMFMADANILYIDPP---------------
SID_11    ------------------------------------------------------------
SID_2     QHNHHHQHQHQHYHSHTSSTTSRASIEAVVGAVPDPSGHRAPPKPR--RPDRNHFGASDR
SID_31    RR---------------ASLEAALSPPSVPPPPLPPAQAPPRKPS--YTVRSRFNSSDS
SID_8     FIFR------------PSEDRTQLPQSLPLIVTLSPLEAPAALSDILNVKSEGAGPGS
SID_9     KSHKRRPSTSEISPRSVSHLRGRSDSPLRHPIPPLPSLPRISTGPSLVEAFRHQASEIGK
SID_10    ------------------------------------------------------------
```

FIG. 9A

CLUSTAL W (1.83) Multiple Sequence Alignment of Ascomycota SSB7
orthologues (Continued)

```
SID_12    IATGHYMRVLELGDHSNFSASSTNAVDPASSHQDHLPLGSSSIAASLFQNPWSR------
SID_13    ----------FAAGNHDSMTLG-------------HLPP---------------------
SID_11    ------------MEDPVNISSS--------------------------------------
SID_2     SATPTLSHFMRAESSMSMRHYESGPLRSMSPNPYGTPAATTTSSTARMPHEQSHDPYAP-
SID_31    GVTPTSVHPMRSESSMSMRHYENGQLRSVSPNPYANP-TTTTSSTARMPHEHSHDPYAP-
SID_8     GTSEPGQSTGARQGGQSLKQFDNSDSPARSVTSTPGSARSMAAYRPNMQYDQDQEAYPPQ
SID_9     QSPAPPRRYYLRPPPDDNAAFWDGAPQIPEDTPGSLPRSHQAAGLLLPPAELAPDHMMPQ
SID_10    ------------------------------------------------------------

SID_12    ---------SGADAQAVNQNSQMLTGREQHHGKRRGHSQKAMLSKALQKANTAVLLDNA
SID_13    ---------HQESASTYPGEGGIFMDGEGEADFRQHGATQKAMLSKALQKANTAVLLDNA
SID_11    ---------YSGEHSARHDHERTESGSTSPQRRRPRGSSQKAMLSKALAKANTAVLLDNA
SID_2     ---------RGHSRDHSGKSSRD-----MGKPRAQKNPSQKAMLSRALQKANTAVQLDNA
SID_31    ---------RGHSRDHSGKSSRD-----LGKPRAQKNPSQKAMLSRALQKANTAVQLDNA
SID_8     ---------RGHSRSRSGKGSND-----KGR---AKPPSQKAMLHRALQKANTAVQLDNA
SID_9     YTQNGDPRGQSRGRSHGAKSSTDSTASTRNRDRQRHRSDKKAMLSEALSKANTAVQLDNG
SID_10    ------------------------------------------------------------

SID_12    ANFEGAMEAYNDACQLLQLVMLRSSGGEDEKSKLQEIRDTYMIRVTELQRMDFSFTEPNS
SID_13    ANFEGAMEAYTDACQLLQLVMLRSNGGDEERIKLQEIRDTYMARITELQRMDFSIMESDG
SID_11    ENFEGAIEAYQDACELLQHVMLRSNGGDVEKYKLLEIRKTYLNRIQELLRIQLPSNLKKD
SID_2     QNFEGAREAYAEACDLLQQVLDRTPG-DEDKRKLEAIHQTYTSRIDELDQLG-PWQVETV
SID_31    QNFEGARESYAEACDLLQQVLDRTSG-DEDKRKLETIRATYTSRIDELDQMG-PWQDENV
SID_8     QNFKGAREAYAEACDLLQQVLQKTTA-DEDKRKLEAIRRTYTSRIDELDQMA-PWQEEET
SID_9     QDFEAARRAYTEACHLLQEVLQRTSV-EVDRRKLEAIHQTYVGRIDELDEML-GDS-LDE
SID_10    ------------------------------------------------------------

SID_12    KALPERPL------SQESYS--EMFQSIEEDENEPSLNESVNSLRRSSDDHQPVLNEANV-
SID_13    KALPERPL------SQESFG--ELLHAVASVQDDPYL-DSQHSAAHSGLRLQAAFDESRP-
SID_11    KALPERPP------SGRSATPQEDEPPIEQDYTDEDGAEEYFARQNAEDDVPPVPSLNTVR
SID_2     KALPARPE------SEEYSASIFIPQDYDMGDEAPRIETARVVSYIAGDNASPFAAAPNQW
SID_31    KALPARPE------SEDYGASIYMHQDYEMMEEAPRIETARVVS-IIGDGSSP---VAHQW
SID_8     KALPARPESLAQHSESESVLRLDDDDDDEPNDTAVFDTATAAR-IDGHSPQPRIVNSPPR
SID_9     KALPEEPES----YDERGYMRTQAYNGEVSDDEPMLSTYTRERSRTREPSLSVQTQFRRQ
SID_10    ------------------------------------------------------------

SID_12    LASDRVPVR-----------------------RQSLLPSAIDDDLCCLTLSTSTT
SID_13    LPSEAIPPR-----------------------RQSLRPSAQSD-----------
SID_11    LPSISGQDL-----------------------NFSFEASKTDIGGANSRESEAVA
SID_2     QQSGGHTASERLQPNR------GLEPGLLQSSFSRAPRSPRRLQSTDDLRAQHQ-EGQYA
SID_31    QQD--YTTTDRQQPAR------TLEPGMLQSSFS---RSPRRLRSTDNLRAQSQQEALYA
SID_8     DDSQGYRRRSAQNKPKPIVTSLTPEPGLLQSSFS---RSPVRLRTPEHFLPQRP-ADPYM
SID_9     PPSGRPPAPPTLTLQT------PGGSNGPTSYLS--EQYSLQSSFSKARFEKAPMDNAYM
SID_10    -----------------------------------------------MDNAYM
```

*FIG. 9B*

CLUSTAL W (1.83) Multiple Sequence Alignment of Ascomycota SSB7 orthologues (Continued)

```
SID_12    KQNSLSQTESFTASRDGHLE--------------------MAMHSESGQASTALSLDDDSA
SID_13    --------------------------------------------RTTPAGLGNN--
SID_11    QGHSSPSP--------------------------------TLQFVSDSADHQGDTET
SID_2     PPPLSPR-SQSPVKTHDHDDDMFAELPPHEPYQYQQEHDHQDHHQDYHQHHRHHNHHHHE
SID_31    PAPLSPR-SPSPMKMHP-----------------------EEYTEMVQEHHEPHHQHYHQ
SID_8     PAPLSPRRPLSPAKEVDDMD--------------------EPVRTDFSMSHDQQNDHAQE
SID_9     PPPLLPRRPLSPAQPPPPPP--------------------APEKDAPRQQVFRPDYSMSG
SID_10    PPPLSPRRPGSPARPSSPP---------------------VEYESPR----RPPPDRPN

SID_12    HHLRYNDWALLS-THAKDAYESTSWLDTIDESGASSPASTRSKVSSLYLRHGGSHHLSHG
SID_13    -LAAYHHGAFLDPTPVLDSNETTSWLDTIDESGASSPSSANSKASSVYLRRRTSRRLSTD
SID_11    RSSTAHASHSSDGQVPVNDNQSTSWLDTIDESGASSPVSTNTKLS-LYLGGTHSHHASNG
SID_2     RQPSETVLSSYELQGHVDGGIQNSWLDPIDESGGSTASSVHSRTSSLGYRRRHIRAVSGN
SID_31    RQPSDSVLP-YDMQDFTEG-TQNSWLDPIDESGASTVSSVHSRTSSLGYRRRHIRAASGN
SID_8     HNVP---------QTHFREDSMNSWLDPIDESGGSTASSVHSRTSSLGFRRKHIRSVSGE
SID_9     AQATSRNYKTNGGHQRDPSHESISWLDPIEESGGSSASSVHSRSSSTGIRRKHIRAASGD
SID_10    AQTEAP--ASSSGHQRANSHESVSWLDPIDESDRSSVTSVHSRSSSR-VVRKHIRAPSGA
                          ****.*:**. *:  *..:: *              : *

SID_12    TEAEFDAALDAAVEAAYDEGFEPVTEPNEQYNGGI------------DNDDDIVANARRNI
SID_13    TEAEFDAALDAAVEAAYDDGLEPVEEYQD------------------EEGDSVVANARRNI
SID_11    TEAEFDAALDAAVEAAYDEGLEPALNEQEGFYDDDDDDYEDHRDDDYDHDDVVSNARRNI
SID_2     TEAEFDTALDAAIEAAYDDGYEPMDSVDYG---TI----------DAGGDNSMAGVLHKV
SID_31    TEAEFDTALDAAIEAAYDDGFEPMETEDYD---AM----------DPR-EDVVASVMQRV
SID_8     TEAEFDTALDAAIEAAYDDGYEPMSPIDQRRTVSV----------DAG-EEVIANAMRKV
SID_9     TEAEFDAALDDAIEAAYDEGFEPEDQYYTDG--------------HDAVTG--------S
SID_10    TEAEFDAALDDAIEAAYDDGYEPESHYPGHSY-------------HDAQVDPIADKLRRV
          ******.*** *:*****.* **

SID_12    ELAKQKVREAEREAQVAMARGREVRNLQQ-PSIIDHSHG-----VGLDYLDEEAEEEERL
SID_13    ELAKQRVREAELEAEAAMSRGRDLRPVQE-QYLLDDAGG-----QTLEYLDEEAEEEERL
SID_11    EIAKQRVREAEREAQAVMARGLQQRLMMQDENVAVSTYN-----VDADYIDEEAEEEERL
SID_2     EMARERARQTEQEAYDELANLRQAHSQNPQHQQEE-DRY---TAEGFYED-DSSEEEERL
SID_31    EKAREQVRQTEQEAYDDLAMLRQAHQQNQHYLQEEEDKY---TPDGFYED-DSSEDEERL
SID_8     ELARQKVRETEQELY-EMERDNRSQPQYQSYEYQG-------TPNDFYND-NSSDEEERI
SID_9     SYPRDQVPDEGMDALELANERERKLRLQQHLEDEEYRKRGWTGHDDFYDEGHDSEEEERF
SID_10    EMARELVRESEREALELATEREQRLRLQQQLEDEEYRKR-VTAGEDFYDG-NDSEEEERL
          . .:: . :                                           ..::***:

SID_12    LEEMTRGYIMDDFNFDLQSKSALPRQSDSSSFSGRAWESSAVSN--TTTTG-VMLSPLVE
SID_13    LEEMTKGYVMDEFEFGLQTKSALPRESDSSNMSGHTWESSLASN--ATGPGSLALSTLAE
SID_11    LEEMTKGYVMDDFEFNLHTKTALPRQSDSSTVSGRTWGSSITSTSANSATAGTSLSTLAE
SID_2     LDEITRDFAIEDFTM----ENP--NGTQVSARQQDAWNEDETRPDFISGVRSFSALSQRP
SID_31    LDEITRDFAIEDFTM----TQPQSNTATVSASQQEAWNEDETRPDFISGVRSFSALSQRP
SID_8     LDEIARDYGLESYRH----RPPPPRESDSSGVTSRTWHSSQG-SNPPTGATSLSTVTELP
SID_9     LEEMTKGYQIEDFAFGPNNKQSIPRESDSSGVTNRTWNSSTG-SNQNTSTTLLSTVSESP
SID_10    LEEAPRTDGMDDFAFGVQQRPPVPRESDSSGMTGRTWHSSMG-SNPATGATLTP-VSEDG
          *:*  .: .:..:.:         .   :: *   .:* .:     :         .
```

*FIG. 9C*

CLUSTAL W (1.83) Multiple Sequence Alignment of Ascomycota SSB7
orthologues (Continued)

```
SID_12     AS--------------------ALPEVSAMTKQVAEPLPTQANGPAVLPKQNPAPTPGP
SID_13     DDDSVLPLDFLDQTLLPTAPPTAALPPIPVSSDFPSLPLPRASVSSPAPPPPPMGPPPIP
SID_11     EG--------------------ILTDATMPSKRLPPVPKIPTGSTQQPIPP-NMSPSA
SID_2      PIPQAY-----------------AANASQPAAPPPTSALPDLP------PGR----
SID_31     PIPQTSNI---------------MQPAAPPPTTTLPPPPTTTLPEVP------KGSDSPSH
SID_8      PP--------------------LTHLTHGPAAPPPTQSLPELP------QRPGSSAQ
SID_9      THPE------------------PKGPLPPLPPPAGALPQLPDRPPGTSGSGASNR
SID_10     THPH------------------RSGPLPPLPPQAAAQVPPQP----GSAGSQSSGQ

SID_12     SVRARRMSGQRTTELKIETKPRLGADSDISSQGQSSEPAALSPPPPLPKDEPSMNFPMRT
SID_13     GVRARRLSGQASTELKIETGSHARSSSTVSNVDPFMIPPTQ-PAPAASKDEASQ------
SID_11     GVRARRFSGSNTKQLKIDTK-RVAAGYEPTKKEPFSAQPAGPPSPVLLPEPKTS----LP
SID_2      -------PGQNPKQLKIETANIVQT-QKSVYDDDEISP--STQE-PPPET----------
SID_31     GVRNRRMSGQNPKQLKIETTNLGQSNTRTVYDDDEISP--STVDRDLVEA----------
SID_8      SVRNRRLSGQNPKQLKIETSKLALPMQSYADANQAKSAPLSSQNVDATVE----------
SID_9      SVRQRRLSGQNLKQLKIETTKLAQ-PGPTTAG--PAFPPQPARSHNYIAQ----------
SID_10     SVRNWRLSGQNPKGLKIETNKLAATAAPATAG--PTFPSQPK-TGSYIVQ----------
                .*.  . ***:*

SID_12     SKTLAPTPVLRSGVR-LNKRNASIGSFSEDTWANASLDKPTTQEEDNNLEISRLPSLARP
SID_13     EPSRSATPSFRANLHPTSRRNPSTGSFVD----HINLIKTRTQE-DEEGGLPVLPAAIRP
SID_11     ILTSSMSKPLPTGPS-EKKGSFDVSALGQ---RSSSLTRIPTLE-GDSVARSAQSSPPRT
SID_2      -LVRTASAQPVRPPIPTESFPSELSAPAS------PTAKKRLLEGE--NVLNASPSIHR-
SID_31     -LVRGASAHPVKQLNAAD---NESKIPGS------PSAKKKLIDGEDATAANASPSIHR-
SID_8      -PDTKAASAKHRQPSPPLFEASPTDMTGSR---PTPSPFGQLGSEKGDDDITGSPNTRK-
SID_9      -QRQALSAGPHRNANPLAARRVVSPSMG-----EGGAPPLPAHLQDDYPPRAGSPSVGR-
SID_10     -QRQALSAGPNRALGPPTSRPGPSPVPGTLDEEPEDAPPRPTALSHDEYPRVGTPSVVRA
                                                              :   . .  :

SID_12     IGKVPSAPDNLGKLNSGP--KSFRARNVSVPGPDT--LIDSPDTPSS-AFPPFDIQKGTG
SID_13     MGKVPSAPDGLDKVGATT--KSFRNRNVSVPIPDT--VPVSPTTPWSGSFSSQETQKASG
SID_11     ISKITSAPGMLRKNTSSSSLAGMRARNMSMSTPD---INESPNTPSSSVFPAFDFQRQLA
SID_2      ----------LRKNFSSSSLRSMKNRNMSVSHLDD-SSDASPGTPLNDPFN------KAP
SID_31     ----------LKKNFSSSSLRSMKNRNMSVSHLDD-NSDVSPGTPNGNPFG------KTP
SID_8      ----------LRKNFSSSSLRSMKSRNMSLTHLEE-GSDLSPGTPGSNPFG------SLN
SID_9      P--------SLKKTFSSSSLRSAH-RKLSVSHNDD-VFDMSPGTPVSNQFGI--SGSTTR
SID_10     P--------NLRKNYSSSSLKSLKTRNLSISHLDEGMSDHSPGTPLSSQFG------AR
                    * *   :. . :*::*:.  :       ** ** . *

SID_12     SAAGPVLPTPTGATFAPNGLPSGG----LYLFDSHIHSPTNLGSPNA---------TATNA
SID_13     IPHMPVLPTPTAPLFTQNGLPTGG----LDLFDCEIHSPTSLGRPNM---------LVHNA
SID_11     NGLVPAMPTPSGASFPL--MTSKS----LHLFDNDIHSPTTPGSPSS---------TVTNA
SID_2      AVPVPALPTPLLA-SFKDHMEAAA-GVGFHLFDDEFHAAAAAGPQSPQSPRSPVVVSMDV
SID_31     AV--PALPTPLIT-SFRDNGEAGG-GAGLHLFDDNFHAAATPGPQSP-------VVSMEV
SID_8      APSVPALPTPLAT-SFRDRSETN--AAGLSLFDDHFYSPTSPGSPNP---------LISDP
SID_9      LPSIPSMPTPIAG-SFRERADTVVGTAGMYLFDAEFHSANDPGSPNG---------TLTDA
SID_10     LPAVPSLPAGILSNHLKDRANSTT-PGGLHLFENDFHSSERPGSPDP---------LTADA
                * .*:              :   :  **. ..::.   *   .    :
```

*FIG. 9D*

CLUSTAL W (1.83) Multiple Sequence Alignment of Ascomycota SSB7
orthologues (Continued)

```
SID_12   PAPLEHCPESFLLRPFWLMRCIYQTIAHPSGGYLTTKLFVPRDVWRVKNVKIKAVEEKVS
SID_13   PLPLEPCPESFLLRPFWLMRCLYQTLSHPQGGYLSEKLFIPRDVWRVKNVKIKALEDKIS
SID_11   PIPLEPCPESFLLRPFWLMRCLYQTIAHPRGGYLSTKLFIPREVWHVKNVRIKAMEDKIS
SID_2    PVPLEPCPNDFMLRPFWLMRCLYQTLVHPKGGYISTKLFVPRDVWRVKGVKIKNVEDKIA
SID_31   PAPLEPCPNDFMLRPFWLMRCLYQTLVHPKGGYVSTKLFVPRDVWRVKGVKIKNVEDKVA
SID_8    PAPLEPCPTDFMLRPFWLMRCLYQTLAHPRGGYISSKLFVSRDVWRVKGVKLKNIEDKVA
SID_9    PAPLEPCPSDVLLRPFWLMRCLYQTLCHPRGGYISNKLFVPRDVWRVKGVKLKYVEEKIS
SID_10   PAPLEPCPTDVMLRPFWLMRALYQTLCHPRGGYLSNRLFVPRDVWRVKGVKLKAVEDKIA
          * *** **  ..:********.:***: ** ***:: :**:.*:**:**.*::* :*:*::

SID_12   NCDLLTAALLKLAKVDTYDADAVLEEMQSFETVLDQVQSSLSKKLG-GEVGVQGAMALFK
SID_13   NCDLLTAALLKLAQVDMFDADAVLDEMQSFESILDQAQMVLSKKLG-NEVGVHAAIPQLR
SID_11   LCDLLTAALLKVAQVDTYDADAVLEEMQTFENILDQAQTTFAKKLG-NEVGVQGALPLFK
SID_2    NCDFLTAALLKLSKVDTLDADAVLEEMQALEGILEQIQPVLARKLG-NEVGVQGSGLLFK
SID_31   NCDFLTAALLKLAKVDTFDADAVLEEMQSLEGVLEQVQSSLARKLG-SEVGVQG-GHIFK
SID_8    NCDFLTAALLKIARVDTYDADAVLEEMQSLEGILEQVQTALSRKLG-NEVGVHGSGALFK
SID_9    QCDLMTAALQKLARVDTCDADAVLEEMQALETVIESVEKFLVKKLGASEVGPHATS--FK
SID_10   NCDLLTAALQKLARVDTCDADAVLEEMQALEGVLEHVQATLSRKLG-SEVGVQGASSMFK
          **:***** *:::**   ******:***::*  :::    :  :*** .***  :.   ::

SID_12   ASQSSDD-AAAVDT--------LPSKTSGGASKSYLTSWRKLRSKNSGFGGTTSQ-SSVK
SID_13   QHASFDD-AAQFET--------SVVKSSSTSNKSYRPTWKRLRSKTSGITTVSSF-SSVR
SID_11   NANNSDESPISTEN--------MASRSSSQSSRSVLTSWRKLRSKSSAAPSTSTAPSTYR
SID_2    DASMMEGDPGSA-----------VPRSGSVSGKASAFSWRRLRPKTSGVGLG----GSYS
SID_31   DASVD-GEGGSN-----------VPRSGSVSGKASAFSWRRLRPKTSGVGLG----GSYS
SID_8    DASTGDGDAATG-----------MPRSASVSGKS-SFSWRRLRSKNSAVGLG----GSYM
SID_9    DPVHAEDGS--------------LPRSASVSAKTSAFSWRRLRSKNSSANLTSAGKGSSS
SID_10   DAAAAAAAAAAGDAAAAGGDAAAMPRSASVAGKASSFSWRRLRSKNSSANLPALAASGYG
                   :..  :  ::           :*::**.*.*.                  .

SID_12   ETTKDN---------------LIINSLPMSSTP-NSQPVKRNTTQLQFNGPNANYMSALA
SID_13   ETSKEQ---------------LTMTSVPMTTAP-SNQ-ARRSVTSLDFSGPNSHYMGALA
SID_11   DSGKGG---------------LSMSTLPMTASPPSGRFTKRDVMQLQLSGPNANYMGALA
SID_2    SRNASAETKEAS---------TLATVPMTPKP-TSRSAKRDVSQVQFIGPNASYMGSLA
SID_31   NRSASMETKEVT---------TLATLPMTPKP-TSRPPKRDVSQAQFIGPNAMYMGSLA
SID_8    SRINTETSKEIP---------SIASLPMTPTP-TNRPPKRDLAQVQFTGPNAMYMSSLA
SID_9    AGGTSGNVASTP--IEGAGKDIICPSLPMTTHP-TNRPMKRDVGNVLFQGPNANYMSSLA
SID_10   NKGGNGAAASTTNLSEGLGKDATLASLPMTTHP-TSRPTKRDINSVSFTGPNANYMSSLA
                            ::**:. *  ..:  :*.  .  :  ***: **.:**
```

*FIG. 9E*

CLUSTAL W (1.83) Multiple Sequence Alignment of Ascomycota SSB7
orthologues (Continued)

```
SID_12    RLCDAAQVLDQIAQQVEDPGLKHSSPTLVGLELSTRHAAEFFGFYICRFALNDIAMMVDK
SID_13    RLFDAAQVLDQVAQQVEDPGLKHSSPTHVGLELSTRHAAEFFGFYICRFALADVGLMLDK
SID_11    RLFDAAQVLDQIARQVEDPGLKHSSPTHVGLELSTRHAAEFFGFYICRFALNDVGLLLDK
SID_2     RLFDAAQAVDQIARQVDDPGLRLADKTQVGLELCTRHAAEFFGFYICRFVLADLGLLLDK
SID_31    RLFDAAQAIDQIARQVEDPGLRHADKTQVGLELCTRHAAEFFGFYICRFVLADLSLLLDK
SID_8     RLFDAAQAIDQIARQVEDPGLRHADKTQVGLELCTRHAAEFFGFYVCRFVLSDLGLLLDK
SID_9     RLFDAAQLVDQIARQVEDPGLRHADKTQVGLELSTRHAAEFFALYICRFVLSDLTLMLDK
SID_10    RLFDAAQTVDQIARQVEDPGLRHADKTQVGLELCARHAAEFFAFYICRFALSDLTLLMDK
          **  ****  :**:*:**:****: :. * *****.:*******.:*:***.* *: :::**

SID_12    FIKRGSEWVLI
SID_13    FIKRGSEWVLI
SID_11    YIKRGTEWVLV
SID_2     FLKRGSEWVMT
SID_31    FLKRGSEWVLT
SID_8     YLKRGSEWVLT
SID_9     FLKRGSEWVLV
SID_10    FVKRGSEWVLA
          ::***:***:
```

*FIG. 9E (Continued)*

SEQUENCE LISTING

<160> NUMBER OF SEQ ID NOS: 38

<210> SEQ ID NO 1
<211> LENGTH: 4067
<212> TYPE: DNA
<213> ORGANISM: Hypocrea jecorina

<400> SEQUENCE: 1

```
atgcagcaac cgccctcctt agttggcgac cgcagcatca ccggcctggg agacgcagcc      60
agccgaccaa atctctcttc atcctcgcct accgtcacca gcgcgccctc ggcaccgaca     120
tcgccaccgc cgcggccgcc aatatcgctg aatccccgt cgcgagagcc tcctggcgtc      180
gagcccgtgc tccgcatcac gccagtcccg cgctccgtct ttgcctctgt ccaccagccg     240
cgcaagtcgt cgctggtcca gacgtcgcac gtcctgccct cgcccaggac cgccgccgca    300
gctcaccatc accatcccgt ctcgcattcc gcctctggca gcagcggcag caacggcagt    360
ggaagcggca gtggcagcgg cagcggcaat ctgctgcgtc aaacgcatcg cgacaccgtg    420
cacccccccg tcaagcggcc atccacccg tcgtcgcatc ccaccagggg cgccagcacc     480
ggagcatcgc cgcagcaggg cgccagctcc cgaaaccgct cgtcgacgtc gcccgtttcg    540
tccccggcga gtcgcacgcc tccttatgca tctcgtcagg cctcagtttc ccattcccgc    600
cagcagcaca accaccatca tcagcaccaa caccagcatt accactccca caccagctcg    660
actaccagtc gcgccagcat cgaggccgta gtcggtgccg tccccgatcc ctcaggtcac    720
cgagcgccgc cgaaaccccg tcgaccggat cgcaaccact ttggcgcgtc agatcgcagc    780
gcaactccca ccctgtcgca cttcatgagg gcagagtcga gcatgtccat gagacattac    840
gagagcggcc ccttacgctc catgtcgccg aaccctacg gaaccctgc cgccaccacg      900 acgtcgtcca ctgccagaat gccgcacgag cagagccacg atccctacgc ccctcgcggc    960
cactctcgcg atcactcggg gaagagcagc agagacatgg gcaagccccg agctcagaag   1020
aatccctcac agaaggcgat gctctcccgt gccctgcaaa aggccaacac cgcagttcag   1080
ctcgacaatg ctcagaactt cgaaggcgct cgagaagcgt acgccgaggc ttgcgacttg   1140
ttgcagcagg tgcttgaccg aacaccggga gatgaggaca gcggaagct cgaagccatt    1200 gtaagtcacg gcggcaaccg gaatgtcgag cccgttgtct gtcattagta gatcacttgg   1260
aactgacaat ttcaatctgt agcaccaaac ttacaccagc cgcatcgatg agctggatca   1320
gttgggccct tggcaggttg agaccgtcaa ggctctgccg gcgcggccag agagcgagga   1380
gtacagcgcg tccatattca taccccagga ttacgacatg ggcgatgaag ctcccaggat   1440
tgagacggca cgggtggtga gctacatcgc tggagacaac gcgtctccct ttgcagcagc   1500
gcccaaccag tggcagcagt cgggaggtca cacggcatct gaacggctgc agcccaaccg   1560
cggtctggaa ccgggtctgc tacagtcgtc cttctctcgg gccccgaggt cgcccaggcg   1620
gctgcagtcc accgatgatc ttcgcgcaca gcatcaggag ggccagtatg cgcctccccc   1680
```

```
actctcgcct cgctcgcagt cgccggtaaa gacgcatgac catgacgacg acatgtttgc   1740
cgaactgcca ccacacgagc cctatcagta ccagcaagag cacgaccatc aagaccacca   1800
tcaagactac catcaacatc accgccatca caaccaccac catcacgaac gacagcccag   1860
cgagactgtc ctatcctcat acgagctcca gggtcatgtg gatggaggaa tccaaaactc   1920
atggctagat ccaattgacg agtcgggagg ctcaacagcg tcgtctgtac actcacgcac   1980
ctcttcgctt ggctaccgtc gacgccatat ccgggccgtg agcgggaaca ccgaggccga   2040
gtttgacacg gcgctggacg ctgctatcga ggctgcctac gacgacggct acgagcccat   2100
ggactctgta gactatggga ccattgatgc tggggggggac aatagcatgg caggcgtatt   2160
gcacaaggtg gagatggcgc gcgaacgagc gagacagacg gagcaggaag cctatgacga   2220
gctggccaac ctccgacagg cgcactcaca gaatccgcag caccagcagg aggaggacag   2280
gtatactgcc gagggattct acgaggacga ctcgtctgaa gaggaggaga gactattgga   2340
cgagattaca cgcgactttg ccattgagga ctttaccatg gaaaacccga atggcacaca   2400
ggtgtcagct aggcagcagg atgcatgaa cgaggacgag acgaggccgg atttcatctc   2460
gggcgtccga tccttttctg ccctgtcgca gaggccaccc attcctcagg cctacgccgc   2520
caacgcctcg cagccagcag ccccccctcc gacatccgca ttgccagacc tgccaccagg   2580
acgccctggt caaaatccaa agcaactcaa gatcgagacg gcaaacattg tacaaaccca   2640
gaagtcggtc tatgacgacg acgaaatctc cccaagcacg caagagccgc cgcccgagac   2700
gctcgtccgg acggcgagcg cgcagcctgt aaggccaccg ataccgacag aaagcttccc   2760
atccgaactc agtgctcccg catcgccaac cgccaagaag aggcttctgg aaggagagaa   2820
tgtgctgaat gcctcgcctt ctatccacag gctacggaag aacttttcgt cttctagctt   2880
gaggagcatg aagaacagga acatgtccgt ctcacatttg gacgcagct cggatgcttc   2940 cccccggcacc ccctgaatg acccccttcaa caaggcacct gccgtgcccg tgcccgcgct   3000
gccgaccccc ttgctcgcgt cgttcaaaga tcatatggag gcagcggccg gtgttggctt   3060
ccacctgttt gacgacgagt ttcatgcagc ggcggctgcc ggcccccaaa gcccgcagag   3120
tcccagaagt cccgttgttg tctccatgga cgtccctgtg cctctggaac cctgtccaaa   3180
cgacttcatg ctgcgaccgt tttggctgat gcgatgccta taccagacac ttgtgcatcc   3240
caagggtggc tacatcagta cgaagctatt cgtgccgcga gacgtctggc gggtcaaagg   3300
tgtcaagatc aagaacgtgg aggacaaaat tgccaactgc gacttttga ctgcagccct   3360 gctgaagctg tccaaagtgg acactctgga tgcggatgcc gtgctggagg agatgcaagc   3420
cctcgagggc attctggagc agatacagcc ggtcctggcc cgaaagcttg gaaacgaagt   3480
gggcgttcaa ggttccggtc tgctgttcaa agacgcctcg atgatggaag gagacccgg   3540 ttcagccgtg ccgcgatcag gaagtgtgtc tggcaaggcg tctgcgtttt cctggcgacg   3600
gcttcggcca agacgtcgg gcgtcgggct gggagggtcg tacagcagcc gcaacgccag   3660
tgctgagacg aaggaggcct caacgctggc aacggtgccc atgacgccga aaccgacaag   3720
ccgttcggcc aagcgagacg tgagccaggt tcagttcatc gggcccaatg cgagctacat   3780
gggctctctc gcgcgcttgt ttgacgctgc gcaggcagtt ggtaagcata ttgcgatacg   3840
cataccggtt acagtgacgg caagctaacg atgatgcaga tcaaattgca aggcaggtcg   3900
acgaccccgg tttgcggctt gcggacaaga ctcaggtcgg cttggagctc tgcacccggc   3960
acgccgctga gttctttggc ttttacattt gccgattcgt cttggccgac ctcggcctgt   4020
tgctggacaa gttcctcaaa cgaggaagcg aatgggtcat gacatga            4067
```

<210> SEQ ID NO 2
<211> LENGTH: 1308
<212> TYPE: PRT
<213> ORGANISM: Hypocrea jecorina

<400> SEQUENCE: 2

```
Met Gln Gln Pro Pro Ser Leu Val Gly Asp Arg Ser Ile Thr Gly Leu
1               5                   10                  15

Gly Asp Ala Ala Ser Arg Pro Asn Leu Ser Ser Ser Pro Thr Val
            20                  25                  30

Thr Ser Ala Pro Ser Ala Pro Thr Ser Pro Pro Arg Pro Pro Ile
            35                  40                  45

Ser Leu Asn Pro Pro Ser Arg Glu Pro Pro Gly Val Glu Pro Val Leu
50                  55                  60

Arg Ile Thr Pro Val Pro Arg Ser Val Phe Ala Ser Val His Gln Pro
65                  70                  75                  80

Arg Lys Ser Ser Leu Val Gln Thr Ser His Val Leu Pro Ser Pro Arg
                85                  90                  95

Thr Ala Ala Ala His His His Pro Val Ser His Ser Ala Ser
            100                 105                 110

Gly Ser Ser Gly Ser Asn Gly Ser Gly Ser Gly Ser Gly Ser
            115                 120                 125

Gly Asn Leu Leu Arg Gln Thr His Arg Asp Thr Val His Pro Pro Val
130                 135                 140

Lys Arg Pro Ser Thr Pro Ser Ser His Pro Thr Arg Gly Ala Ser Thr
145                 150                 155                 160

Gly Ala Ser Pro Gln Gln Gly Ala Ser Ser Arg Asn Arg Ser Ser Thr
                165                 170                 175

Ser Pro Val Ser Ser Pro Ala Ser Arg Thr Pro Pro Tyr Ala Ser Arg
            180                 185                 190

Gln Ala Ser Val Ser His Ser Arg Gln Gln His Asn His His His Gln
            195                 200                 205

His Gln His Gln His Tyr His Ser His Thr Ser Ser Thr Thr Ser Arg
210                 215                 220

Ala Ser Ile Glu Ala Val Val Gly Ala Val Pro Asp Pro Ser Gly His
225                 230                 235                 240

Arg Ala Pro Pro Lys Pro Arg Arg Pro Asp Arg Asn His Phe Gly Ala
                245                 250                 255

Ser Asp Arg Ser Ala Thr Pro Thr Leu Ser His Phe Met Arg Ala Glu
            260                 265                 270

Ser Ser Met Ser Met Arg His Tyr Glu Ser Gly Pro Leu Arg Ser Met
            275                 280                 285

Ser Pro Asn Pro Tyr Gly Thr Pro Ala Ala Thr Thr Thr Ser Ser Thr
290                 295                 300

Ala Arg Met Pro His Glu Gln Ser His Asp Pro Tyr Ala Pro Arg Gly
305                 310                 315                 320

His Ser Arg Asp His Ser Gly Lys Ser Ser Arg Asp Met Gly Lys Pro
                325                 330                 335

Arg Ala Gln Lys Asn Pro Ser Gln Lys Ala Met Leu Ser Arg Ala Leu
            340                 345                 350

Gln Lys Ala Asn Thr Ala Val Gln Leu Asp Asn Ala Gln Asn Phe Glu
            355                 360                 365

Gly Ala Arg Glu Ala Tyr Ala Glu Ala Cys Asp Leu Leu Gln Gln Val
```

```
              370                 375                 380
Leu Asp Arg Thr Pro Gly Asp Glu Asp Lys Arg Lys Leu Glu Ala Ile
385                 390                 395                 400

His Gln Thr Tyr Thr Ser Arg Ile Asp Glu Leu Asp Gln Leu Gly Pro
                405                 410                 415

Trp Gln Val Glu Thr Val Lys Ala Leu Pro Ala Arg Pro Glu Ser Glu
            420                 425                 430

Glu Tyr Ser Ala Ser Ile Phe Ile Pro Gln Asp Tyr Asp Met Gly Asp
                435                 440                 445

Glu Ala Pro Arg Ile Glu Thr Ala Arg Val Val Ser Tyr Ile Ala Gly
        450                 455                 460

Asp Asn Ala Ser Pro Phe Ala Ala Pro Asn Gln Trp Gln Gln Ser
465                 470                 475                 480

Gly Gly His Thr Ala Ser Glu Arg Leu Gln Pro Asn Arg Gly Leu Glu
                485                 490                 495

Pro Gly Leu Leu Gln Ser Ser Phe Ser Arg Ala Pro Arg Ser Pro Arg
            500                 505                 510

Arg Leu Gln Ser Thr Asp Asp Leu Arg Ala Gln His Gln Glu Gly Gln
        515                 520                 525

Tyr Ala Pro Pro Pro Leu Ser Pro Arg Ser Gln Ser Pro Val Lys Thr
        530                 535                 540

His Asp His Asp Asp Met Phe Ala Glu Leu Pro Pro His Glu Pro
545                 550                 555                 560

Tyr Gln Tyr Gln Gln Glu His Asp His Gln Asp His His Gln Asp Tyr
                565                 570                 575

His Gln His His Arg His His Asn His His His Glu Arg Gln Pro
                580                 585                 590

Ser Glu Thr Val Leu Ser Ser Tyr Glu Leu Gln Gly His Val Asp Gly
            595                 600                 605

Gly Ile Gln Asn Ser Trp Leu Asp Pro Ile Asp Glu Ser Gly Gly Ser
        610                 615                 620

Thr Ala Ser Ser Val His Ser Arg Thr Ser Ser Leu Gly Tyr Arg Arg
625                 630                 635                 640

Arg His Ile Arg Ala Val Ser Gly Asn Thr Glu Ala Glu Phe Asp Thr
                645                 650                 655

Ala Leu Asp Ala Ala Ile Glu Ala Ala Tyr Asp Asp Gly Tyr Glu Pro
                660                 665                 670

Met Asp Ser Val Asp Tyr Gly Thr Ile Asp Ala Gly Gly Asp Asn Ser
            675                 680                 685

Met Ala Gly Val Leu His Lys Val Glu Met Ala Arg Glu Arg Ala Arg
        690                 695                 700

Gln Thr Glu Gln Glu Ala Tyr Asp Glu Leu Ala Asn Leu Arg Gln Ala
705                 710                 715                 720

His Ser Gln Asn Pro Gln His Gln Gln Glu Glu Asp Arg Tyr Thr Ala
                725                 730                 735

Glu Gly Phe Tyr Glu Asp Asp Ser Ser Glu Glu Glu Arg Leu Leu
                740                 745                 750

Asp Glu Ile Thr Arg Asp Phe Ala Ile Glu Asp Phe Thr Met Glu Asn
            755                 760                 765

Pro Asn Gly Thr Gln Val Ser Ala Arg Gln Gln Asp Ala Trp Asn Glu
        770                 775                 780

Asp Glu Thr Arg Pro Asp Phe Ile Ser Gly Val Arg Ser Phe Ser Ala
785                 790                 795                 800
```

```
Leu Ser Gln Arg Pro Pro Ile Pro Gln Ala Tyr Ala Ala Asn Ala Ser
                805                 810                 815
Gln Pro Ala Ala Pro Pro Thr Ser Ala Leu Pro Asp Leu Pro Pro
            820                 825                 830
Gly Arg Pro Gly Gln Asn Pro Lys Gln Leu Lys Ile Glu Thr Ala Asn
                835                 840                 845
Ile Val Gln Thr Gln Lys Ser Val Tyr Asp Asp Glu Ile Ser Pro
850                 855                 860
Ser Thr Gln Glu Pro Pro Glu Thr Leu Val Arg Thr Ala Ser Ala
865                 870                 875                 880
Gln Pro Val Arg Pro Pro Ile Pro Thr Glu Ser Phe Pro Ser Glu Leu
                885                 890                 895
Ser Ala Pro Ala Ser Pro Thr Ala Lys Lys Arg Leu Leu Glu Gly Glu
                900                 905                 910
Asn Val Leu Asn Ala Ser Pro Ser Ile His Arg Leu Arg Lys Asn Phe
                915                 920                 925
Ser Ser Ser Ser Leu Arg Ser Met Lys Asn Arg Asn Met Ser Val Ser
            930                 935                 940
His Leu Asp Asp Ser Ser Asp Ala Ser Pro Gly Thr Pro Leu Asn Asp
945                 950                 955                 960
Pro Phe Asn Lys Ala Pro Ala Val Pro Val Pro Ala Leu Pro Thr Pro
                965                 970                 975
Leu Leu Ala Ser Phe Lys Asp His Met Glu Ala Ala Ala Gly Val Gly
            980                 985                 990
Phe His Leu Phe Asp Asp Glu Phe  His Ala Ala Ala  Ala Gly Pro
                995                 1000                1005
Gln Ser  Pro Gln Ser Pro Arg  Ser Pro Val Val Val  Ser Met Asp
    1010                1015                1020
Val Pro  Val Pro Leu Glu Pro  Cys Pro Asn Asp Phe  Met Leu Arg
    1025                1030                1035
Pro Phe  Trp Leu Met Arg Cys  Leu Tyr Gln Thr Leu  Val His Pro
    1040                1045                1050
Lys Gly  Gly Tyr Ile Ser Thr  Lys Leu Phe Val Pro  Arg Asp Val
    1055                1060                1065
Trp Arg  Val Lys Gly Val Lys  Ile Lys Asn Val Glu  Asp Lys Ile
    1070                1075                1080
Ala Asn  Cys Asp Phe Leu Thr  Ala Ala Leu Leu Lys  Leu Ser Lys
    1085                1090                1095
Val Asp  Thr Leu Asp Ala Asp  Ala Val Leu Glu Glu  Met Gln Ala
    1100                1105                1110
Leu Glu  Gly Ile Leu Glu Gln  Ile Gln Pro Val Leu  Ala Arg Lys
    1115                1120                1125
Leu Gly  Asn Glu Val Gly Val  Gln Gly Ser Gly Leu  Leu Phe Lys
    1130                1135                1140
Asp Ala  Ser Met Met Glu Gly  Asp Pro Gly Ser Ala  Val Pro Arg
    1145                1150                1155
Ser Gly  Ser Val Ser Gly Lys  Ala Ser Ala Phe Ser  Trp Arg Arg
    1160                1165                1170
Leu Arg  Pro Lys Thr Ser Gly  Val Gly Leu Gly Gly  Ser Tyr Ser
    1175                1180                1185
Ser Arg  Asn Ala Ser Ala Glu  Thr Lys Glu Ala Ser  Thr Leu Ala
    1190                1195                1200
```

```
Thr Val Pro Met Thr Pro Lys Pro Thr Ser Arg Ser Ala Lys Arg
    1205            1210                1215

Asp Val Ser Gln Val Gln Phe Ile Gly Pro Asn Ala Ser Tyr Met
    1220            1225                1230

Gly Ser Leu Ala Arg Leu Phe Asp Ala Ala Gln Ala Val Asp Gln
    1235            1240                1245

Ile Ala Arg Gln Val Asp Asp Pro Gly Leu Arg Leu Ala Asp Lys
    1250            1255                1260

Thr Gln Val Gly Leu Glu Leu Cys Thr Arg His Ala Ala Glu Phe
    1265            1270                1275

Phe Gly Phe Tyr Ile Cys Arg Phe Val Leu Ala Asp Leu Gly Leu
    1280            1285                1290

Leu Leu Asp Lys Phe Leu Lys Arg Gly Ser Glu Trp Val Met Thr
    1295            1300                1305

<210> SEQ ID NO 3
<211> LENGTH: 2731
<212> TYPE: DNA
<213> ORGANISM: Hypocrea jecorina

<400> SEQUENCE: 3
atgcagcaac cgccctcctt agttggcgac cgcagcatca ccggcctggg agacgcagcc     60
agccgaccaa atctctcttc atcctcgcct accgtcacca gcgcgccctc ggcaccgaca    120
tcgccaccgc cgcggccgcc aatatcgctg aatccccgt cgcgagagcc tcctggcgtc    180
gagcccgtgc tccgcatcac gccagtcccg cgctccgtct ttgcctctgt ccaccagccg    240
cgcaagtcgt cgctggtcca gacgtcgcac gtcctgcccc gcccaggac cgccgccgca    300 gctcaccatc accatcccgt ctcgcattcc gcctctggca gcagcggcag caacggcagt    360
ggaagcggca gtggcagcgg cagcggcaat ctgctgcgtc aaacgcatcg cgacaccgtg    420
cacccccccg tcaagcggcc atccaccccg tcgtcgcatc ccaccagggg cgccagcacc    480
ggagcatcgc cgcagcaggg cgccagctcc cgaaaccgct cgtcgacgtc gcccgtttcg    540
tccccggcga gtcgcacgcc tccttatgca tctcgtcagg cctcagtttc ccattcccgc    600
cagcagcaca ccaccatca tcagcaccaa caccagcatt accactccca caccagctcg    660
actaccagtc gcgccagcat cgaggccgta gtcggtgccg tccccgatcc ctcaggtcac    720
cgagcgccgc cgaaaccccg tcgaccggat cgcaaccact tggcgcgtc agatcgcagc    780 gcaactccca ccctgtcgca cttcatgagg gcagagtcga gcatgtccat gagacattac    840
gagagcggcc ccttacgctc catgtcgccg aaccctacg gaaccctgc cgccaccacg    900 acgtcgtcca ctgccagaat gccgcacgag cagagccacg atccctacgc ccctcgcggc    960
cactctcgcg atcactcggg gaagagcagc agagacatgg gcaagcccg agctcagaag   1020 aatccctcac agaaggcgat gctctcccgt gccctgcaaa aggccaacac cgcagttcag   1080
ctcgacaatg ctcagaactt cgaaggcgct cgagaagcgt acgccgaggc ttgcgacttg   1140
ttgcagcagg tgcttgaccg aacaccggga gatgaggaca agcggaagct cgaagccatt   1200
gtaagtcacg gcggcaaccg gaatgtcgag cccgttgtct gtcattagta gatcacttgg   1260
aactgacaat ttcaatctgt gcaccaaac ttacaccagc cgcatcgatg agctggatca   1320
gttgggccct tggcaggttg agaccgtcaa ggctctgccg gcgcggccag agagcgagga   1380
gtacagcgcg tccatattca taccccagga ttacgcatg ggccgatgaag ctcccaggat   1440 tgagacggca cgggtggtga gctacatcgc tggagacaac gcgtctcccct ttgcagcagc   1500
```

```
gcccaaccag tggcagcagt cgggaggtca cacggcatct gaacggctgc agcccaaccg   1560
cggtctggaa ccgggtctgc tacagtcgtc cttctctcgg ccccgaggt cgcccaggcg    1620 gctgcagtcc accgatgatc ttcgcgcaca gcatcaggag ggccagtatg cgcctccccc   1680
actctcgcct cgctcgcagt cgccggtaaa gacgcatgac catgacgacg acatgtttgc   1740
cgaactgcca ccacacgagc cctatcagta ccagcaagag cacgaccatc aagaccacca   1800
tcaagactac catcaacatc accgccatca caaccaccac catcacgaac dacagcccag   1860
cgagactgtc ctatcctcat acgagctcca gggtcatgtg gatggaggaa tccaaaactc   1920
atggctagat ccaattgacg agtcgggagg ctcaacagcg tcgtctgtac actcacgcac   1980
ctcttcgctt ggctaccgtc gacgccatat ccgggccgtg agcgggaaca ccgaggccga   2040
gtttgacacg cgcctggacg ctgctatcga ggctgcctac gacgacggct acgagcccat   2100
ggactctgta gactatggga ccattgatgc tggggggaca atagcatggc aggcgtattg   2160
cacaaggtgg agatggcgcg cgaacgagcg agacagacgg agcaggaagc ctatgacgag   2220
ctggccaacc tccgacaggc gcactcacag aatccgcagc accagcagga ggaggacagg   2280
tatactgccg agggattcta cgaggacgac tcgtctgaag aggaggagag actattggac   2340
gagattacac gcgactttgc cattgaggac tttaccatgg aaaacccgaa tggcacacag   2400
gtgtcagcta ggcagcagga tgcatggaac gaggacgaga cgaggccgga tttcatctcg   2460
ggcgtccgat cctttctgc cctgtcgcag aggccaccca ttcctcaggc ctacgccgcc   2520
aacgcctcgc agccagcagc ccccctccg acatccgcat gccagacct gccaccagga    2580 cgccctggtc aaaatccaaa gcaactcaag atcgagacgg caaacattgt acaaacccag   2640
aagtcggtct atgacgacga cgaaatctcc ccaagcacgc aagagccgcc gcccgagacg   2700
ctcgtccgga cggcgagcgc gcagcctgta a                                 2731
```

<210> SEQ ID NO 4
<211> LENGTH: 882
<212> TYPE: PRT
<213> ORGANISM: Hypocrea jecorina

<400> SEQUENCE: 4

Met Gln Gln Pro Pro Ser Leu Val Gly Asp Arg Ser Ile Thr Gly Leu
1               5                   10                  15

Gly Asp Ala Ala Ser Arg Pro Asn Leu Ser Ser Ser Pro Thr Val
            20                  25                  30

Thr Ser Ala Pro Ser Ala Pro Thr Ser Pro Pro Arg Pro Ile
        35                  40                  45

Ser Leu Asn Pro Pro Ser Arg Glu Pro Pro Gly Val Glu Pro Val Leu
    50                  55                  60

Arg Ile Thr Pro Val Pro Arg Ser Val Phe Ala Ser Val His Gln Pro
65                  70                  75                  80

Arg Lys Ser Ser Leu Val Gln Thr Ser His Val Leu Pro Ser Pro Arg
                85                  90                  95

Thr Ala Ala Ala Ala His His His His Pro Val Ser His Ser Ala Ser
            100                 105                 110

Gly Ser Ser Gly Ser Asn Gly Ser Gly Ser Gly Ser Gly Ser
        115                 120                 125

Gly Asn Leu Leu Arg Gln Thr His Arg Asp Thr Val His Pro Pro Val
    130                 135                 140

Lys Arg Pro Ser Thr Pro Ser Ser His Pro Thr Arg Gly Ala Ser Thr
145                 150                 155                 160

-continued

```
Gly Ala Ser Pro Gln Gln Gly Ala Ser Ser Arg Asn Arg Ser Ser Thr
                165                 170                 175

Ser Pro Val Ser Ser Pro Ala Ser Arg Thr Pro Pro Tyr Ala Ser Arg
            180                 185                 190

Gln Ala Ser Val Ser His Ser Arg Gln Gln His Asn His His His Gln
        195                 200                 205

His Gln His Gln His Tyr His Ser His Thr Ser Ser Thr Thr Ser Arg
    210                 215                 220

Ala Ser Ile Glu Ala Val Val Gly Ala Val Pro Asp Pro Ser Gly His
225                 230                 235                 240

Arg Ala Pro Pro Lys Pro Arg Arg Pro Asp Arg Asn His Phe Gly Ala
                245                 250                 255

Ser Asp Arg Ser Ala Thr Pro Thr Leu Ser His Phe Met Arg Ala Glu
            260                 265                 270

Ser Ser Met Ser Met Arg His Tyr Glu Ser Gly Pro Leu Arg Ser Met
        275                 280                 285

Ser Pro Asn Pro Tyr Gly Thr Pro Ala Ala Thr Thr Thr Ser Ser Thr
    290                 295                 300

Ala Arg Met Pro His Glu Gln Ser His Asp Pro Tyr Ala Pro Arg Gly
305                 310                 315                 320

His Ser Arg Asp His Ser Gly Lys Ser Ser Arg Asp Met Gly Lys Pro
                325                 330                 335

Arg Ala Gln Lys Asn Pro Ser Gln Lys Ala Met Leu Ser Arg Ala Leu
            340                 345                 350

Gln Lys Ala Asn Thr Ala Val Gln Leu Asp Asn Ala Gln Asn Phe Glu
        355                 360                 365

Gly Ala Arg Glu Ala Tyr Ala Glu Ala Cys Asp Leu Leu Gln Gln Val
    370                 375                 380

Leu Asp Arg Thr Pro Gly Asp Glu Asp Lys Arg Lys Leu Glu Ala Ile
385                 390                 395                 400

His Gln Thr Tyr Thr Ser Arg Ile Asp Glu Leu Asp Gln Leu Gly Pro
                405                 410                 415

Trp Gln Val Glu Thr Val Lys Ala Leu Pro Ala Arg Pro Glu Ser Glu
            420                 425                 430

Glu Tyr Ser Ala Ser Ile Phe Ile Pro Gln Asp Tyr Asp Met Gly Asp
        435                 440                 445

Glu Ala Pro Arg Ile Glu Thr Ala Arg Val Val Ser Tyr Ile Ala Gly
    450                 455                 460

Asp Asn Ala Ser Pro Phe Ala Ala Pro Asn Gln Trp Gln Gln Ser
465                 470                 475                 480

Gly Gly His Thr Ala Ser Glu Arg Leu Gln Pro Asn Arg Gly Leu Glu
                485                 490                 495

Pro Gly Leu Leu Gln Ser Ser Phe Ser Arg Ala Pro Arg Ser Pro Arg
            500                 505                 510

Arg Leu Gln Ser Thr Asp Asp Leu Arg Ala Gln His Gln Glu Gly Gln
        515                 520                 525

Tyr Ala Pro Pro Leu Ser Pro Arg Ser Gln Ser Pro Val Lys Thr
    530                 535                 540

His Asp His Asp Asp Met Phe Ala Glu Leu Pro Pro His Glu Pro
545                 550                 555                 560

Tyr Gln Tyr Gln Gln Glu His Asp His Gln Asp His Gln Asp Tyr
                565                 570                 575
```

```
His Gln His His Arg His Asn His His His Glu Arg Gln Pro
            580                 585                 590

Ser Glu Thr Val Leu Ser Ser Tyr Glu Leu Gln Gly His Val Asp Gly
        595                 600                 605

Gly Ile Gln Asn Ser Trp Leu Asp Pro Ile Asp Glu Ser Gly Gly Ser
    610                 615                 620

Thr Ala Ser Ser Val His Ser Arg Thr Ser Ser Leu Gly Tyr Arg Arg
625                 630                 635                 640

Arg His Ile Arg Ala Val Ser Gly Asn Thr Glu Ala Glu Phe Asp Thr
                645                 650                 655

Ala Leu Asp Ala Ala Ile Glu Ala Ala Tyr Asp Asp Gly Tyr Glu Pro
            660                 665                 670

Met Asp Ser Val Asp Tyr Gly Thr Ile Asp Ala Gly Gly Thr Ile Ala
        675                 680                 685

Trp Gln Ala Tyr Cys Thr Arg Trp Arg Trp Arg Ala Asn Glu Arg Asp
    690                 695                 700

Arg Arg Ser Arg Lys Pro Met Thr Ser Trp Pro Thr Ser Asp Arg Arg
705                 710                 715                 720

Thr His Arg Ile Arg Ser Thr Ser Arg Arg Thr Gly Ile Leu Pro
                725                 730                 735

Arg Asp Ser Thr Arg Thr Thr Arg Leu Lys Arg Arg Arg Asp Tyr Trp
            740                 745                 750

Thr Arg Leu His Ala Thr Leu Pro Leu Arg Thr Leu Pro Trp Lys Thr
        755                 760                 765

Arg Met Ala His Arg Cys Gln Leu Gly Ser Arg Met His Gly Thr Arg
    770                 775                 780

Thr Arg Arg Gly Arg Ile Ser Ser Arg Ala Ser Asp Pro Phe Leu Pro
785                 790                 795                 800

Cys Arg Arg Gly His Pro Phe Leu Arg Pro Thr Pro Thr Pro Arg
                805                 810                 815

Ser Gln Gln Pro Pro Leu Arg His Pro His Cys Gln Thr Cys His Gln
            820                 825                 830

Asp Ala Leu Val Lys Ile Gln Ser Asn Ser Arg Ser Arg Gln Thr
        835                 840                 845

Leu Tyr Lys Pro Arg Ser Arg Ser Met Thr Thr Lys Ser Pro Gln
    850                 855                 860

Ala Arg Lys Ser Arg Arg Pro Arg Arg Ser Ser Gly Arg Arg Ala Arg
865                 870                 875                 880

Ser Leu

<210> SEQ ID NO 5
<211> LENGTH: 1158
<212> TYPE: DNA
<213> ORGANISM: Artificial Sequence
<220> FEATURE:
<223> OTHER INFORMATION: synthetic

<400> SEQUENCE: 5
ctagtgcatg cgcaaattta aagcgctgat gaggtcgccc aggcggctgc agtccaccga    60
tgatcttcgc gcacagcatc aggagggcca gtatgcgcct cccccactct cgcctcgctc   120
gcagtcgccg gtaaagacgc atgaccatga cgacgacatg tttgccgaac tgccaccaca   180
cgagccctat cagtaccagc aagagcacga ccatcaagac caccatcaag actaccatca   240
acatcaccgc catcacaacc accaccatca cgaacgacag cccagcgaga ctgtcctatc   300
```

```
ctcatacgag ctccagggtc atgtggatgg aggaatccaa aactcatggc tagatccaat     360
tgacgagtcg ggaggctcaa cagcgtcgtc tgtacactca cgcacctctt cgcttggcta     420
ccgtcgacgc catatccggg ccgtgagcgg gaacaccgag gccgagtttg acacggcgct     480
ggacgctgct atcgaggctg cctacgacga cggctacgag cccatggact ctgtagacta     540
tgggaccatt gatgctgggg ggacaatagc atggcaggcg tattgcacaa ggtcgagatg     600
gcgcgcgaac gagcgagaca gaccgagcag gaagcctatg acgagctggc caacctccga     660
caggcgcact cacagaatcc gcagcaccag caggaggagg acaggtatac tgccgaggga     720
ttctacgagg acgactcgtc tgaagaggag gagagactat ggacgagat tacacgcgac     780 tttgccattg aggactttac catggaaaac ccgaatggca cacaggtgtc agctaggcag     840
caggatgcat ggaacgagga cgagacgagg ccggatttca tctcgggcgt ccgatccttt     900
tctgccctgt cgcagaggcc acccattcct caggcctacg ccgccaacgc ctcgcagcca     960
gcagcccccc ctccgacatc cgcattgcca gacctgccac caggacgccc tggtcaaaat    1020
ccaaagcaac tcaagatcga gacggcaaac attgtacaaa cccagaagtc ggtctatgac    1080
gacgacgaaa tctccccaag cacgcaagag ccgccgcccg agacgctcat cgatcgcgcg    1140
cagatccata tatagggc                                                  1158

<210> SEQ ID NO 6
<211> LENGTH: 408
<212> TYPE: DNA
<213> ORGANISM: Artificial Sequence
<220> FEATURE:
<223> OTHER INFORMATION: synthetic

<400> SEQUENCE: 6
gaccggccgc tagtctcccg ttatctcact agtggcccac gtggccaatt cctaaagaaa      60
cagcatgaaa tggtattatg taagagctat agtctaaagg cactctgctg ataaaaata     120 gtggctataa gtctgctgca aaactacccc caacctcgta ggtatataag tactgtttga     180
tggtagtcta tcggcaggcg tattgcacaa gggttttaga gctagagttc gtttcggctt     240
ttcctcggaa cccccagagg tcatcagttc gaatcgctaa cagaatagca agttaaaata     300
aggctagtcc gttatcaact tgaaaaagtg gcaccgagtc ggtggtgctt ttttttctct     360
taagcttggc actggccgtc gttttacaac gtcgtgactg ggaaaacc                 408

<210> SEQ ID NO 7
<211> LENGTH: 408
<212> TYPE: DNA
<213> ORGANISM: Artificial Sequence
<220> FEATURE:
<223> OTHER INFORMATION: synthetic

<400> SEQUENCE: 7
gaccggccgc tagtctcccg ttatctcact agtggcccac gtggccaatt cctaaagaaa      60
cagcatgaaa tggtattatg taagagctat agtctaaagg cactctgctg ataaaaata     120 gtggctataa gtctgctgca aaactacccc caacctcgta ggtatataag tactgtttga     180
tggtagtcta tcgcgcgaac gagcgagaca gagttttaga gctagagttc gtttcggctt     240
ttcctcggaa cccccagagg tcatcagttc gaatcgctaa cagaatagca agttaaaata     300
aggctagtcc gttatcaact tgaaaaagtg gcaccgagtc ggtggtgctt ttttttctct     360
taagcttggc actggccgtc gttttacaac gtcgtgactg ggaaaacc                 408
```

```
<210> SEQ ID NO 8
<211> LENGTH: 1310
<212> TYPE: PRT
<213> ORGANISM: Fusarium sp.

<400> SEQUENCE: 8
```

| | | | | | | | | | | | | | | | |
|---|---|---|---|---|---|---|---|---|---|---|---|---|---|---|---|
| Met | His | Asp | Gly | Gln | Ile | Ser | Ser | Ser | Pro | Arg | Gln | Phe | Leu | Asn | His |
| 1 | | | | 5 | | | | | 10 | | | | | 15 | |
| Asn | His | Asn | His | His | His | Asn | Gln | Arg | Pro | Ser | Ala | Ser | Pro | Ser | Ser |
| | | | 20 | | | | | 25 | | | | | 30 | | |
| Ala | Val | Thr | Ala | Thr | Val | Pro | Pro | Pro | Trp | Ala | Leu | Pro | Ala | Tyr | Ala |
| | | | 35 | | | | | 40 | | | | | 45 | | |
| Ser | Ser | Ala | Ser | Val | Ser | Thr | Asp | Ser | Arg | Pro | Ala | Thr | Ala | Thr | Gly |
| | 50 | | | | | 55 | | | | | 60 | | | | |
| Arg | Ser | His | Tyr | Tyr | Pro | His | Arg | Asp | Pro | Ser | Arg | Ser | Ala | Leu | Ser |
| 65 | | | | | 70 | | | | | 75 | | | | | 80 |
| Pro | Ser | Ala | Ser | Pro | Ser | Leu | Asn | Thr | His | Pro | His | His | Lys | Gly | Pro |
| | | | | 85 | | | | | 90 | | | | | 95 | |
| Gly | Pro | Arg | Leu | Pro | Arg | Thr | Ser | Ser | Leu | Leu | Pro | Pro | Pro | His | Ile |
| | | | 100 | | | | | 105 | | | | | 110 | | |
| Glu | Pro | Ser | Pro | Arg | Ala | Val | Thr | Phe | Gln | Arg | Ser | Asp | Arg | Leu | Ser |
| | | | 115 | | | | | 120 | | | | | 125 | | |
| Pro | Thr | Pro | Thr | Pro | Thr | Pro | Gly | Ser | Ser | Asn | Gly | Asn | Gly | Asn |
| | 130 | | | | | 135 | | | | | 140 | | | | |
| Gly | Asn | Gly | Asn | Gly | Ile | Pro | His | Asn | Ala | Ala | Glu | Ser | Ser | Trp | Leu |
| 145 | | | | | 150 | | | | | 155 | | | | | 160 |
| Leu | Asn | Arg | Leu | Ser | Ser | Ser | Thr | Val | Ser | Thr | Asn | Phe | Ser | Arg | Val |
| | | | | 165 | | | | | 170 | | | | | 175 | |
| Ser | Ala | Leu | Pro | Pro | Arg | Ala | Asn | His | Thr | Ser | Ser | Arg | Leu | Gly | Lys |
| | | | 180 | | | | | 185 | | | | | 190 | | |
| Ser | Pro | Ser | Ile | Asp | Ala | Thr | Thr | Phe | Ile | Asp | Asn | Ser | Pro | Pro | Pro |
| | | | 195 | | | | | 200 | | | | | 205 | | |
| Ser | Lys | Pro | Ser | Pro | Arg | Lys | Leu | Gln | Lys | Asn | His | Arg | Pro | Ser | Thr |
| | 210 | | | | | 215 | | | | | 220 | | | | |
| Ser | Val | Ser | Asn | Pro | Asp | Thr | Phe | Ile | Phe | Arg | Pro | Ser | Glu | Asp | Arg |
| 225 | | | | | 230 | | | | | 235 | | | | | 240 |
| Thr | Gln | Leu | Pro | Gln | Ser | Leu | Pro | Leu | Ile | Val | Thr | Leu | Ser | Pro | Leu |
| | | | | 245 | | | | | 250 | | | | | 255 | |
| Glu | Ala | Pro | Ala | Ala | Leu | Ser | Asp | Ile | Leu | Asn | Val | Lys | Ser | Glu | Gly |
| | | | 260 | | | | | 265 | | | | | 270 | | |
| Ala | Gly | Pro | Gly | Ser | Gly | Thr | Ser | Glu | Pro | Gly | Gln | Ser | Thr | Gly | Ala |
| | | | 275 | | | | | 280 | | | | | 285 | | |
| Arg | Gln | Gly | Gly | Gln | Ser | Leu | Lys | Gln | Phe | Asp | Asn | Ser | Asp | Ser | Pro |
| | 290 | | | | | 295 | | | | | 300 | | | | |
| Ala | Arg | Ser | Val | Thr | Ser | Thr | Pro | Gly | Ser | Ala | Arg | Ser | Met | Ala | Ala |
| 305 | | | | | 310 | | | | | 315 | | | | | 320 |
| Tyr | Arg | Pro | Asn | Met | Gln | Tyr | Asp | Gln | Asp | Gln | Glu | Ala | Tyr | Pro | Pro |
| | | | | 325 | | | | | 330 | | | | | 335 | |
| Gln | Arg | Gly | His | Ser | Arg | Ser | Arg | Ser | Gly | Lys | Gly | Ser | Asn | Asp | Lys |
| | | | 340 | | | | | 345 | | | | | 350 | | |
| Gly | Arg | Ala | Lys | Pro | Pro | Ser | Gln | Lys | Ala | Met | Leu | His | Arg | Ala | Leu |
| | | | 355 | | | | | 360 | | | | | 365 | | |
| Gln | Lys | Ala | Asn | Thr | Ala | Val | Gln | Leu | Asp | Asn | Ala | Gln | Asn | Phe | Lys |
| | 370 | | | | | 375 | | | | | 380 | | | | |

```
Gly Ala Arg Glu Ala Tyr Ala Glu Ala Cys Asp Leu Leu Gln Gln Val
385                 390                 395                 400

Leu Gln Lys Thr Thr Ala Asp Glu Asp Lys Arg Lys Leu Glu Ala Ile
            405                 410                 415

Arg Arg Thr Tyr Thr Ser Arg Ile Asp Glu Leu Asp Gln Met Ala Pro
            420                 425                 430

Trp Gln Glu Glu Glu Thr Lys Ala Leu Pro Ala Arg Pro Glu Ser Leu
            435                 440                 445

Ala Gln His Ser Glu Ser Glu Ser Val Leu Arg Leu Asp Asp Asp Asp
    450                 455                 460

Asp Asp Glu Pro Asn Asp Thr Ala Val Phe Asp Thr Ala Thr Ala Ala
465                 470                 475                 480

Arg Ile Asp Gly His Ser Pro Gln Pro Arg Ile Val Asn Ser Pro Pro
            485                 490                 495

Arg Asp Asp Ser Gln Gly Tyr Arg Arg Arg Ser Ala Gln Asn Lys Pro
            500                 505                 510

Lys Pro Ile Val Thr Ser Leu Thr Pro Glu Pro Gly Leu Leu Gln Ser
            515                 520                 525

Ser Phe Ser Arg Ser Pro Val Arg Leu Arg Thr Pro Glu His Phe Leu
    530                 535                 540

Pro Gln Arg Pro Ala Asp Pro Tyr Met Pro Ala Pro Leu Ser Pro Arg
545                 550                 555                 560

Arg Pro Leu Ser Pro Ala Lys Glu Val Asp Met Asp Glu Pro Val
            565                 570                 575

Arg Thr Asp Phe Ser Met Ser His Asp Gln Gln Asn Asp His Ala Gln
            580                 585                 590

Glu His Asn Val Pro Gln Thr His Phe Arg Glu Asp Ser Met Asn Ser
            595                 600                 605

Trp Leu Asp Pro Ile Asp Glu Ser Gly Gly Ser Thr Ala Ser Ser Val
    610                 615                 620

His Ser Arg Thr Ser Ser Leu Gly Phe Arg Arg Lys His Ile Arg Ser
625                 630                 635                 640

Val Ser Gly Glu Thr Glu Ala Glu Phe Asp Thr Ala Leu Asp Ala Ala
            645                 650                 655

Ile Glu Ala Ala Tyr Asp Asp Gly Tyr Glu Pro Met Ser Pro Ile Asp
            660                 665                 670

Gln Arg Arg Thr Val Ser Val Asp Ala Gly Glu Glu Val Ile Ala Asn
            675                 680                 685

Ala Met Arg Lys Val Glu Leu Ala Arg Gln Lys Val Arg Glu Thr Glu
    690                 695                 700

Gln Glu Leu Tyr Glu Met Glu Arg Asp Asn Arg Ser Gln Pro Gln Tyr
705                 710                 715                 720

Gln Ser Tyr Glu Tyr Gln Gly Thr Pro Asn Asp Phe Tyr Asn Asp Asn
            725                 730                 735

Ser Ser Asp Glu Glu Arg Ile Leu Asp Glu Ile Ala Arg Asp Tyr
            740                 745                 750

Gly Leu Glu Ser Tyr Arg His Arg Pro Pro Pro Arg Glu Ser Asp
            755                 760                 765

Ser Ser Gly Val Thr Ser Arg Thr Trp His Ser Ser Gln Gly Ser Asn
            770                 775                 780

Pro Pro Thr Gly Ala Thr Ser Leu Ser Thr Val Thr Glu Leu Pro Pro
785                 790                 795                 800

Pro Leu Thr His Leu Thr His Gly Pro Ala Ala Pro Pro Pro Thr Gln
```

```
                805                 810                 815
Ser Leu Pro Glu Leu Pro Gln Arg Pro Gly Ser Ser Ala Gln Ser Val
            820                 825                 830

Arg Asn Arg Arg Leu Ser Gly Gln Asn Pro Lys Gln Leu Lys Ile Glu
            835                 840                 845

Thr Ser Lys Leu Ala Leu Pro Met Gln Ser Tyr Ala Asp Ala Asn Gln
            850                 855                 860

Ala Lys Ser Ala Pro Leu Ser Ser Gln Asn Val Asp Ala Thr Val Glu
865                 870                 875                 880

Pro Asp Thr Lys Ala Ala Ser Ala Lys His Arg Gln Pro Ser Pro Pro
                885                 890                 895

Leu Phe Glu Ala Ser Pro Thr Asp Met Thr Gly Ser Arg Pro Thr Pro
            900                 905                 910

Ser Pro Phe Gly Gln Leu Gly Ser Glu Lys Gly Asp Asp Ile Thr
            915                 920                 925

Gly Ser Pro Asn Thr Arg Lys Leu Arg Lys Asn Phe Ser Ser Ser
930                 935                 940

Leu Arg Ser Met Lys Ser Arg Asn Met Ser Leu Thr His Leu Glu Glu
945                 950                 955                 960

Gly Ser Asp Leu Ser Pro Gly Thr Pro Gly Ser Asn Pro Phe Gly Ser
                965                 970                 975

Leu Asn Ala Pro Ser Val Pro Ala Leu Pro Thr Pro Leu Ala Thr Ser
            980                 985                 990

Phe Arg Asp Arg Ser Glu Thr Asn Ala Ala Gly Leu Ser Leu Phe Asp
            995                 1000                1005

Asp His Phe Tyr Ser Pro Thr Ser Pro Gly Ser Pro Asn Pro Leu
    1010                1015                1020

Ile Ser Asp Pro Pro Ala Pro Leu Glu Pro Cys Pro Thr Asp Phe
    1025                1030                1035

Met Leu Arg Pro Phe Trp Leu Met Arg Cys Leu Tyr Gln Thr Leu
    1040                1045                1050

Ala His Pro Arg Gly Gly Tyr Ile Ser Ser Lys Leu Phe Val Ser
    1055                1060                1065

Arg Asp Val Trp Arg Val Lys Gly Val Lys Leu Lys Asn Ile Glu
    1070                1075                1080

Asp Lys Val Ala Asn Cys Asp Phe Leu Thr Ala Ala Leu Leu Lys
    1085                1090                1095

Ile Ala Arg Val Asp Thr Tyr Asp Ala Asp Ala Val Leu Glu Glu
    1100                1105                1110

Met Gln Ser Leu Glu Gly Ile Leu Glu Gln Val Gln Thr Ala Leu
    1115                1120                1125

Ser Arg Lys Leu Gly Asn Glu Val Gly Val His Gly Ser Gly Ala
    1130                1135                1140

Leu Phe Lys Asp Ala Ser Thr Gly Asp Gly Asp Ala Ala Thr Gly
    1145                1150                1155

Met Pro Arg Ser Ala Ser Val Ser Gly Lys Ser Ser Phe Ser Trp
    1160                1165                1170

Arg Arg Leu Arg Ser Lys Asn Ser Ala Val Gly Leu Gly Gly Ser
    1175                1180                1185

Tyr Met Ser Arg Ile Asn Thr Glu Thr Ser Lys Glu Ile Pro Ser
    1190                1195                1200

Ile Ala Ser Leu Pro Met Thr Pro Thr Pro Thr Asn Arg Pro Pro
    1205                1210                1215
```

```
Lys Arg Asp Leu Ala Gln Val Gln Phe Thr Gly Pro Asn Ala Met
    1220                1225                1230

Tyr Met Ser Ser Leu Ala Arg Leu Phe Asp Ala Ala Gln Ala Ile
    1235                1240                1245

Asp Gln Ile Ala Arg Gln Val Glu Asp Pro Gly Leu Arg His Ala
    1250                1255                1260

Asp Lys Thr Gln Val Gly Leu Glu Leu Cys Thr Arg His Ala Ala
    1265                1270                1275

Glu Phe Phe Gly Phe Tyr Val Cys Arg Phe Val Leu Ser Asp Leu
    1280                1285                1290

Gly Leu Leu Leu Asp Lys Tyr Leu Lys Arg Gly Ser Glu Trp Val
    1295                1300                1305

Leu Thr
    1310

<210> SEQ ID NO 9
<211> LENGTH: 1370
<212> TYPE: PRT
<213> ORGANISM: Neurospora sp.

<400> SEQUENCE: 9

Met Pro Leu Pro His Phe Thr Ile Ala Pro Pro Pro Ala Pro Pro
1               5                   10                  15

Ala Pro Ala Thr Ser Thr Ser Thr Ser Ser Lys Ile Pro Thr Ser Ser
                20                  25                  30

Asn Asn Pro Gly Ser Ser Ala Ser Ala Thr Asp Leu Ser Ser Ala Arg
            35                  40                  45

Thr Pro Pro Ala Thr Val Thr Thr Phe Ala Gly Ser Ala Ser Tyr Ala
    50                  55                  60

Ser Ser Pro Ser Pro Arg Thr Arg Leu Pro Asp Arg Asp Phe Ile Ser
65                  70                  75                  80

Pro Gly Leu Arg Asn Pro Tyr Pro Gln Gly Gln Gln Arg Pro Ser Arg
                85                  90                  95

Pro Pro Pro Pro Pro Pro Arg Gln Arg Gln Gln Gln Gln Gln Gln Pro
            100                 105                 110

Gln Gln His Ser Glu Arg Phe Gly Thr Val Thr Val Pro Thr Ala Ala
        115                 120                 125

Glu His Asn Gln Ser Thr Phe Ser Pro Phe Pro Asp Arg Leu Pro
    130                 135                 140

Pro Lys Val Pro Thr Asp Ser Arg Pro Ser Gln Asp Leu Leu Glu Ser
145                 150                 155                 160

Phe Asn Glu Pro Leu Leu His Gly Pro Ala Thr Pro Asp Ser Thr Lys
                165                 170                 175

Gly Leu Lys Pro Pro Ser His Lys Arg Gly His Ser Arg Ser Gly Ser
            180                 185                 190

Ser Ser Ser Ile Gly Asp Arg Leu Arg Asn Phe Asn Arg Trp Ser Val
        195                 200                 205

Ser Ser Ala Ser Ser Lys Gly Ser Asn Gly Gly Ser Ser Trp Arg
    210                 215                 220

Ile Gly Trp Asp Ser Gly Lys Glu Arg Glu Asp Ser Pro Gly Gln Lys
225                 230                 235                 240

Ser His Lys Arg Arg Pro Ser Thr Ser Glu Ile Ser Pro Arg Ser Val
                245                 250                 255

Ser His Leu Arg Gly Arg Ser Asp Ser Pro Leu Arg His Pro Ile Pro
```

```
            260                 265                 270
Pro Leu Pro Ser Leu Pro Arg Ile Ser Thr Gly Pro Ser Leu Val Glu
            275                 280                 285

Ala Phe Arg His Gln Ala Ser Glu Ile Gly Lys Gln Ser Pro Ala Pro
            290                 295                 300

Pro Arg Arg Tyr Tyr Leu Arg Pro Pro Asp Asn Ala Ala Phe
305                 310                 315                 320

Trp Asp Gly Ala Pro Gln Ile Pro Glu Asp Thr Pro Gly Ser Leu Pro
                325                 330                 335

Arg Ser His Gln Ala Ala Gly Leu Leu Leu Pro Pro Ala Glu Leu Ala
            340                 345                 350

Pro Asp His Met Met Pro Gln Tyr Thr Gln Asn Gly Asp Pro Arg Gly
            355                 360                 365

Gln Ser Arg Gly Arg Ser His Gly Ala Lys Ser Thr Asp Ser Thr
            370                 375                 380

Ala Ser Thr Arg Asn Arg Asp Arg Gln Arg His Arg Ser Asp Lys Lys
385                 390                 395                 400

Ala Met Leu Ser Glu Ala Leu Ser Lys Ala Asn Thr Ala Val Gln Leu
                405                 410                 415

Asp Asn Gly Gln Asp Phe Glu Ala Ala Arg Arg Ala Tyr Thr Glu Ala
                420                 425                 430

Cys His Leu Leu Gln Glu Val Leu Gln Arg Thr Ser Val Glu Val Asp
            435                 440                 445

Arg Arg Lys Leu Glu Ala Ile His Gln Thr Tyr Val Gly Arg Ile Asp
            450                 455                 460

Glu Leu Asp Glu Met Leu Gly Asp Ser Leu Asp Glu Lys Ala Leu Pro
465                 470                 475                 480

Glu Glu Pro Glu Ser Tyr Asp Glu Arg Gly Tyr Met Arg Thr Gln Ala
                485                 490                 495

Tyr Asn Gly Glu Val Ser Asp Asp Glu Pro Met Leu Ser Thr Tyr Thr
                500                 505                 510

Arg Glu Arg Ser Arg Thr Arg Glu Pro Ser Leu Ser Val Gln Thr Gln
            515                 520                 525

Phe Arg Arg Gln Pro Pro Ser Gly Arg Pro Pro Ala Pro Pro Thr Leu
            530                 535                 540

Thr Leu Gln Thr Pro Gly Gly Ser Asn Gly Pro Thr Ser Tyr Leu Ser
545                 550                 555                 560

Glu Gln Tyr Ser Leu Gln Ser Ser Phe Ser Lys Ala Arg Phe Glu Lys
                565                 570                 575

Ala Pro Met Asp Asn Ala Tyr Met Pro Pro Leu Leu Pro Arg Arg
                580                 585                 590

Pro Leu Ser Pro Ala Gln Pro Pro Pro Pro Ala Pro Glu Lys
            595                 600                 605

Asp Ala Pro Arg Gln Gln Val Phe Arg Pro Asp Tyr Ser Met Ser Gly
            610                 615                 620

Ala Gln Ala Thr Ser Arg Asn Tyr Lys Thr Asn Gly Gly His Gln Arg
625                 630                 635                 640

Asp Pro Ser His Glu Ser Ile Ser Trp Leu Asp Pro Ile Glu Glu Ser
                645                 650                 655

Gly Gly Ser Ser Ala Ser Ser Val His Ser Arg Ser Ser Thr Gly
                660                 665                 670

Ile Arg Arg Lys His Ile Arg Ala Ala Ser Gly Asp Thr Glu Ala Glu
            675                 680                 685
```

-continued

```
Phe Asp Ala Ala Leu Asp Asp Ile Glu Ala Ala Tyr Asp Glu Gly
    690                 695                 700
Phe Glu Pro Glu Asp Gln Tyr Tyr Thr Asp Gly His Asp Ala Val Thr
705                 710                 715                 720
Gly Ser Ser Tyr Pro Arg Asp Gln Val Pro Asp Glu Gly Met Asp Ala
                725                 730                 735
Leu Glu Leu Ala Asn Glu Arg Glu Arg Lys Leu Arg Leu Gln Gln His
                    740                 745                 750
Leu Glu Asp Glu Glu Tyr Arg Lys Arg Gly Trp Thr Gly His Asp Asp
            755                 760                 765
Phe Tyr Asp Glu Gly His Asp Ser Glu Glu Glu Arg Phe Leu Glu
    770                 775                 780
Glu Met Thr Lys Gly Tyr Gln Ile Glu Asp Phe Ala Phe Gly Pro Asn
785                 790                 795                 800
Asn Lys Gln Ser Ile Pro Arg Glu Ser Asp Ser Ser Gly Val Thr Asn
                805                 810                 815
Arg Thr Trp Asn Ser Ser Thr Gly Ser Asn Gln Asn Thr Ser Thr Thr
                    820                 825                 830
Leu Leu Ser Thr Val Ser Glu Ser Pro Thr His Pro Glu Pro Lys Gly
            835                 840                 845
Pro Leu Pro Pro Leu Pro Pro Pro Ala Gly Ala Leu Pro Gln Leu
    850                 855                 860
Pro Asp Arg Pro Pro Gly Thr Ser Gly Ser Gly Ala Ser Asn Arg Ser
865                 870                 875                 880
Val Arg Gln Arg Arg Leu Ser Gly Gln Asn Leu Lys Gln Leu Lys Ile
                885                 890                 895
Glu Thr Thr Lys Leu Ala Gln Pro Gly Pro Thr Thr Ala Gly Pro Ala
                    900                 905                 910
Phe Pro Pro Gln Pro Ala Arg Ser His Asn Tyr Ile Ala Gln Gln Arg
            915                 920                 925
Gln Ala Leu Ser Ala Gly Pro His Arg Asn Ala Asn Pro Leu Ala Ala
    930                 935                 940
Arg Arg Val Val Ser Pro Ser Met Gly Glu Gly Gly Ala Pro Pro Leu
945                 950                 955                 960
Pro Ala His Leu Gln Asp Asp Tyr Pro Pro Arg Ala Gly Ser Pro Ser
                965                 970                 975
Val Gly Arg Pro Ser Leu Lys Lys Thr Phe Ser Ser Ser Ser Leu Arg
                    980                 985                 990
Ser Ala His Arg Lys Leu Ser Val Ser His Asn Asp Asp Val Phe Asp
            995                 1000                1005
Met Ser Pro Gly Thr Pro Val Ser Asn Gln Phe Gly Ile Ser Gly
    1010                1015                1020
Ser Thr Thr Arg Leu Pro Ser Ile Pro Ser Met Pro Thr Pro Ile
    1025                1030                1035
Ala Gly Ser Phe Arg Glu Arg Ala Asp Thr Val Val Gly Thr Ala
    1040                1045                1050
Gly Met Tyr Leu Phe Asp Ala Glu Phe His Ser Ala Asn Asp Pro
    1055                1060                1065
Gly Ser Pro Asn Gly Thr Leu Thr Asp Ala Pro Ala Pro Leu Glu
    1070                1075                1080
Pro Cys Pro Ser Asp Val Leu Leu Arg Pro Phe Trp Leu Met Arg
    1085                1090                1095
```

```
Cys Leu Tyr Gln Thr Leu Cys His Pro Arg Gly Gly Tyr Ile Ser
    1100                1105                1110

Asn Lys Leu Phe Val Pro Arg Asp Val Trp Arg Val Lys Gly Val
    1115                1120                1125

Lys Leu Lys Tyr Val Glu Glu Lys Ile Ser Gln Cys Asp Leu Met
    1130                1135                1140

Thr Ala Ala Leu Gln Lys Leu Ala Arg Val Asp Thr Cys Asp Ala
    1145                1150                1155

Asp Ala Val Leu Glu Glu Met Gln Ala Leu Glu Thr Val Ile Glu
    1160                1165                1170

Ser Val Glu Lys Phe Leu Val Lys Lys Leu Gly Ala Ser Glu Val
    1175                1180                1185

Gly Pro His Ala Thr Ser Phe Lys Asp Pro Val His Ala Glu Asp
    1190                1195                1200

Gly Ser Leu Pro Arg Ser Ala Ser Val Ser Ala Lys Thr Ser Ala
    1205                1210                1215

Phe Ser Trp Arg Arg Leu Arg Ser Lys Asn Ser Ser Ala Asn Leu
    1220                1225                1230

Thr Ser Ala Gly Lys Gly Ser Ser Ser Ala Gly Gly Thr Ser Gly
    1235                1240                1245

Asn Val Ala Ser Thr Pro Ile Glu Gly Ala Gly Lys Asp Ile Ile
    1250                1255                1260

Cys Pro Ser Leu Pro Met Thr Thr His Pro Thr Asn Arg Pro Met
    1265                1270                1275

Lys Arg Asp Val Gly Asn Val Leu Phe Gln Gly Pro Asn Ala Asn
    1280                1285                1290

Tyr Met Ser Ser Leu Ala Arg Leu Phe Asp Ala Ala Gln Leu Val
    1295                1300                1305

Asp Gln Ile Ala Arg Gln Val Glu Asp Pro Gly Leu Arg His Ala
    1310                1315                1320

Asp Lys Thr Gln Val Gly Leu Glu Leu Ser Thr Arg His Ala Ala
    1325                1330                1335

Glu Phe Phe Ala Leu Tyr Ile Cys Arg Phe Val Leu Ser Asp Leu
    1340                1345                1350

Thr Leu Met Leu Asp Lys Phe Leu Lys Arg Gly Ser Glu Trp Val
    1355                1360                1365

Leu Val
    1370

<210> SEQ ID NO 10
<211> LENGTH: 805
<212> TYPE: PRT
<213> ORGANISM: Myceliophthora sp.

<400> SEQUENCE: 10

Met Asp Asn Ala Tyr Met Pro Pro Leu Ser Pro Arg Arg Pro Gly
1               5                   10                  15

Ser Pro Ala Arg Pro Ser Ser Pro Val Glu Tyr Glu Ser Pro Arg
                20                  25                  30

Arg Pro Pro Pro Asp Arg Pro Asn Ala Gln Thr Glu Ala Pro Ala Ser
            35                  40                  45

Ser Ser Gly His Gln Arg Ala Asn Ser His Glu Ser Val Ser Trp Leu
        50                  55                  60

Asp Pro Ile Asp Glu Ser Asp Arg Ser Ser Val Thr Ser Val His Ser
65                  70                  75                  80
```

```
Arg Ser Ser Ser Arg Val Val Arg Lys His Ile Arg Ala Pro Ser Gly
            85                  90                  95

Ala Thr Glu Ala Glu Phe Asp Ala Ala Leu Asp Asp Ala Ile Glu Ala
           100                 105                 110

Ala Tyr Asp Asp Gly Tyr Glu Pro Glu Ser His Tyr Pro Gly His Ser
           115                 120                 125

Tyr His Asp Ala Gln Val Asp Pro Ile Ala Asp Lys Leu Arg Arg Val
       130                 135                 140

Glu Met Ala Arg Glu Leu Val Arg Glu Ser Glu Arg Glu Ala Leu Glu
145                 150                 155                 160

Leu Ala Thr Glu Arg Glu Gln Arg Leu Arg Leu Gln Gln Gln Leu Glu
               165                 170                 175

Asp Glu Glu Tyr Arg Lys Arg Val Thr Ala Gly Glu Asp Phe Tyr Asp
               180                 185                 190

Gly Asn Asp Ser Glu Glu Glu Arg Leu Leu Glu Glu Ala Pro Arg
       195                 200                 205

Thr Asp Gly Met Asp Asp Phe Ala Phe Gly Val Gln Gln Arg Pro Pro
       210                 215                 220

Val Pro Arg Glu Ser Asp Ser Ser Gly Met Thr Gly Arg Thr Trp His
225                 230                 235                 240

Ser Ser Met Gly Ser Asn Pro Ala Thr Gly Ala Thr Leu Thr Pro Val
               245                 250                 255

Ser Glu Asp Gly Thr His Pro His Arg Ser Gly Pro Leu Pro Pro Leu
               260                 265                 270

Pro Pro Gln Ala Ala Gln Val Pro Gln Pro Gly Ser Ala Gly
               275                 280                 285

Ser Gln Ser Ser Gly Gln Ser Val Arg Asn Trp Arg Leu Ser Gly Gln
290                 295                 300

Asn Pro Lys Gly Leu Lys Ile Glu Thr Asn Lys Leu Ala Ala Thr Ala
305                 310                 315                 320

Ala Pro Ala Thr Ala Gly Pro Thr Phe Pro Ser Gln Pro Lys Thr Gly
               325                 330                 335

Ser Tyr Ile Val Gln Gln Arg Gln Ala Leu Ser Ala Gly Pro Asn Arg
               340                 345                 350

Ala Leu Gly Pro Pro Thr Ser Arg Pro Gly Pro Ser Pro Val Pro Gly
               355                 360                 365

Thr Leu Asp Glu Glu Pro Glu Asp Ala Pro Pro Arg Pro Thr Ala Leu
       370                 375                 380

Ser His Asp Glu Tyr Pro Arg Val Gly Thr Pro Ser Val Val Arg Ala
385                 390                 395                 400

Pro Asn Leu Arg Lys Asn Tyr Ser Ser Ser Leu Lys Ser Leu Lys
               405                 410                 415

Thr Arg Asn Leu Ser Ile Ser His Leu Asp Glu Gly Met Ser Asp His
               420                 425                 430

Ser Pro Gly Thr Pro Leu Ser Ser Gln Phe Gly Ala Arg Leu Pro Ala
               435                 440                 445

Val Pro Ser Leu Pro Ala Gly Ile Leu Ser Asn His Leu Lys Asp Arg
450                 455                 460

Ala Asn Ser Thr Thr Pro Gly Gly Leu His Leu Phe Glu Asn Asp Phe
465                 470                 475                 480

His Ser Ser Glu Arg Pro Gly Ser Pro Asp Pro Leu Thr Ala Asp Ala
               485                 490                 495
```

```
Pro Ala Pro Leu Glu Pro Cys Pro Thr Asp Val Met Leu Arg Pro Phe
                500                 505                 510

Trp Leu Met Arg Ala Leu Tyr Gln Thr Leu Cys His Pro Arg Gly Gly
            515                 520                 525

Tyr Leu Ser Asn Arg Leu Phe Val Pro Arg Asp Val Trp Arg Val Lys
        530                 535                 540

Gly Val Lys Leu Lys Ala Val Glu Asp Lys Ile Ala Asn Cys Asp Leu
545                 550                 555                 560

Leu Thr Ala Ala Leu Gln Lys Leu Ala Arg Val Asp Thr Cys Asp Ala
                565                 570                 575

Asp Ala Val Leu Glu Glu Met Gln Ala Leu Glu Gly Val Leu Glu His
            580                 585                 590

Val Gln Ala Thr Leu Ser Arg Lys Leu Gly Ser Glu Val Gly Val Gln
        595                 600                 605

Gly Ala Ser Ser Met Phe Lys Asp Ala Ala Ala Ala Ala Ala Ala Ala
610                 615                 620

Ala Ala Gly Asp Ala Ala Ala Gly Gly Asp Ala Ala Ala Met Pro
625                 630                 635                 640

Arg Ser Ala Ser Val Ala Gly Lys Ala Ser Ser Phe Ser Trp Arg Arg
                645                 650                 655

Leu Arg Ser Lys Asn Ser Ser Ala Asn Leu Pro Ala Leu Ala Ala Ser
            660                 665                 670

Gly Tyr Gly Asn Lys Gly Gly Asn Gly Ala Ala Ser Thr Thr Asn
        675                 680                 685

Leu Ser Glu Gly Leu Gly Lys Asp Ala Thr Leu Ala Ser Leu Pro Met
690                 695                 700

Thr Thr His Pro Thr Ser Arg Pro Thr Lys Arg Asp Ile Asn Ser Val
705                 710                 715                 720

Ser Phe Thr Gly Pro Asn Ala Asn Tyr Met Ser Ser Leu Ala Arg Leu
                725                 730                 735

Phe Asp Ala Ala Gln Thr Val Asp Gln Ile Ala Arg Gln Val Glu Asp
            740                 745                 750

Pro Gly Leu Arg His Ala Asp Lys Thr Gln Val Gly Leu Glu Leu Cys
        755                 760                 765

Ala Arg His Ala Ala Glu Phe Phe Ala Phe Tyr Ile Cys Arg Phe Ala
770                 775                 780

Leu Ser Asp Leu Thr Leu Leu Met Asp Lys Phe Val Lys Arg Gly Ser
785                 790                 795                 800

Glu Trp Val Leu Ala
                805

<210> SEQ ID NO 11
<211> LENGTH: 1004
<212> TYPE: PRT
<213> ORGANISM: Talaroymyces sp.

<400> SEQUENCE: 11

Met Glu Asp Pro Val Asn Ile Ser Ser Ser Tyr Ser Gly Glu His Ser
1               5                   10                  15

Ala Arg His Asp His Glu Arg Thr Glu Ser Gly Ser Thr Ser Pro Gln
            20                  25                  30

Arg Arg Arg Pro Arg Gly Ser Ser Gln Lys Ala Met Leu Ser Lys Ala
        35                  40                  45

Leu Ala Lys Ala Asn Thr Ala Val Leu Leu Asp Asn Ala Glu Asn Phe
50                  55                  60
```

```
Glu Gly Ala Ile Glu Ala Tyr Gln Asp Ala Cys Glu Leu Leu Gln His
 65                  70                  75                  80

Val Met Leu Arg Ser Asn Gly Gly Asp Val Glu Lys Tyr Lys Leu Leu
             85                  90                  95

Glu Ile Arg Lys Thr Tyr Leu Asn Arg Ile Gln Glu Leu Leu Arg Ile
            100                 105                 110

Gln Leu Pro Ser Asn Leu Lys Lys Asp Lys Ala Leu Pro Glu Arg Pro
        115                 120                 125

Pro Ser Gly Arg Ser Ala Thr Pro Gln Glu Asp Glu Pro Pro Ile Glu
130                 135                 140

Gln Asp Tyr Thr Asp Glu Asp Gly Ala Glu Glu Tyr Phe Ala Arg Gln
145                 150                 155                 160

Asn Ala Glu Asp Val Pro Pro Val Pro Ser Leu Asn Thr Val Arg
                165                 170                 175

Leu Pro Ser Ile Ser Gly Gln Asp Leu Asn Phe Ser Phe Glu Ala Ser
            180                 185                 190

Lys Thr Asp Ile Gly Gly Ala Asn Ser Arg Glu Ser Glu Ala Val Ala
        195                 200                 205

Gln Gly His Ser Ser Pro Ser Pro Thr Leu Gln Phe Val Ser Asp Ser
210                 215                 220

Ala Asp His Gln Gly Asp Thr Glu Thr Arg Ser Ser Thr Ala His Ala
225                 230                 235                 240

Ser His Ser Ser Asp Gly Gln Val Pro Val Asn Asp Asn Gln Ser Thr
                245                 250                 255

Ser Trp Leu Asp Thr Ile Asp Glu Ser Gly Ala Ser Ser Pro Val Ser
            260                 265                 270

Thr Asn Thr Lys Leu Ser Leu Tyr Leu Gly Gly Thr His Ser His His
        275                 280                 285

Ala Ser Asn Gly Thr Glu Ala Glu Phe Asp Ala Ala Leu Asp Ala Ala
290                 295                 300

Val Glu Ala Ala Tyr Asp Glu Gly Leu Glu Pro Ala Leu Asn Glu Gln
305                 310                 315                 320

Glu Gly Phe Tyr Asp Asp Asp Asp Tyr Glu Asp His Arg Asp
                325                 330                 335

Asp Asp Tyr Asp His Asp Asp Val Val Ser Asn Ala Arg Arg Asn Ile
            340                 345                 350

Glu Ile Ala Lys Gln Arg Val Arg Glu Ala Arg Glu Ala Gln Ala
        355                 360                 365

Val Met Ala Arg Gly Leu Gln Gln Arg Leu Met Met Gln Asp Glu Asn
370                 375                 380

Val Ala Val Ser Thr Tyr Asn Val Asp Ala Asp Tyr Ile Asp Glu Glu
385                 390                 395                 400

Ala Glu Glu Glu Glu Arg Leu Leu Glu Glu Met Thr Lys Gly Tyr Val
                405                 410                 415

Met Asp Asp Phe Glu Phe Asn Leu His Thr Lys Thr Ala Leu Pro Arg
            420                 425                 430

Gln Ser Asp Ser Ser Thr Val Ser Gly Arg Thr Trp Gly Ser Ser Ile
        435                 440                 445

Thr Ser Thr Ser Ala Asn Ser Ala Thr Ala Gly Thr Ser Leu Ser Thr
450                 455                 460

Leu Ala Glu Glu Gly Ile Leu Thr Asp Ala Thr Met Pro Ser Lys Arg
465                 470                 475                 480
```

-continued

```
Leu Pro Pro Val Pro Lys Ile Pro Thr Gly Ser Thr Gln Gln Pro Ile
            485                 490                 495

Pro Pro Asn Met Ser Pro Ser Ala Gly Val Arg Ala Arg Phe Ser
        500                 505                 510

Gly Ser Asn Thr Lys Gln Leu Lys Ile Asp Thr Lys Arg Val Ala Ala
            515                 520                 525

Gly Tyr Glu Pro Thr Lys Lys Glu Pro Phe Ser Ala Gln Pro Ala Gly
            530                 535                 540

Pro Pro Ser Pro Val Leu Leu Pro Glu Pro Lys Thr Ser Leu Pro Ile
545                 550                 555                 560

Leu Thr Ser Ser Met Ser Lys Pro Leu Pro Thr Gly Pro Ser Glu Lys
                565                 570                 575

Lys Gly Ser Phe Asp Val Ser Ala Leu Gly Gln Arg Ser Ser Ser Leu
                580                 585                 590

Thr Arg Ile Pro Thr Leu Glu Gly Asp Ser Val Ala Arg Ser Ala Gln
        595                 600                 605

Ser Ser Pro Pro Arg Thr Ile Ser Lys Ile Thr Ser Ala Pro Gly Met
        610                 615                 620

Leu Arg Lys Asn Thr Ser Ser Ser Ser Leu Ala Gly Met Arg Ala Arg
625                 630                 635                 640

Asn Met Ser Met Ser Thr Pro Asp Ile Asn Glu Ser Pro Asn Thr Pro
                645                 650                 655

Ser Ser Ser Val Phe Pro Ala Phe Phe Gln Arg Gln Leu Ala Asn
                660                 665                 670

Gly Leu Val Pro Ala Met Pro Thr Pro Ser Gly Ala Ser Phe Pro Leu
        675                 680                 685

Met Thr Ser Lys Ser Leu His Leu Phe Asp Asn Asp Ile His Ser Pro
690                 695                 700

Thr Thr Pro Gly Ser Pro Ser Ser Thr Val Thr Asn Ala Pro Ile Pro
705                 710                 715                 720

Leu Glu Pro Cys Pro Glu Ser Phe Leu Leu Arg Pro Phe Trp Leu Met
                725                 730                 735

Arg Cys Leu Tyr Gln Thr Ile Ala His Pro Arg Gly Gly Tyr Leu Ser
        740                 745                 750

Thr Lys Leu Phe Ile Pro Arg Glu Val Trp His Val Lys Asn Val Arg
        755                 760                 765

Ile Lys Ala Met Glu Asp Lys Ile Ser Leu Cys Asp Leu Leu Thr Ala
770                 775                 780

Ala Leu Leu Lys Val Ala Gln Val Asp Thr Tyr Asp Ala Asp Ala Val
785                 790                 795                 800

Leu Glu Glu Met Gln Thr Phe Glu Asn Ile Leu Asp Gln Ala Gln Thr
                805                 810                 815

Thr Phe Ala Lys Lys Leu Gly Asn Glu Val Gly Val Gln Gly Ala Leu
                820                 825                 830

Pro Leu Phe Lys Asn Ala Asn Asn Ser Asp Glu Ser Pro Ile Ser Thr
        835                 840                 845

Glu Asn Met Ala Ser Arg Ser Ser Ser Gln Ser Ser Arg Ser Val Leu
        850                 855                 860

Thr Ser Trp Arg Lys Leu Arg Ser Lys Ser Ala Ala Pro Ser Thr
865                 870                 875                 880

Ser Thr Ala Pro Ser Thr Tyr Arg Asp Ser Gly Lys Gly Gly Leu Ser
                885                 890                 895

Met Ser Thr Leu Pro Met Thr Ala Ser Pro Pro Ser Gly Arg Phe Thr
```

```
            900             905             910
Lys Arg Asp Val Met Gln Leu Gln Leu Ser Gly Pro Asn Ala Asn Tyr
            915             920             925

Met Gly Ala Leu Ala Arg Leu Phe Asp Ala Ala Gln Val Leu Asp Gln
            930             935             940

Ile Ala Arg Gln Val Glu Asp Pro Gly Leu Lys His Ser Ser Pro Thr
945             950             955             960

His Val Gly Leu Glu Leu Ser Thr Arg His Ala Ala Glu Phe Phe Gly
            965             970             975

Phe Tyr Ile Cys Arg Phe Ala Leu Asn Asp Val Gly Leu Leu Leu Asp
            980             985             990

Lys Tyr Ile Lys Arg Gly Thr Glu Trp Val Leu Val
            995             1000
```

<210> SEQ ID NO 12
<211> LENGTH: 1215
<212> TYPE: PRT
<213> ORGANISM: Aspergillus sp.

<400> SEQUENCE: 12

```
Met Ala His Asn Leu Thr Ser Glu Gly His Gly Arg Ser Ser Arg Pro
1               5               10              15

Met Ser Pro Glu Tyr Pro Phe Thr Ala Asp Thr Ala Ala Pro Arg Leu
            20              25              30

Ser Arg Ala Asn Ser Trp Asn Arg Phe Lys Lys Gly Ser Asp Ser
            35              40              45

Thr Glu Leu Ala Ser Arg Phe Gly Ala Val Thr Pro Thr Arg Pro Glu
    50              55              60

Leu Val Ser Glu Leu Ile Thr Gly Ser Pro Ser Thr Ser Pro Gly Asp
65              70              75              80

His Ile Gln Glu Gly Leu Gly Ser Leu Asn Arg Trp Ser Gln Ser Thr
            85              90              95

Ser Ser Ser Lys Gly Ser Pro Lys Tyr Asp Ser Tyr His Lys Gly Ile
            100             105             110

Pro Phe Lys Ala Ser Val Asp His Asp Tyr Thr Ser Pro Lys Ala Arg
            115             120             125

Ala Ser Pro Glu Arg Asn Ala Ile Ser Gly Leu Ser Pro Leu Val Ala
    130             135             140

Ala Pro Thr Asn Asn Glu Ser Pro Leu Gln Gly His Ser Ser Asp
145             150             155             160

Ser Ile Ala Thr Gly His Tyr Met Arg Val Leu Glu Leu Gly Asp His
            165             170             175

Ser Asn Phe Ser Ala Ser Ser Thr Asn Ala Val Asp Pro Ala Ser Ser
            180             185             190

His Gln Asp His Leu Pro Leu Gly Ser Ser Ile Ala Ala Ser Leu
            195             200             205

Phe Gln Asn Pro Trp Ser Arg Ser Gly Ala Asp Ala Gln Ala Val Asn
    210             215             220

Gln Asn Ser Gln Met Leu Thr Gly Arg Glu Gln His Gly Lys Arg
225             230             235             240

Arg Arg Gly His Ser Gln Lys Ala Met Leu Ser Lys Ala Leu Gln Lys
            245             250             255

Ala Asn Thr Ala Val Leu Leu Asp Asn Ala Ala Asn Phe Glu Gly Ala
            260             265             270
```

-continued

```
Met Glu Ala Tyr Asn Asp Ala Cys Gln Leu Leu Gln Leu Val Met Leu
            275                 280                 285

Arg Ser Ser Gly Gly Glu Asp Glu Lys Ser Lys Leu Gln Glu Ile Arg
    290                 295                 300

Asp Thr Tyr Met Ile Arg Val Thr Glu Leu Gln Arg Met Asp Phe Ser
305                 310                 315                 320

Phe Thr Glu Pro Asn Ser Lys Ala Leu Pro Glu Arg Pro Leu Ser Gln
                325                 330                 335

Glu Ser Tyr Ser Glu Met Phe Gln Ser Ile Glu Asp Glu Asn Glu
                340                 345                 350

Pro Ser Leu Asn Glu Ser Val Asn Ser Leu Arg Arg Ser Ser Asp Asp
                355                 360                 365

His Gln Pro Val Leu Asn Glu Ala Asn Val Leu Ala Ser Asp Arg Val
    370                 375                 380

Pro Val Arg Arg Gln Ser Leu Leu Pro Ser Ala Ile Asp Asp Asp Leu
385                 390                 395                 400

Cys Cys Leu Thr Leu Ser Thr Ser Thr Lys Gln Asn Ser Leu Ser
                405                 410                 415

Gln Thr Glu Ser Phe Thr Ala Ser Arg Asp Gly His Leu Glu Met Ala
                420                 425                 430

Met His Ser Glu Ser Gly Gln Ala Ser Thr Ala Leu Ser Leu Asp Asp
    435                 440                 445

Asp Ser Ala His His Leu Arg Tyr Asn Asp Trp Ala Leu Leu Ser Thr
    450                 455                 460

His Ala Lys Asp Ala Tyr Glu Ser Thr Ser Trp Leu Asp Thr Ile Asp
465                 470                 475                 480

Glu Ser Gly Ala Ser Ser Pro Ala Ser Thr Arg Ser Lys Val Ser Ser
                485                 490                 495

Leu Tyr Leu Arg His Gly Gly Ser His His Leu Ser His Gly Thr Glu
                500                 505                 510

Ala Glu Phe Asp Ala Ala Leu Asp Ala Ala Val Glu Ala Ala Tyr Asp
    515                 520                 525

Glu Gly Phe Glu Pro Val Thr Glu Pro Asn Glu Gln Tyr Asn Gly Gly
    530                 535                 540

Ile Asp Asn Asp Asp Asp Ile Val Ala Asn Ala Arg Arg Asn Ile Glu
545                 550                 555                 560

Leu Ala Lys Gln Lys Val Arg Glu Ala Arg Glu Ala Gln Val Ala
                565                 570                 575

Met Ala Arg Gly Arg Glu Val Arg Asn Leu Gln Gln Pro Ser Ile Ile
    580                 585                 590

Asp His Ser His Gly Val Gly Leu Asp Tyr Leu Asp Glu Glu Ala Glu
    595                 600                 605

Glu Glu Glu Arg Leu Leu Glu Glu Met Thr Arg Gly Tyr Ile Met Asp
    610                 615                 620

Asp Phe Asn Phe Asp Leu Gln Ser Lys Ser Ala Leu Pro Arg Gln Ser
625                 630                 635                 640

Asp Ser Ser Ser Phe Ser Gly Arg Ala Trp Glu Ser Ser Ala Val Ser
                645                 650                 655

Asn Thr Thr Thr Thr Gly Val Met Leu Ser Pro Leu Val Glu Ala Ser
                660                 665                 670

Ala Leu Pro Glu Val Ser Ala Met Thr Lys Gln Val Ala Glu Pro Leu
                675                 680                 685

Pro Thr Gln Ala Asn Gly Pro Ala Val Leu Pro Lys Gln Asn Pro Ala
```

```
            690                 695                 700
Pro Thr Pro Gly Pro Ser Val Arg Ala Arg Arg Met Ser Gly Gln Arg
705                 710                 715                 720

Thr Thr Glu Leu Lys Ile Glu Thr Lys Pro Arg Leu Gly Ala Asp Ser
            725                 730                 735

Asp Ile Ser Ser Gln Gly Gln Ser Ser Glu Pro Ala Ala Leu Ser Pro
                740                 745                 750

Pro Pro Pro Leu Pro Lys Asp Glu Pro Ser Met Asn Phe Pro Met Arg
            755                 760                 765

Thr Ser Lys Thr Leu Ala Pro Thr Pro Val Leu Arg Ser Gly Val Arg
        770                 775                 780

Leu Asn Lys Arg Asn Ala Ser Ile Gly Ser Phe Ser Glu Asp Thr Trp
785                 790                 795                 800

Ala Asn Ala Ser Leu Asp Lys Pro Thr Thr Gln Glu Glu Asp Asn Asn
                805                 810                 815

Leu Glu Ile Ser Arg Leu Pro Ser Leu Ala Arg Pro Ile Gly Lys Val
            820                 825                 830

Pro Ser Ala Pro Asp Asn Leu Gly Lys Leu Asn Ser Gly Pro Lys Ser
        835                 840                 845

Phe Arg Ala Arg Asn Val Ser Val Pro Gly Pro Asp Thr Leu Ile Asp
850                 855                 860

Ser Pro Asp Thr Pro Ser Ser Ala Phe Pro Pro Phe Asp Ile Gln Lys
865                 870                 875                 880

Gly Thr Gly Ser Ala Ala Gly Pro Val Leu Pro Thr Pro Thr Gly Ala
                885                 890                 895

Thr Phe Ala Pro Asn Gly Leu Pro Ser Gly Gly Leu Tyr Leu Phe Asp
            900                 905                 910

Ser His Ile His Ser Pro Thr Asn Leu Gly Ser Pro Asn Ala Thr Ala
        915                 920                 925

Thr Asn Ala Pro Ala Pro Leu Glu His Cys Pro Glu Ser Phe Leu Leu
930                 935                 940

Arg Pro Phe Trp Leu Met Arg Cys Ile Tyr Gln Thr Ile Ala His Pro
945                 950                 955                 960

Ser Gly Gly Tyr Leu Thr Thr Lys Leu Phe Val Pro Arg Asp Val Trp
            965                 970                 975

Arg Val Lys Asn Val Lys Ile Lys Ala Val Glu Glu Lys Val Ser Asn
        980                 985                 990

Cys Asp Leu Leu Thr Ala Ala Leu Leu Lys Leu Ala Lys Val Asp Thr
                995                 1000                1005

Tyr Asp Ala Asp Ala Val Leu Glu Glu Met Gln Ser Phe Glu Thr
    1010                1015                1020

Val Leu Asp Gln Val Gln Ser Ser Leu Ser Lys Lys Leu Gly Gly
    1025                1030                1035

Glu Val Gly Val Gln Gly Ala Met Ala Leu Phe Lys Ala Ser Gln
    1040                1045                1050

Ser Ser Asp Asp Ala Ala Ala Val Asp Thr Leu Pro Ser Lys Thr
    1055                1060                1065

Ser Gly Gly Ala Ser Lys Ser Tyr Leu Thr Ser Trp Arg Lys Leu
    1070                1075                1080

Arg Ser Lys Asn Ser Gly Phe Gly Gly Thr Thr Ser Gln Ser Ser
    1085                1090                1095

Val Lys Glu Thr Thr Lys Asp Asn Leu Ile Ile Asn Ser Leu Pro
    1100                1105                1110
```

```
Met Ser Ser Thr Pro Asn Ser Gln Pro Val Lys Arg Asn Thr Thr
1115                1120                1125

Gln Leu Gln Phe Asn Gly Pro Asn Ala Asn Tyr Met Ser Ala Leu
    1130                1135                1140

Ala Arg Leu Cys Asp Ala Ala Gln Val Leu Asp Gln Ile Ala Gln
1145                1150                1155

Gln Val Glu Asp Pro Gly Leu Lys His Ser Ser Pro Thr Leu Val
    1160                1165                1170

Gly Leu Glu Leu Ser Thr Arg His Ala Ala Glu Phe Phe Gly Phe
1175                1180                1185

Tyr Ile Cys Arg Phe Ala Leu Asn Asp Ile Ala Met Met Val Asp
    1190                1195                1200

Lys Phe Ile Lys Arg Gly Ser Glu Trp Val Leu Ile
1205                1210                1215
```

<210> SEQ ID NO 13
<211> LENGTH: 1098
<212> TYPE: PRT
<213> ORGANISM: Penicillium sp.

<400> SEQUENCE: 13

```
Met Leu Tyr Arg Ala Ala Val Glu Asp Glu Pro Arg Ser Phe His Pro
1               5                   10                  15

Arg Arg Pro Ser Gly Pro Leu Thr Glu Pro Pro Ser Gly Pro Leu Pro
            20                  25                  30

His Arg Pro Ser Ser Arg Ile Ser Arg Ser Ala Ser Arg Asn Arg Leu
        35                  40                  45

Ala His Pro Ala Gly Gly Gly Ala Arg Ile Ala Ser Thr Ser Pro Asp
    50                  55                  60

Pro Leu Ala Asp Leu Thr Pro Ser Ser Pro Ile Lys Glu Gly Leu Gly
65                  70                  75                  80

Asn Leu Asn Arg Cys Pro Ser Arg Thr Pro Ala Arg Ala Glu Leu Pro
                85                  90                  95

Glu Val Ser Val Pro Glu Leu Arg Ala Ser Glu Met Phe Met Ala Asp
            100                 105                 110

Ala Asn Ile Leu Tyr Ile Asp Pro Pro Phe Ala Ala Gly Asn His Asp
        115                 120                 125

Ser Met Thr Leu Gly His Leu Pro Pro His Gln Glu Ser Ala Ser Thr
    130                 135                 140

Tyr Pro Gly Glu Gly Gly Ile Phe Met Asp Gly Glu Gly Glu Ala Asp
145                 150                 155                 160

Phe Arg Gln His Gly Ala Thr Gln Lys Ala Met Leu Ser Lys Ala Leu
                165                 170                 175

Gln Lys Ala Asn Thr Ala Val Leu Leu Asp Asn Ala Ala Asn Phe Glu
            180                 185                 190

Gly Ala Met Glu Ala Tyr Thr Asp Ala Cys Gln Leu Leu Gln Leu Val
        195                 200                 205

Met Leu Arg Ser Asn Gly Gly Asp Glu Glu Arg Ile Lys Leu Gln Glu
    210                 215                 220

Ile Arg Asp Thr Tyr Met Ala Arg Ile Thr Glu Leu Gln Arg Met Asp
225                 230                 235                 240

Phe Ser Ile Met Glu Ser Asp Gly Lys Ala Leu Pro Glu Arg Pro Leu
                245                 250                 255

Ser Gln Glu Ser Phe Gly Glu Leu Leu His Ala Val Ala Ser Val Gln
```

```
                260                 265                 270
Asp Asp Pro Tyr Leu Asp Ser Gln His Ser Ala Ala His Ser Gly Leu
            275                 280                 285

Arg Leu Gln Ala Ala Phe Asp Glu Ser Arg Pro Leu Pro Ser Glu Ala
            290                 295                 300

Ile Pro Pro Arg Arg Gln Ser Leu Arg Pro Ser Ala Gln Ser Asp Arg
305                 310                 315                 320

Thr Thr Pro Ala Gly Leu Gly Asn Asn Leu Ala Ala Tyr His His Gly
            325                 330                 335

Ala Phe Leu Asp Pro Thr Pro Val Leu Asp Ser Asn Glu Thr Thr Ser
            340                 345                 350

Trp Leu Asp Thr Ile Asp Glu Ser Gly Ala Ser Ser Pro Ser Ser Ala
            355                 360                 365

Asn Ser Lys Ala Ser Ser Val Tyr Leu Arg Arg Thr Ser Arg Arg
            370                 375                 380

Leu Ser Thr Asp Thr Glu Ala Glu Phe Asp Ala Ala Leu Asp Ala Ala
385                 390                 395                 400

Val Glu Ala Ala Tyr Asp Asp Gly Leu Glu Pro Val Glu Glu Tyr Gln
            405                 410                 415

Asp Glu Glu Gly Asp Ser Val Val Ala Asn Ala Arg Arg Asn Ile Glu
            420                 425                 430

Leu Ala Lys Gln Arg Val Arg Glu Ala Glu Leu Glu Ala Glu Ala Ala
            435                 440                 445

Met Ser Arg Gly Arg Asp Leu Arg Pro Val Gln Glu Gln Tyr Leu Leu
            450                 455                 460

Asp Asp Ala Gly Gly Gln Thr Leu Glu Tyr Leu Asp Glu Glu Ala Glu
465                 470                 475                 480

Glu Glu Glu Arg Leu Leu Glu Glu Met Thr Lys Gly Tyr Val Met Asp
            485                 490                 495

Glu Phe Glu Phe Gly Leu Gln Thr Lys Ser Ala Leu Pro Arg Glu Ser
            500                 505                 510

Asp Ser Ser Asn Met Ser Gly His Thr Trp Glu Ser Ser Leu Ala Ser
            515                 520                 525

Asn Ala Thr Gly Pro Gly Ser Leu Ala Leu Ser Thr Leu Ala Glu Asp
            530                 535                 540

Asp Asp Ser Val Leu Pro Leu Asp Phe Leu Asp Gln Thr Leu Leu Pro
545                 550                 555                 560

Thr Ala Pro Pro Thr Ala Ala Leu Pro Pro Ile Pro Val Ser Ser Asp
            565                 570                 575

Phe Pro Ser Leu Pro Leu Pro Arg Ala Ser Val Ser Ser Pro Ala Pro
            580                 585                 590

Pro Pro Pro Pro Met Gly Pro Pro Ile Pro Gly Val Arg Ala Arg
            595                 600                 605

Arg Leu Ser Gly Gln Ala Ser Thr Glu Leu Lys Ile Glu Thr Gly Ser
            610                 615                 620

His Ala Arg Ser Ser Ser Thr Val Ser Asn Val Asp Pro Phe Met Ile
625                 630                 635                 640

Pro Pro Thr Gln Pro Ala Pro Ala Ala Ser Lys Asp Glu Ala Ser Gln
            645                 650                 655

Glu Pro Ser Arg Ser Ala Thr Pro Ser Phe Arg Ala Asn Leu His Pro
            660                 665                 670

Thr Ser Arg Arg Asn Pro Ser Thr Gly Ser Phe Val Asp His Ile Asn
            675                 680                 685
```

```
Leu Ile Lys Thr Arg Thr Gln Glu Asp Glu Glu Gly Leu Pro Val
690                 695                 700

Leu Pro Ala Ala Ile Arg Pro Met Gly Lys Val Pro Ser Ala Pro Asp
705                 710                 715                 720

Gly Leu Asp Lys Val Gly Ala Thr Thr Lys Ser Phe Arg Asn Arg Asn
                725                 730                 735

Val Ser Val Pro Ile Pro Asp Thr Val Pro Val Ser Pro Thr Thr Pro
                740                 745                 750

Trp Ser Gly Ser Phe Ser Ser Gln Glu Thr Gln Lys Ala Ser Gly Ile
            755                 760                 765

Pro His Met Pro Val Leu Pro Thr Pro Thr Ala Pro Leu Phe Thr Gln
        770                 775                 780

Asn Gly Leu Pro Thr Gly Gly Leu Asp Leu Phe Asp Cys Glu Ile His
785                 790                 795                 800

Ser Pro Thr Ser Leu Gly Arg Pro Asn Met Leu Val His Asn Ala Pro
                805                 810                 815

Leu Pro Leu Glu Pro Cys Pro Glu Ser Phe Leu Leu Arg Pro Phe Trp
                820                 825                 830

Leu Met Arg Cys Leu Tyr Gln Thr Leu Ser His Pro Gln Gly Gly Tyr
            835                 840                 845

Leu Ser Glu Lys Leu Phe Ile Pro Arg Asp Val Trp Arg Val Lys Asn
850                 855                 860

Val Lys Ile Lys Ala Leu Glu Asp Lys Ile Ser Asn Cys Asp Leu Leu
865                 870                 875                 880

Thr Ala Ala Leu Leu Lys Leu Ala Gln Val Asp Met Phe Asp Ala Asp
                885                 890                 895

Ala Val Leu Asp Glu Met Gln Ser Phe Glu Ser Ile Leu Asp Gln Ala
                900                 905                 910

Gln Met Val Leu Ser Lys Lys Leu Gly Asn Glu Val Gly Val His Ala
            915                 920                 925

Ala Ile Pro Gln Leu Arg Gln His Ala Ser Phe Asp Asp Ala Ala Gln
930                 935                 940

Phe Glu Thr Ser Val Val Lys Ser Ser Ser Thr Ser Asn Lys Ser Tyr
945                 950                 955                 960

Arg Pro Thr Trp Lys Arg Leu Arg Ser Lys Thr Ser Gly Ile Thr Thr
                965                 970                 975

Val Ser Ser Phe Ser Ser Val Arg Glu Thr Thr Lys Glu Gln Leu Thr
                980                 985                 990

Met Thr Ser Val Pro Met Thr Thr Ala Pro Ser Asn Gln Ala Arg Arg
            995                 1000                1005

Ser Val Thr Ser Leu Asp Phe Ser Gly Pro Asn Ser His Tyr Met
    1010                1015                1020

Gly Ala Leu Ala Arg Leu Phe Asp Ala Ala Gln Val Leu Asp Gln
    1025                1030                1035

Val Ala Gln Gln Val Glu Asp Pro Gly Leu Lys His Ser Ser Pro
    1040                1045                1050

Thr His Val Gly Leu Glu Leu Ser Thr Arg His Ala Ala Glu Phe
    1055                1060                1065

Phe Gly Phe Tyr Ile Cys Arg Phe Ala Leu Ala Asp Val Gly Leu
    1070                1075                1080

Met Leu Asp Lys Phe Ile Lys Arg Gly Ser Glu Trp Val Leu Ile
    1085                1090                1095
```

<210> SEQ ID NO 14
<211> LENGTH: 364
<212> TYPE: PRT
<213> ORGANISM: Hypocrea jecorina

<400> SEQUENCE: 14

Met Lys Gly Leu Ile Leu Val Gly Gly Phe Gly Thr Arg Leu Arg Pro
1               5                   10                  15

Leu Thr Leu Thr Leu Pro Lys Pro Leu Val Glu Phe Cys Asn Lys Pro
            20                  25                  30

Met Ile Val His Gln Ile Glu Ala Leu Val Ala Ala Gly Val Thr Asp
        35                  40                  45

Ile Val Leu Ala Val Asn Tyr Arg Pro Glu Ile Met Glu Lys Phe Leu
50                  55                  60

Ala Glu Tyr Glu Glu Lys Tyr Asn Ile Asn Ile Glu Phe Ser Val Glu
65                  70                  75                  80

Ser Glu Pro Leu Asp Thr Ala Gly Pro Leu Lys Leu Ala Glu Arg Ile
                85                  90                  95

Leu Gly Lys Asp Asp Ser Pro Phe Phe Val Leu Asn Ser Asp Val Ile
            100                 105                 110

Cys Asp Tyr Pro Phe Lys Glu Leu Leu Glu Phe His Lys Ala His Gly
        115                 120                 125

Asp Glu Gly Thr Ile Val Val Thr Lys Val Glu Pro Ser Lys Tyr
130                 135                 140

Gly Val Val Val His Lys Pro Asn His Pro Ser Arg Ile Asp Arg Phe
145                 150                 155                 160

Val Glu Lys Pro Val Glu Phe Val Gly Asn Arg Ile Asn Ala Gly Met
                165                 170                 175

Tyr Ile Phe Asn Pro Ser Val Leu Lys Arg Ile Glu Leu Arg Pro Thr
            180                 185                 190

Ser Ile Glu Lys Glu Thr Phe Pro Ala Met Val Ala Asp Asn Gln Leu
        195                 200                 205

His Ser Phe Asp Leu Glu Gly Phe Trp Met Asp Val Gly Gln Pro Lys
210                 215                 220

Asp Phe Leu Ser Gly Thr Cys Leu Tyr Leu Ser Ser Leu Thr Lys Lys
225                 230                 235                 240

Gly Ser Lys Glu Leu Thr Pro Pro Thr Glu Pro Tyr Val His Gly Gly
                245                 250                 255

Asn Val Met Ile His Pro Ser Ala Lys Ile Gly Lys Asn Cys Arg Ile
            260                 265                 270

Gly Pro Asn Val Thr Ile Gly Pro Asp Val Val Gly Asp Gly Val
        275                 280                 285

Arg Leu Gln Arg Cys Val Leu Leu Lys Gly Ser Lys Val Lys Asp His
290                 295                 300

Ala Trp Val Lys Ser Thr Ile Val Gly Trp Asn Ser Thr Val Gly Arg
305                 310                 315                 320

Trp Ala Arg Leu Glu Asn Val Thr Val Leu Gly Asp Asp Val Thr Ile
                325                 330                 335

Gly Asp Glu Ile Tyr Val Asn Gly Gly Ser Val Leu Pro His Lys Ser
            340                 345                 350

Ile Lys Ala Asn Val Asp Val Pro Ala Ile Ile Met
        355                 360

<210> SEQ ID NO 15

```
<211> LENGTH: 1042
<212> TYPE: PRT
<213> ORGANISM: Hypocrea jecorina

<400> SEQUENCE: 15
```

| | | | | | | | | | | | | | | |
|---|---|---|---|---|---|---|---|---|---|---|---|---|---|---|
| Met | Asp | Tyr | Thr | Gln | Tyr | His | Ala | Leu | Gly | His | Gly | Glu | Val | Leu | Asp |
| 1 | | | | 5 | | | | | 10 | | | | | 15 | |
| Pro | Asn | Asp | Pro | Asn | Lys | Thr | Ser | Ala | Pro | Ala | Ala | Pro | Gln | Phe | Gln |
| | | | 20 | | | | | 25 | | | | | 30 | | |
| Pro | Pro | Ser | Ser | Pro | Tyr | Val | Pro | Pro | Gly | Ser | Pro | Tyr | Gly | Ala | Pro |
| | | | 35 | | | | | 40 | | | | | 45 | | |
| Pro | Tyr | His | Gly | Gly | His | Gln | Ala | Pro | Pro | Met | Ala | Met | Pro | Pro | Pro |
| | 50 | | | | | 55 | | | | | 60 | | | | |
| Ser | Thr | Pro | Gly | Tyr | Gly | Pro | Pro | Gln | Gly | Gln | Ser | Phe | Pro | Gly | Ser |
| 65 | | | | | 70 | | | | | 75 | | | | | 80 |
| Pro | Met | Pro | Ser | Gln | Asp | Ala | Gly | Leu | Ala | Ala | Gln | Phe | Gly | Gly | Met |
| | | | | 85 | | | | | 90 | | | | | 95 | |
| Ser | Leu | Gly | Ala | Asp | Ala | Gly | Gly | Ala | Ala | Ala | Arg | Lys | Lys | Lys | Lys |
| | | | 100 | | | | | 105 | | | | | 110 | | |
| Asp | Arg | His | Ala | Tyr | His | Ser | Val | Glu | Pro | Thr | Gly | Ser | Ser | Gln | Ala |
| | | | 115 | | | | | 120 | | | | | 125 | | |
| Phe | Asn | Gly | Leu | Pro | Pro | Gly | Thr | Pro | Ala | Glu | Gln | Phe | Leu | Asn | Val |
| | 130 | | | | | 135 | | | | | 140 | | | | |
| Asn | Asn | Pro | Gln | Gly | Ile | Pro | Ala | Leu | Gly | Gly | Gln | Phe | Gly | Ser | Pro |
| 145 | | | | | 150 | | | | | 155 | | | | | 160 |
| Leu | Ala | Ser | Pro | Met | Gly | Thr | Pro | His | Met | Ala | Asn | Pro | Gly | Gln | Phe |
| | | | | 165 | | | | | 170 | | | | | 175 | |
| Pro | Ala | Pro | Thr | Ser | Pro | Phe | Thr | Pro | Ser | Ala | Pro | Val | Ser | Pro | Ala |
| | | | 180 | | | | | 185 | | | | | 190 | | |
| Glu | Phe | Ala | Ser | Arg | Phe | Gly | Ser | Pro | Asp | Ala | Ala | Thr | Ser | Ile | Gly |
| | | | 195 | | | | | 200 | | | | | 205 | | |
| Ser | Ala | Gly | Pro | Ser | Gln | Val | Ser | Pro | Asp | Asp | Met | Pro | Ser | Ile | Pro |
| | 210 | | | | | 215 | | | | | 220 | | | | |
| Ala | Ser | Arg | Asp | Ala | Ile | Gln | Glu | His | Phe | Phe | Lys | Asn | Val | Tyr | Pro |
| 225 | | | | | 230 | | | | | 235 | | | | | 240 |
| Thr | Phe | Glu | Arg | His | Val | Pro | Pro | Ala | Thr | Val | Ser | Phe | Val | Ala | |
| | | | | 245 | | | | | 250 | | | | | 255 | |
| Phe | Asp | Gln | Gly | Asn | Ala | Ser | Pro | Lys | Phe | Thr | Arg | Leu | Thr | Leu | Asn |
| | | | 260 | | | | | 265 | | | | | 270 | | |
| Asn | Ile | Pro | Thr | Thr | Ala | Glu | Gly | Leu | His | Ala | Thr | Gly | Leu | Pro | Leu |
| | | | 275 | | | | | 280 | | | | | 285 | | |
| Gly | Met | Leu | Ile | Gln | Pro | Leu | Ala | Pro | Leu | Gln | Ala | Gly | Glu | Ala | Glu |
| | 290 | | | | | 295 | | | | | 300 | | | | |
| Ile | Pro | Val | Leu | Asp | Phe | Gly | Asp | Ala | Gly | Pro | Pro | Arg | Cys | Arg | Arg |
| 305 | | | | | 310 | | | | | 315 | | | | | 320 |
| Cys | Arg | Ala | Tyr | Ile | Asn | Pro | Phe | Met | Met | Phe | Arg | Ser | Gly | Gly | Asn |
| | | | | 325 | | | | | 330 | | | | | 335 | |
| Lys | Phe | Val | Cys | Asn | Leu | Cys | Ser | Tyr | Pro | Asn | Glu | Thr | Pro | Pro | Glu |
| | | | 340 | | | | | 345 | | | | | 350 | | |
| Tyr | Phe | Cys | Ala | Val | Ser | Pro | Gln | Gly | Val | Arg | Leu | Asp | Arg | Asp | Gln |
| | | | 355 | | | | | 360 | | | | | 365 | | |
| Arg | Pro | Glu | Leu | His | Arg | Gly | Thr | Val | Glu | Phe | Val | Pro | Lys | Glu | |
| | 370 | | | | | 375 | | | | | 380 | | | | |
| Tyr | Trp | Thr | Arg | Glu | Pro | Val | Gly | Leu | Arg | Trp | Leu | Phe | Val | Ile | Asp |

```
385                 390                 395                 400
Val Thr Gln Glu Ser Tyr Asn Lys Gly Phe Met Glu Thr Phe Cys Glu
                405                 410                 415
Gly Ile Leu Ala Ala Leu Tyr Gly Gly Asn Asp Glu Glu Asn Asp Glu
                420                 425                 430
Asp Gly Glu Pro Lys Arg Arg Ile Pro Lys Gly Ala Lys Val Gly Phe
            435                 440                 445
Ile Thr Tyr Asp Lys Asp Ile His Phe Tyr Asn Ile Asn Pro His Leu
        450                 455                 460
Asp Gln Ala His Met Met Ile Met Pro Asp Leu Glu Asp Pro Phe Leu
465                 470                 475                 480
Pro Leu Gly Glu Gly Leu Phe Val Asp Pro Tyr Glu Ser Lys Ala Ile
                485                 490                 495
Ile Thr Ser Leu Leu Thr Arg Leu Pro Glu Met Phe Ser Thr Ile Lys
                500                 505                 510
Asn Pro Glu Pro Ala Leu Leu Ala Thr Leu Asn Ala Ala Val Ala Ala
                515                 520                 525
Leu Glu Ala Thr Gly Gly Lys Val Val Cys Ser Cys Ser Thr Leu Pro
        530                 535                 540
Thr Trp Gly Pro Gly Arg Leu Phe Met Arg Asp Asp Gly Asn His Pro
545                 550                 555                 560
Gly Gly Glu Leu Asp Lys Lys Leu Tyr Thr Thr Glu His Pro Ala Trp
                565                 570                 575
Lys Lys Val Ser Glu Lys Met Ala Ser Ser Gly Ile Gly Val Asp Phe
                580                 585                 590
Phe Leu Ala Ala Pro Ser Gly Gly Tyr Leu Asp Ile Ala Thr Ile Gly
            595                 600                 605
His Val Ala Ala Thr Thr Gly Gly Glu Thr Phe Tyr Tyr Pro Asn Phe
        610                 615                 620
Ile Ala Pro Arg Asp Gly Ala Arg Leu Ser Met Glu Ile Thr His Ala
625                 630                 635                 640
Ile Thr Arg Glu Thr Gly Phe Gln Ala Leu Met Lys Val Arg Cys Ser
                645                 650                 655
Thr Gly Leu Gln Val Ala Ala Tyr His Gly Asn Phe Val Gln His Thr
                660                 665                 670
Phe Gly Ala Asp Leu Glu Ile Gly Val Ile Asp Ala Asp Lys Ala Leu
            675                 680                 685
Gly Val Ser Phe Ser His Asp Gly Lys Leu Asp Pro Lys Leu Asp Ala
        690                 695                 700
His Phe Gln Thr Ala Leu Leu Tyr Thr Thr Ala Ser Gly Gln Arg Arg
705                 710                 715                 720
Val Arg Cys Ser Asn Val Ile Ala Ser Val Ser Asp Thr Ser Lys Glu
                725                 730                 735
Ser Asn Thr Lys Glu Leu Ala Ile Arg Gln Cys Leu Lys Phe Val Asp
                740                 745                 750
Gln Asp Ala Val Val Gly Ile Phe Ala Lys Glu Ala Ser Thr Lys Leu
            755                 760                 765
Ala Thr Thr Ser Ala Asn Leu Gln Asp Val Arg Asn Trp Leu Thr Glu
        770                 775                 780
Arg Thr Ile Asp Ile Met Ala Tyr Tyr Lys Lys His Ser Ala Asn Gln
785                 790                 795                 800
Phe Pro Pro Ser Gln Leu Val Met Pro Glu Arg Leu Lys Glu Phe Cys
                805                 810                 815
```

```
Met Tyr Met Leu Gly Met Leu Lys Cys Arg Ala Phe Lys Gly Gly Ile
            820                 825                 830

Glu Asn Ser Asp Arg Arg Val His Glu Leu Arg Met Val Arg Ser Met
            835                 840                 845

Gly Pro Leu Glu Leu Ser Leu Tyr Leu Tyr Pro Arg Met Ile Ala Leu
        850                 855                 860

His Asn Leu Gln Pro Glu Glu Gly Phe Ala Asp Pro Glu Thr Gly His
865                 870                 875                 880

Leu Lys Met Pro Pro Ser Val Arg Thr Ser Phe Ser Arg Val Glu Pro
                885                 890                 895

Gly Gly Val Tyr Leu Val Asp Asn Gly Gln Gln Cys Leu Leu Trp Phe
        900                 905                 910

His Ala Gln Thr Ser Pro Asn Leu Ile Thr Asp Leu Phe Gly Glu Gly
        915                 920                 925

His Asp Ser Leu Lys Gly Leu Asp Pro Tyr Thr Ser Thr Leu Pro Val
    930                 935                 940

Leu Glu Thr His Leu Ser Ala Gln Val Arg Asn Ile Ile Glu Phe Leu
945                 950                 955                 960

Lys Ser Met Arg Gly Ser Lys Gly Met Thr Ile Gln Leu Ala Arg Gln
                965                 970                 975

Gly Ile Asp Gly Ala Glu Tyr Glu Phe Ala Arg Met Leu Val Glu Asp
            980                 985                 990

Arg Asn Asn Glu Ala Lys Ser Tyr Val Asp Trp Leu Val His Ile His
            995                 1000                1005

Arg Gly Val Gln Leu Glu Leu Ser Gly Gln Arg Lys Lys Glu Gly
    1010                1015                1020

Asp Gly Glu Ala Thr Ala Val Met Ala Asn Phe Ala Gly Leu Arg
    1025                1030                1035

Pro Ala Tyr Trp
    1040

<210> SEQ ID NO 16
<211> LENGTH: 534
<212> TYPE: PRT
<213> ORGANISM: Hypocrea jecorina

<400> SEQUENCE: 16

Met Asp Gly Met Met Ser Gln Pro Met Gly Gln Gln Ala Phe Tyr Phe
1               5                   10                  15

Tyr Asn His Glu His Lys Met Ser Pro Arg Gln Val Ile Phe Ala Gln
            20                  25                  30

Gln Met Ala Ala Tyr Gln Met Met Pro Ser Leu Pro Pro Thr Pro Met
        35                  40                  45

Tyr Ser Arg Pro Asn Ser Ser Cys Ser Gln Pro Pro Thr Leu Tyr Ser
    50                  55                  60

Asn Gly Pro Ser Val Met Thr Pro Thr Ser Thr Pro Pro Leu Ser Ser
65                  70                  75                  80

Arg Lys Pro Met Leu Val Asp Thr Glu Phe Gly Asp Asn Pro Tyr Phe
                85                  90                  95

Pro Ser Thr Pro Pro Leu Ser Ala Ser Gly Ser Thr Val Gly Ser Pro
            100                 105                 110

Lys Ala Cys Asp Met Leu Gln Thr Pro Met Asn Pro Met Phe Ser Gly
        115                 120                 125

Leu Glu Gly Ile Ala Ile Lys Asp Ser Ile Asp Ala Thr Glu Ser Leu
```

```
            130                 135                 140
Val Leu Asp Trp Ala Ser Ile Ala Ser Pro Pro Leu Ser Pro Val Tyr
145                 150                 155                 160

Leu Gln Ser Gln Thr Ser Ser Gly Lys Val Pro Ser Leu Thr Ser Ser
                165                 170                 175

Pro Ser Asp Met Leu Ser Thr Thr Ala Ser Cys Pro Ser Leu Ser Pro
            180                 185                 190

Ser Pro Thr Pro Tyr Ala Arg Ser Val Thr Ser Glu His Asp Val Asp
                195                 200                 205

Phe Cys Asp Pro Arg Asn Leu Thr Val Ser Val Gly Ser Asn Pro Thr
            210                 215                 220

Leu Ala Pro Glu Phe Thr Leu Leu Ala Asp Asp Ile Lys Gly Glu Pro
225                 230                 235                 240

Leu Pro Thr Ala Ala Gln Pro Ser Phe Asp Phe Asn Pro Ala Leu Pro
                245                 250                 255

Ser Gly Leu Pro Thr Phe Glu Asp Phe Ser Asp Leu Glu Ser Glu Ala
                260                 265                 270

Asp Phe Ser Ser Leu Val Asn Leu Gly Glu Ile Asn Pro Val Asp Ile
            275                 280                 285

Ser Arg Pro Arg Ala Cys Thr Gly Ser Ser Val Val Ser Leu Gly His
290                 295                 300

Gly Ser Phe Ile Gly Asp Glu Asp Leu Ser Phe Asp Glu Ala Phe
305                 310                 315                 320

His Phe Pro Ser Leu Pro Ser Pro Thr Ser Ser Val Asp Phe Cys Asp
                325                 330                 335

Val His Gln Asp Lys Arg Gln Lys Asp Arg Lys Glu Ala Lys Pro
                340                 345                 350

Val Met Asn Ser Ala Ala Gly Gly Ser Gln Ser Gly Asn Glu Gln Ala
                355                 360                 365

Gly Ala Thr Glu Ala Ala Ser Ala Ala Ser Asp Ser Asn Ala Ser Ser
                370                 375                 380

Ala Ser Asp Glu Pro Ser Ser Met Pro Ala Pro Thr Asn Arg Arg
385                 390                 395                 400

Gly Arg Lys Gln Ser Leu Thr Glu Asp Pro Ser Lys Thr Phe Val Cys
                405                 410                 415

Asp Leu Cys Asn Arg Arg Phe Arg Arg Gln Glu His Leu Lys Arg His
                420                 425                 430

Tyr Arg Ser Leu His Thr Gln Glu Lys Pro Phe Glu Cys Asn Glu Cys
                435                 440                 445

Gly Lys Lys Phe Ser Arg Ser Asp Asn Leu Ala Gln His Ala Arg Thr
            450                 455                 460

His Ser Gly Gly Ala Ile Val Met Asn Leu Ile Glu Glu Ser Ser Glu
465                 470                 475                 480

Val Pro Ala Tyr Asp Gly Ser Met Met Ala Gly Pro Val Gly Asp Asp
                485                 490                 495

Tyr Ser Thr Tyr Gly Lys Val Leu Phe Gln Ile Ala Ser Glu Ile Pro
                500                 505                 510

Gly Ser Ala Ser Glu Leu Ser Ser Glu Glu Gly Glu Gln Gly Lys Lys
                515                 520                 525

Lys Arg Lys Arg Ser Asp
                530

<210> SEQ ID NO 17
```

<211> LENGTH: 668
<212> TYPE: PRT
<213> ORGANISM: Hypocrea jecorina

<400> SEQUENCE: 17

```
Arg Gly Arg Ser Pro Ser Ala Gly Gly Phe Gln Ser Asp Ile Asn Gln
1               5                   10                  15

Ser His Ser Pro Ala Arg Ser Pro Leu Ala Pro Thr Asn Glu Gln Pro
            20                  25                  30

Ser Ala Gly Leu Gly Val Gly Leu Gly Gln Gln Gln Arg Ala Phe
        35                  40                  45

Ala Ala Pro Leu His Pro Asn Tyr Asp Ser Phe Gly Ala Asn Gly Phe
50                  55                  60

Leu Gly Ala Gln Ala Asn Ala Val Asp Pro Thr Asn Gly Phe Asp Pro
65                  70                  75                  80

Ser Ala Ser Phe Gly Gln Gln Pro Ala Thr Gly Pro Asp Ser Thr Leu
                85                  90                  95

Ser Leu Asn Ala Gln Ala Gln His Asn Tyr Leu Ser Pro Asn Leu His
            100                 105                 110

Asp Gly Asp Phe Ser Leu Phe Pro Ser Ala Ala Glu Gln Gly Asp Gln
            115                 120                 125

Tyr Asn Ala Pro Leu Phe Glu Gln Pro Leu Gly Asp Leu Asn Ala
        130                 135                 140

Met Thr Ser Pro His Ser His Gln Ser Pro Thr Pro Pro Gln Leu Phe
145                 150                 155                 160

Gln Pro Asp Ser Leu Gln Ser Pro Pro Phe Asn Arg His Gln Phe Ser
                165                 170                 175

Ser Pro Pro Thr His Ser Arg Asn Ala Ser Leu Gly Pro Glu Ala Ala
            180                 185                 190

Leu Leu Pro Ser Gln Ile Gly Asp Trp Thr Gln Pro Gln Phe Gln Gly
        195                 200                 205

His Arg Arg Thr Pro Ser Glu Tyr Ser Asp Val Ser Ser Val Ala Pro
        210                 215                 220

Ser Pro His Leu Val Ser Ser Asp Thr Phe Asp Ala Asp Gln Ser Gly
225                 230                 235                 240

His Ser Pro Leu Gln Arg Pro Ala Asp Val Ser Leu Tyr Gln Glu Val
                245                 250                 255

Leu Gly Ile Gly Ser Phe Ser Leu Ala Asp His Gly Ser Pro Gly Tyr
            260                 265                 270

His Gly Arg Ser Pro Ser His Ser Pro Ala Ile Ser Pro Arg Ile Met
        275                 280                 285

Pro Gln Gln Met Pro Asp Thr Met Gln Pro Ser Phe Asn Leu Ile Pro
290                 295                 300

Pro Asn Gly Gly Phe Asp Gly Val Ser Gly Tyr Pro Asp Leu Gln Pro
305                 310                 315                 320

Ser His Glu Ser Phe Pro Ser Leu Ser Gly Gly Met Gly Gly Asp Met
                325                 330                 335

His Gln Met Ala Pro Pro Ala Ile Asn Ile Asp Phe Ala Pro Thr Asn
            340                 345                 350

Ser Arg Gln Gly Ser Phe Glu Pro Lys Ser Gln Met Asp Gln Asp
        355                 360                 365

Ser Leu Thr Pro Pro Glu Arg Gly Arg Pro Lys Ser Arg Pro Arg Ala
        370                 375                 380

Val Thr Asp Pro Phe His Pro Gly Ser Gly Ile Leu Pro Pro Gly Asn
```

```
385                 390                 395                 400

Leu Gly Ser Ser Leu Gly Val Asp Leu Ala Ala Arg Ser Asp Thr Ala
                405                 410                 415

Ser Arg Ser Leu Ser Pro Leu Asp Arg Ser Gly Thr Ser Ser Pro Ala
                420                 425                 430

Ser Arg Arg Arg Gln Ser Thr Ser Val Pro Asn Asn Val Ile Ala
                435                 440                 445

Leu Arg Leu Ala Asp Pro Glu Tyr Gln Asn Ser Gln Glu Ala Gly Thr
450                 455                 460

Ser Lys Arg Met Gln Lys His Pro Ala Thr Phe Gln Cys Thr Leu Cys
465                 470                 475                 480

Pro Lys Arg Phe Thr Arg Ala Tyr Asn Leu Arg Ser His Leu Arg Thr
                485                 490                 495

His Thr Asp Glu Arg Pro Phe Val Cys Thr Val Cys Gly Lys Ala Phe
                500                 505                 510

Ala Arg Gln His Asp Arg Lys Arg His Glu Ser Leu His Ser Gly Glu
                515                 520                 525

Lys Lys Phe Val Cys Lys Gly Asp Leu Lys Thr Gly Gly Gln Trp Gly
                530                 535                 540

Cys Gly Arg Arg Phe Ala Arg Ala Asp Ala Leu Gly Arg His Phe Arg
545                 550                 555                 560

Ser Glu Ala Gly Arg Ile Cys Ile Lys Pro Leu Leu Asp Glu Glu Met
                565                 570                 575

Val Glu Arg Gln Arg Gln Trp Gln Glu Gln Arg Met Gln Gln Asn Met
                580                 585                 590

Ala Gln Asn Met Ala Asn Pro Gln Val Met Gly Met Asp Ala Gly Pro
                595                 600                 605

Ala Tyr Pro Met Asp Ala Ser Gly Asn Tyr Thr Leu Pro Gln Ala Leu
                610                 615                 620

Leu Ala Gln Tyr Pro Ala Leu Ala Gln Met Asn Trp Ser Ala Thr Asp
625                 630                 635                 640

Met Gly Gly Gly Leu Asp Asp Glu Leu Ser Gly Arg Ser Ser Phe Asp
                645                 650                 655

Ala Ser Asp Tyr Asp Asp Gly Asp Gly Gly Tyr
                660                 665

<210> SEQ ID NO 18
<211> LENGTH: 540
<212> TYPE: PRT
<213> ORGANISM: Hypocrea jecorina

<400> SEQUENCE: 18

Met Ser Leu Ser Lys Leu Ser Val Ser Leu Leu Ala Leu Ala Gly Ser
1               5                   10                  15

Ala Ile Ala Gly Asp Leu Pro Ser Ile Thr Ala Lys Gly Ser Lys Phe
                20                  25                  30

Phe Tyr Pro Asn Gly Thr Gln Phe Phe Ile Lys Gly Val Ala Tyr Gln
                35                  40                  45

Gln Asp Val Gly Gln Ala Gly Ser Thr Asp Ser Ser Thr Ser Thr Phe
                50                  55                  60

Ile Asp Pro Leu Ser Ser Glu Ala Asn Cys Lys Arg Asp Val Pro Leu
65                  70                  75                  80

Leu Lys Gln Leu Gly Thr Asn Val Ile Arg Thr Tyr Ala Ile Asp Pro
                85                  90                  95
```

```
Lys Ala Asp His Ser Ala Cys Met Lys Leu Leu Asn Asp Ala Gly Ile
                100                 105                 110

Tyr Val Phe Ser Asp Leu Gly Glu Pro Ser Leu Ser Ile Asn Arg Asp
            115                 120                 125

Thr Pro Ala Trp Asn Thr Glu Leu Phe Asp Arg Tyr Lys Ala Val Val
        130                 135                 140

Asp Glu Met Ser Gln Tyr Pro Asn Val Ile Gly Tyr Phe Ala Gly Asn
145                 150                 155                 160

Glu Val Ser Asn Ala Lys Asn Asn Thr Gly Ala Ser Ala Tyr Val Lys
                165                 170                 175

Ala Ala Val Arg Asp Thr Lys Ala Tyr Ile Lys Ser Lys Lys Tyr Arg
            180                 185                 190

Trp Gln Gly Val Gly Tyr Ala Ala Asn Asp Asp Val Asp Ile Arg Ala
        195                 200                 205

Glu Ile Ala Asp Tyr Phe Asn Cys Gly Asp Gln Asp Glu Ala Ile Asp
210                 215                 220

Phe Trp Gly Tyr Asn Ile Tyr Ser Trp Cys Gly Gln Ser Ser Met Gln
225                 230                 235                 240

Lys Ser Gly Tyr Asp Glu Gln Thr Thr Phe Phe Ser Asn Tyr Ser Val
            245                 250                 255

Pro Val Phe Phe Ala Glu Tyr Gly Cys Asn Leu Pro Ser Gly Ala Ala
        260                 265                 270

Ala Arg Ile Phe Gln Glu Thr Ala Ala Leu Tyr Ser Asp Glu Met Thr
        275                 280                 285

Lys Val Phe Ser Gly Gly Ile Val Tyr Met Tyr Phe Glu Glu Asp Asn
290                 295                 300

Asp Tyr Gly Leu Val Lys Val Asn Asn Gly Ala Val Ser Lys Leu Lys
305                 310                 315                 320

Asp Phe Ser Ala Leu Gln Thr Gln Val Thr Lys Ala Asp Pro Lys Gly
            325                 330                 335

Val Asp Ala Asp Asp Tyr Lys Pro Thr Asn Lys Pro Ala Ser Cys Pro
        340                 345                 350

Ala Leu Thr Asp Asp Trp Gln Ala Ile Asn Ser Leu Pro Pro Thr Pro
        355                 360                 365

Asp Ala Ser Leu Cys Thr Cys Met Gln Ser Ser Leu Ser Cys Val His
370                 375                 380

Ala Asp Asp Leu Asp Thr Lys Asp Phe Gly Asp Ile Phe Gly Phe Ile
385                 390                 395                 400

Cys Gly Lys Ser Pro Glu Val Cys Ala Gly Ile Asn Gly Asp Pro Ser
            405                 410                 415

Thr Gly Val Tyr Gly Ala Tyr Ser Met Cys Glu Asp Ala Ala Lys Leu
        420                 425                 430

Asp Tyr Val Leu Asp Ala Tyr Tyr Gln Ser Gln Lys Lys Ala Ser Thr
        435                 440                 445

Ala Cys Asp Phe Asn Gly Gln Ala Gln Val Val Ser Pro Lys Ala Ala
450                 455                 460

Ser Thr Cys Ser Ala Ala Leu Ala Ser Ala Ile Asn Lys Gln
465                 470                 475                 480

Ala Ala Thr Ala Thr Ala Pro Val Gly Ala Gly Ser Thr Ser Gly Ser
            485                 490                 495

Lys Gly Ala Ala Thr Ser Thr Asn Ala Ala Val Ala Gly Arg Pro Val
        500                 505                 510

Ser His Leu Leu Ser Met Gly Glu Ile Ser Val Ala Leu Tyr Met Gly
```

```
         515                 520                 525
Val Ala Met Leu Ala Gly Gly Ala Met Ile Val Leu
    530                 535                 540

<210> SEQ ID NO 19
<211> LENGTH: 1200
<212> TYPE: DNA
<213> ORGANISM: Hypocrea jecorina

<400> SEQUENCE: 19
atgcagcaac cgccctcctt agttggcgac cgcagcatca ccggcctggg agacgcagcc      60
agccgaccaa atctctcttc atcctcgcct accgtcacca gcgcgccctc ggcaccgaca     120
tcgccaccgc cgcggccgcc aatatcgctg aatccccgt cgcgagagcc tcctggcgtc     180
gagcccgtgc tccgcatcac gccagtcccg cgctccgtct ttgcctctgt ccaccagccg     240
cgcaagtcgt cgctggtcca gacgtcgcac gtcctgccct cgcccaggac gccgccgca     300
gctcaccatc accatcccgt ctcgcattcc gcctctggca gcagcggcag caacggcagt     360
ggaagcggca gtggcagcgg cagcggcaat ctgctgcgtc aaacgcatcg cgacaccgtg     420
cacccccccg tcaagcggcc atccacccg tcgtcgcatc ccaccagggg cgccagcacc     480
ggagcatcgc cgcagcaggg cgccagctcc cgaaaccgct cgtcgacgtc gcccgtttcg     540
tccccggcga gtcgcacgcc tccttatgca tctcgtcagg cctcagtttc ccattcccgc     600
cagcagcaca accaccatca tcagcaccaa caccagcatt accactccca caccagctcg     660
actaccagtc gcgccagcat cgaggccgta gtcggtgccg tccccgatcc ctcaggtcac     720
cgagcgccgc cgaaaccccg tcgaccggat cgcaaccact ttggcgcgtc agatcgcagc     780
gcaactccca ccctgtcgca cttcatgagg gcagagtcga gcatgtccat gagacattac     840
gagagcggcc ccttacgctc catgtcgccg aaccctacg gaaccctgc cgccaccacg     900
acgtcgtcca ctgccagaat gccgcacgag cagagccacg atccctacgc ccctcgcggc     960
cactctcgcg atcactcggg gaagagcagc agagacatgg gcaagccccg agctcagaag    1020
aatccctcac agaaggcgat gctctcccgt gccctgcaaa aggccaacac cgcagttcag    1080
ctcgacaatg ctcagaactt cgaaggcgct cgagaagcgt acgccgaggc ttgcgacttg    1140
ttgcagcagg tgcttgaccg aacaccggga gatgaggaca gcggaagct cgaagccatt    1200

<210> SEQ ID NO 20
<211> LENGTH: 2539
<212> TYPE: DNA
<213> ORGANISM: Hypocrea jecorina

<400> SEQUENCE: 20
caccaaactt acaccagccg catcgatgag ctggatcagt tgggcccttg gcaggttgag      60
accgtcaagg ctctgccggc gcggccagag agcgaggagt acagcgcgtc catattcata     120
ccccaggatt acgacatggg cgatgaagct cccaggattg agacggcacg ggtggtgagc     180
tacatcgctg agacaacgc gtctcccttt gcagcagcgc ccaaccagtg gcagcagtcg     240
ggaggtcaca cggcatctga acggctgcag cccaaccgcg gtctggaacc gggtctgcta     300
cagtcgtcct tctctcgggc cccgaggtcg ccaggcggc tgcagtccac cgatgatctt     360
cgcgcacagc atcaggaggg ccagtatgcg cctcccccac tctcgcctcg ctcgcagtcg     420
ccggtaaaga cgcatgacca tgacgacgac atgtttgccg aactgccacc acacgagccc     480
tatcagtacc agcaagagca cgaccatcaa gaccaccatc aagactacca tcaacatcac     540
```

| | |
|---|---|
| cgccatcaca accaccacca tcacgaacga cagcccagcg agactgtcct atcctcatac | 600 |
| gagctccagg gtcatgtgga tggaggaatc caaaactcat ggctagatcc aattgacgag | 660 |
| tcgggaggct caacagcgtc gtctgtacac tcacgcacct cttcgcttgg ctaccgtcga | 720 |
| cgccatatcc gggccgtgag cgggaacacc gaggccgagt ttgacacggc gctggacgct | 780 |
| gctatcgagg ctgcctacga cgacggctac gagcccatgg actctgtaga ctatgggacc | 840 |
| attgatgctg gggggacaa tagcatggca ggcgtattgc acaaggtgga gatgcgcgc | 900 |
| gaacgagcga gacagacgga gcaggaagcc tatgacgagc tggccaacct ccgacaggcg | 960 |
| cactcacaga tccgcagca ccagcaggag gaggacaggt atactgccga gggattctac | 1020 |
| gaggacgact cgtctgaaga ggaggagaga ctattggacg agattacacg cgactttgcc | 1080 |
| attgaggact ttaccatgga aaacccgaat ggcacacagg tgtcagctag gcagcaggat | 1140 |
| gcatggaacg aggacgagac gaggccggat ttcatctcgg gcgtccgatc cttttctgcc | 1200 |
| ctgtcgcaga ggccacccat tcctcaggcc tacgccgcca acgcctcgca gccagcagcc | 1260 |
| cccctccga catccgcatt gccagacctg ccaccaggac gccctggtca aaatccaaag | 1320 |
| caactcaaga tcgagacggc aaacattgta caaacccaga agtcggtcta tgacgacgac | 1380 |
| gaaatctccc caagcacgca agagccgccg cccgagacgc tcgtccggac ggcgagcgcg | 1440 |
| cagcctgtaa ggccaccgat accgacagaa agcttcccat ccgaactcag tgctcccgca | 1500 |
| tcgccaaccg ccaagaagag gcttctggaa ggagagaatg tgctgaatgc ctcgccttct | 1560 |
| atccacaggc tacggaagaa cttttcgtct tctagcttga ggagcatgaa gaacaggaac | 1620 |
| atgtccgtct cacatttgga cgacagctcg gatgcttccc ccggcacccc cctgaatgac | 1680 |
| cccttcaaca aggcacctgc cgtgcccgtg cccgcgctgc cgacccccctt gctcgcgtcg | 1740 |
| ttcaaagatc atatggaggc agcggccggt gttggcttcc acctgtttga cgacgagttt | 1800 |
| catgcagcgg cggctgccgg cccccaaagc ccgcagagtc ccagaagtcc cgttgttgtc | 1860 |
| tccatggacg tccctgtgcc tctggaaccc tgtccaaacg acttcatgct gcgaccgttt | 1920 |
| tggctgatgc gatgcctata ccagacactt gtgcatccca agggtggcta catcagtacg | 1980 |
| aagctattcg tgccgcgaga cgtctggcgg gtcaaaggtg tcaagatcaa gaacgtggag | 2040 |
| gacaaaattg ccaactgcga cttttttgact gcagccctgc tgaagctgtc caaagtggac | 2100 |
| actctgatcg cggatgccgt gctggaggag atgcaagccc tcgagggcat tctgagcag | 2160 |
| atacagccgg tcctggcccg aaagcttgga aacgaagtgg gcgttcaagg ttccggtctg | 2220 |
| ctgttcaaag acgcctcgat gatggaagga ccccggtt cagccgtgcc gcgatcagga | 2280 |
| agtgtgtctg gcaaggcgtc tgcgttttcc tggcgacggc ttcggccaaa gacgtcgggc | 2340 |
| gtcgggctgg gagggtcgta cagcagccgc aacgccagtg ctgagacgaa ggaggcctca | 2400 |
| acgctggcaa cggtgcccat gacgccgaaa ccgacaagcc gttcggccaa gcgagacgtg | 2460 |
| agccaggttc agttcatcgg gcccaatgcg agctacatgg gctctctcgc gcgcttgttt | 2520 |
| gacgctgcgc aggcagttg | 2539 |

<210> SEQ ID NO 21
<211> LENGTH: 188
<212> TYPE: DNA
<213> ORGANISM: Hypocrea jecorina

<400> SEQUENCE: 21

| | |
|---|---|
| atcaaattgc aaggcaggtc gacgaccccg gtttgcggct tgcggacaag actcaggtcg | 60 |
| gcttggagct ctgcacccgg cacgccgctg agttctttgg cttttacatt tgccgattcg | 120 | tcttggccga cctcggcctg ttgctggaca agttcctcaa acgaggaagc gaatgggtca    180 tgacatga    188

<210> SEQ ID NO 22
<211> LENGTH: 87
<212> TYPE: PRT
<213> ORGANISM: Hypocrea jecorina

<400> SEQUENCE: 22

Ser Gln Lys Ala Met Leu Ser Arg Ala Leu Gln Lys Ala Asn Thr Ala
1               5                   10                  15

Val Gln Leu Asp Asn Ala Gln Asn Phe Glu Gly Ala Arg Glu Ala Tyr
            20                  25                  30

Ala Glu Ala Cys Asp Leu Leu Gln Gln Val Leu Asp Arg Thr Pro Gly
        35                  40                  45

Asp Glu Asp Lys Arg Lys Leu Glu Ala Ile His Gln Thr Tyr Thr Ser
    50                  55                  60

Arg Ile Asp Glu Leu Asp Gln Leu Gly Pro Trp Gln Val Glu Thr Val
65                  70                  75                  80

Lys Ala Leu Pro Ala Arg Pro
            85

<210> SEQ ID NO 23
<211> LENGTH: 60
<212> TYPE: PRT
<213> ORGANISM: Hypocrea jecorina

<400> SEQUENCE: 23

Ser Trp Leu Asp Pro Ile Asp Glu Ser Gly Gly Ser Thr Ala Ser Ser
1               5                   10                  15

Val His Ser Arg Thr Ser Ser Leu Gly Tyr Arg Arg His Ile Arg
            20                  25                  30

Ala Val Ser Gly Asn Thr Glu Ala Glu Phe Asp Thr Ala Leu Asp Ala
        35                  40                  45

Ala Ile Glu Ala Ala Tyr Asp Asp Gly Tyr Glu Pro
    50                  55                  60

<210> SEQ ID NO 24
<211> LENGTH: 118
<212> TYPE: PRT
<213> ORGANISM: Hypocrea jecorina

<400> SEQUENCE: 24

Leu Glu Pro Cys Pro Asn Asp Phe Met Leu Arg Pro Phe Trp Leu Met
1               5                   10                  15

Arg Cys Leu Tyr Gln Thr Leu Val His Pro Lys Gly Gly Tyr Ile Ser
            20                  25                  30

Thr Lys Leu Phe Val Pro Arg Asp Val Trp Arg Val Lys Gly Val Lys
        35                  40                  45

Ile Lys Asn Val Glu Asp Lys Ile Ala Asn Cys Asp Phe Leu Thr Ala
    50                  55                  60

Ala Leu Leu Lys Leu Ser Lys Val Asp Thr Leu Asp Ala Asp Ala Val
65                  70                  75                  80

Leu Glu Glu Met Gln Ala Leu Glu Gly Ile Leu Glu Gln Ile Gln Pro
            85                  90                  95

Val Leu Ala Arg Lys Leu Gly Asn Glu Val Gly Val Gln Gly Ser Gly
            100                 105                 110

Leu Leu Phe Lys Asp Ala
        115

<210> SEQ ID NO 25
<211> LENGTH: 84
<212> TYPE: PRT
<213> ORGANISM: Hypocrea jecorina

<400> SEQUENCE: 25

Thr Val Pro Met Thr Pro Lys Pro Thr Ser Arg Ser Ala Lys Arg Asp
1               5                   10                  15

Val Ser Gln Val Gln Phe Ile Gly Pro Asn Ala Ser Tyr Met Gly Ser
            20                  25                  30

Leu Ala Arg Leu Phe Asp Ala Ala Gln Ala Val Asp Gln Ile Ala Arg
        35                  40                  45

Gln Val Asp Asp Pro Gly Leu Arg Leu Ala Asp Lys Thr Gln Val Gly
    50                  55                  60

Leu Glu Leu Cys Thr Arg His Ala Ala Glu Phe Phe Gly Phe Tyr Ile
65                  70                  75                  80

Cys Arg Phe Val

<210> SEQ ID NO 26
<211> LENGTH: 60
<212> TYPE: PRT
<213> ORGANISM: Hypocrea jecorina

<400> SEQUENCE: 26

Ser Trp Leu Asp Pro Ile Asp Glu Ser Gly Gly Ser Thr Ala Ser Ser
1               5                   10                  15

Val His Ser Arg Thr Ser Ser Leu Gly Tyr Arg Arg His Ile Arg
            20                  25                  30

Ala Val Ser Gly Asn Thr Glu Ala Glu Phe Asp Thr Ala Leu Asp Ala
        35                  40                  45

Ala Ile Glu Ala Ala Tyr Asp Asp Gly Tyr Glu Pro
    50                  55                  60

<210> SEQ ID NO 27
<211> LENGTH: 22
<212> TYPE: PRT
<213> ORGANISM: Hypocrea jecorina

<400> SEQUENCE: 27

Asp Ser Ser Glu Glu Glu Glu Arg Leu Leu Asp Glu Ile Thr Arg Asp
1               5                   10                  15

Phe Ala Ile Glu Asp Phe
            20

<210> SEQ ID NO 28
<211> LENGTH: 119
<212> TYPE: PRT
<213> ORGANISM: Hypocrea jecorina

<400> SEQUENCE: 28

Pro Val Pro Leu Glu Pro Cys Pro Asn Asp Phe Met Leu Arg Pro Phe
1               5                   10                  15

Trp Leu Met Arg Cys Leu Tyr Gln Thr Leu Val His Pro Lys Gly Gly
            20                  25                  30

Tyr Ile Ser Thr Lys Leu Phe Val Pro Arg Asp Val Trp Arg Val Lys
        35                  40                  45

```
Gly Val Lys Ile Lys Asn Val Glu Asp Lys Ile Ala Asn Cys Asp Phe
            50                  55                  60

Leu Thr Ala Ala Leu Leu Lys Leu Ser Lys Val Asp Thr Leu Asp Ala
 65                  70                  75                  80

Asp Ala Val Leu Glu Glu Met Gln Ala Leu Glu Gly Ile Leu Glu Gln
                 85                  90                  95

Ile Gln Pro Val Leu Ala Arg Lys Leu Gly Asn Glu Val Gly Val Gln
            100                 105                 110

Gly Ser Gly Leu Leu Phe Lys
            115

<210> SEQ ID NO 29
<211> LENGTH: 24
<212> TYPE: PRT
<213> ORGANISM: Hypocrea jecorina

<400> SEQUENCE: 29

Val Pro Arg Ser Gly Ser Val Ser Gly Lys Ala Ser Ala Phe Ser Trp
 1               5                   10                  15

Arg Arg Leu Arg Pro Lys Thr Ser
            20

<210> SEQ ID NO 30
<211> LENGTH: 96
<212> TYPE: PRT
<213> ORGANISM: Hypocrea jecorina

<400> SEQUENCE: 30

Thr Ser Arg Ser Ala Lys Arg Asp Val Ser Gln Val Gln Phe Ile Gly
 1               5                   10                  15

Pro Asn Ala Ser Tyr Met Gly Ser Leu Ala Arg Leu Phe Asp Ala Ala
            20                  25                  30

Gln Ala Val Asp Gln Ile Ala Arg Gln Val Asp Asp Pro Gly Leu Arg
            35                  40                  45

Leu Ala Asp Lys Thr Gln Val Gly Leu Glu Leu Cys Thr Arg His Ala
 50                  55                  60

Ala Glu Phe Phe Gly Phe Tyr Ile Cys Arg Phe Val Leu Ala Asp Leu
 65                  70                  75                  80

Gly Leu Leu Leu Asp Lys Phe Leu Lys Arg Gly Ser Glu Trp Val Met
                 85                  90                  95

<210> SEQ ID NO 31
<211> LENGTH: 1235
<212> TYPE: PRT
<213> ORGANISM: Trichoderma atraviride

<400> SEQUENCE: 31

Met Gln Gln Ser His Pro Phe Asp Asp Asn Ile Ile Ser Arg Arg Ala
 1               5                   10                  15

Thr Arg Ala Pro Ile Glu Pro Ser Pro Pro Pro Pro Pro Pro Pro Gln
            20                  25                  30

Ala Ser Ser Arg Glu Ala Pro Gly Ile Glu Ala Val Leu Ser Ser Pro
            35                  40                  45

Lys Thr Pro Val Leu Arg Ser Val Phe Ser Ser Ala Arg Leu Pro Arg
 50                  55                  60

Ser Ser Ser Leu Ile Pro Pro Leu His Gly Ser Pro Pro Ser Ala Ser
 65                  70                  75                  80
```

```
Thr Ala Ala Ala Ile Asn Thr Asn Ser Pro His His Ala Asn Ala
                85              90              95

Ser Gln His Thr His Arg Gly Pro Val His Pro Val Ser Leu Lys
            100             105             110

Arg Pro Ser Thr Pro Ser Ser Gln Leu Asn Arg Gly Ala Ser Ser Gly
            115             120             125

Ala Ser Pro Gln Glu Ala Ser Arg Thr Arg Asn Arg Trp Ser Thr Ser
        130             135             140

Ser Ile Ser Ser Ala Ser Ser Arg Thr Ser Pro Tyr Ala Ser Arg Gln
145             150             155             160

Ala Ser Ile Ser Asn Ser Arg Ile Arg Arg Ala Ser Leu Glu Ala Ala
                165             170             175

Leu Ser Pro Pro Ser Val Pro Pro Pro Leu Pro Pro Ala Gln Ala
                180             185             190

Pro Pro Arg Lys Pro Ser Tyr Thr Val Arg Ser Arg Phe Asn Ser Ser
            195             200             205

Asp Ser Gly Val Thr Pro Thr Ser Val His Pro Met Arg Ser Glu Ser
    210             215             220

Ser Met Ser Met Arg His Tyr Glu Asn Gly Gln Leu Arg Ser Val Ser
225             230             235             240

Pro Asn Pro Tyr Ala Asn Pro Thr Thr Thr Ser Ser Thr Ala Arg
                245             250             255

Met Pro His Glu His Ser His Asp Pro Tyr Ala Pro Arg Gly His Ser
            260             265             270

Arg Asp His Ser Gly Lys Ser Ser Arg Asp Leu Gly Lys Pro Arg Ala
            275             280             285

Gln Lys Asn Pro Ser Gln Lys Ala Met Leu Ser Arg Ala Leu Gln Lys
    290             295             300

Ala Asn Thr Ala Val Gln Leu Asp Asn Ala Gln Asn Phe Glu Gly Ala
305             310             315             320

Arg Glu Ser Tyr Ala Glu Ala Cys Asp Leu Leu Gln Gln Val Leu Asp
            325             330             335

Arg Thr Ser Gly Asp Glu Asp Lys Arg Lys Leu Glu Thr Ile Arg Ala
            340             345             350

Thr Tyr Thr Ser Arg Ile Asp Glu Leu Asp Gln Met Gly Pro Trp Gln
            355             360             365

Asp Glu Asn Val Lys Ala Leu Pro Ala Arg Pro Glu Ser Glu Asp Tyr
    370             375             380

Gly Ala Ser Ile Tyr Met His Gln Asp Tyr Glu Met Met Glu Glu Ala
385             390             395             400

Pro Arg Ile Glu Thr Ala Arg Val Val Ser Ile Ile Gly Asp Gly Ser
            405             410             415

Ser Pro Val Ala His Gln Trp Gln Gln Asp Tyr Thr Thr Thr Asp Arg
            420             425             430

Gln Gln Pro Ala Arg Thr Leu Glu Pro Gly Met Leu Gln Ser Ser Phe
            435             440             445

Ser Arg Ser Pro Arg Arg Leu Arg Ser Thr Asp Asn Leu Arg Ala Gln
    450             455             460

Ser Gln Gln Glu Ala Leu Tyr Ala Pro Ala Pro Leu Ser Pro Arg Ser
465             470             475             480

Pro Ser Pro Met Lys Met His Pro Glu Glu Tyr Thr Glu Met Val Gln
                485             490             495

Glu His His Glu Pro His His Gln His Tyr His Gln Arg Gln Pro Ser
```

```
                500             505             510
Asp Ser Val Leu Pro Tyr Asp Met Gln Asp Phe Thr Glu Gly Thr Gln
            515                 520                 525
Asn Ser Trp Leu Asp Pro Ile Asp Glu Ser Gly Ala Ser Thr Val Ser
            530                 535                 540
Ser Val His Ser Arg Thr Ser Ser Leu Gly Tyr Arg Arg Arg His Ile
545                 550                 555                 560
Arg Ala Ala Ser Gly Asn Thr Glu Ala Glu Phe Asp Thr Ala Leu Asp
                565                 570                 575
Ala Ala Ile Glu Ala Ala Tyr Asp Asp Gly Phe Glu Pro Met Glu Thr
            580                 585                 590
Glu Asp Tyr Asp Ala Met Asp Pro Arg Glu Asp Val Ala Ser Val
            595                 600                 605
Met Gln Arg Val Glu Lys Ala Arg Glu Gln Val Arg Gln Thr Glu Gln
            610                 615                 620
Glu Ala Tyr Asp Asp Leu Ala Met Leu Arg Gln Ala His Gln Gln Asn
625                 630                 635                 640
Gln His Tyr Leu Gln Glu Glu Asp Lys Tyr Thr Pro Asp Gly Phe
                645                 650                 655
Tyr Glu Asp Asp Ser Ser Glu Asp Glu Arg Leu Leu Asp Glu Ile
                660                 665                 670
Thr Arg Asp Phe Ala Ile Glu Asp Phe Thr Met Thr Gln Pro Gln Ser
                675                 680                 685
Asn Thr Ala Thr Val Ser Ala Ser Gln Gln Glu Ala Trp Asn Glu Asp
            690                 695                 700
Glu Thr Arg Pro Asp Phe Ile Ser Gly Val Arg Ser Phe Ser Ala Leu
705                 710                 715                 720
Ser Gln Arg Pro Pro Ile Pro Gln Thr Ser Asn Ile Met Gln Pro Ala
                725                 730                 735
Ala Pro Pro Pro Thr Thr Thr Leu Pro Pro Pro Thr Thr Thr Leu
            740                 745                 750
Pro Glu Val Pro Lys Gly Ser Asp Ser Pro Ser His Gly Val Arg Asn
            755                 760                 765
Arg Arg Met Ser Gly Gln Asn Pro Lys Gln Leu Lys Ile Glu Thr Thr
            770                 775                 780
Asn Leu Gly Gln Ser Asn Thr Arg Thr Val Tyr Asp Asp Glu Ile
785                 790                 795                 800
Ser Pro Ser Thr Val Asp Arg Asp Leu Val Glu Ala Leu Val Arg Gly
                805                 810                 815
Ala Ser Ala His Pro Val Lys Gln Leu Asn Ala Ala Asp Asn Glu Ser
                820                 825                 830
Lys Ile Pro Gly Ser Pro Ser Ala Lys Lys Leu Ile Asp Gly Glu
            835                 840                 845
Asp Ala Thr Ala Ala Asn Ala Ser Pro Ser Ile His Arg Leu Lys Lys
            850                 855                 860
Asn Phe Ser Ser Ser Leu Arg Ser Met Lys Asn Arg Asn Met Ser
865                 870                 875                 880
Val Ser His Leu Asp Asp Asn Ser Asp Val Ser Pro Gly Thr Pro Asn
                885                 890                 895
Gly Asn Pro Phe Gly Lys Thr Pro Ala Val Pro Ala Leu Pro Thr Pro
                900                 905                 910
Leu Ile Thr Ser Phe Arg Asp Asn Gly Glu Ala Gly Gly Gly Ala Gly
            915                 920                 925
```

Leu His Leu Phe Asp Asp Asn Phe His Ala Ala Ala Thr Pro Gly Pro
930 935 940

Gln Ser Pro Val Val Ser Met Glu Val Pro Ala Pro Leu Glu Pro Cys
945 950 955 960

Pro Asn Asp Phe Met Leu Arg Pro Phe Trp Leu Met Arg Cys Leu Tyr
965 970 975

Gln Thr Leu Val His Pro Lys Gly Gly Tyr Val Ser Thr Lys Leu Phe
980 985 990

Val Pro Arg Asp Val Trp Arg Val Lys Gly Val Lys Ile Lys Asn Val
995 1000 1005

Glu Asp Lys Val Ala Asn Cys Asp Phe Leu Thr Ala Ala Leu Leu
1010 1015 1020

Lys Leu Ala Lys Val Asp Thr Phe Asp Ala Asp Ala Val Leu Glu
1025 1030 1035

Glu Met Gln Ser Leu Glu Gly Val Leu Glu Gln Val Gln Ser Ser
1040 1045 1050

Leu Ala Arg Lys Leu Gly Ser Glu Val Gly Val Gln Gly Gly His
1055 1060 1065

Ile Phe Lys Asp Ala Ser Val Asp Gly Glu Gly Ser Asn Val
1070 1075 1080

Pro Arg Ser Gly Ser Val Ser Gly Lys Ala Ser Ala Phe Ser Trp
1085 1090 1095

Arg Arg Leu Arg Pro Lys Thr Ser Gly Val Gly Leu Gly Gly Ser
1100 1105 1110

Tyr Ser Asn Arg Ser Ala Ser Met Glu Thr Lys Glu Val Thr Thr
1115 1120 1125

Leu Ala Thr Leu Pro Met Thr Pro Lys Pro Thr Ser Arg Pro Pro
1130 1135 1140

Lys Arg Asp Val Ser Gln Ala Gln Phe Ile Gly Pro Asn Ala Met
1145 1150 1155

Tyr Met Gly Ser Leu Ala Arg Leu Phe Asp Ala Ala Gln Ala Ile
1160 1165 1170

Asp Gln Ile Ala Arg Gln Val Glu Asp Pro Gly Leu Arg His Ala
1175 1180 1185

Asp Lys Thr Gln Val Gly Leu Glu Leu Cys Thr Arg His Ala Ala
1190 1195 1200

Glu Phe Phe Gly Phe Tyr Ile Cys Arg Phe Val Leu Ala Asp Leu
1205 1210 1215

Ser Leu Leu Asp Lys Phe Leu Lys Arg Gly Ser Glu Trp Val
1220 1225 1230

Leu Thr
1235

<210> SEQ ID NO 32
<211> LENGTH: 4694
<212> TYPE: DNA
<213> ORGANISM: Hypocrea jecorina

<400> SEQUENCE: 32
atggatcagc gctgtgggcg gttcgttcag ggccatcgcc aggcacaggc acaggcacag    60
gcacagaggc tcaggcacga ggtaccggta cctgggccgg ccaattgga tgcaccacca    120 cggcctgacc tgcgtttccg caactcccac gcttgcctcc ccacgatcca cagcgccagg    180
gacgtccaaa tccccgatag tattcccagt cgaggaccag cagcgattga gtgagtgagt    240

```
gactgactga gggacgactg aggtactgac ggatcccaga ggacagcacg acaccgcacc      300
gcaccgctca gcacaggccc gttgctggga gtgctgtcga tccgctgagt ggcctctctc      360
tctctctctg tctctcctcc ttcgcatcag cctcgtgagc accgcaaaga cagaagaacc      420
cgccattgtc tcgaggtcat ggccggctgc cacacgcgcg caatacatcc aatcccacga      480
ctgcgacccc cgacccacgc tgtacgagta agattggccg gaagaggcga ccattggctg      540
agacggcagc ccgcaccagt ccagcaaccg caactgcaag tgctgcacgt cgtacgaacc      600
tgatttggcc atagccagcg ccagagcatg cagcaaccgc cctccttagt tggcgaccgc      660
agcatcaccg gcctgggaga cgcagccagc cgaccaaatc tctcttcatc ctcgcctacc      720
gtcaccagcg cgccctcggc accgacatcg ccaccgccgc ggccgccaat atcgctgaat      780
cccccgtcgc gagagcctcc tggcgtcgag cccgtgctcc gcatcacgcc agtcccgcgc      840
tccgtctttg cctctgtcca ccagccgcgc aagtcgtcgc tggtccagac gtcgcacgtc      900
ctgccctcgc ccaggaccgc cgccgcagct caccatcacc atcccgtctc gcattccgcc      960
tctggcagca gcggcagcaa cggcagtgga agcggcagtg gcagcggcag cggcaatctg     1020
ctgcgtcaaa cgcatcgcga caccgtgcac cccccgtca agcggccatc caccccgtcg     1080
tcgcatccca ccaggggcgc cagcaccgga gcatcgccgc agcagggcgc cagctcccga     1140
aaccgctcgt cgacgtcgcc cgtttcgtcc ccggcgagtc gcacgcctcc ttatgcatct     1200
cgtcaggcct cagtttccca ttcccgccag cagcacaacc accatcatca gcaccaacac     1260
cagcattacc actcccacac cagctcgact accagtcgcg ccagcatcga ggccgtagtc     1320
ggtgccgtcc ccgatccctc aggtcaccga gcgccgccga aaccccgtcg accggatcgc     1380
aaccactttg gcgcgtcaga tcgcagcgca actcccaccc tgtcgcactt catgagggca     1440
gagtcgagca tgtccatgag acattacgag agcggcccct acgctccat gtcgccgaac      1500
ccctacggaa cccctgccgc caccacgacg tcgtccactg ccagaatgcc gcacgagcag     1560
agccacgatc cctacgcccc tcgcggccac tctcgcgatc actcggggaa gagcagcaga     1620
gacatgggca agccccgagc tcagaagaat ccctcacaga aggcgatgct ctcccgtgcc     1680
ctgcaaaagg ccaacaccgc agttcagctc gacaatgctc agaacttcga aggcgctcga     1740
gaagcgtacg ccgaggcttg cgacttgttg cagcaggtgc ttgaccgaac accgggagat     1800
gaggacaagc ggaagctcga agccattgta agtcacggcg gcaaccggaa tgtcgagccc     1860
gttgtctgtc attagtagat cacttggaac tgacaatttc aatctgtagc accaaactta     1920
caccagccgc atcgatgagc tggatcagtt gggcccttgg caggttgaga ccgtcaaggc     1980
tctgccggcg cggccagaga gcgaggagta cagcgcgtcc atattcatac cccaggatta     2040
cgacatgggc gatgaagctc ccaggattga acggcacgg tggtgagct acatcgctgg      2100
agacaacgcg tctccctttg cagcagcgcc caaccagtgg cagcagtcgg gaggtcacac     2160
ggcatctgaa cggctgcagc ccaaccgcgg tctggaaccg gtctgctac agtcgtcctt      2220
ctctcgggcc ccgaggtcgc ccaggcggct gcagtccacc gatgatcttc gcgcacagca     2280
tcaggagggc cagtatgcgc ctccccccact ctcgcctcgc tcgcagtcgc cggtaaagac     2340
gcatgaccat gacgacgaca tgtttgccga actgccacca cacgagccct atcagtacca     2400
gcaagagcac gaccatcaag accaccatca agactaccat caacatcacc gccatcacaa     2460
ccaccaccat cacgaacgac agcccagcga gactgtccta tcctcatacg agctccaggg     2520
tcatgtggat ggaggaatcc aaaactcatg gctagatcca attgacgagt cgggaggctc     2580
```

-continued

| | |
|---|---|
| aacagcgtcg tctgtacact cacgcacctc ttcgcttggc taccgtcgac gccatatccg | 2640 |
| ggccgtgagc gggaacaccg aggccgagtt tgacacggcg ctggacgctg ctatcgaggc | 2700 |
| tgcctacgac gacggctacg agcccatgga ctctgtagac tatgggacca ttgatgctgg | 2760 |
| gggggacaat agcatggcag gcgtattgca caaggtggag atggcgcgcg aacgagcgag | 2820 |
| acagacggag caggaagcct atgacgagct ggccaacctc cgacaggcgc actcacagaa | 2880 |
| tccgcagcac cagcaggagg aggacaggta tactgccgag ggattctacg aggacgactc | 2940 |
| gtctgaagag gaggagagac tattggacga gattacacgc gactttgcca ttgaggactt | 3000 |
| taccatggaa aacccgaatg cacacaggt gtcagctagg cagcaggatg catggaacga | 3060 |
| ggacgagacg aggccggatt tcatctcggg cgtccgatcc ttttctgccc tgtcgcagag | 3120 |
| gccacccatt cctcaggcct acgccgccaa cgcctcgcag ccagcagccc ccctccgac | 3180 |
| atccgcattg ccagacctgc caccaggacg ccctggtcaa aatccaaagc aactcaagat | 3240 |
| cgagacggca acattgtac aaacccagaa gtcggtctat gacgacgacg aaatctcccc | 3300 |
| aagcacgcaa gagccgccgc ccgagacgct cgtccggacg cgagcgcgc agcctgtaag | 3360 |
| gccaccgata ccgacagaaa gcttcccatc cgaactcagt gctcccgcat cgccaaccgc | 3420 |
| caagaagagg cttctggaag gagagaatgt gctgaatgcc tcgccttcta tccacaggct | 3480 |
| acggaagaac ttttcgtctt ctagcttgag gagcatgaag aacaggaaca tgtccgtctc | 3540 |
| acatttggac gacagctcgg atgcttcccc cggcaccccc ctgaatgacc ccttcaacaa | 3600 |
| ggcacctgcc gtgcccgtgc ccgcgctgcc gaccccttg ctcgcgtcgt tcaaagatca | 3660 |
| tatgggaggca gcggccggtg ttggcttcca cctgtttgac gacgagtttc atgcagcggc | 3720 |
| ggctgccggc ccccaaagcc cgcagagtcc cagaagtccc gttgttgtct ccatggacgt | 3780 |
| ccctgtgcct ctggaaccct gtccaaacga cttcatgctg cgaccgtttt ggctgatgcg | 3840 |
| atgcctatac cagacacttg tgcatcccaa gggtggctac atcagtacga agctattcgt | 3900 |
| gccgcgagac gtctggcggg tcaaaggtgt caagatcaag aacgtggagg acaaaattgc | 3960 |
| caactgcgac ttttttgactg cagccctgct gaagctgtcc aaagtggaca ctctggatgc | 4020 |
| ggatgccgtg ctggaggaga tgcaagcccc cgagggcatt ctggagcaga tacagccggt | 4080 |
| cctggcccga aagcttggaa acgaagtggg cgttcaaggt tccggtctgc tgttcaaaga | 4140 |
| cgcctcgatg atggaaggag accccggttc agccgtgccg cgatcaggaa gtgtgtctgg | 4200 |
| caaggcgtct gcgttttcct ggcgacggct tcggccaaag acgtcgggcg tcgggctggg | 4260 |
| agggtcgtac agcagccgca acgccagtgc tgagacgaag gaggcctcaa cgctggcaac | 4320 |
| ggtgcccatg acgccgaaac cgacaagccg ttcggccaag cgagacgtga gccaggttca | 4380 |
| gttcatcggg cccaatgcga gctacatggg ctctctcgcg cgcttgtttg acgctgcgca | 4440 |
| ggcagttggt aagcatattg cgatacgcat accggttaca gtgacggcaa gctaacgatg | 4500 |
| atgcagatca aattgcaagg caggtcgacg accccggttt gcggcttgcg gacaagactc | 4560 |
| aggtcggctt ggagctctgc acccggcacg ccgctgagtt ctttggcttt tacatttgcc | 4620 |
| gattcgtctt ggccgacctc ggcctgttgc tggacaagtt cctcaaacga ggaagcgaat | 4680 |
| gggtcatgac atga | 4694 |

<210> SEQ ID NO 33
<211> LENGTH: 1465
<212> TYPE: PRT
<213> ORGANISM: Hypocrea jecorina

<400> SEQUENCE: 33

-continued

```
Met Asp Gln Arg Cys Gly Arg Phe Val Gln Gly His Arg Gln Ala Gln
1               5                   10                  15

Ala Gln Ala Gln Ala Gln Arg Leu Arg His Glu Val Pro Val Pro Gly
            20                  25                  30

Pro Gly Gln Leu Asp Ala Pro Pro Arg Pro Asp Leu Arg Phe Arg Asn
            35                  40                  45

Ser His Ala Cys Leu Pro Thr Ile His Ser Ala Arg Asp Val Gln Ile
        50                  55                  60

Pro Asp Ser Ile Pro Ser Arg Gly Pro Ala Ala Ile Glu Gly Gln His
65                  70                  75                  80

Asp Thr Ala Pro His Arg Ser Ala Gln Ala Arg Cys Trp Glu Cys Cys
                85                  90                  95

Arg Ser Ala Glu Trp Pro Leu Ser Leu Ser Leu Ser Leu Leu Leu Arg
            100                 105                 110

Ile Ser Leu Val Ser Thr Ala Lys Thr Glu Glu Pro Ala Ile Val Ser
        115                 120                 125

Arg Ser Trp Pro Ala Ala Thr Arg Ala Gln Tyr Ile Gln Ser His Asp
    130                 135                 140

Cys Asp Pro Arg Pro Thr Leu Tyr Asp Gln Arg Gln Ser Met Gln Gln
145                 150                 155                 160

Pro Pro Ser Leu Val Gly Asp Arg Ser Ile Thr Gly Leu Gly Asp Ala
            165                 170                 175

Ala Ser Arg Pro Asn Leu Ser Ser Ser Pro Thr Val Thr Ser Ala
        180                 185                 190

Pro Ser Ala Pro Thr Ser Pro Pro Arg Pro Ile Ser Leu Asn
        195                 200                 205

Pro Pro Ser Arg Glu Pro Pro Gly Val Glu Pro Val Leu Arg Ile Thr
    210                 215                 220

Pro Val Pro Arg Ser Val Phe Ala Ser Val His Gln Pro Arg Lys Ser
225                 230                 235                 240

Ser Leu Val Gln Thr Ser His Val Leu Pro Ser Pro Arg Thr Ala Ala
            245                 250                 255

Ala Ala His His His His Pro Val Ser His Ser Ala Ser Gly Ser Ser
            260                 265                 270

Gly Ser Asn Gly Ser Gly Ser Gly Ser Gly Ser Gly Asn Leu
    275                 280                 285

Leu Arg Gln Thr His Arg Asp Thr Val His Pro Pro Val Lys Arg Pro
    290                 295                 300

Ser Thr Pro Ser Ser His Pro Thr Arg Gly Ala Ser Thr Gly Ala Ser
305                 310                 315                 320

Pro Gln Gln Gly Ala Ser Ser Arg Asn Arg Ser Ser Thr Ser Pro Val
            325                 330                 335

Ser Ser Pro Ala Ser Arg Thr Pro Pro Tyr Ala Ser Arg Gln Ala Ser
        340                 345                 350

Val Ser His Ser Arg Gln Gln His Asn His His His Gln His
            355                 360                 365

Gln His Tyr His Ser His Thr Ser Ser Thr Thr Ser Arg Ala Ser Ile
    370                 375                 380

Glu Ala Val Val Gly Ala Val Pro Asp Pro Ser Gly His Arg Ala Pro
385                 390                 395                 400

Pro Lys Pro Arg Arg Pro Asp Arg Asn His Phe Gly Ala Ser Asp Arg
            405                 410                 415
```

```
Ser Ala Thr Pro Thr Leu Ser His Phe Met Arg Ala Glu Ser Ser Met
            420                 425                 430
Ser Met Arg His Tyr Glu Ser Gly Pro Leu Arg Ser Met Ser Pro Asn
        435                 440                 445
Pro Tyr Gly Thr Pro Ala Ala Thr Thr Thr Ser Ser Thr Ala Arg Met
    450                 455                 460
Pro His Glu Gln Ser His Asp Pro Tyr Ala Pro Arg Gly His Ser Arg
465                 470                 475                 480
Asp His Ser Gly Lys Ser Arg Asp Met Gly Lys Pro Arg Ala Gln
                485                 490                 495
Lys Asn Pro Ser Gln Lys Ala Met Leu Ser Arg Ala Leu Gln Lys Ala
            500                 505                 510
Asn Thr Ala Val Gln Leu Asp Asn Ala Gln Asn Phe Glu Gly Ala Arg
        515                 520                 525
Glu Ala Tyr Ala Glu Ala Cys Asp Leu Leu Gln Gln Val Leu Asp Arg
    530                 535                 540
Thr Pro Gly Asp Glu Asp Lys Arg Lys Leu Glu Ala Ile His Gln Thr
545                 550                 555                 560
Tyr Thr Ser Arg Ile Asp Glu Leu Asp Gln Leu Gly Pro Trp Gln Val
                565                 570                 575
Glu Thr Val Lys Ala Leu Pro Ala Arg Pro Glu Ser Glu Glu Tyr Ser
            580                 585                 590
Ala Ser Ile Phe Ile Pro Gln Asp Tyr Asp Met Gly Asp Glu Ala Pro
        595                 600                 605
Arg Ile Glu Thr Ala Arg Val Val Ser Tyr Ile Ala Gly Asp Asn Ala
    610                 615                 620
Ser Pro Phe Ala Ala Ala Pro Asn Gln Trp Gln Gln Ser Gly Gly His
625                 630                 635                 640
Thr Ala Ser Glu Arg Leu Gln Pro Asn Arg Gly Leu Glu Pro Gly Leu
                645                 650                 655
Leu Gln Ser Ser Phe Ser Arg Ala Pro Arg Ser Pro Arg Arg Leu Gln
            660                 665                 670
Ser Thr Asp Asp Leu Arg Ala Gln His Gln Glu Gly Gln Tyr Ala Pro
        675                 680                 685
Pro Pro Leu Ser Pro Arg Ser Gln Ser Pro Val Lys Thr His Asp His
    690                 695                 700
Asp Asp Asp Met Phe Ala Glu Leu Pro Pro His Glu Pro Tyr Gln Tyr
705                 710                 715                 720
Gln Gln Glu His Asp His Gln Asp His His Gln Asp Tyr His Gln His
                725                 730                 735
His Arg His His Asn His His His His Glu Arg Gln Pro Ser Glu Thr
            740                 745                 750
Val Leu Ser Ser Tyr Glu Leu Gln Gly His Val Asp Gly Gly Ile Gln
        755                 760                 765
Asn Ser Trp Leu Asp Pro Ile Asp Glu Ser Gly Gly Ser Thr Ala Ser
    770                 775                 780
Ser Val His Ser Arg Thr Ser Ser Leu Gly Tyr Arg Arg His Ile
785                 790                 795                 800
Arg Ala Val Ser Gly Asn Thr Glu Ala Glu Phe Asp Thr Ala Leu Asp
                805                 810                 815
Ala Ala Ile Glu Ala Ala Tyr Asp Asp Gly Tyr Glu Pro Met Asp Ser
        820                 825                 830
Val Asp Tyr Gly Thr Ile Asp Ala Gly Gly Asp Asn Ser Met Ala Gly
```

-continued

```
                835                 840                 845
Val Leu His Lys Val Glu Met Ala Arg Glu Arg Ala Arg Gln Thr Glu
        850                 855                 860

Gln Glu Ala Tyr Asp Glu Leu Ala Asn Leu Arg Gln Ala His Ser Gln
865                 870                 875                 880

Asn Pro Gln His Gln Glu Glu Asp Arg Tyr Thr Ala Glu Gly Phe
                885                 890                 895

Tyr Glu Asp Asp Ser Glu Glu Glu Arg Leu Leu Asp Glu Ile
            900                 905                 910

Thr Arg Asp Phe Ala Ile Glu Asp Phe Thr Met Glu Asn Pro Asn Gly
            915                 920                 925

Thr Gln Val Ser Ala Arg Gln Asp Ala Trp Asn Glu Asp Glu Thr
        930                 935                 940

Arg Pro Asp Phe Ile Ser Gly Val Arg Ser Phe Ser Ala Leu Ser Gln
945                 950                 955                 960

Arg Pro Pro Ile Pro Gln Ala Tyr Ala Ala Asn Ala Ser Gln Pro Ala
                965                 970                 975

Ala Pro Pro Pro Thr Ser Ala Leu Pro Asp Leu Pro Pro Gly Arg Pro
            980                 985                 990

Gly Gln Asn Pro Lys Gln Leu Lys Ile Glu Thr Ala Asn Ile Val Gln
        995                 1000                1005

Thr Gln Lys Ser Val Tyr Asp Asp Glu Ile Ser Pro Ser Thr
    1010                1015                1020

Gln Glu Pro Pro Pro Glu Thr Leu Val Arg Thr Ala Ser Ala Gln
    1025                1030                1035

Pro Val Arg Pro Pro Ile Pro Thr Glu Ser Phe Pro Ser Glu Leu
    1040                1045                1050

Ser Ala Pro Ala Ser Pro Thr Ala Lys Lys Arg Leu Leu Glu Gly
    1055                1060                1065

Glu Asn Val Leu Asn Ala Ser Pro Ser Ile His Arg Leu Arg Lys
    1070                1075                1080

Asn Phe Ser Ser Ser Leu Arg Ser Met Lys Asn Arg Asn Met
    1085                1090                1095

Ser Val Ser His Leu Asp Asp Ser Ser Asp Ala Ser Pro Gly Thr
    1100                1105                1110

Pro Leu Asn Asp Pro Phe Asn Lys Ala Pro Ala Val Pro Val Pro
    1115                1120                1125

Ala Leu Pro Thr Pro Leu Leu Ala Ser Phe Lys Asp His Met Glu
    1130                1135                1140

Ala Ala Ala Gly Val Gly Phe His Leu Phe Asp Asp Glu Phe His
    1145                1150                1155

Ala Ala Ala Ala Ala Gly Pro Gln Ser Pro Gln Ser Pro Arg Ser
    1160                1165                1170

Pro Val Val Val Ser Met Asp Val Pro Val Pro Leu Glu Pro Cys
    1175                1180                1185

Pro Asn Asp Phe Met Leu Arg Pro Phe Trp Leu Met Arg Cys Leu
    1190                1195                1200

Tyr Gln Thr Leu Val His Pro Lys Gly Gly Tyr Ile Ser Thr Lys
    1205                1210                1215

Leu Phe Val Pro Arg Asp Val Trp Arg Val Lys Gly Val Lys Ile
    1220                1225                1230

Lys Asn Val Glu Asp Lys Ile Ala Asn Cys Asp Phe Leu Thr Ala
    1235                1240                1245
```

```
Ala Leu Leu Lys Leu Ser Lys Val Asp Thr Leu Asp Ala Asp Ala
    1250            1255            1260

Val Leu Glu Glu Met Gln Ala Leu Glu Gly Ile Leu Glu Gln Ile
1265            1270            1275

Gln Pro Val Leu Ala Arg Lys Leu Gly Asn Glu Val Gly Val Gln
    1280            1285            1290

Gly Ser Gly Leu Leu Phe Lys Asp Ala Ser Met Met Glu Gly Asp
    1295            1300            1305

Pro Gly Ser Ala Val Pro Arg Ser Gly Ser Val Ser Gly Lys Ala
    1310            1315            1320

Ser Ala Phe Ser Trp Arg Arg Leu Arg Pro Lys Thr Ser Gly Val
    1325            1330            1335

Gly Leu Gly Gly Ser Tyr Ser Ser Arg Asn Ala Ser Ala Glu Thr
    1340            1345            1350

Lys Glu Ala Ser Thr Leu Ala Thr Val Pro Met Thr Pro Lys Pro
1355            1360            1365

Thr Ser Arg Ser Ala Lys Arg Asp Val Ser Gln Val Gln Phe Ile
    1370            1375            1380

Gly Pro Asn Ala Ser Tyr Met Gly Ser Leu Ala Arg Leu Phe Asp
    1385            1390            1395

Ala Ala Gln Ala Val Asp Gln Ile Ala Arg Gln Val Asp Asp Pro
    1400            1405            1410

Gly Leu Arg Leu Ala Asp Lys Thr Gln Val Gly Leu Glu Leu Cys
    1415            1420            1425

Thr Arg His Ala Ala Glu Phe Phe Gly Phe Tyr Ile Cys Arg Phe
    1430            1435            1440

Val Leu Ala Asp Leu Gly Leu Leu Leu Asp Lys Phe Leu Lys Arg
    1445            1450            1455

Gly Ser Glu Trp Val Met Thr
    1460            1465

<210> SEQ ID NO 34
<211> LENGTH: 4067
<212> TYPE: DNA
<213> ORGANISM: Hypocrea jecorina

<400> SEQUENCE: 34
atgcagcaac cgccctcctt agttggcgac cgcagcatca ccggcctggg agacgcagcc      60
agccgaccaa atctctcttc atcctcgcct accgtcacca gcgcgccctc ggcaccgaca     120
tcgccaccgc cgcggccgcc aatatcgctg aatccccgt cgcgagagcc tcctggcgtc      180
gagcccgtgc tccgcatcac gccagtcccg cgctccgtct ttgcctctgt ccaccagccg     240
cgcaagtcgt cgctggtcca gacgtcgcac gtcctgcccg cgcccaggac cgccgccgca     300
gctcaccatc accatcccgt ctcgcattcc gcctctggca gcagcggcag caacggcagt     360
ggaagcggca gtggcagcgg cagcggcaat ctgctgcgtc aaacgcatcg cgacaccgtg     420 caccccccg tcaagcggcc atccaccccg tcgtcgcatc ccaccagggg cgccagcacc      480
ggagcatcgc cgcagcaggg cgccagctcc cgaaaccgct cgtcgacgtc gcccgtttcg     540
tccccggcga gtcgcacgcc tccttatgca tctcgtcagg cctcagtttc ccattcccgc     600
cagcagcaca ccaccatca tcagcaccaa caccagcatt accactccca caccagctcg     660
actaccagtc gcgccagcat cgaggccgta gtcggtgccg tccccgatcc ctcaggtcac     720
cgagcgccgc cgaaaccccg tcgaccggat cgcaaccact ttggcgcgtc agatcgcagc     780
```

```
gcaactccca ccctgtcgca cttcatgagg gcagagtcga gcatgtccat gagacattac    840
gagagcggcc ccttacgctc catgtcgccg aaccccctacg gaaccccctgc cgccaccacg   900 acgtcgtcca ctgccagaat gccgcacgag cagagccacg atccctacgc ccctcgcggc    960
cactctcgcg atcactcggg gaagagcagc agagacatgg gcaagcccgg agctcagaag   1020
aatccctcac agaaggcgat gctctcccgt gccctgcaaa aggccaacac cgcagttcag   1080
ctcgacaatg ctcagaactt cgaaggcgct cgagaagcgt acgccgaggc ttgcgacttg   1140
ttgcagcagg tgcttgaccg aacaccggga gatgaggaca agcggaagct cgaagccatt   1200
gtaagtcacg gcggcaaccg gaatgtcgag cccgttgtct gtcattagta gatcacttgg   1260
aactgacaat ttcaatctgt agcaccaaac ttacaccagc cgcatcgatg agctggatca   1320 gttgggcccct tggcaggttg agaccgtcaa ggctctgccg gcgcggccag agagcgagga   1380
gtacagcgcg tccatattca taccccagga ttacgacatg ggcgatgaag ctcccaggat   1440
tgagacggca cgggtggtga gctacatcgc tggagacaac gcgtctccct ttgcagcagc   1500
gcccaaccag tggcagcagt cgggaggtca cacggcatct gaacggctgc agcccaaccg   1560
cggtctggaa ccgggtctgc tacagtcgtc cttctctcgg gccccgaggt cgcccaggcg   1620
gctgcagtcc accgatgatc ttcgcgcaca gcatcaggag ggccagtatg cgcctccccc   1680
actctcgcct cgctcgcagt cgccggtaaa gacgcatgac catgacgacg acatgtttgc   1740
cgaactgcca ccacacgagc cctatcagta ccagcaagag cacgaccatc aagaccacca   1800
tcaagactac catcaacatc accgccatca caaccaccac catcacgaac gacagcccag   1860
cgagactgtc ctatcctcat acgagctcca gggtcatgtg gatggaggaa tccaaaactc   1920
atggctagat ccaattgacg agtcgggagg ctcaacagcg tcgtctgtac actcacgcac   1980
ctcttcgctt ggctaccgtc gacgccatat ccgggccgtg agcgggaaca ccgaggccga   2040
gtttgacacg gcgctggacg ctgctatcga ggctgcctac gacgacggct acgagcccat   2100
ggactctgta gactatggga ccattgatgc tgggggggac aatagcatgg caggcgtatt   2160
gcacaaggtg gagatggcgc gcgaacgagc gagacagacg gagcaggaag cctatgacga   2220
gctggccaac ctccgacagg cgcactcaca gaatccgcag caccagcagg aggaggacag   2280
gtatactgcc gagggattct acgaggacga ctcgtctgaa gaggaggaga gactattgga   2340
cgagattaca cgcgactttg ccattgagga ctttaccatg gaaaacccga atggcacaca   2400
ggtgtcagct aggcagcagg atgcatggaa cgaggacgag acgaggccgg atttcatctc   2460
gggcgtccga tccttttctg ccctgtcgca gaggccaccc attcctcagg cctacgccgc   2520
caacgcctcg cagccagcag cccccccctcc gacatccgca ttgccagacc tgccaccagg   2580
acgccctggt caaaatccaa agcaactcaa gatcgagacg gcaaacattg tacaaaccca   2640
gaagtcggtc tatgacgacg acgaaatctc cccaagcacg caagagccgc cgcccgagac   2700
gctcgtccgg acggcgagcg cgcagccgtg aaggccaccg ataccgacag aaagcttccc   2760
atccgaactc agtgctcccg catcgccaac cgccaagaag aggcttctgg aaggagagaa   2820
tgtgctgaat gcctcgcctt ctatccacag gctacggaag aactttttcgt cttctagctt   2880 gaggagcatg aagaacagga acatgtccgt ctcacatttg gacgacagct cggatgcttc   2940 cccccggcacc ccccctgaatg accccttcaa caaggcacct gccgtgcccg tgcccgcgct   3000
gccgaccccc ttgctcgcgt cgttcaaaga tcatatggag gcagcggccg gtgttggctt   3060
ccacctgttt gacgacgagt ttcatgcagc ggcggctgcc ggcccccaaa gcccgcagag   3120
```

-continued

```
tcccagaagt cccgttgttg tctccatgga cgtccctgtg cctctggaac cctgtccaaa    3180
cgacttcatg ctgcgaccgt tttggctgat gcgatgccta taccagacac ttgtgcatcc    3240
caagggtggc tacatcagta cgaagctatt cgtgccgcga gacgtctggc gggtcaaagg    3300
tgtcaagatc aagaacgtgg aggacaaaat tgccaactgc gacttttga ctgcagccct     3360 gctgaagctg tccaaagtgg acactctgga tgcggatgcc gtgctggagg agatgcaagc    3420
cctcgaggga attctggagc agatacagcc ggtcctggcc cgaaagcttg gaaacgaagt    3480
gggcgttcaa ggttccggtc tgctgttcaa agacgcctcg atgatggaag agacccccgg    3540
ttcagccgtg ccgcgatcag gaagtgtgtc tggcaaggcg tctgcgtttt cctggcgacg    3600
gcttcggcca aagacgtcgg gcgtcgggct gggagggtcg tacagcagcc gcaacgccag    3660
tgctgagacg aaggaggcct caacgctggc aacggtgccc atgacgccga aaccgacaag    3720
ccgttcggcc aagcgagacg tgagccaggt tcagttcatc gggcccaatg cgagctacat    3780
gggctctctc gcgcgcttgt ttgacgctgc gcaggcagtt ggtaagcata ttgcgatacg    3840
cataccggtt acagtgacgg caagctaacg atgatgcaga tcaaattgca aggcaggtcg    3900
acgaccccgg tttgcggctt gcggacaaga ctcaggtcgg cttggagctc tgcacccggc    3960
acgccgctga gttctttggc ttttacattt gccgattcgt cttggccgac ctcggcctgt    4020
tgctggacaa gttcctcaaa cgaggaagcg aatgggtcat gacatga                  4067
```

<210> SEQ ID NO 35
<211> LENGTH: 1285
<212> TYPE: PRT
<213> ORGANISM: Hypocrea jecorina

<400> SEQUENCE: 35

```
Met Gln Gln Pro Pro Ser Leu Val Gly Asp Arg Ser Ile Thr Gly Leu
1               5                   10                  15

Gly Asp Ala Ala Ser Arg Pro Asn Leu Ser Ser Ser Pro Thr Val
            20                  25                  30

Thr Ser Ala Pro Ser Ala Pro Thr Ser Pro Pro Arg Pro Pro Ile
        35                  40                  45

Ser Leu Asn Pro Pro Ser Arg Glu Pro Pro Gly Val Glu Pro Val Leu
    50                  55                  60

Arg Ile Thr Pro Val Pro Arg Ser Val Phe Ala Ser Val His Gln Pro
65                  70                  75                  80

Arg Lys Ser Ser Leu Val Gln Thr Ser His Val Leu Pro Ser Pro Arg
                85                  90                  95

Thr Ala Ala Ala Ala His His His Pro Val Ser His Ser Ala Ser
            100                 105                 110

Gly Ser Ser Gly Ser Asn Gly Ser Gly Ser Gly Ser Gly Ser
        115                 120                 125

Gly Asn Leu Leu Arg Gln Thr His Arg Asp Thr Val His Pro Pro Val
130                 135                 140

Lys Arg Pro Ser Thr Pro Ser Ser His Pro Thr Arg Gly Ala Ser Thr
145                 150                 155                 160

Gly Ala Ser Pro Gln Gln Gly Ala Ser Arg Asn Arg Ser Ser Thr
                165                 170                 175

Ser Pro Val Ser Ser Pro Ala Ser Arg Thr Pro Pro Tyr Ala Ser Arg
            180                 185                 190

Gln Ala Ser Val Ser His Ser Arg Gln Gln His Asn His His Gln
        195                 200                 205
```

```
His Gln His Gln His Tyr His Ser His Thr Ser Ser Thr Ser Arg
    210             215                 220

Ala Ser Ile Glu Ala Val Val Gly Ala Val Pro Asp Pro Ser Gly His
225             230                 235                 240

Arg Ala Pro Pro Lys Pro Arg Arg Pro Asp Arg Asn His Phe Gly Ala
            245                 250                 255

Ser Asp Arg Ser Ala Thr Pro Thr Leu Ser His Phe Met Arg Ala Glu
        260                 265                 270

Ser Ser Met Ser Met Arg His Tyr Glu Ser Gly Pro Leu Arg Ser Met
            275                 280                 285

Ser Pro Asn Pro Tyr Gly Thr Pro Ala Ala Thr Thr Thr Ser Ser Thr
290                 295                 300

Ala Arg Met Pro His Glu Gln Ser His Asp Pro Tyr Ala Pro Arg Gly
305                 310                 315                 320

His Ser Arg Asp His Ser Gly Lys Ser Ser Arg Asp Met Gly Lys Pro
                325                 330                 335

Arg Ala Gln Lys Asn Pro Ser Gln Lys Ala Met Leu Ser Arg Ala Leu
            340                 345                 350

Gln Lys Ala Asn Thr Ala Val Gln Leu Asp Asn Ala Gln Asn Phe Glu
        355                 360                 365

Gly Ala Arg Glu Ala Tyr Ala Glu Ala Cys Asp Leu Leu Gln Gln Val
370                 375                 380

Leu Asp Arg Thr Pro Gly Asp Glu Asp Lys Arg Lys Leu Glu Ala Ile
385                 390                 395                 400

His Gln Thr Tyr Thr Ser Arg Ile Asp Glu Leu Asp Gln Leu Gly Pro
                405                 410                 415

Trp Gln Val Glu Thr Val Lys Ala Leu Pro Ala Arg Pro Glu Ser Glu
            420                 425                 430

Glu Tyr Ser Ala Ser Ile Phe Ile Pro Gln Asp Tyr Asp Met Gly Asp
        435                 440                 445

Glu Ala Pro Arg Ile Glu Thr Ala Arg Val Val Ser Tyr Ile Ala Gly
450                 455                 460

Asp Asn Ala Ser Pro Phe Ala Ala Ala Pro Asn Gln Trp Gln Gln Ser
465                 470                 475                 480

Gly Gly His Thr Ala Ser Glu Arg Leu Gln Pro Asn Arg Gly Leu Glu
                485                 490                 495

Pro Gly Leu Leu Gln Ser Ser Phe Ser Arg Ala Pro Arg Ser Pro Arg
            500                 505                 510

Arg Leu Gln Ser Thr Asp Asp Leu Arg Ala Gln His Gln Glu Gly Gln
        515                 520                 525

Tyr Ala Pro Pro Leu Ser Pro Arg Ser Gln Ser Pro Gln Glu His
530                 535                 540

Asp His Gln Asp His His Gln Asp Tyr His Gln His His Arg His His
545                 550                 555                 560

Asn His His His His Glu Arg Gln Pro Ser Glu Thr Val Leu Ser Ser
                565                 570                 575

Tyr Glu Leu Gln Gly His Val Asp Gly Gly Ile Gln Asn Ser Trp Leu
            580                 585                 590

Asp Pro Ile Asp Glu Ser Gly Gly Ser Thr Ala Ser Ser Val His Ser
        595                 600                 605

Arg Thr Ser Ser Leu Gly Tyr Arg Arg Arg His Ile Arg Ala Val Ser
610                 615                 620

Gly Asn Thr Glu Ala Glu Phe Asp Thr Ala Leu Asp Ala Ala Ile Glu
```

```
            625                 630                 635                 640
Ala Ala Tyr Asp Asp Gly Tyr Glu Pro Met Asp Ser Val Asp Tyr Gly
                    645                 650                 655

Thr Ile Asp Ala Gly Gly Asp Asn Ser Met Ala Gly Val Leu His Lys
                    660                 665                 670

Val Glu Met Ala Arg Glu Arg Ala Arg Gln Thr Gln Glu Ala Tyr
            675                 680                 685

Asp Glu Leu Ala Asn Leu Arg Gln Ala His Ser Gln Asn Pro Gln His
            690                 695                 700

Gln Gln Glu Glu Asp Arg Tyr Thr Ala Glu Gly Phe Tyr Glu Asp Asp
705                 710                 715                 720

Ser Ser Glu Glu Glu Arg Leu Leu Asp Glu Ile Thr Arg Asp Phe
            725                 730                 735

Ala Ile Glu Asp Phe Thr Met Glu Asn Pro Asn Gly Thr Gln Val Ser
                    740                 745                 750

Ala Arg Gln Gln Asp Ala Trp Asn Glu Asp Glu Thr Arg Pro Asp Phe
            755                 760                 765

Ile Ser Gly Val Arg Ser Phe Ser Ala Leu Ser Gln Arg Pro Pro Ile
            770                 775                 780

Pro Gln Ala Tyr Ala Ala Asn Ala Ser Gln Pro Ala Ala Pro Pro Pro
785                 790                 795                 800

Thr Ser Ala Leu Pro Asp Leu Pro Pro Gly Arg Pro Gly Gln Asn Pro
                    805                 810                 815

Lys Gln Leu Lys Ile Glu Thr Ala Asn Ile Val Gln Thr Gln Lys Ser
                    820                 825                 830

Val Tyr Asp Asp Asp Glu Ile Ser Pro Ser Thr Gln Glu Pro Pro Pro
            835                 840                 845

Glu Thr Leu Val Arg Thr Ala Ser Ala Gln Pro Val Arg Pro Pro Ile
            850                 855                 860

Pro Thr Glu Ser Phe Pro Ser Glu Leu Ser Ala Pro Ala Ser Pro Thr
865                 870                 875                 880

Ala Lys Lys Arg Leu Leu Glu Gly Glu Asn Val Leu Asn Ala Ser Pro
                    885                 890                 895

Ser Ile His Arg Leu Arg Lys Asn Phe Ser Ser Ser Leu Arg Ser
                    900                 905                 910

Met Lys Asn Arg Asn Met Ser Val Ser His Leu Asp Asp Ser Ser Asp
                    915                 920                 925

Ala Ser Pro Gly Thr Pro Leu Asn Asp Pro Phe Asn Lys Ala Pro Ala
            930                 935                 940

Val Pro Val Pro Ala Leu Pro Thr Pro Leu Leu Ala Ser Phe Lys Asp
945                 950                 955                 960

His Met Glu Ala Ala Ala Gly Val Gly Phe His Leu Phe Asp Asp Glu
                    965                 970                 975

Phe His Ala Ala Ala Ala Ala Gly Pro Gln Ser Pro Gln Ser Pro Arg
                    980                 985                 990

Ser Pro Val Val Val Ser Met Asp Val Pro Val Pro Leu Glu Pro Cys
            995                 1000                1005

Pro Asn Asp Phe Met Leu Arg Pro Phe Trp Leu Met Arg Cys Leu
            1010                1015                1020

Tyr Gln Thr Leu Val His Pro Lys Gly Gly Tyr Ile Ser Thr Lys
            1025                1030                1035

Leu Phe Val Pro Arg Asp Val Trp Arg Val Lys Gly Val Lys Ile
            1040                1045                1050
```

Lys Asn Val Glu Asp Lys Ile Ala Asn Cys Asp Phe Leu Thr Ala
     1055                1060                1065

Ala Leu Leu Lys Leu Ser Lys Val Asp Thr Leu Asp Ala Asp Ala
    1070                1075                1080

Val Leu Glu Glu Met Gln Ala Leu Glu Gly Ile Leu Glu Gln Ile
    1085                1090                1095

Gln Pro Val Leu Ala Arg Lys Leu Gly Asn Glu Val Gly Val Gln
    1100                1105                1110

Gly Ser Gly Leu Leu Phe Lys Asp Ala Ser Met Met Glu Gly Asp
    1115                1120                1125

Pro Gly Ser Ala Val Pro Arg Ser Gly Ser Val Ser Gly Lys Ala
    1130                1135                1140

Ser Ala Phe Ser Trp Arg Arg Leu Arg Pro Lys Thr Ser Gly Val
    1145                1150                1155

Gly Leu Gly Gly Ser Tyr Ser Ser Arg Asn Ala Ser Ala Glu Thr
    1160                1165                1170

Lys Glu Ala Ser Thr Leu Ala Thr Val Pro Met Thr Pro Lys Pro
    1175                1180                1185

Thr Ser Arg Ser Ala Lys Arg Asp Val Ser Gln Val Gln Phe Ile
    1190                1195                1200

Gly Pro Asn Ala Ser Tyr Met Gly Ser Leu Ala Arg Leu Phe Asp
    1205                1210                1215

Ala Ala Gln Ala Val Asp Gln Ile Ala Arg Gln Val Asp Asp Pro
    1220                1225                1230

Gly Leu Arg Leu Ala Asp Lys Thr Gln Val Gly Leu Glu Leu Cys
    1235                1240                1245

Thr Arg His Ala Ala Glu Phe Phe Gly Phe Tyr Ile Cys Arg Phe
    1250                1255                1260

Val Leu Ala Asp Leu Gly Leu Leu Asp Lys Phe Leu Lys Arg
    1265                1270                1275

Gly Ser Glu Trp Val Met Thr
    1280                1285

<210> SEQ ID NO 36
<211> LENGTH: 462
<212> TYPE: DNA
<213> ORGANISM: Hypocrea jecorina

<400> SEQUENCE: 36
atccacagcg ccagggacgt ccaaatcccc gatagtattc ccagtcgagg accagcagcg      60
attgagtgag tgagtgactg actgagggac gactgaggta ctgacggatc ccagaggaca     120
gcacgacacc gcaccgcacc gctcagcaca ggcccgttgc tgggagtgct gtcgatccgc     180
tgagtggcct ctctctctct ctctgtctct cctccttcgc atcagcctcg tgagcaccgc     240
aaagacagaa gaacccgcca ttgtctcgag gtcatggccg gctgccacac gcgcgcaata     300
catccaatcc cacgactgcg acccccgacc cacgctgtac gagtaagatt ggccggaaga     360
ggcgaccatt ggctgagacg gcagcccgca ccagtccagc aaccgcaact gcaagtgctg     420
cacgtcgtac gaacctgatt tggccatagc cagcgccaga gc                       462

<210> SEQ ID NO 37
<211> LENGTH: 373
<212> TYPE: DNA
<213> ORGANISM: Hypocrea jecorina

<400> SEQUENCE: 37

```
agaaagagaa ggagaccgtt ttttgtcat tgaaagcaag cttgtgtgtt ttatcctatg    60
cgatacctaa tgagcaagag gcgggataat tgatctgaga ttttggtata acgttcatga   120
cgacggaacg atgagaagca gcaaaaggcg cgtttgttcg gaattcagtt gcggacatgc   180
ggcagcctgc tatatatcaa gaggaggttg gctgctttgg tgatccagac atcgaaaggc   240
atacatgtgt gtattttata gtatatatat ctctctcttt cctgaagcgt cttttctctg   300
gaagagacgg gatacatgat cgaacagcaa gcgagaagac atctgaaaga tttaatctga   360
agaaatggtc atg                                                      373
```

<210> SEQ ID NO 38
<211> LENGTH: 1343
<212> TYPE: PRT
<213> ORGANISM: Hypocrea jecorina

<400> SEQUENCE: 38

```
Met Ile Glu Asp Thr Ala Ala Leu Ala Ala Ala Glu Leu Ile Ala
1               5                   10                  15

Ser Leu Ala Cys Asp Pro Ala Ser Ala Ser Ser Ser Leu Val
            20                  25                  30

Ser Val Gly Pro Gly Ser Ser Ile Lys Leu Pro Gly Arg Glu Asn Pro
        35                  40                  45

Ala Lys Arg Thr Leu Glu Ile Glu Leu Glu Lys Leu Val Leu Arg Ile
    50                  55                  60

Ser Gln Leu Glu Ser Arg Ala Ser Ala Ser Ala Asn Ala Ser Val Phe
65                  70                  75                  80

Pro Glu Thr Pro Asn Glu Val Asn Asp Thr Leu Phe Asn Asp Val
                85                  90                  95

Asp Pro Ser Val Asn Gly Arg Pro Val Ala Pro Gln Pro Arg Leu
            100                 105                 110

Ser Gln Ala Gln Gln Gly Ser Leu Asp Ser Pro Ile Phe Val Ser Arg
        115                 120                 125

Gln Leu Thr Lys Glu Ala Leu Gln Gly Leu Arg Asp His Val Asp Asp
    130                 135                 140

Gln Ser Lys Leu Leu Asp Ser Gln Arg Gln Glu Leu Ala Gly Val Asn
145                 150                 155                 160

Ala Gln Leu Leu Glu Gln Lys Gln Leu Gln Glu Arg Ala Leu Ala Met
                165                 170                 175

Leu Glu Gln Glu Arg Val Ala Thr Leu Glu Arg Glu Leu Trp Lys His
            180                 185                 190

Gln Lys Ala Asn Glu Ala Phe Gln Lys Ala Leu Arg Glu Ile Gly Glu
        195                 200                 205

Ile Val Thr Ala Val Ala Arg Gly Asp Leu Thr Met Lys Val Arg Met
    210                 215                 220

Asn Ser Val Glu Met Asp Pro Glu Ile Thr Thr Phe Lys Arg Thr Ile
225                 230                 235                 240

Asn Ala Met Met Asp Gln Leu Gln Thr Phe Ala Ser Glu Val Ser Arg
                245                 250                 255

Val Ala Arg Glu Val Gly Thr Glu Leu Leu Gly Gly Gln Ala Arg
            260                 265                 270

Ile Gly Gly Val Asp Gly Val Trp Lys Glu Leu Thr Asp Asn Val Asn
        275                 280                 285

Ile Met Ala Gln Asn Leu Thr Asp Gln Val Arg Glu Ile Ala Ser Val
```

-continued

```
            290                 295                 300
Thr Thr Ala Val Ala His Gly Asp Leu Thr Lys Lys Ile Glu Arg Pro
305                 310                 315                 320

Ala Lys Gly Glu Ile Leu Gln Leu Gln Gln Thr Ile Asn Thr Met Val
                325                 330                 335

Asp Gln Leu Arg Thr Phe Ala Ser Glu Val Thr Arg Val Ala Arg Asp
                340                 345                 350

Val Gly Thr Glu Gly Ile Leu Gly Gly Gln Ala Asp Val Gly Gly Val
                355                 360                 365

Lys Gly Met Trp Asn Asp Leu Thr Val Asn Val Asn Ala Met Ala Asn
                370                 375                 380

Asn Leu Thr Thr Gln Val Arg Asp Ile Ile Lys Val Thr Thr Ala Val
385                 390                 395                 400

Ala Lys Gly Asp Leu Thr Gln Lys Val Gln Ala Glu Cys Arg Gly Glu
                405                 410                 415

Met Phe Lys Leu Lys Ser Thr Ile Asn Ser Met Val Asp Gln Leu Gln
                420                 425                 430

Gln Phe Ala Arg Glu Val Thr Lys Ile Ala Arg Glu Val Gly Thr Glu
                435                 440                 445

Gly Arg Leu Gly Gly Gln Ala Thr Val His Asp Val Glu Gly Thr Trp
450                 455                 460

Arg Asp Leu Thr Glu Asn Val Asn Gly Met Ala Met Asn Leu Thr Thr
465                 470                 475                 480

Gln Val Arg Glu Ile Ala Lys Val Thr Thr Ala Val Ala Arg Gly Asp
                485                 490                 495

Leu Thr Lys Lys Ile Gly Val Glu Val Lys Gly Glu Ile Leu Glu Leu
                500                 505                 510

Lys Asn Thr Ile Asn Gln Met Val Asp Arg Leu Gly Thr Phe Ala Val
                515                 520                 525

Glu Val Ser Lys Val Ala Arg Glu Val Gly Thr Asp Gly Thr Leu Gly
                530                 535                 540

Gly Gln Ala Gln Val Ala Asn Val Glu Gly Lys Trp Lys Asp Leu Thr
545                 550                 555                 560

Glu Asn Val Asn Thr Met Ala Ser Asn Leu Thr Val Gln Val Arg Ser
                565                 570                 575

Ile Ser Ala Val Thr Gln Ala Ile Ala Asn Gly Asp Met Ser Gln Thr
                580                 585                 590

Ile Asp Val Glu Ala Asn Gly Glu Ile Gln Val Leu Lys Glu Thr Ile
                595                 600                 605

Asn Asn Met Val Ser Arg Leu Ser Ser Phe Cys Tyr Glu Val Gln Arg
                610                 615                 620

Val Ala Lys Asp Val Gly Val Asp Gly Lys Met Gly Ala Gln Ala Asp
625                 630                 635                 640

Val Ala Gly Leu Asn Gly Arg Trp Lys Glu Ile Thr Thr Asp Val Asn
                645                 650                 655

Thr Met Ala Ser Asn Leu Thr Thr Gln Val Arg Ala Phe Ser Asp Ile
                660                 665                 670

Thr Asn Leu Ala Thr Asp Gly Asp Phe Thr Lys Leu Val Asp Val Glu
                675                 680                 685

Ala Ser Gly Glu Met Asp Glu Leu Lys Lys Lys Ile Asn Gln Met Ile
                690                 695                 700

Ser Asn Leu Arg Asp Ser Ile Gln Arg Asn Thr Gln Ala Arg Glu Ala
705                 710                 715                 720
```

-continued

Ala Glu Leu Ala Asn Lys Thr Lys Ser Glu Phe Leu Ala Asn Met Ser
            725                 730                 735

His Glu Ile Arg Thr Pro Met Asn Gly Ile Ile Gly Met Thr Gln Leu
            740                 745                 750

Thr Leu Asp Thr Asp Leu Thr Gln Tyr Gln Arg Glu Met Leu Asn Ile
            755                 760                 765

Val Asn Asp Leu Ala Asn Ser Leu Leu Thr Ile Ile Asp Asp Ile Leu
            770                 775                 780

Asp Leu Ser Lys Ile Glu Ala Arg Arg Met Val Ile Glu Glu Ile Pro
785                 790                 795                 800

Tyr Thr Leu Arg Gly Thr Val Phe Asn Ala Leu Lys Thr Leu Ala Val
            805                 810                 815

Lys Ala Asn Glu Lys Phe Leu Asp Leu Thr Tyr Lys Val Asp Ser Ser
            820                 825                 830

Val Pro Asp Tyr Val Ile Gly Asp Ser Phe Arg Leu Arg Gln Ile Ile
            835                 840                 845

Leu Asn Leu Val Gly Asn Ala Ile Lys Phe Thr Glu His Gly Glu Val
            850                 855                 860

Ser Leu Thr Ile Gln Glu Gln Glu Asp Lys Arg His Val Gly Pro Gly
865                 870                 875                 880

Glu Tyr Ala Ile Glu Phe Ile Val Glu Asp Thr Gly Ile Gly Ile Ala
            885                 890                 895

Lys Asp Lys Leu Asn Leu Ile Phe Asp Thr Phe Gln Gln Ala Asp Gly
            900                 905                 910

Ser Met Thr Arg Lys Phe Gly Gly Thr Gly Leu Gly Leu Ser Ile Ser
            915                 920                 925

Lys Arg Phe Val Asn Leu Met Gly Gly Asp Leu Trp Val Asn Ser Glu
            930                 935                 940

Val Gly Lys Gly Ser Glu Phe His Phe Thr Cys Arg Val Lys Leu Ala
945                 950                 955                 960

Asp Val His Ala Glu Ser Val Gln Gln Gln Leu Lys Pro Tyr Arg Gly
            965                 970                 975

His Gln Val Leu Phe Val Asp Lys Ser Gln Ser Asn Ala Ala Thr His
            980                 985                 990

Ile Gly Glu Met Leu Glu Glu Ile Gly Leu His Pro Val Val Asn
            995                 1000                1005

Ser Glu Lys Ser Ser Ala Leu Thr Arg Leu Lys Glu Gly Gly Ala
            1010                1015                1020

Leu Pro Tyr Asp Ala Ile Ile Val Asp Ser Ile Asp Thr Ala Arg
            1025                1030                1035

Arg Leu Arg Ala Val Asp Asp Phe Lys Tyr Leu Pro Ile Val Leu
            1040                1045                1050

Leu Ala Pro Val Val His Val Ser Leu Lys Ser Cys Leu Asp Leu
            1055                1060                1065

Gly Ile Thr Ser Tyr Met Thr Met Pro Cys Lys Leu Ile Asp Leu
            1070                1075                1080

Ser Asn Gly Met Ile Pro Ala Leu Glu Asn Arg Ala Thr Pro Ser
            1085                1090                1095

Leu Ala Asp Val Thr Lys Ser Phe Glu Ile Leu Leu Ala Glu Asp
            1100                1105                1110

Asn Thr Val Asn Gln Lys Leu Ala Val Lys Ile Leu Glu Lys Tyr
            1115                1120                1125

-continued

```
His His Val Val Thr Val Val Gly Asn Gly Trp Glu Ala Val Glu
    1130            1135            1140

Ala Val Lys Gln Lys Lys Phe Asp Val Ile Leu Met Asp Val Gln
    1145            1150            1155

Met Pro Ile Met Gly Gly Phe Glu Ala Thr Gly Lys Ile Arg Glu
    1160            1165            1170

Tyr Glu Arg Gly Met Gly Thr His Arg Thr Pro Ile Ile Ala Leu
    1175            1180            1185

Thr Ala His Ala Met Met Gly Asp Arg Glu Lys Cys Ile Gln Ala
    1190            1195            1200

Gln Met Asp Glu Tyr Leu Ser Lys Pro Leu Gln Gln Asn Gln Leu
    1205            1210            1215

Ile Gln Thr Ile Leu Lys Cys Ala Thr Leu Gly Gly Ala Leu Leu
    1220            1225            1230

Glu Lys Asn Arg Glu Arg Glu Leu Ala Leu Gln Ala Glu Ala Lys
    1235            1240            1245

Ala Ser Gly Arg Leu Asp Gly Glu Arg Gly Met Leu Arg Pro Gly
    1250            1255            1260

Leu Glu Gly Arg Ser Phe Thr Thr Arg Glu Pro Met Thr Lys Ser
    1265            1270            1275

Arg Pro Ser Leu Thr Lys Ala Thr Ser Lys Ala Leu Glu Glu Ala
    1280            1285            1290

Arg Asn Ala Ala Ala Ala Asn Ala Gly Leu Arg Phe Ser Glu Leu
    1295            1300            1305

Thr Gly Phe Ser Ala Asp Leu Met Glu Glu Leu Asp Asn Met Glu
    1310            1315            1320

Asp Glu Asp Ser Phe Thr Lys Ala Arg Glu Asp Leu Ala Asp Arg
    1325            1330            1335

Arg Ser Leu Ser Ser
    1340
```

FILAMENTOUS FUNGAL STRAINS COMPRISING REDUCED VISCOSITY PHENOTYPES

CROSS-REFERENCE TO RELATED APPLICATIONS

The present application claims priority to U.S. Provisional Patent Application Ser. No. 62/661,658, filed Apr. 24, 2018, which is hereby incorporated by reference in its entirety.

TECHNICAL FIELD

The present disclosure is generally related to the fields of biology, molecular biology, rheology, filamentous fungi, industrial protein production and the like. More particularly, the present strains and methods of the disclosure relate to genetic modifications in filamentous fungi that give rise to variant strains having altered phenotypes, altered morphologies, altered growth characteristics and the like. More specifically, as presented and described herein, such variant strains of filamentous fungi are well-suited for growth in submerged cultures (e.g., for the large-scale production of enzymes and other proteins or metabolites for commercial applications).

REFERENCE TO A SEQUENCE LISTING

The contents of the electronic submission of the text file Sequence Listing, named "NB40808-WO-PCT_Sequence-Listing.txt" was created on Apr. 5, 2019 and is 184 KB in size, which is hereby incorporated by reference in its entirety.

BACKGROUND

Filamentous fungi are capable of expressing native and heterologous proteins to high levels, making them well-suited for the large-scale production of enzymes and other proteins and/or metabolites for industrial, pharmaceutical, animal health, food and beverage applications and the like. Filamentous fungi are typically grown in mycelial submerged cultures in bioreactors (fermentors), which bioreactors are adapted to introduce and distribute oxygen and nutrients into the culture medium (i.e., culture broth). The morphological characteristics of the mycelium affect the rheological properties of the culture medium (broth), thereby affecting bioreactor performance.

For example, in the filamentous fungal host *Trichoderma reesei*, many native and heterologous proteins are efficiently secreted, resulting in both high specific productivity (Qp) and yield on glucose. However, capacity requirements for *Trichoderma* processes (i.e., filamentous fungi in general) are very high due to low volumetric productivity. For example, low volumetric productivity is caused by the need to restrict biomass levels due to high culture broth viscosity and oxygen transfer limitations Generally, the higher the viscosity of the broth, the less uniform the distribution of oxygen and nutrients, and the more energy required to agitate the culture. For example, in some cases, the viscosity of the culture broth becomes sufficiently high to significantly interfere with the dissolution of oxygen and nutrients, thereby adversely affecting the growth of the fungi and/or product production by the fungi. Additionally, the power required to mix and aerate viscous broth in the bioreactor can significantly increase the cost of production, and incur higher capital expenditures in terms of motors and power supplies. Thus, as generally described above, many ongoing and unmet needs remain in the art, including, but not limited to, improved volumetric efficiencies, enhanced/uniform oxygen distribution, reduced cell broth viscosity, high specific productivities, improved yield on carbon source, reduced bioreactor operating costs, altered (cell) phenotypes, altered (cell) morphologies, altered (cell) growth characteristics and the like.

SUMMARY

Described herein are strains, methods, constructs and the like relating to filamentous fungi having genetic modifications that give rise to variant strains having altered phenotypes, altered morphologies, altered growth characteristics and the like. For example, certain embodiments of the disclosure are related to a variant strain of filamentous fungus derived from a parental strain, wherein the variant strain comprises a genetic modifications of a gene encoding a SSB7 protein.

Thus, in certain embodiments, the disclosure is related to variant strains of filamentous fungus derived from parental strains, wherein the variant strain comprise genetic modifications of a gene encoding a SSB7 protein comprising about 50% sequence identity to any one of SEQ ID NO: 2, SEQ ID NO: 8, SEQ ID NO: 9, SEQ ID NO: 10, SEQ ID NO: 11, SEQ ID NO: 12, SEQ ID NO: 13, SEQ ID NO: 31, SEQ ID NO: 33 and SEQ ID NO: 35, wherein the cells of the variant strain comprise a reduced viscosity phenotype relative to the parental cells. Thus, in certain other embodiments, such variant strains comprising a reduced viscosity phenotype (a) produce during aerobic fermentation in submerged culture a cell broth that requires a reduced amount of agitation to maintain a preselected dissolved oxygen content, relative to the cells of the parental strain and/or (b) produce a cell broth that maintains an increased dissolved oxygen content at a preselected amount of agitation, relative to the cells of the parental strain.

Thus, in other embodiments, a genetic modification of a gene encoding a SSB7 protein comprises deleting or disrupting at least a 3' region of the gene encoding the SSB7 protein. In other embodiments, a SSB7 protein encoded by the gene comprises a deletion of at least the last 400 amino acid positions of the SSB7 C-terminus, a deletion of at least the last 600 amino acid positions of the SSB7 C-terminus, a deletion of at least the last 800 amino acid positions of the SSB7 C-terminus, or a deletion of at least the last 1,000 amino acid positions of the SSB7 C-terminus. In other embodiments, the SSB7 protein encoded by the gene is completely deleted.

Thus, in certain other embodiments, the ssb7 gene is disrupted in the 3' region encoding the last 400 amino acid positions of the SSB7 C-terminus, the ssb7 gene is disrupted in the 3' region encoding the last 600 amino acid positions of the SSB7 C-terminus, the ssb7 gene is disrupted in the 3' region encoding the last 800 amino acid positions of the SSB7 C-terminus, or the ssb7 gene is disrupted in the 3' region encoding the last 1,000 amino acid positions of the SSB7 C-terminus.

In related embodiments, the parental and variant strains comprise gene encoding the same protein of interest (POI). In other embodiments, the variant strain produces substantially the same amount of the protein of interest per unit amount of biomass relative to the parental strain. In other embodiments, the variant strain produces more of the protein of interest per unit amount of biomass as the parental strain.

In other embodiments, the filamentous fungus is of the phylum Ascomycota. In other embodiments, the filamentous fungus is selected from the group consisting of a *Trichoderma* sp. fungus, a *Fusarium* sp. fungus, a *Neurospora* sp. fungus, a *Myceliophthora* sp. fungus, a *Talaromyces* sp. fungus, an *Aspergillus* sp. fungus and a *Penicillium* sp. fungus.

Thus, in certain other embodiments the disclosure is directed to one or more proteins of interest produced by a reduced viscosity variant of the disclosure.

In certain other embodiments, the variant strain further comprises a genetic modification of one or more genes encoding a MPG1 protein, a SFB3 protein, a SEB1 protein, a CRZ1 protein and/or a GAS1 protein.

In other embodiments, a gene encoding a SSB7 protein hybridizes with the ssb7 gene of SEQ ID NO: 1 or the complementary sequence thereof, under stringent hybridization conditions. In other embodiments, a gene encoding a SSB7 protein hybridizes with the ssb7 exon of SEQ ID NO: 19 or the complementary sequence thereof, under stringent hybridization conditions. In other embodiments, a gene encoding a SSB7 protein hybridizes with the ssb7 exon of SEQ ID NO: 20 or the complementary sequence thereof, under stringent hybridization conditions. In other embodiments, a gene encoding a SSB7 protein hybridizes with the ssb7 exon of SEQ ID NO: 21 or the complementary sequence thereof, under stringent hybridization conditions.

In yet other embodiments, a gene encoding a SSB7 protein hybridizes with a nucleic acid sequence encoding region A of SEQ ID NO: 22 under stringent hybridization conditions. In other embodiments, a gene encoding a SSB7 protein hybridizes with a nucleic acid sequence encoding region B of SEQ ID NO: 23 under stringent hybridization conditions. In other embodiments, a gene encoding the SSB7 protein hybridizes with a nucleic acid sequence encoding region C of SEQ ID NO: 24 under stringent hybridization conditions. In other embodiments, a gene encoding a SSB7 protein hybridizes with a nucleic acid sequence encoding region D of SEQ ID NO: 25 under stringent hybridization conditions.

In other embodiments, a gene encoding a SSB7 protein hybridizes with a nucleic acid sequence encoding a conserved amino acid sequence of the SSB7 protein under stringent hybridization conditions, the conserved sequence selected from the group consisting of SEQ ID NOs: 26-30 under stringent hybridization conditions.

In certain other embodiments, the disclosure is directed to methods for constructing reduced viscosity strains of filamentous fungus cells, such methods comprising (a) obtaining a parental strain of filamentous fungus cells and genetically modifying a gene encoding a SSB7 protein comprising at least 50% sequence identity to SEQ ID NO: 2, SEQ ID NO: 8, SEQ ID NO: 9, SEQ ID NO: 10, SEQ ID NO: 11, SEQ ID NO: 12, SEQ ID NO: 13, SEQ ID NO: 31, SEQ ID NO: 33 or SEQ ID NO: 35, and (b) isolating the variant strain modified in step (a), wherein the cells of the variant strain comprise a reduced viscosity phenotype relative to the parental cells. Thus, in related embodiments, the variant strain during aerobic fermentation in submerged culture (a) produces a cell broth that requires a reduced amount of agitation to maintain a preselected dissolved oxygen content, relative to the cells of the parental strain and/or (b) produces a cell broth that maintains an increased dissolved oxygen content at a preselected amount of agitation, relative to the cells of the parental strain.

Thus, in other embodiments of the method, a genetic modification of a gene encoding a SSB7 protein comprises deleting or disrupting at least a 3' region of the gene encoding the SSB7 protein.

In certain other embodiments, a SSB7 protein encoded by the gene comprises a deletion of at least the last 400 amino acid positions of the SSB7 C-terminus, a deletion of at least the last 600 amino acid positions of the SSB7 C-terminus, a deletion of at least the last 800 amino acid positions of the SSB7 C-terminus, a deletion of at least the last 1,000 amino acid positions of the SSB7 C-terminus and the like. In other embodiments of the method, a SSB7 protein encoded by the gene is completely deleted.

In certain other embodiments of the methods, a ssb7 gene is disrupted in the 3' region encoding the last 400 amino acid positions of the SSB7 C-terminus, a ssb7 gene is disrupted in the 3' region encoding the last 600 amino acid positions of the SSB7 C-terminus, a ssb7 gene is disrupted in the 3' region encoding the last 800 amino acid positions of the SSB7 C-terminus, a ssb7 gene is disrupted in the 3' region encoding the last 1,000 amino acid positions of the SSB7 C-terminus and the like.

Thus, certain other embodiments such fungal cells comprise a gene encoding a protein of interest. In other embodiments, the variant strain produces substantially the same amount of the protein of interest per unit amount of biomass relative to the parental strain. In other embodiments, the variant strain produces more of the protein of interest per unit amount of biomass as the parental strain. Thus, in certain other embodiments, the disclosure is directed to a protein of interest produced by a variant strain of the disclosure.

In certain other embodiments of the methods, the filamentous fungus is of the phylum Ascomycota. In other embodiments, the filamentous fungus is selected from the group consisting of a *Trichoderma* sp. fungus, a *Fusarium* sp. fungus, a *Neurospora* sp. fungus, a Myceliophthora sp. fungus, a *Talaromyces* sp. fungus, an *Aspergillus* sp. fungus and a *Penicillium* sp.

In other embodiments of the methods, the variant strain further comprises a genetic modification of one or more genes encoding a MPG1 protein, a SFB3 protein, a SEB1 protein, a CRZ1 protein and/or a GAS1 protein.

In other embodiments of the methods, a gene encoding a SSB7 protein hybridizes with the ssb7 gene of SEQ ID NO: 1 or the complementary sequence thereof, under stringent hybridization conditions. In certain other embodiments, a gene encoding a SSB7 protein hybridizes with the ssb7 exon of SEQ ID NO: 19 or the complementary sequence thereof, under stringent hybridization conditions. In other embodiments, a gene encoding a SSB7 protein hybridizes with the ssb7 exon of SEQ ID NO: 20 or the complementary sequence thereof, under stringent hybridization conditions. In another embodiment, a gene encoding a SSB7 protein hybridizes with the ssb7 exon of SEQ ID NO: 21 or the complementary sequence thereof, under stringent hybridization conditions.

In other embodiments of the methods, a gene encoding a SSB7 protein hybridizes with a nucleic acid sequence encoding region A of SEQ ID NO: 22 under stringent hybridization conditions. In other embodiments, a gene encoding a SSB7 protein hybridizes with a nucleic acid sequence encoding region B of SEQ ID NO: 23 under stringent hybridization conditions. In another embodiment, a gene encoding a SSB7 protein hybridizes with a nucleic acid sequence encoding region C of SEQ ID NO: 24 under stringent hybridization conditions. In other embodiments, a gene encoding a SSB7 protein hybridizes with a nucleic acid sequence encoding region D of SEQ ID NO: 25 under stringent hybridization conditions. In other embodiments of the methods, a gene encoding a SSB7 protein hybridizes with a nucleic acid sequence encoding a conserved amino acid sequence of the SSB7 protein under stringent hybridization conditions, the conserved sequence selected from the group consisting of SEQ ID NOs: 26-30.

In certain other embodiments, the disclosure is directed to a method for screening and isolating a variant strain of filamentous fungus cells comprising a reduced viscosity phenotype, the method comprising (a) genetically modifying a gene in a parental fungal strain encoding a SSB7 protein comprising at least 50% sequence identity to SEQ ID NO: 2, SEQ ID NO: 8, SEQ ID NO: 9, SEQ ID NO: 10, SEQ ID NO: 11, SEQ ID NO: 12, SEQ ID NO: 13, SEQ ID NO: 31, SEQ ID NO: 33 or SEQ ID NO: 35, (b) screening cell morphology of the modified variant strain of step (a) for a reduced viscosity phenotype relative to cell morphology of the parental strain, and (c) isolating a modified variant strain of step (b) comprising a reduced viscosity phenotype, wherein the variant strain during aerobic fermentation in submerged culture (a) produces a cell broth that requires a reduced amount of agitation to maintain a preselected dissolved oxygen content, relative to the cells of the parental strain and/or (b) produces a cell broth that maintains an increased dissolved oxygen content at a preselected amount of agitation, relative to the cells of the parental strain. In other embodiments, the variant strain of step (c) comprises a reduced viscosity phenotype related to shorter hyphal filaments (FIG. 2), relative to the parental strain from which it was derived.

BRIEF DESCRIPTION OF THE BIOLOGICAL SEQUENCES

SEQ ID NO: 1 is a nucleic acid sequence of the wild-type *T. reesei* ssb7 gene encoding a native SSB7 protein of SEQ ID NO: 2.

SEQ ID NO: 2 is the amino acid sequence of the native *T. reesei* SSB7 protein encoded by SEQ ID NO: 1.

SEQ ID NO: 3 is a nucleic acid sequence of allele ssb7(fs), comprising a deletion of G (ΔG) in exon 2, resulting in a frame-shift (fs) mutation, and a premature stop codon prior to the last intron of the ssb7 gene.

SEQ ID NO: 4 is the amino acid sequence of the variant SSB7 protein encoded by allele ssb7(fs) of SEQ ID NO: 3.

SEQ ID NO: 5 is a synthetic gBlock nucleic acid sequence presented in FIG. 6A.

SEQ ID NO: 6 is a synthetic gBlock single-guide RNA (sgRNA) expression cassette targeting TS1 of the ssb7 gene presented in FIG. 6B.

SEQ ID NO: 7 is a synthetic gBlock single-guide RNA (sgRNA) expression cassette targeting TS2 of the ssb7 gene presented in FIG. 6C.

SEQ ID NO: 8 is the amino acid sequence of a *Fusarium* sp. SSB7 protein orthologue.

SEQ ID NO: 9 is the amino acid sequence of a *Neurospora* sp. SSB7 protein orthologue.

SEQ ID NO: 10 is the amino acid sequence of a *Myceliophthora* sp. SSB7 protein orthologue.

SEQ ID NO: 11 is the amino acid sequence of a *Talaroymyces* sp. SSB7 protein orthologue.

SEQ ID NO: 12 is the amino acid sequence of an *Aspergillus* sp. SSB7 protein orthologue.

SEQ ID NO: 13 is the amino acid sequence of a *Penicillium* sp. SSB7 protein orthologue.

SEQ ID NO: 14 is the amino acid sequence of a *T. reesei* MPG1 protein.

SEQ ID NO: 15 is the amino acid sequence of a *T. reesei* SFB3 protein.

SEQ ID NO: 16 is the amino acid sequence of a *T. reesei* SEB1 protein.

SEQ ID NO: 17 is the amino acid sequence of a *T. reesei* CRZ1 protein.

SEQ ID NO: 18 is the amino acid sequence of a *T. reesei* GAS1 protein.

SEQ ID NO: 19 is a nucleic acid sequence of the wild-type *T. reesei* ssb7 gene exon 1.

SEQ ID NO: 20 is a nucleic acid sequence of the wild-type *T. reesei* ssb7 gene exon 2.

SEQ ID NO: 21 is a nucleic acid sequence of the wild-type *T. reesei* ssb7 gene exon 3.

SEQ ID NO: 22 is a *T. reesei* nucleic acid sequence encoding the SSB7 protein Region A.

SEQ ID NO: 23 is a *T. reesei* nucleic acid sequence encoding the SSB7 protein Region B.

SEQ ID NO: 24 is a *T. reesei* nucleic acid sequence encoding the SSB7 protein Region C.

SEQ ID NO: 25 is a *T. reesei* nucleic acid sequence encoding the SSB7 protein Region D.

SEQ ID NO: 26 is a conserved SSB7 amino acid sequence as shown in FIG. 9C.

SEQ ID NO: 27 is a conserved SSB7 amino acid sequence as shown in FIG. 9C.

SEQ ID NO: 28 is a conserved SSB7 amino acid sequence as shown in FIG. 9D.

SEQ ID NO: 29 is a conserved SSB7 amino acid sequence as shown in FIG. 9D.

SEQ ID NO: 30 is a conserved SSB7 amino acid sequence as shown in FIG. 9E.

SEQ ID NO: 31 is the amino acid sequence of a *T. atroviride* SSB7 protein.

SEQ ID NO: 32 is a nucleic acid sequence prediction of the *T. reesei* (QM6a strain) ssb7 gene encoding the predicted SSB7 protein of SEQ ID NO: 33.

SEQ ID NO: 33 is the amino acid sequence of the *T. reesei* (QM6a strain) predicted SSB7 protein encoded by SEQ ID NO: 32.

SEQ ID NO: 34 is a nucleic acid sequence prediction of the *T. reesei* (RUT-C30 strain) ssb7 gene encoding the predicted SSB7 protein of SEQ ID NO: 35.

SEQ ID NO: 35 is the amino acid sequence of the *T. reesei* (RUT-C30 strain) predicted SSB7 protein encoded by SEQ ID NO: 34.

SEQ ID NO: 36 is the 5'-UTR (untranslated region) of the *T. reesei* ssb7 gene transcript.

SEQ ID NO: 37 is the 3'-UTR (untranslated region) of the *T. reesei* ssb7 gene transcript.

SEQ ID NO: 38 is the amino acid sequence of a native *T. reesei* Nik1 protein.

BRIEF DESCRIPTION OF THE DRAWINGS

As shown in FIG. 2, DNA fragment 1 (FIG. 2, Panel 1A and Panel 1B) and DNA fragment 6 (FIG. 2, Panel 6A and Panel 6B) represent independent transformants for each DNA fragment (i.e., DNA fragment 1 and 6). Transformants carrying most DNA fragments retained the hyper-branching and thick hyphae phenotype observed for the mutant strain, Morph 77B7. For example, as shown in FIG. 2, Panels 1A and 1B, transformants comprising DNA fragment 1 (encoding one of the other mutant loci in strain Morph 77B7 (i.e., PID 112328), exemplifies this hyper-branching and thick hyphae phenotype. In contrast, as shown in FIG. 2, Panels 6A and 6B, only the transformants comprising DNA fragment 6 (i.e., encoding PID 108712/SSB7), reversed this phenotype, at least partially, with thinner and less-branched hyphae.

FIG. 3 presents the nucleic acid sequence of a *T. reesei* wild-type ssb7 gene (FIG. 3A, SEQ ID NO: 1) encoding a native SSB7 protein (FIG. 3B, SEQ ID NO: 2) and the nucleic acid sequence of *T. reesei* mutant ssb7 allele (ssb7 (fs), FIG. 3C, SEQ ID NO: 3) encoding a variant SSB7 protein (i.e., a C-terminal truncated) SSB7 protein, wherein the coding sequence regions are presented in CAPITAL letters and introns are presented in italicized lower case. As shown in FIG. 3C, the adjacent nucleotides to the site of the (ΔG) frame-shift mutation in the nucleic acid sequence of the mutant ssb7 allele are presented as bold CAPITAL and underlined letters GA.

FIG. 4 presents the *T. reesei* ssb7 gene (ORF) coding sequences as exon 1 (FIG. 4A, SEQ ID NO: 19), exon 2 (FIG. 4B, SEQ ID NO: 20) and exon 3 (FIG. 4C, SEQ ID NO: 21).

FIG. 5 is a graphical representation of a MUSCLE alignment of three hundred and fifty-three (353) Ascomycete homologs, excluding short protein predictions lacking amino acids spanning the N-terminal MIT domain. At the bottom of FIG. 5 are boxes representing the amino acid sequence of the *T. reesei* SSB7 protein wherein amino acid (residues) are presented in black shaded boxes if conserved in greater than 85% of the aligned sequences (or are light grey otherwise). As presented in FIG. 5, amino acid sequence gaps in the sequence alignment are presented as grey shaded lines between the residues. A single grey box below the residues represents the MIT domain, annotated in the downloaded GeneBank EGR47392 sequence for PID 108712/SSB7. The mean hydrophobicity and isoelectric point (PI) are also plotted and presented in FIG. 5. The amino acid identity in the alignment is plotted just above the residues. Bar height is proportional to amino acid identity. The grey bars represent residues identical in at least 30% of sequences in the alignment and black bars less than 30%. The alignment reveals four (4) regions of conservation in SSB7 homologs, Regions A through D, represented as boxes labeled A-D. Region A corresponds to the MIT domain.

FIG. 6 presents the synthetic DNA sequences added to pTrex2g MoCas for cas9-mediated genome editing at the ssb7 locus. For example, SEQ ID NO: 5 (FIG. 6A) is an IDT gBlock nucleic acid sequence with the sequence information to edit the ssb7 locus, SEQ ID NO: 6 (FIG. 6B) is an IDT gBlock for expression of 77B7 TS1 sgRNA and SEQ ID NO: 7 (FIG. 6C) is an IDT gBlock for expression of 77B7 TS2 sgRNA. As presented in FIG. 6A, single underlined nucleotides show regions of sequence identity to pTrex2gHyg MoCas used for in vitro plasmid assembly, double underlined nucleotides indicate the 20-nt target sites corresponding to the guide RNA sequences, UPPER CASE BOLD residues represent G to C nucleotide changes that alter the protospacer adjacent motif (PAM) sites adjacent to the target sites and gray shaded nucleotides show six (6) G residues that are seven (7) G's in the wild-type gene. As presented in FIG. 6B and FIG. 6C, single underlined nucleotides show regions of sequence identity to pTrex2gHyg MoCas used for in vitro plasmid assembly, lower case nucleotides show the target sites in the *T. reesei* genome, double underlined nucleotides indicate the sequence of the sgRNAs, and gray shaded nucleotides show intron sequences.

FIG. 7 shows "Agitation" and "Dissolved Oxygen (DO)" profiles for Bioreactor fermentations of (parental) TrGA 29-9 and (daughter) ssb7 mutant derived strains. The amount of agitation (FIG. 7, left y-axis (RPM) marked with 'x'; trend upward before t=0) and Dissolved Oxygen (FIG. 7, right y-axis (DO %, marked with '|'; trend downward before t=0) was plotted against the feed start adjusted fermentation time (x-axis) for the time window (plus and minus 10 hours) used to calculate the Agitation-addition and DO-limitation measurements. Profiles of parental TrGA 29-9 ("29-9": black) and two ssb7 mutant (daughter) strains (TrGA 29-9 ssb7(311): grey) and (TrGA 29-9 ssb7(TS1): white) were plotted.

FIG. 8 generally shows the amino acid composition and related properties of the wild-type *T. reesei* SSB7 protein (SEQ ID NO: 2). FIG. 8A, shows a PEPSTATS analysis of the SEQ ID NO: 2, wherein the SSB7 protein comprises 1,308 residues, an estimated (theoretical) molecular weight of 142,540 (Da), an isoelectric point of approximately 6.8 and an approximate net charge of $^{+}10$. On a mole percent (%) basis, the SSB7 protein comprises approximately 12.0% (157) serine (S) residues, 9.6% (126) alanine (A) residues, 9.6% (126) proline (P) residues, 6.8% (89) leucine (L) residues, 5.8% (76) glutamine (Q), and the like, as presented in FIG. 8A. FIG. 8C-FIG. 8F present hydropathy plots of the SSB7 protein scanning the 1,308 residues of the SSB7 protein's sequence (SEQ ID NO: 2) in approximately 320 residue windows starting from the N-terminus (residue 1) and ending at the C-terminus (residue 1,308) of SEQ ID NO: 2, wherein FIG. 8C shows a hydropathy plot of the SSB7 protein residues 1-320 (SEQ ID NO:2), FIG. 8D shows a hydropathy plot of the SSB7 protein residues 321-640 (SEQ ID NO:2), FIG. 8E shows a hydropathy plot of the SSB7 protein residues 641-961 (SEQ ID NO: 2) and FIG. 8F shows a hydropathy plot of the SSB7 protein residues 962-1,308 (SEQ ID NO: 2). FIG. 8G shows the Kyle-Doolittle amino acid hydropathy scores used in FIG. 8B-8F. Thus, as presented in FIG. 8B-8G, hydrophobic regions of the SSB7 protein sequence are indicated as score values greater than zero and hydrophilic regions of the SSB7 protein sequence are indicated as score values less than zero (e.g., see residue values FIG. 8G). For example, FIG. 8C presents a hydropathy plot of the SSB7 protein (N-terminal residues 1-320), wherein the single letter amino acid sequence of residues 1-320 are shown directly above the hydropathy plot.

FIG. 9 presents a CLUSTAL W (1.83) multiple sequence alignment of the wild-type *Trichoderma reesei* SSB7 protein (abbreviated "SID_2"; presented in bold CAPITAL amino acid residues) and a wild-type *Trichoderma atroviride* SSB7 protein (abbreviated "SID_31") aligned with six (6) different Ascomycota SSB7 protein orthologues. More particularly, as presented in FIG. 9A-9E, a *Fusarium* sp. SSB7 protein (SEQ ID NO: 8; abbreviated "SID_8"), a *Neurospora* sp. SSB7 protein (SEQ ID NO: 9; abbreviated "SID 9"), a *Myceliophthora* sp. SSB7 protein (SEQ ID NO: 10; abbreviated "SID 10), a *Talaroymyces* sp. SSB7 protein (SEQ ID NO: 11; abbreviated "SID_11"), an *Aspergillus* sp. SSB7 protein (SEQ ID NO: 12; abbreviated "SID_12"), a *Penicillium* sp. SSB7 protein (SEQ ID NO: 13; abbreviated "SID_13") and the wild-type *Trichoderma atroviride* SSB7 protein (SEQ ID NO: 31) were aligned with the *T. reesei* SSB7 protein (SEQ ID NO: 2). As presented in FIG. 9A-9E (i.e., below the aligned amino residues), an asterisk (*) indicates positions which have a single, fully conserved residue, a colon (:) indicates conservation between groups of strongly similar properties (i.e., scoring>0.5 in the Gonnet PAM 250 matrix) and a period (.) indicates conservation between groups of weakly similar properties (i.e., scoring<0.5 in the Gonnet PAM 250 matrix).

DETAILED DESCRIPTION

Figure 1A:
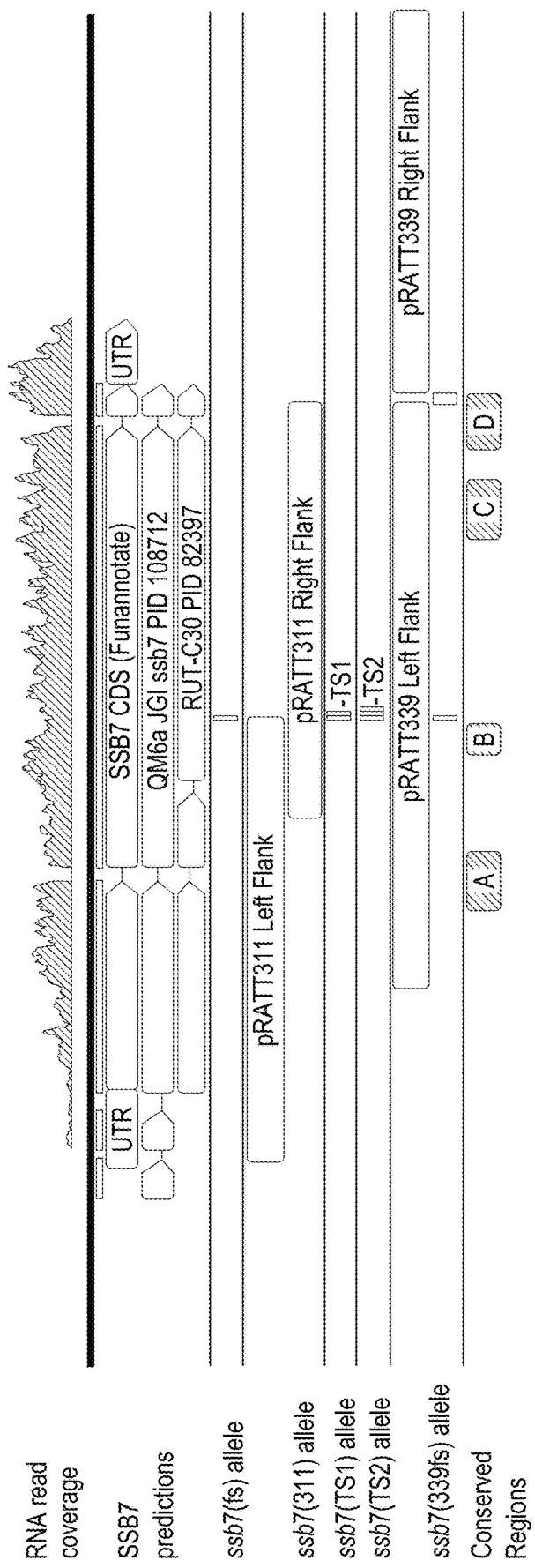
FIG. 1 is a schematic diagram of the ssb7 locus, which illustrates the ssb7 alleles disclosed and exemplified herein. More specifically, as presented and described in the Examples section, such variant strains of filamentous fungus (i.e., comprising a mutated ssb7 allele) comprise a reduced viscosity phenotype/morphology (i.e., producing a reduced viscosity fermentation broth), relative to a parental (control) strain comprising a wild-type ssb7 allele. Thus, as presented in FIG. 1A, the regions corresponding to the predicted SSB7 protein coding sequence (i.e., exons) for the ssb7 gene are represented as arrows, with the lines in between exons showing the position of the introns. The gene predictions for different versions of ssb7 are indicated by their label (e.g., "QM6a JGI ssb7 PID 108712" and "RUT-C30 PID 82397"), as well as the prediction described herein ("SSB7 CDS (funannotate)"). A summary of RNA-sequencing reads mapped to this locus are shown in a coverage map (RNA read coverage). The 5' and 3'-untranslated regions (UTR) predicted by funannotate are also indicated and labeled as such. Each track below the sequence illustrates the five (5) different alleles disclosed and exemplified herein (e.g., allele ssb7(fs), allele ssb7(311), allele ssb7(TS1), allele ssb7(TS2) and allele ssb7(339fs)). The boxes (e.g., labeled "pRATT311 Left Flank", "pRATT311 Right Flank", "pRATT339 Left Flank" and "pRATT339 Right Flank") show the homology boxes used to target integration of markers (e.g., pyr2) at the ssb7 locus; the boxes (e.g., labeled "TS1" and "TS2") show the Target Sequences (TS) used for cas9-mediated gene editing. Polymorphisms (i.e., mutations and indels) present in the alleles are presented as small unlabeled boxes (i.e., as best as possible at this resolution). Furthermore, below the allele annotations are boxes labeled A-D, indicating the location in the coding sequence of the four (4) regions of amino acid conservation therein (i.e., FIG. 1A, Regions A-D), as further described below in Example 1. For clarity, at a higher sequence resolution.
FIG. 1B presents all the genetic modifications around the frame-shift (fs) site identified in strain Morph 77B7 for each of the alleles (ssb7(fs), ssb7(311), ssb7(TS1), ssb7(TS2) and ssb7(399fs)). In particular, the first row of FIG. 1B (labeled "DNA") shows the nucleotide sub-sequence of the fs site identified in the mutant ssb7(fs) allele of SEQ ID NO: 3 and the second row of FIG. 1B (labeled "Amino Acid) shows the amino acid sub-sequence encoded by the mutant ssb7(fs) allele of SEQ ID NO: 3, which amino acid sub-sequence is present in SSB7 variant protein SEQ ID NO: 4.

As set forth and described herein, the present disclosure addresses certain ongoing and unmet needs in the art of filamentous fungi protein production and methods thereof, including but not limited to, improved volumetric efficiencies, enhanced/uniform oxygen distribution, reduced cell broth viscosity, high specific productivities, improved yield on carbon source, reduced bioreactor (fermentor) operating costs, altered (cell) phenotypes, altered (cell) morphologies, altered (cell) growth characteristics and the like. Thus, the present strains and methods of the disclosure generally relate to genetic modifications in filamentous fungi that give rise to variant strains having such altered phenotypes, altered morphologies, altered growth characteristics, and the like. More particularly, as presented and described herein, such variant strains of filamentous fungi are well-suited for growth in submerged cultures for the large-scale production of enzymes and other proteins, or metabolites.

Thus, in certain embodiments, the disclosure is related to variant strains of filamentous fungus derived from parental strains described herein. In certain embodiments, such variant strains comprise a genetic modification of a gene encoding a SSB7 protein. More particularly, in certain other embodiments, a variant strain of the disclosure (i.e., comprising a genetic modification of a gene encoding a SSB7 protein) produces a cell broth that requires a reduced amount of agitation to maintain a preselected dissolved oxygen (DO) content (i.e., during aerobic fermentation in submerged culture), and/or produces a cell mass that maintains an increased DO content at a preselected amount of agitation, relative to the cells of the parental strain (i.e., during aerobic fermentation in submerged culture).

For example, in certain embodiments, such variant strains of filamentous fungus constructed and described herein comprise altered cell morphology phenotypes (e.g., see, Examples 1-3 and FIG. 2), particularly referred to herein as "reduced viscosity" phenotypes. More particularly, as presented in Example 1, a *T. reesei* mutant named "Morph 77B7" was observed to have an altered morphology (phenotype) in submerged liquid culture, particularly having shorter and thicker filaments than its parent, wherein the Morph 77B7 mutant also showed a higher level of dissolved oxygen (DO) during growth, compared to cultures containing the parent (see, Example 1, TABLE 1).

Furthermore, as set forth in Example 1, only one wild-type locus complemented the mutant (Morph 77B7) phenotype, which was herein named "ssb7", wherein the ssb7 gene encodes a newly predicted protein, SSB7, that partly overlaps with other protein predictions on the same DNA sequence, e.g. *Trichoderma reesei* QM6a Protein ID (PID) 108712 (The Genome Portal of the Department of Energy Joint Genome Institute, Grigoriev et al., *Nucleic Acids Res.*, 2011). Likewise, the ssb7 mutant allele identified comprises a single guanine (G) nucleotide deletion (ΔG) in exon 2 (*T. reesei* QM6a Scaffold 13, 167404), wherein a deletion of G in exon 2 (of the ssb7 mutant allele) results in a frame-shift (fs) mutation and a premature stop codon prior to the last intron (intron 2) of the ssb7 gene, which mutant allele was named "ssb7(fs)".

Example 2 of the disclosure further validates that the ssb7 mutation is causative for the fermentation (culture) broth viscosity reduction (i.e., altered morphology/phenotype), wherein the ssb7 locus was specifically mutated in a parental *T. reesei* strain. For example, two (2) different methods were used to target ssb7 mutagenesis by homologous recombination, generating alleles herein named "ssb7(311)" and "ssb7 (TS1)", wherein both alleles of ssb7 exhibited a reduced viscosity phenotype.

Example 3 of the disclosure additionally tested and confirmed the utility of such ssb7 mutants, wherein three (3) mutant alleles of ssb7, named "ssb7(311)", "ssb7(339fs)"

and "ssb7(TS2)", were also evaluated in a different *Trichoderma reesei* lineage (named "T4abc") expressing the native cocktail of cellulases. These mutants derived of this background also demonstrated reduced viscosity phenotypes described herein.

Thus, as further exemplified and described herein, such variant strains of filamentous fungus comprising a reduced viscosity phenotype of the disclosure, produce a cell broth that requires a reduced amount of agitation to maintain a preselected dissolved oxygen (DO) content during aerobic fermentation in submerged culture and/or produce a cell mass that maintains an increased DO content at a preselected amount of agitation during aerobic fermentation in submerged culture, relative to the cells of the parental strain. For example, the cell mass of such variant (daughter) strains of filamentous fungus cells exhibit a reduced viscosity phenotype compared to the cell mass of the (unmodified) parental strain, which reduced viscosity accounts for the observations relating to dissolved oxygen (DO) content and added agitation, as further described in the Examples section below.

Thus, certain other embodiments of the disclosure are related to methods of constructing such variant strains of filamentous fungal cells, methods of screening such variant strains, methods for producing proteins of interest using such variant strains and the like, wherein the variant strains produce a cell broth that requires a reduced amount of agitation to maintain a preselected dissolved oxygen (DO) content, and/or produce a cell mass that maintains an increased DO content at a preselected amount of agitation during aerobic fermentation in submerged culture relative to the cells of the parental strain.

I. Definitions

Prior to describing the present strains and methods in detail, the following terms are defined for clarity. Terms not defined should be accorded their ordinary meanings as used in the relevant art. Unless defined otherwise, all technical and scientific terms used herein have the same meaning as commonly understood by one of ordinary skill in the art to which the present compositions and methods apply.

Although any methods and materials similar or equivalent to those described herein can also be used in the practice or testing of the present compositions and methods, representative illustrative methods and materials are now described. All publications and patents cited herein are incorporated by reference in their entirety.

As used herein, the singular articles "a," "an," and "the" encompass the plural referents unless the context clearly dictates otherwise.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or a proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Filamentous fungus cells for manipulation, construction and use as described herein are generally from the phylum Ascomycota, subphylum Pezizomycotina, particularly fungi that have a vegetative hyphae state. Such organisms include filamentous fungus cells used for the production of commercially important industrial and pharmaceutical proteins, including, but not limited to *Trichoderma* sp., *Aspergillus* sp., *Fusarium* sp., *Penicillium* sp., *Chrysosporium* sp., *Cephalosporium* sp., *Talaromyces* sp., *Geosmithia* sp., *Neurospora* sp., *Myceliophthora* sp. and the like. For example, in certain embodiments, filamentous fungus cells and strains thereof include, but are not limited to *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Neurospora crassa*, *Penicillium funiculosum*, *Penicillium chrysogenum*, *Talaromyces* (*Geosmithia*) *emersonii*, *Fusarium venenatum*, *Myceliophthora thermophila*, *Chrysosporium lucknowense* (C1) and the like.

As used herein, genomic coordinates (e.g., Scaffold 13, 167404) reference Version 2 of the *Trichoderma reesei* QM6a genome sequence assembly generated by the Department of Energy Joint Genome Institute (JGI). (The Genome Portal of the Department of Energy Joint Genome Institute, Grigoriev et al., *Nucleic Acids Res* 2012 January; 40(Database issue): D26-32. doi: 10.1093/nar/gkr947). The JGI assembled Scaffold sequences have also been deposited in GeneBank (The National Center for Biotechnology) under the nucleotide accession numbers GL985056.1 through GL985132.1.

In certain embodiments, filamentous fungus cells for manipulation, construction and use as described herein are generally from the phylum Ascomycota, subphylum Pezizomycotina, particularly fungi that have a vegetative hyphae state and comprising a gene (or gene homologue) of a ssb7 gene (SEQ ID NO: 1).

In other embodiments, a variant strain of the disclosure (i.e., comprising a genetic modification of a gene encoding a SSB7 protein), further comprises a genetic modification of a gene encoding a MPG1, SFB3, SEB1, CRZ1 and/or GAS1 protein.

As used herein, a *T. reesei* MPG1 protein comprises an amino acid sequence of SEQ ID NO: 14, as described in International PCT Publication No. WO2012/145584 (incorporated herein by reference in its entirety).

As used herein, a *T. reesei* SFB3 protein comprises an amino acid sequence of SEQ ID NO: 15, as described in International PCT Publication No. WO2012/027580 (incorporated herein by reference in its entirety).

As used herein, a *T. reesei* SEB1 protein comprises an amino acid sequence of SEQ ID NO: 16, as described in International PCT Publication No. WO2012/145595 (incorporated herein by reference in its entirety).

As used herein, a *T. reesei* CRZ1 protein comprises an amino acid sequence of SEQ ID NO: 17, as described in International PCT Publication No. WO2012/145596 (incorporated herein by reference in its entirety).

As used herein, a *T. reesei* GAS1 protein comprises an amino acid sequence of SEQ ID NO: 18, as described in International PCT Publication Nos. WO2012/145596 and WO2012/145592 (each incorporated herein by reference in their entirety).

In other embodiments, a *Trichoderma* sp. strain of the disclosure comprises a Nik1$^{M743}$ mutation described in International PCT Publication No. WO2016/130523, which Nik1$^{M743}$ protein comprises a methionine substitution at position 743 of SEQ ID NO: 38.

In certain other embodiments, an *Aspergillus* sp. strain of the disclosure comprises a Nik1$^{M786}$ mutation, which Nik1$^{M776}$ protein comprises a methionine substitution at position 786, as described in International PCT Publication No. WO2016/130523 (incorporated herein by reference in its entirety). As used herein, phrases such as a "parental cell", a "parental fungal cell", a "parental strain", a "parental fungal strain", a "parental strain of filamentous fungus cells", "reference strain" and the like may be used interchangeably, and refer to "unmodified" parental filamentous fungal cells. For example, a "parental strain of filamentous fungus cells" refers to any cell or strain of filamentous fungi in which the genome of the "parental" cell is modified or modifiable (e.g., via only one genetic modification introduced into the parental cell) to generate a variant (daughter) strain of filamentous fungus cells such that "parental" and "daughter" cells differ by only one genetic modification.

As used herein, phrases such as a "variant cell", a "daughter cell", a "variant strain", a "daughter strain", a "variant or daughter fungal strain", a "variant or daughter strain of filamentous fungus cells" and the like may be used interchangeably, and refer to variant strains of filamentous fungus cells that are derived from (i.e., obtained from or obtainable from) a parental (or reference) strain of filamentous fungus cells, wherein the variant strain comprises only one genetic modification which is not present in the parental strain, such that, by comparison, phenotypic differences between the "parental" and "variant" strains can be attributed to the one genetic modification. In other terms, parental and variant strains are otherwise isogenic except for the single genetic modification "introduced" to the variant strain. Thus, in the present disclosure, parental and variant strains can be described as having certain characteristics, such as genetic modifications, expression phenotypes, morphology phenotypes and the like; however, the skilled person will appreciate that it is technically the cells of the parental or variant strain that have such characteristics, and the "strains" are referred to for convenience.

In certain embodiments, unmodified (parental) cells may be referred to as "control cells" or "reference cells", particularly when being compared (vis-à-vis) with genetically modified (variant/daughter) cells derived therefrom.

As used herein, when a phenotype/morphology of (unmodified) parental cells (i.e., control cells) are being compared to a phenotype/morphology of variant (daughter) cells, it will be understood that the "parental" (unmodified) and "daughter" (modified) cells are grown/cultivated/fermented under the same conditions (e.g., the same conditions such as media, temperature, pH and the like).

Likewise, when describing the production of a protein of interest (POI) in an (unmodified) parental cell (i.e., a control cell) vis-à-vis the production of the same POI in a variant (modified) daughter cell, it will be understood that the "parental" and "variant" cells are grown/cultivated/fermented under essentially the same conditions (e.g., the same conditions such as media, temperature, pH and the like).

As used herein, a "protein of interest" or "POI" is a protein that is desired to be produced in a submerged culture of filamentous fungus cells. Such a protein (POI) can be an enzyme, a substrate-binding protein, a surface-active protein, a structural protein, an antibody and the like, and can be expressed at high levels. Thus, a POI can be encoded by an endogenous gene, or a heterologous gene, relative to the variant strain and/or the parental strain. A heterologous gene (encoding a POI) can be introduced (e.g., transformed) into a parental and/or variant fungal strain (e.g., prior, during or after performing one or more genetic modifications of the disclosure). The POI can be expressed intracellularly, or as a secreted protein. Generally, POIs are commercially important for industrial, pharmaceutical, animal health, food and beverage use, making them desirable to produce in large quantities.

As used herein, "aerobic fermentation" refers to growth in the presence of oxygen.

As used herein, the terms "broth", "cell broth", "fermentation broth" and/or "culture broth" are used interchangeably, and refer collectively to (i) the fermentation (culture) medium and (ii) the cells, in a liquid (submerged) culture.

As used herein, the term "cell mass" refers to the cell component (including intact and lysed cells) present in a liquid (submerged) culture. Cell mass can be expressed in dry cell weight or wet cell weight.

As used herein, "viscosity" is a measure of the resistance of a fluid to deformation by mechanical stress (e.g., such as shear stress or tensile stress).

In the context of the present disclosure, viscosity also refers to the resistance of a "cell broth" (defined above) to deformation by mechanical stress. Thus, in certain embodiments, "viscosity" is herein defined as "a measure of the resistance of a cell broth" to such mechanical stress (e.g., as provided/induced by a rotor/impeller). However, because the viscosity of a cell broth can be difficult to measure directly, indirect measurements of viscosity can be used, such as the dissolved oxygen (DO) content of the culture broth at a preselected amount of agitation, the amount of agitation required to maintain a preselected DO content, the amount of power required to agitate the cell broth to maintain a preselected DO content, or even hyphal morphology.

As used herein, a "reduced viscosity" variant strain of filamentous fungus cells refers to a variant strain that produces a cell broth that has a reduced viscosity (i.e., reduced resistance to shear or tensile stress) compared to an equivalent cell broth produced by a parental strain. Generally, equivalent cell broths have comparable cell masses. In certain embodiments, the difference between a variant 'reduced viscosity' strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cell broths are described herein.

As used herein, "dissolved oxygen" (DO) refers to the amount of oxygen ($O_2$) present in a liquid medium, as measured in volume/volume units. The DO level can be maintained at a high level, e.g., between 170-100% and 20%, between 100-80% and 20%, between 70% and 20%, between 65% and 20%, between 60% and 20%, between 55% and 20%, between 50% and 20%, between 45% and 20%, between 44% and 20%, between 43% and 20%, between 42% and 20%, between 41% and 20%, between 40% and 20%, between 35% and 20%, between 30% and 20%, and between 25% and 20% throughout the fermentation. In particular, the DO can be high at the beginning of the fermentation and to be permitted to fall as the fermentation progresses. The DO level can be controlled by the rate at which the fermentation medium is agitated (e.g., stirred, and/or by the rate of addition of air or oxygen). The culture can be agitated (e.g., stirred at between 400-700 RPM) and the DO level is maintained above 20%, above 25%, above 30%, above 35%, above 40%, above 45%, above 50% and above 55% or more, by altering the air or oxygen flow rate and impeller speed.

As used herein, the terms "wild-type" and "native" are used interchangeably and refer to genes, proteins or strains found in nature.

As used herein, a "primary genetic determinant" refers to a gene, or genetic manipulation thereof, that is necessary and sufficient to confer a specified phenotype in the absence of other genes, or genetic manipulations thereof. More particularly, as set forth in Examples section of the disclosure, a filamentous fungus gene, herein named "ssb7" is the "primary genetic determinant" necessary and sufficient to confer the "reduced" viscosity phenotype described herein.

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins". Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 30%, about 40%, about 50%, about 60%, about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement of amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. It is not intended that homologues necessarily be evolutionarily related. Thus, it is intended that the term encompass the same, similar, or corresponding protein (s) (i.e., in terms of structure and function) obtained from different organisms. In certain embodiments, homologue can share at least about 30%, about 40%, about 50%, about 60%, about 70%, at least about 75%, at least about 80%, at least about 85%, at least about 90%, at least about 91%, at least about 92%, at least about 93%, at least about 94%, at least about 95%, at least about 96%, at least about 9'7%, at least about 98%, or even at least about 99%, or more, amino acid sequence identity with a reference protein. In some embodiments, it is desirable to identify a homologue that has a quaternary, tertiary and/or primary structure similar to the reference protein. In some embodiments, homologous proteins induce similar immunological response(s) as a reference protein. In some embodiments, homologous proteins are engineered to produce enzymes with desired activity (ies).

The degree of amino acid identity between sequences can be determined using any suitable method known in the art (see, e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI); and Devereux et al., 1984).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (1987). The method is similar to that described by Higgins and Sharp (1989). Useful PILEUP parameters including a default gap weight of 3.00, a default gap length weight of 0.10, and weighted end gaps. Another example of a useful algorithm is the BLAST algorithm, described by Altschul et al., 1990 and Karlin et al., 1993. One particularly useful BLAST program is the WU-BLAST-2 program (see, e.g., Altschul et al., 1996). Parameters "W," "T," and "X" determine the sensitivity and speed of the alignment. The BLAST program uses as defaults a word-length (W) of 11, the BLOSUM62 scoring matrix (see, e.g., Henikoff and Henikoff, 1989) alignments (B) of 50, expectation (E) of 10, M'5, N'-4, and a comparison of both strands.

As used herein, the phrases "substantially similar" and "substantially identical", in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters. (See, e.g., Altschul, et al., 1990; Henikoff et al., 1989; Karlin et al., 1993; and Higgins et al., 1988). Software for performing BLAST analyses is publicly available through the National Center for Biotechnology Information. Also, databases can be searched using FASTA (Pearson et al., 1988). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to transcription, post-transcriptional modification, translation, post-translational modification, secretion and the like.

As used herein, the combined term "expresses/produces", as used in phrases such as (i) a "variant strain of filamentous fungus cells expresses/produces an 'increased' amount of a protein of interest (POI)" and (ii) a "variant strain of filamentous fungus cells expresses/produces a 'reduced' amount of a native SSB7 protein", the term "expresses/produces" is meant to include any steps involved in the expression and production of a protein in such variant filamentous fungus strains of the disclosure. For example, means of generating variant strains of filamentous fungus cells expressing/producing a 'reduced' amount of a native SSB7 protein include, but are not limited to, genetic modifications (e.g., mutations, disruptions, truncations, deletions, etc.) of the ssb7 gene's protein coding sequence, promoter sequence, 5'-UTR sequence, 3'-UTR sequence, combinations thereof and the like.

As used herein, phrases a "full length SSB7 protein" and "native SSB7 protein" may be used interchangeably, and particularly refer to a SSB7 protein sequence derived or obtained from a parental fungal cell of the disclosure. For example, in certain embodiments, a native SSB7 protein comprises amino acid positions 1-1,308 of SEQ ID NO: 2. In other embodiments, a native SSB7 protein comprises amino acid positions 1-1,235 of SEQ ID NO: 31. In other embodiments, a native SSB7 protein comprises amino acid positions 1-1,465 of SEQ ID NO: 33. In other embodiments, a native SSB7 protein comprises amino acid positions 1-1,285 of SEQ ID NO: 35. In other embodiments, a native SSB7 protein comprises amino acid positions 1-1,310 of SEQ ID NO: 8. In other embodiments, a native SSB7 protein comprises amino acid positions 1-1,370 of SEQ ID NO: 9. In other embodiments, a native SSB7 protein comprises amino acid positions 1-805 of SEQ ID NO: 10. In other embodiments, a native SSB7 protein comprises amino acid positions 1-1,004 of SEQ ID NO: 11. In other embodiments, a native SSB7 protein comprises amino acid positions 1-1,215 of SEQ ID NO: 12. In other embodiments, a native SSB7 protein comprises amino acid positions 1-1,098 of SEQ ID NO: 13.

Thus, in certain other embodiments, a variant strain of filamentous fungus cells expresses/produces a reduced amount of a native SSB7 protein relative to the parental strain.

In certain other embodiments, the disclosure is related to variant strains of Trichoderma sp. fungal cells comprising a genetic modification of a gene encoding a SSB7 protein comprising at least about 50% sequence identity to SEQ ID NO: 2 or SEQ ID NO: 31, wherein variant strain produces a cell broth that requires a reduced amount of agitation to maintain a preselected dissolved oxygen (DO) content and/ or produces a cell mass that maintains an increased DO content at a preselected amount of agitation during aerobic fermentation in submerged culture. In certain embodiments, a Trichoderma sp. gene encoding a SSB7 protein comprises at least about 55% to 99% sequence identity to SEQ ID NO: 1, SEQ ID NO: 32 or SEQ ID NO: 34. In other embodiments, a Trichoderma sp. ssb7 gene comprises a nucleic acid sequence of SEQ ID NO: 1, SEQ ID NO: 32 or SEQ ID NO: 34. In certain other embodiments, a variant Trichoderma sp. strain comprising a reduced viscosity phenotype of the disclosure comprises an allele selected from ssb7(fs), ssb7 (311), ssb7(339fs), ssb7(TS1) and ssb7(TS2).

Thus, as set forth above and further described below in the Examples section, the ssb7 gene is the primary genetic determinant necessary and sufficient to confer the reduced viscosity phenotype described herein. Thus, particular embodiments of the disclosure are related to such variant Trichoderma sp. strains comprising genetic modifications of a gene encoding a SSB7 protein, which variant strains comprise reduced viscosity phenotypes.

Thus, in certain embodiments, a variant fungal strain comprising a reduced viscosity phenotype of the disclosure comprises a genetic modification of a gene encoding a SSB7 protein, wherein the genetic modification of the gene encoding the SSB7 protein occurs within any one (1) of exons 1-3 of the ssb7 gene of SEQ ID NO: 1.

In certain other embodiments, a variant strain comprises a genetic modification of the gene encoding the SSB7 protein, wherein the genetic modification of the gene encoding the SSB7 protein occurs within any two (2) of exons 1-3 of the ssb7 gene of SEQ ID NO: 1.

In certain other embodiments, a variant strain comprises a genetic modification of the gene encoding the SSB7 protein, wherein the genetic modification of the gene encoding the SSB7 protein occurs within all three (3) of exons 1-3 of the ssb7 gene of SEQ ID NO: 1.

In another embodiment, a variant strain comprises a genetic modification of the gene encoding the SSB7 protein, wherein the genetic modification of the gene encoding the SSB7 protein occurs within exon 2 of the ssb7 gene of SEQ ID NO: 1.

In other embodiments, a variant fungal strain comprising a reduced viscosity phenotype of the disclosure comprises genetic modifications of a gene encoding a SSB7 protein, wherein the genetic modifications of the gene encoding the SSB7 protein occur within or disrupts conserved Region A, Region B, Region C and/or Region D of the SSB7 protein, as set forth in FIG. 1A. In another embodiment, a variant strain comprising a reduced viscosity phenotype of the disclosure comprises genetic modifications of a gene encoding a SSB7 protein, wherein the genetic modifications of the gene encoding the SSB7 protein occur within or disrupts conserved Region A of the SSB7 protein, as set forth in FIG. 1A. In another embodiment, a variant strain comprising a reduced viscosity phenotype of the disclosure comprises genetic modifications of a gene encoding a SSB7 protein, wherein or disrupts the genetic modifications of the gene encoding the SSB7 protein occur within conserved Region B of the SSB7 protein, as set forth in FIG. 1A. In another embodiment, a variant strain comprising a reduced viscosity phenotype of the disclosure comprises genetic modifications of a gene encoding a SSB7 protein, wherein the genetic modifications of the gene encoding the SSB7 protein occur within or disrupts conserved Region C of the SSB7 protein, as set forth in FIG. 1A. In another embodiment, a variant strain comprising a reduced viscosity phenotype of the disclosure comprises genetic modifications of a gene encoding a SSB7 protein, wherein the genetic modifications of the gene encoding the SSB7 protein occur within or disrupts conserved Regions D of the SSB7 protein, as set forth in FIG. 1A.

In certain other embodiments, a gene encoding a SSB7 protein comprising "substantial sequence homology" refers to DNA or RNA (nucleic acid) sequences that have de minimus sequence variations from the corresponding nucleic acid sequences (to which comparison is made) and retain substantially the same biological functions as the corresponding nucleic acid sequences (to which comparison is made). For example, in certain embodiments, a nucleic acid sequence comprising substantial sequence homology to a gene (or ORF) encoding a SSB7 protein is assessed by identifying the encoded gene product (SSB7 protein), as described herein.

In certain other embodiments, a nucleic acid sequence comprising substantial sequence homology to a gene (or ORF) encoding a SSB7 protein is determined/identified using nucleic acid hybridization methods. For example, in certain embodiments, a DNA/RNA sequence comprising substantial sequence homology to a gene or polynucleotide of the disclosure (e.g., SEQ ID NO: 1) encoding a SSB7 protein is identified by the ability of such DNA/RNA sequence to hybridize with a specified nucleic acid sequence of the disclosure, under stringent conditions.

As used herein, "hybridizes under stringent conditions" is intended to describe conditions for hybridization and washing under which nucleotide sequences that are significantly identical or homologous to each other remain hybridized to each other. Such stringent conditions are well known to those skilled in the art (see, e.g., Ausubel et al., 1995; Sambrook et al., 1989). For example, in certain embodiments, a non-limiting example of stringent hybridization conditions includes hybridization in 4× sodium chlorine/sodium citrate (SSC), at about 65-70° C. (or hybridization in 4×SSC plus 50% formamide at about 42-50° C.), followed by one or more washes in 1×SSC, at about 65-70° C. Likewise, a non-limiting example of highly stringent hybridization conditions includes hybridization in 1×SSC, at about 65-70° C. (or hybridization in 4×SSC plus 50% formamide at about 42-50° C.), followed by one or more washes in 0.3×SSC, at about 65-70° C. Thud, highly stringent hybridization conditions include hybridization in 4×SSC, at about 50-60° C. (or alternatively hybridization in 6×SSC plus 50% formamide at about 40-45° C.), followed by one or more washes in 2×SSC, at about 50-60° C. Ranges intermediate to the above-recited values, e.g., at 65-70° C. or at 42-50° C. are also intended to be encompassed by the present disclosure. In certain embodiments, SSPE (1×SSPE is 0.15 M NaCl, 10 mM NaH2PO4, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional, non-limiting example of stringent hybridization conditions is hybridization in 0.25-0.5M NaH2PO4, 7% SDS at about 65° C., followed by one or more washes at 0.02M NaH2PO4, 1% SDS at 65° C. or alternatively 0.2×SSC, 1% SDS (see, e.g., Church and Gilbert, 1984).

Thus, in certain other embodiments of the disclosure, an Ascomycota fungal gene encoding a SSB7 protein comprises a nucleic sequence which hybridizes under high stringency conditions with an ssb7 gene of SEQ ID NO: 1 or the complementary sequence thereof. In certain other embodiments, an Ascomycota fungal gene encoding a SSB7 protein comprises a nucleic sequence which hybridizes under high stringency conditions with an ssb7 gene of SEQ ID NO: 31 or the complementary sequence thereof. In certain other embodiments, an Ascomycota fungal gene encoding a SSB7 protein comprises a nucleic sequence which hybridizes under high stringency conditions with an ssb7 gene of SEQ ID NO: 32 or the complementary sequence thereof. In other embodiments, an Ascomycota fungal gene encoding a SSB7 protein comprises a nucleic sequence which hybridizes under high stringency conditions with an ssb7 gene of SEQ ID NO: 34 or the complementary sequence thereof. In other embodiments, an Ascomycota fungal gene encoding a SSB7 protein comprises a nucleic sequence which hybridizes under high stringency conditions with an open reading frame (ORF) of a ssb7 gene of SEQ ID NO: 1, SEQ ID NO: 32, SEQ ID NO: 34 or a complimentary sequence thereof.

In certain other embodiments, an Ascomycota fungal gene encoding a SSB7 protein comprises a nucleic sequence which hybridizes under high stringency conditions with exon 1 of SEQ ID NO: 19 or the complementary sequence thereof. In another embodiment, an Ascomycota fungal gene encoding a SSB7 protein comprises a nucleic sequence which hybridizes under high stringency conditions with exon 2 of SEQ ID NO: 20 or the complementary sequence thereof. In another embodiment, an Ascomycota fungal gene encoding a SSB7 protein comprises a nucleic sequence which hybridizes under high stringency conditions with exon 3 of SEQ ID NO: 21 or the complementary sequence thereof.

In certain other embodiments, an Ascomycota fungal gene encoding a SSB7 protein comprises a nucleic sequence which hybridizes under high stringency conditions with a nucleic acid sequence encoding conserved Region A (SEQ ID NO: 22) of the SSB7 protein. In other embodiments, an Ascomycota fungal gene encoding a SSB7 protein comprises a nucleic sequence which hybridizes under high stringency conditions with a nucleic acid sequence encoding conserved Region B (SEQ ID NO: 23) of the SSB7 protein. In other embodiments, an Ascomycota fungal gene encoding a SSB7 protein comprises a nucleic sequence which hybridizes under high stringency conditions with a nucleic acid sequence encoding conserved Region C (SEQ ID NO: 24) of the SSB7 protein. In another embodiment, an Ascomycota fungal gene encoding a SSB7 protein comprises a nucleic sequence which hybridizes under high stringency conditions with a nucleic acid sequence encoding conserved Region D (SEQ ID NO: 25) of the SSB7 protein.

In certain other embodiments, an Ascomycota fungal gene encoding a SSB7 protein comprises a nucleic sequence which hybridizes under high stringency conditions with a nucleic acid sequence encoding conserved sequence 1 (SEQ ID NO: 26) of the SSB7 protein. In other embodiments, an Ascomycota fungal gene encoding a SSB7 protein comprises a nucleic sequence which hybridizes under high stringency conditions with a nucleic acid sequence encoding conserved sequence 2 (SEQ ID NO: 27) of the SSB7 protein. In other embodiments, an Ascomycota fungal gene encoding a SSB7 protein comprises a nucleic sequence which hybridizes under high stringency conditions with a nucleic acid sequence encoding conserved sequence 3 (SEQ ID NO: 28) of the SSB7 protein. In certain other embodiments, an Ascomycota fungal gene encoding a SSB7 protein comprises a nucleic sequence which hybridizes under high stringency conditions with a nucleic acid sequence encoding conserved sequence 4 (SEQ ID NO: 29) of the SSB7 protein. In yet other embodiments, an Ascomycota fungal gene encoding a SSB7 protein comprises a nucleic sequence which hybridizes under high stringency conditions with a nucleic acid sequence encoding conserved sequence 5 (SEQ ID NO: 30) of the SSB7 protein.

Thus, as generally set forth above, the variant strains of filamentous fungus cells comprise "genetic modifications" of a gene encoding a SSB7, wherein the genetic modifications are relative to the (unmodified) parental cells.

As used herein, the terms "modification" and "genetic modification" are used interchangeably and include, but are not limited to: (a) the introduction, substitution, or removal of one or more nucleotides in a gene, or the introduction, substitution, or removal of one or more nucleotides in a regulatory element required for the transcription or translation of the gene, (b) gene disruption, (c) gene conversion, (d) gene deletion, (e) the down-regulation of a gene (e.g., antisense RNA, siRNA, miRNA, and the like), (f) specific mutagenesis (including, but not limited to, CRISPR/Cas9 based mutagenesis) and/or (g) random mutagenesis of any one or more the genes disclosed herein. For example, as used herein, a variant strain of filamentous fungus comprising a genetic modification includes, but is not limited to a genetic modification of a ssb7 gene disclosed herein. Thus, as described in further detail below, various molecular biological methods are well known and available to one skilled in the art for generating/constructing such variant strains of filamentous fungus cells comprising a genetic modification of a gene encoding a SSB7 protein.

As used herein, "the introduction, substitution, or removal of one or more nucleotides in a gene encoding a SSB7 protein", such genetic modifications include, but are not limited to, the gene's coding sequence (i.e., exons), non-coding intervening (introns) sequences, promoter sequences, 5'-UTR sequences, 3'-UTR sequences, and the like.

Thus, in certain embodiments, a variant strain of filamentous fungus comprising a genetic modification is constructed by a gene deletion technique to eliminate the endogenous gene encoding the SSB7 protein. As used herein, "deletion of a gene" or "gene deletion" refers to the complete removal of the gene's coding sequence from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "partial deletion of a gene" or "partially deleted gene" refers to the partial removal of the gene's coding sequence from the genome of a host cell. For example, the ssb7 gene of SEQ ID NO: 1, encoding the *Trichoderma reesei* SSB7 protein of SEQ ID NO: 2, comprises a coding sequence (CDS) of exons 1-3 (SEQ ID NOs: 19-23, respectively). For example, in certain embodiments set forth below, the "partial deletion" of a ssb7 gene includes, but is not limited to the deletion of any one (or more) of exons 1-3 of the ssb7 gene.

Where a target gene includes control elements (e.g., enhancer elements) that are not located immediately adjacent to the coding sequence of a gene, "partial deletion" of a gene refers to the partial deletion of the coding sequence, and optionally adjacent enhancer elements, including but not limited to e.g., promoter and/or terminator sequences.

As used herein, "disruption of a gene", "gene disruption", "inactivation of a gene" and "gene inactivation" are used interchangeably and refer broadly to any genetic modification that substantially disrupts/inactivates a target gene. Exemplary methods of gene disruptions include, but are not limited to, the complete or partial deletion of any portion of a gene, including a polypeptide coding sequence (CDS), a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the expression/production of the functional gene product. In certain embodiments of the disclosure, such gene disruptions prevent a host cell from expressing/producing the encoded ssb7 gene product.

In other embodiments, a gene encoding a SSB7 protein is down-regulated using established anti-sense (gene-silencing) techniques, i.e., using a nucleotide sequence complementary to the nucleic acid sequence of the gene (e.g., RNAi, siRNA, miRNA and the like).

In certain other embodiments, a gene encoding a SSB7 protein is genetically modified using an established gene editing technique, such as CRISPR/Cas9 gene editing, zinc-finger nuclease (ZFN) gene editing, transcription activatorlike effector nuclease editing (TALEN), homing (mega) nuclease editing, and the like.

In certain other embodiments, a variant strain of filamentous fungus is constructed (i.e., genetically modified) by the process of gene conversion (e.g., see Iglesias and Trautner, 1983).

In other embodiments, a variant strain of filamentous fungus is constructed (i.e., genetically modified) by random or specific mutagenesis, using methods well known in the art, including, but not limited to chemical mutagenesis (see, e.g., Hopwood, 1970) and transposition (see, e.g., Youngman et al., 1983).

For example, such genetic modifications of one or more of the genes disclosed herein reduce the efficiency of the gene's promoter, reduce the efficiency of an enhancer, interfere with the splicing or editing of the gene's mRNA, interfere with the translation of the gene's mRNA, introduce a stop codon into the gene's-coding sequence to prevent the translation of full-length protein, change the coding sequence of the protein to produce a less active or inactive protein, reduce the protein interaction with other nuclear protein components, change the coding sequence of the protein to produce a less stable protein, or target the protein for destruction, or cause the protein to misfold or be incorrectly modified (e.g., by glycosylation), or interfere with cellular trafficking of the protein.

In certain embodiments, genetic modifications of a gene encoding a SSB7 protein reduce the amount of native SSB7 expressed/produced by the variant host cell, wherein the reduced amount of native SSB7 protein expressed/produced" is detected, measured, assayed, and the like, using methods know to one skilled in the art. Thus, one of skill in the art may readily adapt and/or modify the screening methods set forth in the Example section herewith to identify such (mutagenized) variant strains of filamentous fungus cells comprising a reduced viscosity phenotype of the disclosure. For example, in certain embodiments, a reduced amount of native SSB7 expressed/produced is readily correlated to the reduced viscosity phenotype disclosed herein, wherein the skilled artisan may readily identify such variant host strains comprising a reduced viscosity phenotype by screening the morphology differences between the parental strain and variant strain derived therefrom. Thus, the skilled artisan may readily identify such variant strains comprising a reduced viscosity phenotype by screening the parental and variant strains for a reduced viscosity phenotype, which include, but are not limited to, identifying variant strains producing a cell broth that requires a reduced amount of agitation to maintain a preselected dissolved oxygen (DO) content during aerobic fermentation in submerged culture (relative to the parental strains) and/or (ii) identifying variant strains producing a cell mass that maintains an increased DO content at a preselected amount of agitation during aerobic fermentation in submerged culture (relative to the parental strains).

In other embodiments, a reduced amount of a native SSB7 expressed/produced is detected, identified, measured, assayed and the like, by protein quantification methods, gene transcription methods, mRNA translation methods and the like, including, but not limited to protein migration/mobility (SDS-PAGE), mass spectrometry, HPLC, size exclusion, ultracentrifugation sedimentation velocity analysis, transcriptomics, proteomics, fluorescent tags, epitope tags, fluorescent protein (GFP, RFP, etc.) chimeras/hybrids and the like.

As used herein, functionally and/or structurally similar proteins are considered to be "related proteins". Such related proteins can be derived from organisms of different genera and/or species, or even different classes of organisms (e.g., bacteria and fungi). Related proteins also encompass homologues and/or orthologues determined by primary sequence analysis, determined by secondary or tertiary structure analysis, or determined by immunological cross-reactivity.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation. A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a fungal cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection and the like.

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in the cell that is to be transformed).

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the fungal cell chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, an incoming sequence is a non-functional sequence inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the fungal cell chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the fungal cell chromosome a DNA construct is integrated and directs what part of the fungal cell chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As defined herein, a host cell "genome", a fungal cell "genome", or a filamentous fungus cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "vector" refers to any nucleic acid that can be replicated (propagated) in cells and can carry new genes or DNA segments (e.g., an "incoming sequence") into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously) or can integrate into the chromosome of a host cell.

A used herein, a "transformation cassette" refers to a specific vector comprising a gene (or ORF thereof), and having elements in addition to the gene that facilitate transformation of a particular host cell.

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing genetic modifications into the chromosome of a host cell through homologous recombination. In some embodiments, a targeting vector comprises other non-homologous sequences, e.g., added to the ends (i.e., stuffer sequences or flanking sequences). The ends can be closed such that the targeting vector forms a closed circle, such as, for example, insertion into a vector.

As used herein, a variant strain produces "substantially the same amount" of protein per unit amount of biomass as a parental strain if the amount of protein produced by the variant strain is no more than 20% reduced, no more than 15% reduced, no more than 10% reduced, an even no more than 5% reduced compared to the amount of protein produced by the parental strain, wherein the amount of protein is normalized to the total amount of biomass of cells from which protein production is measured, wherein biomass can be expressed in terms of either wet weight (e.g., of cell pellet) or dry weight.

As used herein, a variant strain produces "substantially more protein per unit amount of biomass" than a parental strain if the amount of protein produced by the variant strain is at least 5% increased, at least 10% increased, at least 15% increased, or more, compared to the parental strain, wherein the amount of protein is normalized to the total amount of biomass of cells from which protein production is measured, wherein biomass can be expressed in terms of either wet (e.g., of cell pellet) or dry weight.

As used herein, "fluorochromes" are fluorescent dyes. Preferred fluorochromes bind to cellulose and/or chitin in the cell walls of fungi.

II. *Trichoderma* Strains Comprising Reduced Viscosity Phenotypes

As generally set forth above, and further described in the Examples section below, certain embodiments of the disclosure are related variant strains of filamentous fungus derived from parental strains. More particularly, certain embodiments are related to variant strains of filamentous fungus and methods thereof, wherein such variant strains comprise improved volumetric efficiencies, enhanced/uniform oxygen distribution, reduced cell broth viscosity, high specific productivities, improved yield on carbon source, reduced bioreactor (fermentor) operating costs, altered (cell) phenotypes, altered (cell) morphologies, altered (cell) growth characteristics and the like.

For example, as described and presented herein, such variant strains of the disclosure (i.e., comprising a genetic modification of a gene encoding a SSB7 protein) produce a cell broth that requires a reduced amount of agitation to maintain a preselected dissolved oxygen (DO) content (i.e., during aerobic fermentation in submerged culture), and/or produce a cell mass that maintains an increased DO content at a preselected amount of agitation, relative to the cells of the parental strain (i.e., during aerobic fermentation in submerged culture). More particularly, the variant strains of filamentous fungus constructed and described herein comprise altered cell morphology phenotypes (e.g., see Examples 1-3 and FIG. 2), particularly referred to herein as "reduced viscosity" phenotypes.

Thus, as described in Example 1, a *T. reesei* mutant named "Morph 77B7" was observed to have an altered morphology (phenotype) in submerged liquid culture, particularly having shorter and thicker filaments than its parent, wherein the Morph 77B7 mutant also showed a higher level of dissolved oxygen (DO) during growth, compared to cultures containing the parent (see, Example 1, TABLE 1), wherein only one locus complemented the mutant (Morph 77B7) phenotype (which was named "ssb7"). The ssb7 gene encodes a newly predicted protein, SSB7, that partly overlaps with other protein predictions on the same DNA sequence, e.g. *Trichoderma reesei* QM6a Protein ID (PID) 108712 (The Genome Portal of the Department of Energy Joint Genome Institute, Grigoriev et al., 2011) (see FIG. 1). The ssb7 mutant allele identified in strain Morph 77B7 comprises a single guanine (G) nucleotide deletion (ΔG) in exon 2 (*T. reesei* QM6a Scaffold 13, 167404; SEQ ID NO: 3), resulting in a frameshift (fs) mutation and a premature stop codon prior to the last intron (intron 2) of the ssb7 gene, which mutant allele was named "ssb7(fs)". Example 2 further validates that the ssb7 mutation is causative for the fermentation (culture) broth viscosity reduction (altered morphology/phenotype), wherein the ssb7 locus was specifically mutated (via two different methods) in parental *T. reesei* strains and both alleles of ssb7 exhibited a reduced viscosity phenotype. Likewise, Example 3 additionally tested and confirmed the utility of such ssb7 mutants, wherein three (3) mutant alleles of ssb7 were also evaluated in a different *Trichoderma reesei* lineage (named "T4abc") expressing the native cocktail of cellulases, wherein each of these mutant alleles demonstrated reduced viscosity phenotypes described herein.

Thus, certain embodiments of the disclosure are related to variant strains of filamentous fungi comprising a reduced viscosity phenotype. Certain other embodiments are related to compositions and methods of constructing such variant strains of filamentous fungal cells, screening such variant strains of filamentous fungal cells, producing proteins of interest using such variant strains of filamentous fungal cells and the like.

III. Constructing Variant Filamentous Fungal Strains Comprising Reduced Viscosity Phenotypes In certain embodiments, variant strains (cells) of filamentous fungus are derived from parental strains (cells) of filamentous fungus, wherein the variant strains comprise at least one genetic modification of a gene encoding a SSB7 protein/SSB7 orthologue (i.e., relative to the parental strains), wherein such variant strains comprise a reduced viscosity phenotype relative to the parental strains. More particularly, certain other embodiments of the disclosure are directed to such variant strains (cells) of filamentous fungus comprising a genetic modification of a gene encoding a SSB7 protein/SSB7 orthologue, wherein the variant strains produce, during aerobic fermentation in submerged culture, a cell broth that (i) requires a reduced amount of agitation to maintain a preselected dissolved oxygen (DO) content and/

III.A Constructing Variant *Trichoderma* Strains Comprising Reduced Viscosity Phenotypes As generally set forth above, certain embodiments of the disclosure are directed to variant *Trichoderma* sp. strains derived from parental *Trichoderma* sp. strains, wherein the variant strains comprise a reduced viscosity phenotype. In certain embodiments, a variant *Trichoderma* sp. strain comprises genetic modifications of a gene encoding a SSB7 protein comprising at least about 50% sequence identity to a SSB7 protein of SEQ ID NO: 2 or SEQ ID NO: 31, wherein the variant strain comprises a reduced viscosity phenotype. In certain other embodiments, a variant *Trichoderma* sp. strain comprises genetic modifications of a ssb7 gene comprising at least about 50% sequence identity to the ssb7 gene of SEQ ID NO: 1, wherein the variant strain comprises a reduced viscosity phenotype. In certain other embodiments, a variant *Trichoderma* sp. strain comprises genetic modifications of a ssb7 gene comprising at least about 50% sequence identity to the ssb7 gene of SEQ ID NO: 32, wherein the variant strain comprises a reduced viscosity phenotype. In certain other embodiments, a variant *Trichoderma* sp. strain comprises genetic modifications of a ssb7 gene comprising at least about 50% sequence identity to the ssb7 gene of SEQ ID NO: 34, wherein the variant strain comprises a reduced viscosity phenotype.

In other embodiments, a variant *Trichoderma* sp. strain comprises genetic modifications of a gene encoding a SSB7 protein, wherein the modifications of the gene encoding the SSB7 protein occur within conserved Regions A through D of the SSB7 protein (see, FIG. 1A and SEQ ID NO: 22-25). In certain other embodiments, a variant *Trichoderma* sp. strain comprises genetic modifications of at least one (1) exon selected from the group consisting of exon 1 (SEQ ID NO: 19), exon 2 (SEQ ID NO: 20) and exon 3 (SEQ ID NO: 21), wherein the variant strain comprises a reduced viscosity phenotype. In another embodiment, a variant *Trichoderma* sp. strain comprises genetic modifications of a gene encoding a SSB7 protein, wherein the modifications occur in the promoter sequence of the gene encoding the SSB7 protein and/or occur in an untranslated region (UTR) of the gene encoding the SSB7 protein, wherein the variant strain comprises a reduced viscosity phenotype.

In certain other embodiments, a variant *Trichoderma* sp. strain comprises genetic modifications of a gene encoding a SSB7 protein, wherein the modifications of the gene encoding the SSB7 protein convert one or more encoded SSB7 protein hydrophobic sequence regions as presented in FIG. 8B-8F into a hydrophilic sequence region thereof, or vice versa, wherein the variant strain comprises a reduced viscosity phenotype. For example, the hydropathy plots (per Kyte-Doolittle (KD) Index) of the SSB7 protein sequence of SEQ ID NO: 2 (set forth in FIG. 8B-8F) provide a quantitative analysis of the degree of hydrophobicity or hydrophilicity of certain amino acids within the SSB7 protein sequence. Thus, the hydropathy plots shown in FIG. 8B-8F present the (1°) amino acid sequence of the SSB7 protein on the x-axis and degree (score) of hydrophobicity (>0) and hydrophilicity (<0) on the y-axis, wherein the amino acid hydropathy scores using the KD Index are show in FIG. 8G. For example, it is generally understood by one skilled in the art that analyzing the shape of such plots provide particularly relevant information regarding the partial structure of the protein. For instance, if a stretch of amino acids (i.e., approximately a 10 residue window for a globular (non-membrane spanning) protein) show a positive score (>0) for hydrophobicity, these amino acids are likely buried within the SSB7 proteins 3° structure (i.e., not surface exposed in aqueous solvent). In contrast, amino acid sequence regions with high hydrophilicity scores (<0) indicate that these amino acid residues are in contact with aqueous solvent, and as such, these residues are predominately located on the outer surface of the SSB7 protein.

Thus, as described herein, a ssb7 gene (or a subsequence thereof) encoding such hydrophilic or hydrophobic SSB7 protein sequence regions, may readily be modified to encode the opposite sequence region thereof (e.g., swap hydrophobic sequence with hydrophilic or vice versa). As known in the art, the introduction of such genetic modifications (e.g., which convert at least one (1) hydrophilic amino acid residue into a hydrophobic residue or vice versa, preferably converting at least 2-3 consecutive hydrophilic residues into hydrophobic residues or vice versa, are particularly useful in constructing variant *Trichoderma* sp. strains expressing/producing a reduced amount of native SSB7 protein. For example, the (non-native) SSB7 protein encoded by a modified ssb7 gene (or a subsequence thereof) described above will have a high propensity for misfolding and/or unfolding, thereby resulting in protein aggregation, precipitation, proteolytic cleavage, degradation and the like. Thus, one skilled in the art can assay a parental strain comprising a wild-type gene encoding a native SSB7 protein vis-à-vis a modified (daughter) strain expressing/producing a reduced amount of the native SSB7 protein, by assaying the parent and daughter for a reduced viscosity phenotype of the disclosure.

Thus, by reference to the ssb7 gene of SEQ ID NO: 1, the SSB7 protein of SEQ ID NO: 2, the SSB7 protein of SEQ ID NO: 31, hydropathy plots (FIG. 8B-8G), the SSB7 protein's amino acid composition (FIG. 8A) and the like, one skilled in the art may readily construct such variant *Trichoderma* sp. strains comprising genetic modifications of a gene encoding a native SSB7 protein, wherein such variant strains comprise a reduced viscosity phenotype. For example, one skilled in the art may genetically modify ssb7 gene sequences using routine and conventional molecular biology methods know in the art, and readily identify variant strains thereof comprising reduced viscosity phenotypes of the disclosure.

III.B Constructing Variant Ascomycota Strains Comprising Reduced Viscosity Phenotypes As set forth above, certain embodiments are directed to variant strains (cells) of filamentous fungus derived from parental strains (cells) of filamentous fungus, wherein the variant strains comprise genetic modifications of a gene encoding a SSB7 protein, wherein the variant strains comprise a reduced viscosity phenotype. More particularly, certain embodiments are related to variant strains of filamentous fungus, including, but not limited to *Trichoderma* sp., *Aspergillus* sp., *Fusarium* sp., *Penicillium* sp., *Chrysosporium* sp., *Cephalosporium* sp., *Talaromyces* sp., *Geosmithia* sp., *Neurospora* sp., *Myceliophthora* sp. and the like. Thus, in certain embodiments, the disclosure is related to variant *Fusarium* sp. strains comprising genetic modifications of a gene encoding a SSB7 protein orthologue of SEQ ID NO: 8. In other embodiments, the disclosure is related to variant *Neurospora* sp. strains comprising genetic modifications of a gene encoding a SSB7 protein orthologue of SEQ ID NO: 9. In other embodiments, the disclosure is related to variant *Myceliophthora* sp. strains comprising genetic modifications of a gene encoding a SSB7 protein orthologue of SEQ ID NO: 10. In other embodiments, the disclosure is related to variant *Talaroymyces* sp. strains comprising genetic modifications of a gene encoding a SSB7 protein orthologue of SEQ ID NO: 11. In other embodiments, the disclosure is related to variant *Aspergillus* sp. strains comprising genetic modifications of a gene encoding a SSB7 protein orthologue of SEQ ID NO: 12. In other embodiments, the disclosure is related to variant *Penicillium* sp. strains comprising genetic modifications of a gene encoding a SSB7 protein orthologue of SEQ ID NO: 13.

Figure 5:
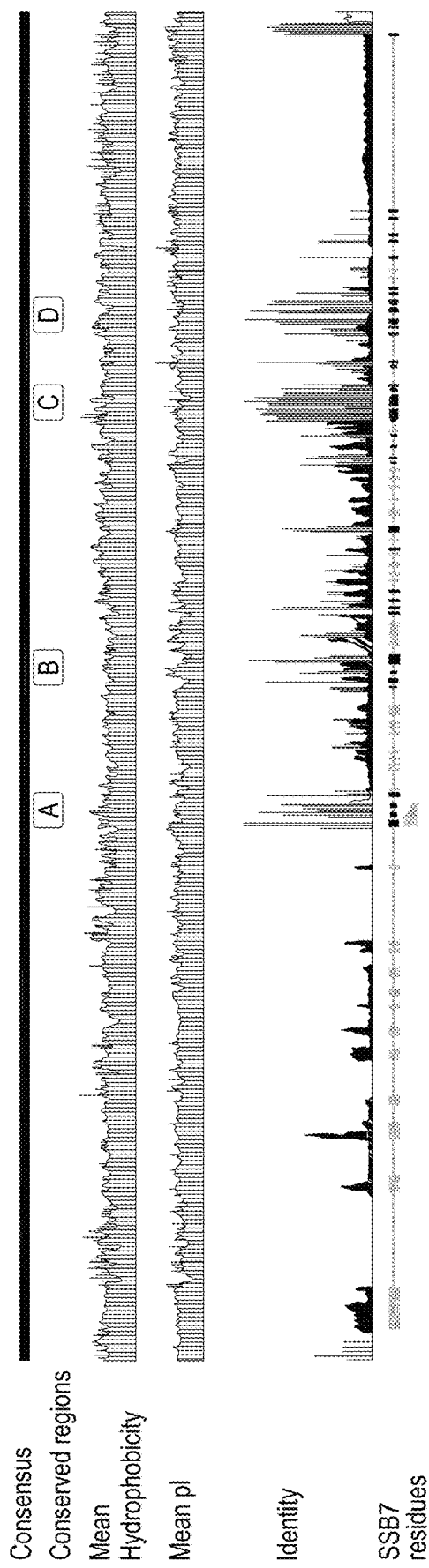
FIG. 5 is a graphical representation illustrating amino acid conservation of the SSB7 protein. More specifically.

More particularly, as generally set forth above, a wild-type *Trichoderma* sp. ssb7 gene of SEQ ID NO: 1, encodes for the newly predicted protein, SSB7, of SEQ ID NO: 2 (which protein is uncharacterized in the literature). The Joint Genome Institute (JGI) *Trichoderma reesei* v2.0 database (strain QM6a) predicts a different gene structure for this same DNA sequence as PID 108712. More specifically, analysis of the ssb7 protein sequence described herein contains a microtubule interacting and trafficking (MIT) domain. Likewise, BLAST searches have shown that SSB7 protein orthologues are present in *Fusarium* sp. (SEQ ID NO: 8), *Neurospora* sp. (SEQ ID NO: 9), *Myceliophthora* sp. (SEQ ID NO: 10), *Talaroymyces* sp. (SEQ ID NO: 11), *Aspergillus* sp. (SEQ ID NO: 12) and *Penicillium* sp. (SEQ ID NO: 13) fungal strains, but not Saccharomycetes. For example, as presented and described in FIG. 5, the SSB7 protein comprises several regions of protein sequence conservation. FIG. 5 is a graphical representation of a MUSCLE alignment of three hundred and fifty-three (353) Ascomycete homologs excluding short protein predictions lacking amino acids spanning the N-terminal MIT domain. More specifically, the alignment reveals four (4) regions of conservation in SSB7 homologues/orthologues, defined herein as "Region A" (SEQ ID NO:22), "Region B" (SEQ ID NO:23), "Region C" (SEQ ID NO:24) and "Region D" (SEQ ID NO:25). As presented in FIG. 5, Region A corresponds to the MIT domain referenced above.

In addition, CLUSTAL alignment of such SSB7 orthologues (SEQ ID NOs: 8-13) with the wild-type *Trichoderma reesei* SSB7 protein (SEQ ID NO: 2) and the wild-type *Trichoderma atroviride* SSB7 protein (SEQ ID NO: 31) are presented in FIG. 9A-FIG. 9E, showing several regions of amino acid sequence conservation.

Thus, in certain other embodiments, a variant strain of the disclosure comprises genetic modifications of a gene encoding a SSB7 protein, wherein the gene is modified in a nucleic acid sequence region encoding a "conserved 1" SSB7 protein amino acid of SEQ ID NO: 26. In other embodiments, a variant strain of the disclosure comprises genetic modifications of a gene encoding a SSB7 protein, wherein the gene is modified in a nucleic acid sequence region encoding a "conserved 2" SSB7 protein amino acid of SEQ ID NO: 27. In another embodiment, a variant strain of the disclosure comprises genetic modifications of a gene encoding a SSB7 protein, wherein the gene is modified in a nucleic acid sequence region encoding a "conserved 3" SSB7 protein amino acid of SEQ ID NO: 28. In other embodiments, a variant strain of the disclosure comprises genetic modifications of a gene encoding a SSB7 protein, wherein the gene is modified in a nucleic acid sequence region encoding a "conserved 4" SSB7 protein amino acid of SEQ ID NO: 29. In another embodiment, a variant strain of the disclosure comprises genetic modifications of a gene encoding a SSB7 protein, wherein the gene is modified in a nucleic acid sequence region encoding a "conserved 5" SSB7 protein amino acid of SEQ ID NO: 30.

Thus, vis-à-vis the guidance set forth above in Section III, the Examples presented below and by reference to the amino acid sequences (e.g., SEQ ID NOs: 2, 4, 8-13, 22-31, 33 and 35) and the nucleic acid sequences (e.g., SEQ ID NOs: 1, 3, 5-7, 19-21, 32 or 34) disclosed herein, one skilled in the art may readily construct such variant strains of filamentous fungus comprising a reduced viscosity phenotype of the disclosure.

IV. Variant Fungal Strains Further Comprising a Gene Encoding a MPG1, SFB3, SEB1, CRZ1 and/or GAS1 Protein In certain embodiments, the present disclosure is related to variant strain of filamentous fungus comprising a genetic modification of a gene encoding a SSB7 protein, and one or more genetic modifications of a gene encoding a MPG1 protein (SEQ ID NO: 14), a SFB3 protein (SEQ ID NO: 15), a SEB1 protein (SEQ ID NO: 16), a CRZ1 protein (SEQ ID NO: 17) and/or a GAS1 protein (SEQ ID NO: 18)

For example, variant filamentous fungus strains comprising a genetic modification of a gene encoding a MPG1 protein, a SFB3 protein, a SEB1 protein, a CRZ1 protein and/or a GAS1 protein comprise a reduced viscosity phenotype, relative to the parental strains from which they were derived (see, e.g., International PCT Publication Nos. WO2012/145584, WO2012/027580, WO2012/145595, WO2012/145596, WO2012/145596 and WO2012/145592, which describe the above referenced reduced viscosity phenotypes).

Thus, in certain embodiments, a variant strain of filamentous fungus comprises a genetic modification of a gene encoding a SSB7 and one or more genetic modifications of a gene encoding a protein selected from MPG1, SFB3, SEB1, CRZ1 and/or GAS1.

In certain embodiments, a variant strain of filamentous fungus comprising a genetic modification of a ssb7 gene and at least one genetic modification of a mpg1, sfb3, seb1, crz1 and/or gas1 gene, further comprises a reduced viscosity phenotype relative to a variant strain of filamentous fungus comprising only the genetic modification of a ssb7 gene alone. More specifically, such variant strains of filamentous fungus produce during aerobic fermentation in submerged culture a cell broth that (i) requires a reduced amount of agitation to maintain a preselected dissolved oxygen (DO) content, and/or a (ii) maintains an increased DO content at a preselected amount of agitation (relative to the cells of the parental strain and/or variant strains thereof comprising a genetic modification of ssb7 alone).

V. Molecular Biology

As generally described above, certain embodiments of the disclosure are directed to variant strains of filamentous fungus derived from parental strains of filamentous fungus. The cells of these variant strains subsequently produce, during aerobic fermentation in submerged culture, a cell broth that requires a reduced amount of agitation to maintain a preselected dissolved oxygen (DO) content, and/or a cell broth that maintains an increased DO content at a preselected amount of agitation, compared to the cells of the parental strain. Thus, in certain embodiments, the variant strains of the disclosure comprising a reduced viscosity phenotype comprise genetic modifications of a gene encoding a SSB7 (i.e., relative to cells of the parental strain).

Thus, a variant strain of filamentous fungus described herein comprises genetic modifications of a gene encoding a SSB7 protein, wherein the genetic modifications include, but are not limited to: (a) the introduction, substitution, or removal of one or more nucleotides in a gene (or ORF), or the introduction, substitution, or removal of one or more nucleotides in a regulatory element required for the transcription or translation of the gene (or ORF thereof), (b) a gene disruption, (c) a gene conversion, (d) a gene deletion, (e) a gene down-regulation, (f) specific mutagenesis and/or (g) random mutagenesis of the SSB7 protein disclosed herein. In other embodiments, a variant strain of filamentous fungus comprising a genetic modification of a gene encoding a SSB7, further comprises a genetic modification of one or more genes encoding a MPG1, SFB3, SEB1, CRZ1 and/or GAS1 protein.

Thus, in certain embodiments, a variant strain of filamentous fungus comprising genetic modifications of a gene encoding a SSB7 protein is constructed by gene deletion to eliminate the expression/production of the native SSB7 protein. In other embodiments, a variant strain of filamentous fungus comprising a genetic modification is constructed by partial gene deletion to eliminate the expression/production of a native SSB7 protein. For example, in certain embodiments, a modified filamentous fungal strain comprises a partial deletion of the ssb7 gene, wherein a partial deletion includes the partial deletion of any portion of the ssb7 gene's coding sequence. Thus, such variant strains comprising a reduced viscosity phenotype do not express/produce a native SSB7 protein. For example, gene deletion techniques enable the partial or complete removal of the gene, thereby eliminating the expression/production of the native protein. In such methods, the deletion of the gene may be accomplished by homologous recombination using an integration plasmid/vector that has been constructed to contiguously contain the 5' and 3' regions flanking the gene. The contiguous 5' and 3' regions may be introduced into a filamentous fungal cell, for example, on an integrative plasmid/vector in association with a selectable marker to allow the plasmid to become integrated in the cell.

In other embodiments, a variant strain of filamentous fungus comprises genetic modifications which disrupt or inactivate a gene encoding the protein (e.g., SSB7). Exemplary methods of gene disruption/inactivation include disrupting any portion of the gene, including the polypeptide coding sequence (CDS), promoter, enhancer, or another regulatory element, which disruption includes substitutions, insertions, deletions, inversions, and combinations thereof and variations thereof.

Thus, in certain embodiments, a variant strain of filamentous fungus is constructed by a gene disruption technique. A non-limiting example of a gene disruption technique includes inserting (integrating) into one or more of the genes of the disclosure an integrative plasmid containing a nucleic acid fragment homologous to the (e.g., ssb7) gene, which will create a duplication of the region of homology and incorporate (insert) vector DNA between the duplicated regions. For example, as set forth in the Examples section, such variant strains of filamentous fungus (i.e., comprising a ssb7 gene disruption) comprise a reduced viscosity phenotype of the disclosure.

Thus, in certain other non-limiting examples, a gene disruption technique includes inserting into a gene (e.g., a gene encoding a SSB7 protein) an integrative plasmid containing a nucleic acid fragment homologous to the (e.g., ssb7) gene, which will create a duplication of the region of homology and incorporate (insert) vector DNA between the duplicated regions, wherein the vector DNA inserted separates, e.g., the promoter of the ssb7 gene from the SSB7 protein coding region, or interrupts (disrupts) the coding, or non-coding, sequence of the ssb7 gene, resulting in a reduced viscosity phenotype strain thereof. Thus, a disrupting construct may be a selectable marker gene (e.g., pyr2) accompanied by 5' and 3' regions homologous to the ssb7 gene. The selectable marker enables identification of transformants containing the disrupted gene. Thus, in certain embodiments, gene disruption includes modification of control elements of the gene, such as the promoter, untranslated regions (UTRs), codon changes, and the like.

In other embodiments, a variant strain of filamentous fungus is constructed (i.e., genetically modified) by introducing, substituting, or removing one or more nucleotides in the gene, or a regulatory element required for the transcription or translation thereof. For example, nucleotides may be inserted or removed so as to result in the introduction of a stop codon, the removal of the start codon, or a frame-shift of the open reading frame (ORF), e.g., see allele ssb7(fs). Such a modification may be accomplished by site-directed mutagenesis or PCR generated mutagenesis in accordance with methods known in the art (e.g., see, Botstein and Shortie, 1985; Lo et al., 1985; Higuchi et al., 1988; Shimada, 1996; Ho et al., 1989; Horton et al., 1989 and Sarkar and Sommer, 1990).

In another embodiment, a variant strain of filamentous fungus is constructed (i.e., genetically modified) by the process of gene conversion (e.g., see Iglesias and Trautner, 1983). For example, in the gene conversion method, a nucleic acid sequence corresponding to the target gene is mutagenized in vitro to produce a defective nucleic acid sequence, which is then transformed into the parental cell to produce a variant cell comprising a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993).

In other embodiments, a variant strain of filamentous fungus is constructed by established anti-sense (gene-silencing) techniques, using a nucleotide sequence complementary to the nucleic acid sequence of the ssb7 gene (Parish and Stoker, 1997). More specifically, expression of a gene by a filamentous fungus strain may be reduced (down-regulated) or eliminated by introducing a nucleotide sequence complementary to the nucleic acid sequence of the gene, which is transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a variant strain of filamentous fungus is constructed (i.e., genetically modified) by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. For example, one of skill in the art may readily adapt and/or modify the screening methods set forth in the Example section herewith to identify such (mutagenized) variant strains of filamentous fungus cells comprising a reduced viscosity phenotype.

The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods. Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

For example, such genetic modifications in the one or more of the genes disclosed herein can reduce the efficiency of the gene's promoter, reduce the efficiency of an enhancer, interfere with the splicing or editing of the gene's mRNA, interfere with the translation of the gene's mRNA, introduce a stop codon into the gene's-coding sequence to prevent the translation of full-length protein, change the coding sequence of the protein to produce a less active or inactive protein, reduce the protein interaction with other nuclear protein components, change the coding sequence of the protein to produce a less stable protein, or target the protein for destruction, or cause the protein to misfold or be incorrectly modified (e.g., by glycosylation), or interfere with cellular trafficking of the protein.

In certain other embodiments, a variant strain of filamentous fungus is constructed (i.e., genetically modified) by means of site specific gene editing techniques. For example, in certain embodiments, a variant strain of filamentous fungus is constructed (i.e., genetically modified) by use of transcriptional activator like endonucleases (TALENs), zinc-finger endonucleases (ZFNs), homing (mega) endonuclease and the like. More particularly, the portion of the gene to be modified (e.g., a coding region, a non-coding region, a leader sequence, a pro-peptide sequence, a signal sequence, a transcription terminator, a transcriptional activator, or other regulatory elements required for expression of the coding region) is subjected genetic modification by means of ZFN gene editing, TALEN gene editing, homing (mega) endonuclease and the like, which modification methods are well known and available to one skilled in the art.

Thus, in certain embodiments, a variant strain of filamentous fungus is constructed (i.e., genetically modified) by means of CRISPR/Cas9 editing (e.g., see Examples herewith). More specifically, compositions and methods for fungal genome modification by CRISPR/Cas9 systems are described and well known in the art (e.g., see, International PCT Publication Nos: WO2016/100571, WO2016/100568, WO2016/100272, WO2016/100562 and the like). Thus, a gene encoding a SSB7 protein can be disrupted, deleted, mutated or otherwise genetically modified by means of nucleic acid guided endonucleases, that find their target DNA by binding either a guide RNA (e.g., Cas9) or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (e.g., a Cas9 from *S. pyogenes*, or a codon optimized gene encoding the Cas9 nuclease) is operably linked to a promoter active in the filamentous fungal cell and a terminator active in filamentous fungal cell, thereby creating a filamentous fungal Cas9 expression cassette. Likewise, one or more target sites unique to the gene of interest are readily identified by a person skilled in the art.

For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a filamentous fungal expression cassette for the gRNA is created by operably linking the DNA encoding the gRNA to a promoter active in filamentous fungal cells and a terminator active in filamentous fungal cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the filamentous fungal host's machinery to repair the DNA break generated by the RGEN (RNA-guided endonuclease).

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR, by amplifying the target locus with a forward and reverse primer. These primers can amplify the wild-type locus or the modified locus that has been edited by the RGEN. These fragments are then sequenced using a sequencing primer to identify edited colonies.

Another way in which a gene encoding a SSB7 protein of the disclosure can be genetically modified is by altering the expression level of the gene of interest. For example, nuclease-defective variants of such nucleotide-guided endonucleases (e.g., Cas9 D10A, N863A or Cas9 D10A, H840A) can be used to modulate gene expression levels by enhancing or antagonizing transcription of the target gene. These Cas9 variants are inactive for all nuclease domains present in the protein sequence, but retain the RNA-guided DNA binding activity (i.e., these Cas9 variants are unable to cleave either strand of DNA when bound to the cognate target site).

Thus, the nuclease-defective proteins (i.e., Cas9 variants) can be expressed as a filamentous fungus expression cassette and when combined with a filamentous fungus gRNA expression cassette, such that the Cas9 variant protein is directed to a specific target sequence within the cell. The binding of the Cas9 (variant) protein to specific gene target sites can block the binding or movement of transcription machinery on the DNA of the cell, thereby decreasing the amount of a gene product produced. Thus, any of the genes disclosed herein can be targeted for reduced gene expression using this method. Gene silencing can be monitored in cells containing the nuclease-defective Cas9 expression cassette and the gRNA expression cassette(s) by using methods such as RNAseq.

VI. Utility

As generally described above, and further presented in the Examples section below, use of the reduced viscosity strains of filamentous fungi disclosed herein improves the distribution of oxygen and nutrients in a submerged culture, reduces the amount of energy required to agitate a submerged culture, and enables increased cell mass concentrations present in the culture, leading to increased protein production. Moreover, the variant strains of filamentous fungus disclosed herein comprise fully defined genomes, making them well-suited for subsequent genetic manipulation, complementation, mating, and the like. Likewise, the present strains are not adversely affected in protein production, for example, by the manipulation(s) that resulted in the attendant viscosity reduction. Furthermore, these variant strains of filamentous fungus (i.e., reduced viscosity strains) disclosed herein can be produced from essentially any parental strain, including parental strains that already produce a protein intended for high level expression (i.e., an endogenous or a heterologous protein of interest), already encode a selectable marker, or already include other features that are desirable in a production host. Thus, the present strain and methods eliminate the need to transfer a gene encoding a protein of interest into a pre-existing reduced viscosity production strain.

Thus, the present strains and methods find use in the production of commercially important proteins in submerged cultures of filamentous fungi. For example, commercially important proteins include, but are not limited to, cellulases, xylanases, mannanases, hemicellulases, pectinases, lyases, proteases, kinases, amylases, pullulanases, lipases, esterases, perhydrolases, transferases, laccases, catalases, oxidases, reductases, chlorophyllases, hydrophobins, chymosins, carbonic anhydrases, thymidylate synthases, dihydrofolate reductases, tyrosine kinases, multidrug resistance proteins (e.g., ABC P-gp proteins), CAD (carbamyl-P synthase, aspartate transcarbamylase, dihydroorotase), topoisomerases, ribonucleotide reductase, antibodies and other enzymes, and non-enzyme proteins capable of being expressed in filamentous fungi. Such proteins are suitable for industrial, pharmaceutical, animal health, food and beverage use and the like.

VII. Proteins of Interest

As briefly stated in the preceding section, the present strains and methods find use in the production of commercially important proteins in submerged cultures of filamentous fungi. A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) sub-units, wherein the POI or a variant POI thereof is preferably one with properties of interest.

In certain embodiments, a POI or a variant POI is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

In certain embodiments, a POI or a variant POI is selected from an Enzyme Commission (EC) Number selected from the group consisting of EC 1, EC 2, EC 3, EC 4, EC 5 or EC 6.

For example, in certain embodiments a POI is an oxidoreductase enzyme, including, but not limited to, an EC1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase), EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease S1), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-(3-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.- (e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate: coenzyme A ligase) and EC 6.3.2.28 (e.g., L-amino-acid alpha-ligase).

These and other aspects and embodiments of the present strains and methods will be apparent to the skilled person in view of the present description and the following Examples.

EXAMPLES

Certain aspects of the present disclosure may be further understood in light of the following examples, which should not be construed as limiting. Modifications to materials and methods will be apparent to those skilled in the art.

Example 1

Identification of the ssb7 Gene as Responsible for Morphological Changes in Filamentous Fungus A. Overview

*Trichoderma reesei* is an aerobic filamentous fungus that produces thick, viscous fermentation broths when used in commercial fermentations. For example, the high viscosity of such fermentation broths particularly reduces oxygen transfer, thereby limiting the amount of cell mass, which concomitantly reduces the volumetric productivity that is achieved in *T. reesei* commercial fermentations. Isolation of reduced viscosity mutants can result in mutant strains that produce lower viscosity fermentation broths. With such mutant strains, fermentations can utilize more cell mass, leading to increases in volumetric productivity. More particularly, one such mutant, Morph 77B7, was isolated from a genetic screen, wherein the causative mutation was identified as a frame-shift mutation in the gene, ssb7, encoding a previously uncharacterized MIT domain containing protein. In the instant Example (and Examples 2 and 3 that follow), different mutant alleles of ssb7 are disclosed, illustrating that mutation of ssb7 results in fermentation broth viscosity reductions. The ssb7 locus and the mutant ssb7 alleles disclosed herein are presented in FIG. 1.

B. Screening for Morphology Mutants

A glucoamylase (GA) expressing *Trichoderma* strain named "TrGA 29-9" (see, U.S. Pat. No. 9,725,727, specifically incorporated herein by referenced in its entirety) was mutated with NTG (N-methyl-N'-nitro-N-nitrosoguanidine) until a 10% kill was obtained. The surviving cells were plated on PDA (potato dextrose agar) and allowed to sporulate. Spores were scraped from the plate after being suspended in water. The spores were grown in YEG (yeast extract glucose broth) for 48-72 hours, and the resulting mycelia were sieved through a 200 micrometer (μm) filter that was subsequently washed with copious amounts of water. The filtrate was spun down, the mycelia were collected, and re-inoculated into YEG. This exact procedure was repeated several times, except the mycelia were sieved through smaller filters each time. In the final step, after growth in YEG, the mycelia were filtered through a 40 μm filter, the mycelia were recovered from the filtrate, and plated on PDA.

A spore library was made and a colony picker was used to prepare ninety-six (96) well libraries. Using microscopy the libraries were screened in liquid culture, and mutants were recovered that showed alterations in morphology (i.e., phenotype). Mutants from this screen were evaluated further in high cell density shake flasks. Mutants with low viscosity broths were evaluated further in 14 L fermenters for reduced viscosity (phenotypes), oxygen transfer properties, and protein production under standard and high cell density conditions.

C. Isolation and Characterization of *T. reesei* Morph 77B7

A *T. reesei* mutant named "Morph 77B7" (i.e., obtained as described above in Example 1B), was observed to have an altered morphology (phenotype) in submerged liquid culture, particularly having shorter and thicker filaments than its parent. For example, in liquid medium, cultures containing the Morph 77B7 mutant also showed a higher level of dissolved oxygen (DO) during growth, compared to cultures containing the parent (see TABLE 1).

More particularly, *T. reesei* strains TrGA 29-9 and Morph 77B7 were grown under similar conditions in submerged (liquid) culture and their growth phenotypes were compared. Briefly, spores of each strain were added separately to 500-mL of minimal medium in a 3-L flask with both side and bottom baffles with 60% glucose added to a final concentration of 27.5 g/L. The cultures were grown for 48 hours at 34° C. in a shaking incubator.

After 48 hours, the contents of each flask were added separately to 14-L fermentors containing 9.5-L of medium (containing 4.7 g/L $KH_2PO_4$, 1.0 g/L $MgSO_4 \cdot 7H_2O$, 4.3 g/L $(NH_4)_2SO_4$ and 2.5 mL/L of a 400× trace element solution containing 175 g/L citric acid, 200 g/L $FeSO_4 \cdot 7H_2O$, 16 g/L $ZnSO_4 \cdot 7H_2O$, 3.2 g/L $CuSO_4 \cdot 5H_2O$, 1.4 g/L $MnSO_4 \cdot H_2O$, and 0.8 g/L $H_3BO_3$). These components were heat sterilized together at 121° C. for 30 minutes. A solution of 60% glucose and 0.48% $CaCl_2 \cdot 2H_2O$ was separately autoclaved, cooled and added to the fermentor to a final concentration of 75 g/L glucose and 0.6 g/L $CaCl_2 \cdot 2H_2O$. The medium was adjusted to pH 3.5 with 28% $NH_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 RPM.

As the cultures grew, DO content levels dropped, at least partly as a consequence of the increased viscosity of the fermentation broth, due to the proliferation of filamentous fungus hyphae. When DO content levels fell below 40%, the agitation rate was increased to maintain the dissolved oxygen at 40%. Upon reaching 750 RPM agitation, DO content level would be allowed to drop below 40%. If the DO content did not fall below 40%, then it was unnecessary to increase the agitation rate during the fermentation run, and the initial agitation rate was higher than necessary. When the glucose was completely consumed, the amount of biomass produced in each fermenter was measured, and found to be substantially the same for both strains.

Thus, the DO content level in each fermenter at a given level of agitation, and the amount of agitation required to maintain a given DO content level are indirect measures of the viscosity of the different broths (i.e., due to the different strain growth phenotypes) Although it would be ideal to vary only one variable (i.e., DO or agitation) and measure the other, it is desirable to prevent the DO from falling below 40%, to ensure sufficient biomass in each fermentor, thereby permitting a more meaningful comparison between the growth of the different strains.

As shown in TABLE 1, strain Morph 77B7 has a reduction in fermentation broth viscosity compared to the (parental) TrGA 29-9 strain. For example, at the end of the batch growth phase (i.e., when all the glucose had been consumed), both strains had achieved a similar biomass concentration and similar peak carbon evolution rates (CER). To get there, the control strain saw agitation increase to the maximum set point of 750 RPM and the DO dropped down below the minimum set point to 15%. In contrast, the Morph 7B77 mutant strain did not require as much agitation to achieve the same biomass concentration, wherein the agitation rate only increased to 616 RPM to maintain the DO at the 40% set point.

TABLE 1

Fermentation Broth Viscosity of TrGA 29-9 Compared to Morph 77B7

| Strain Name | Minimum DO | Peak Agitation | Biomass at end of growth phase | Peak CER |
|---|---|---|---|---|
| TrGA 29-9 | 15% | 750 RPM | 40 g/kg | 147 mmol/L/hr |
| Morph 77B7 | 40% | 616 RPM | 40 g/kg | 141 mmol/L/hr |

D. Identification of the Causative ssb7(fs) Mutant Allele in *T. reesei* Morph 77B7

The genomes of the *T. reesei* TrGA 29-9 parent and the Morph 77B7 mutant strains were sequenced (as generally described in PCT Publication No. WO2012/027580), leading to the identification of eight (8) new mutations predicted to alter a coding sequence in the Morph 77B7 genome, any of which mutations alone, or in combination, might be necessary for the observed altered morphology phenotype and viscosity reductions described herein. Thus, to determine which of these mutations were of importance, complementation analysis was performed.

More particularly, only one locus complemented the mutant phenotype, herein named "ssb7". Thus, the ssb7 gene of SEQ ID NO: 1 encodes a newly predicted protein, SSB7, that partly overlaps with other protein predictions on the same DNA sequence, e.g. *Trichoderma reesei* QM6a Protein ID (PID) 108712 (The Genome Portal of the Department of Energy Joint Genome Institute, Grigoriev et al., 2011, hereinafter abbreviated, the "JGI portal"). In the mutant strain Morph 77B7, the ssb7 mutant allele comprises a single guanine (G) nucleotide deletion (ΔG) in exon 2 (*T. reesei* QM6a Scaffold 13, 167404). For example, a deletion of G in exon 2 (i.e., in the ssb7 mutant allele) results in a frame-shift mutation, and a premature stop prior to the last intron of the ssb7 gene. This allele is referred to herein as "ssb7(fs)".

Figure 2:
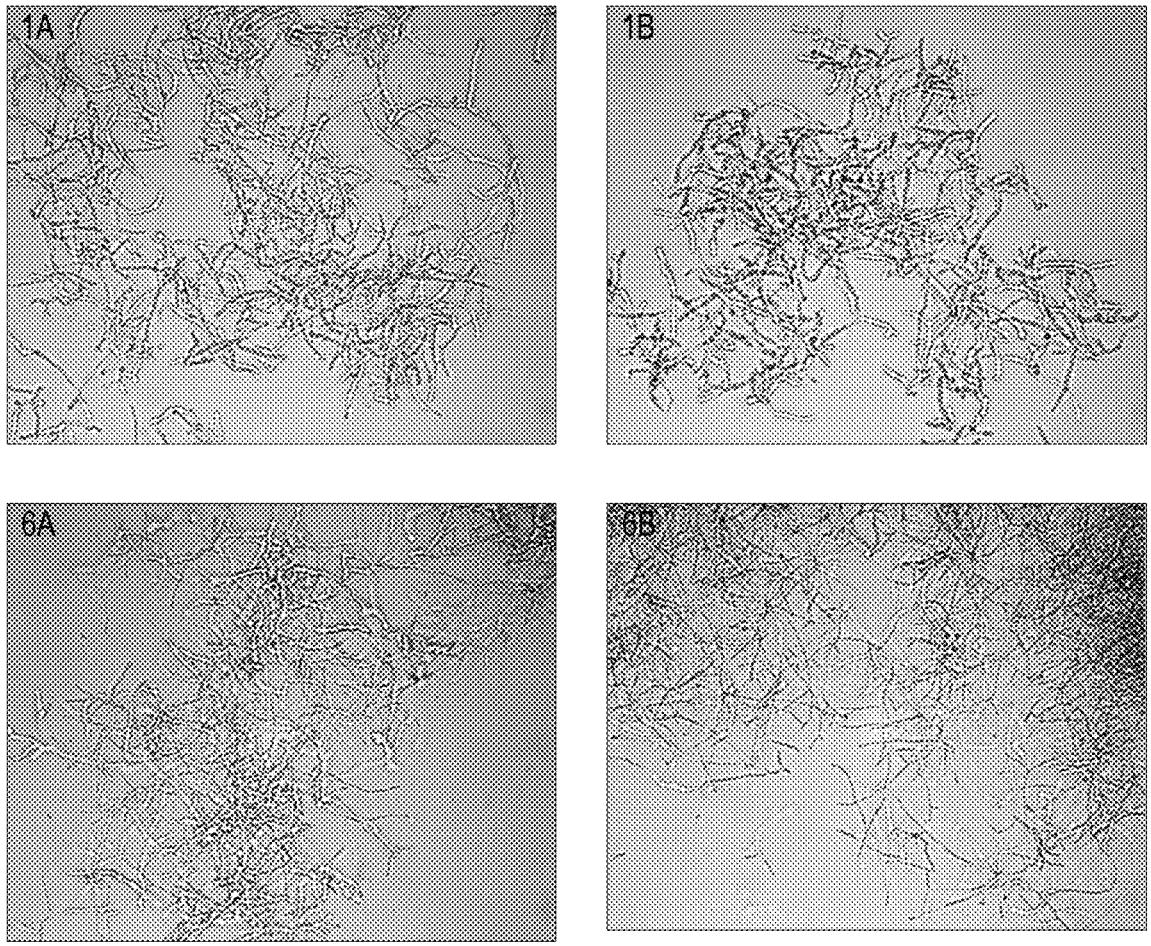
FIG. 2 shows complementation of *T. reesei* mutant strain Morph 77B7 hyphal phenotype by transformation with DNA fragments 1 and 6.
Figure 3A:
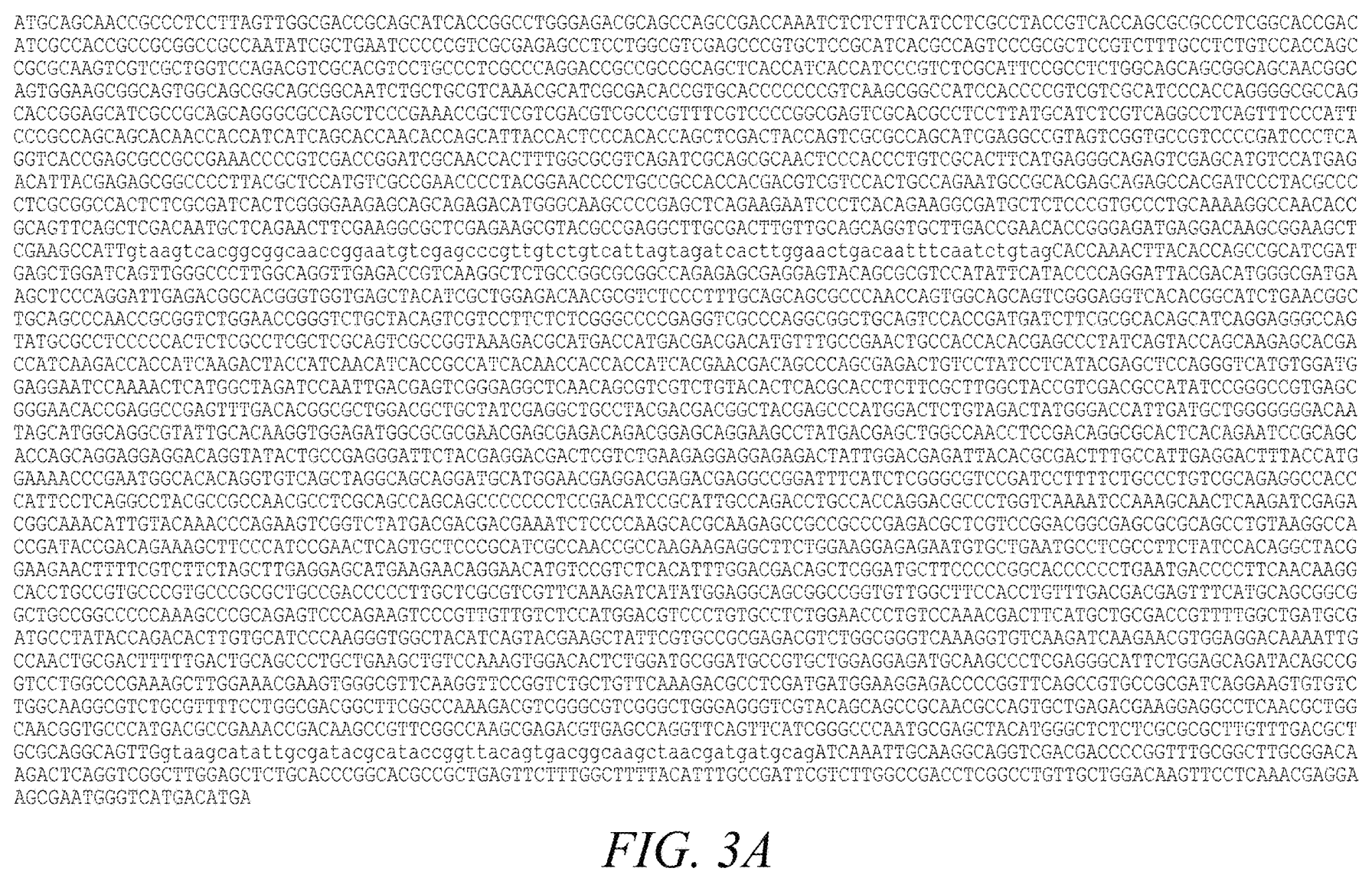

Complementation of the *T. reesei* mutant strain Morph 77B7 hyphal phenotype by transformation with DNA fragments was performed as follows. For each of the eight (8) mutant loci detected in mutant Morph 77B7, plasmids were developed containing transformation selection markers and a DNA fragment corresponding to the wild-type locus sequence with sufficient flanking sequences to ensure expression. Mutant strain Morph 77B7 protoplasts were transformed with each of these plasmids separately. Two (2) transformants from each of the plasmids were transferred to shake flasks with selective liquid media and grown for 3 days at 33° C. Transformants carrying most DNA fragments retained the hyper-branching and thick hyphae phenotype observed for the Morph 77B7 mutant strain. Transformants for DNA fragment 1 (encoding one of the other mutant loci in Morph 77B7, i.e., the gene encoding PID 112328), exemplifies this mutant phenotype. In contrast, only transformants comprising DNA fragment 6 (i.e., encoding PID 108712/SSB7), reversed this phenotype, at least partially, with thinner and less-branched hyphae. As shown in FIG. 2, DNA fragment 1 (FIG. 2, panels 1A and 1B) and DNA fragment 6 (FIG. 2, panels 6A and 6B) represent independent transformants for each DNA fragment 1 and 6. The nucleic acid sequence of the mutant ssb7(fs) allele (SEQ ID NO: 3) encoding the variant SSB7 protein of SEQ ID NO: 4 is presented in FIG. 3.

Thus, as generally set forth above, the nucleic acid sequence of the wild-type *T. reesei* ssb7 gene(SEQ ID NO: 1) encodes SS87 (SEQ ID NO: 2), which is uncharacterized in the literature. For example, the JGI portal *T. reesei* QM6a v2.0 database PID for SS87 is 108712 (genome.jgi-pstiorg/cgibin/dispGeneModel?db=Trire2&id=108712; SEQ ID NO: 33), while the JGI *T. reesei* RUT-C30 database PID for SS87 is 82397 (Jourdier et al., 2017; SEQ ID NO: 35). Thus, the DNA sequences are identical at this locus between the two (2) *T. reesei* strains, however, the coding regions are predicted to be slightly different (see, FIG. 1A; "QM6a JGI ssb7 PID 108712" and "RUT-C30 PID 82397"). Specifically, the N-45terminus of the strain QM6a gene model (SEQ ID NO: 32 encoding PID 108712/SEQ ID NO: 33) harbors two (2) extra exons than strain RUT-C30 gene model (SEQ ID NO: 34 encoding PID 82397/SEQ ID NO: 35), while the strain RUT-C30 gene model contains an additional intron. To resolve the gene model prediction at this locus, we utilized RNA-sequencing data from *T. reesei* coupled with the funannotate fungal genome annotation pipeline (J M Palmer. 2019. Funannotate genome annotation pipeline. Zenodo. lit-t-p4kdoi.org/10.5281/zenodo. 1 134477). Funannotate predicted a gene model that was supported by RNA sequencing read mapping, while both the model predictions from JGI in QM6a and RUT-C30 had incompatible intron-exon boundaries with the RNA-sequencing data. (see, FIG. 1A). The SSB7 gene prediction results in a translated protein of 1308 amino acids that is translated from a 4762 bp transcript that containing 3 exons (SEQ ID: 19, SEQ ID: 20, and SEQ ID: 21), a462 bp 5'UTR(SEQ ID: 36), and a 373 bp 3'UTR (SED ID: 37). Herein Applicant will refer to coordinates of the ssb7 gene and SSB7 protein using the prediction derived from the funannotate software. Herein Applicant will refer to coordinates of the ssb7 gene (SEQ ID NO: 1) and SSB7 protein (SEQ ID NO: 2) using the prediction derived from the funannotate software whereas genomic coordinates, will still refer to the JGI QM6a v2 assembly.

E. Function Based on Homology

BLAST searches performed herein shown that SSB7 protein orthologues are present in *Fusarium* sp. (SEQ ID NO: 8), *Neurospora* sp. (SEQ ID NO: 9), *Myceliophthora* sp. (SEQ ID NO: 10), *Talaroymyces* sp. (SEQ ID NO: 11), *Aspergillus* sp. (SEQ ID NO: 12), and *Penicillium* sp. (SEQ ID NO: 13), but not Saccharomycetes. For example, the *T. reesei* ssb7 gene encodes an uncharacterized, but highly conserved SSB7 protein, comprising a predicted microtubule interacting and trafficking (MIT) domain (see, TABLE 2, Region A and FIG. 5) and unknown SSB7 protein domains set forth as Region B, Region C and Region D of TABLE 2. More particularly, three-hundred and fifty-three (353) Ascomycete homologs (excluding short protein predictions lacking amino acids spanning the N-terminal MIT domain), were aligned using the MUSCLE method (Edgar RC (2004). "MUSCLE: multiple sequence alignment with high accuracy and high throughput". *Nucleic Acids Research*. 32 (5): 1792-97. doi:10.1093/nar/gkh340) in the software package Geneious. The graphical output is presented in FIG. 5, wherein four (4) regions (A-D) of amino acid conservation were identified from the alignment. Region A overlapped with the MIT domain. Conservation implies that these four regions are important for SSB7 function, although the precise enzymatic or structural function is not suggested by the amino acid sequence, based on current scientific knowledge.

TABLE 2

Conserved Amino Acid Regions of Ascomycete SSB7 Protein Homologues

| Region | Domain | Amino Acid Length | First Amino Acid SSB7 Protein | Last amino acid SSB7 | Pairwise BLSM62 positive | SEQ ID NO |
|---|---|---|---|---|---|---|
| A | MIT | 87 | S343 | P429 | 68.9% | 22 |
| B | Unknown | 60 | S613 | P672 | 63.9% | 23 |
| C | Unknown | 118 | L1028 | A1145 | 77.3% | 24 |
| D | Unknown | 84 | T1204 | V1287 | 66.7% | 25 |

Example 2

Re-Creation of Morph 77B7-Phenotype by Disruption of ssb7 in Parental Strain TrGA 29-9

A. Overview

To further validate that the ssb7 mutation was causative for the viscosity reduction, the ssb7 locus was specifically mutated in parental strain TrGA 29-9. Thus, two (2) methods were used to target ssb7 mutagenesis by homologous recombination. One method, using a linear DNA cassette from plasmid pRATT311, targeted the insertion of disruptive DNA at the site of the ΔG identified in strain Morph 77B7 (allele "ssb7(311)").

Figure 1B:
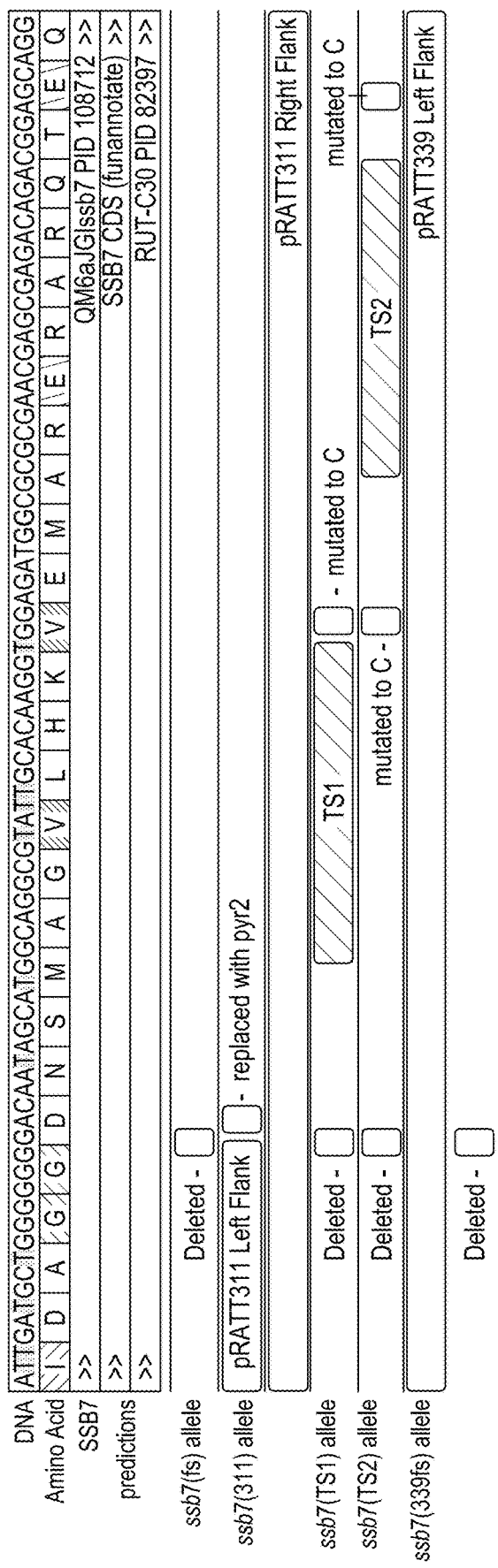

The second method, using circular plasmid pTrex2g MoCas 77b7-HR1, introduced the ΔG mutation identified in strain Morph 77B7, along with one synonymous codon change (relative to original frame) downstream of the frame-shift mutation (allele "ssb7(TS1)"; see FIG. 1 for comparison of alleles). Thus, both alleles of ssb7 exhibited reduced viscosity, wherein the frame-shift allele, ssb7(TS1), had better viscosity reduction.

B. Allele ssb7(311) in Strain TrGA 29-9

The *T. reesei* ssb7 disruption cassette plasmid pRATT311 was prepared using standard molecular biology procedures. Thus, one skilled in the art may readily recreate this plasmid from the relevant DNA parts disclosed. This plasmid included a DNA sequence having a 2.6 Kb homology box homologous to the DNA sequence corresponding to Scaffold 13, 164849 to 167403 (Left Flank). Also included within the plasmid was a DNA sequence having a 1.8 Kb homology box homologous to the DNA sequence corresponding to Scaffold 13, 167405 to 169218 (Right Flank). These sequences were designed to target the ssb7 gene and replace the nucleotide of the genome between the Left and Right Flanks (Scaffold 13, 167404) with the intervening cassette sequences. These intervening cassette sequences included a pyr2 selection marker from *Trichoderma atroviride*. Immediately downstream of the pyr2 selection marker was a DNA sequence having a 0.6 Kb region corresponding to Scaffold 13, 167403 to 166833, homologous to the 3'-most region of the Left Flank (Repeat). These repeated sequences facilitate the subsequent loss of the pyr2 marker, enabling use of this marker in future strain development, while leaving the single nucleotide G deletion mutation (Scaffold 13, 167404) in the ssb7 gene as the only new targeted genome modification. Note that data presented herewith is from a pRATT311 transformant containing the pyr2 marker and Repeat disrupting the ssb7 coding sequence (FIG. 1).

A spontaneous pyr2 mutant derivative of strain TrGA 29-9 was isolated by 5-fluoro-orotic acid (FOA) selection. This TrGA 29-9 pyr2 strain was transformed with the ssb7 disruption cassette from pRATT311, using PEG-mediated protoplast transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the ssb7 disruption cassette integrated at the ssb7 locus by homologous recombination as could be performed by one skilled in the art as per guidance below.

Only a subset of recombinant cells may successfully utilize the homologous flanks to correctly target the disruption of the gene of interest, so many transformants may need to be screened to identify one with the desired event. PCR can be used to test which recombinant cells have the desired targeted disruption. Primers must be designed that amplify across each of the homology box regions, where one primer primes at a location within the selectable marker greater than 100 bp from the closest end and the other primes at a location greater than 100 bp beyond the end of a homology box region within the adjacent genomic sequence. Cells likely containing the correct targeted disruption will successfully create PCR products spanning the Left Flank and Right Flank of the disruption cassette, whereas unsuccessful transformation events will not generate a product of the expected size. At this stage the culture may be a mix of transformed and untransformed cells, so a step of purification may be needed. Purification of the culture can be tested by PCR for loss of a short PCR product spanning the disruption site. The generated strain with confirmed homologous integration of the ssb7 disruption cassette was named "TrGA 29-9 ssb7(311)".

C. Allele ssb7(TS1) in Strain TrGA 29-9

The methods for vector and strain development used for cas9-mediated editing of ssb7 in strain TrGA 29-9 described herein, were performed essentially as described in PCT Publication Nos. PCT/US2015/65693 and WO2016/100272, wherein Example 3 and Example 4 therein describe building pTrex2gHyg MoCas; Example 5 describes adding the guide RNA (gRNA) expression cassette into this vector; and Example 8 further describes adding in a region of homology for HR-directed genome editing, transformation and screening.

A gBlock DNA sequence (SEQ ID NO: 5) shown in FIG. 6A was ordered from Integrated DNA Technologies, Inc. (IDT, Coralville, IA), wherein the sequences underlined at either 5'-end or 3'-end were added to allow Gibson assembly with pTrex2gHyg MoCas, after digestion with EcoRV. Between these underlined sequence is 1,098 bp from the *T. reesei* genome within the ssb7 gene. The grey highlighting shows the six (6) G residues of the mutant ssb7(fs) allele, that are seven (7) G residues in the wild-type ssb7 gene. The internal double underlined sequences are the 20-nucleotide (nt) target sites corresponding to the guide RNA (gRNA) sequences. The first 20-nt target is referred to as "TS1" and the second 20-nt target is referred to as "TS2", wherein the bold font c residues represent the G to C changes that alter the PAM sites adjacent to the target sites.

Two gBlocks were ordered from IDT to encode the expression cassettes for two different single guide RNAs (sgRNAs), one targeting TS1 (SEQ ID NO: 6, FIG. 6B) in the ssb7 gene and one targeting TS2 (SEQ ID NO: 7, FIG. 6C) in the ssb7 gene. Thus, the sequences underlined at either end of the two gBlocks were added to allow Gibson assembly with pTrex2gHyg MoCas after digestion with SilI and AflII.

Thus, two final vectors were constructed. One, pTrex2g MoCas 77b7-HR1, had the ssb7 homology region and the TS1 sgRNA cassette. The second, pTrex2g MoCas 77b7-HR2, had the ssb7 homology region and the TS2 sgRNA cassette. DNA sequencing verified the desired insertion of the gBlocks.

Thus, two (2) of the ssb7 alleles disclosed herein were generated with these plasmids, "ssb7(TS1)" and "ssb7(TS2)". Allele ssb7(TS1) was generated from target sequence 1 (TS1) and contains the original frame shift mutation at Scaffold 13, 167404, as well as a G to C mutation at Scaffold 13, 167436 to inactivate the TS1 recognition sequence (see, FIG. 1). The generated strain with confirmed homologous engineering of the ssb7 locus was named "TrGA 29-9 ssb7(TS1)". For example, PCT Publication No. WO2016/100272 (PCT Application Serial No. PCT/US2015/065693) describes recombinant fungal cells comprising/expressing CAS endonucleases (e.g., expressed via recombinant DNA constructs), recombinant fungal cells comprising/expressing guide RNAs (gRNA), recombinant fungal cells comprising a non-functional, or reduced activity, non-homologous end joining (NHEJ) pathway, methods and compositions of transforming filamentous fungal cells, methods and compositions for screening such transformed fungal cells and the like. Thus, one skilled in the relevant arts, by reference to PCT Publication No. WO2016/100272, may similarly construct allele ssb7(TS1), or any other modified allele disclosed herein, in any filamentous fungal strain of the disclosure.

D. Viscosity Reduction in Bioreactors

*Trichoderma reesei* strains were grown under similar conditions in submerged (liquid) culture and their growth phenotypes were compared. Briefly, spores of each strain were added separately to 50 mL of citrate minimal medium in a 250 ml flask with both side and bottom baffles. The cultures were grown for 48 hours at 30° C. at 170 RPM in a shaking incubator with a 5 cm throw. After 48 hours, the contents of each flask were added separately to 2 L fermentors (bioreactors) for inoculation. Prior to inoculation, 0.95 kg of medium containing 4.7 g/L $KH_2PO_4$, 1.0 g/L $MgSO_4·7H_2O$, 9 g/L $(NH_4)_2SO_4$ and 2.5 mL/L trace element solution were added to the 2 L bioreactors and then heat sterilized together at 121° C. for 30 minutes. Post-sterile additions were added before inoculation to the tank: sterilized 4.8 mL of 50% glucose and 0.96 mL of 0.48% $CaCl_2·2H_2O$. The medium was adjusted to pH 3.5 with 14% $NH_3$ and the temperature was maintained at 30° C., and the pH at 3.5 for the entire growth period.

A dissolved oxygen (DO) probe was calibrated to 100% when there was no added pressure in the headspace (i.e., 0 bar gauge, 1 bar absolute). The bioreactor contained a four-blade Rushton impeller in between two marine impellers, which provided mixing via a variable speed motor that was initially set at 800 RPM.

As the cultures grew, DO levels dropped, at least partly as a consequence of the increased viscosity of the fermentation broth, due to the proliferation of filamentous fungus hyphae. The control of dissolved oxygen inside the bioreactor was based on a control loop adjusting several set-points. When DO fell below 30%, the agitation rate was increased to maintain the dissolved oxygen at 30%, with a maximum agitation set point of 1,200 RPM. If the DO could not hold at 30%, oxygen enrichment was increased from 21% to up to 40%. If the DO still could not hold, then the gas flow was increased from 60 sL/h to up to 80 sL/h. When the glucose was completely consumed, the amount of biomass produced in each bioreactor was measured, and found to be substantially the same for all strains (about 50 g/kg dry cell weight). Following exhaustion of batched glucose, a slow feed of glucose and mixed disaccharides was started to maintain the cells in a glucose-limited state and encourage protein production. Agitation and DO profiles in the bioreactor for the parental TrGA 29-9 strain and the two ssb7 mutant (derived) strains TrGA 29-9 ssb7(311) and TrGA 29-9 ssb7(TS1) are presented in FIG. 7 for clarity.

Figure 7:
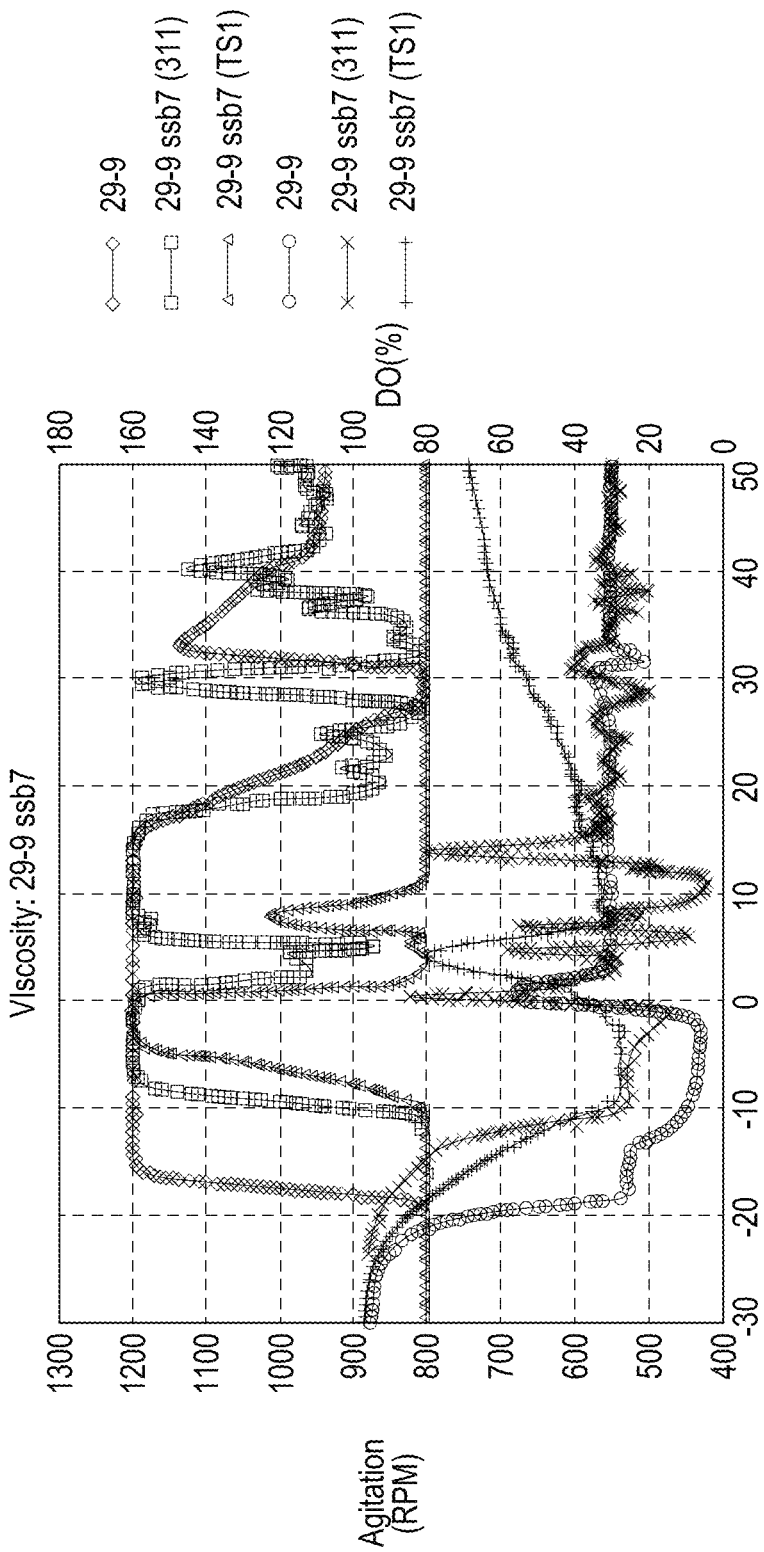
FIG. 7 presents data showing fermentation broth viscosity reductions with allele ssb7(311) and allele ssb7(TS1). More specifically.
Figure 8B:
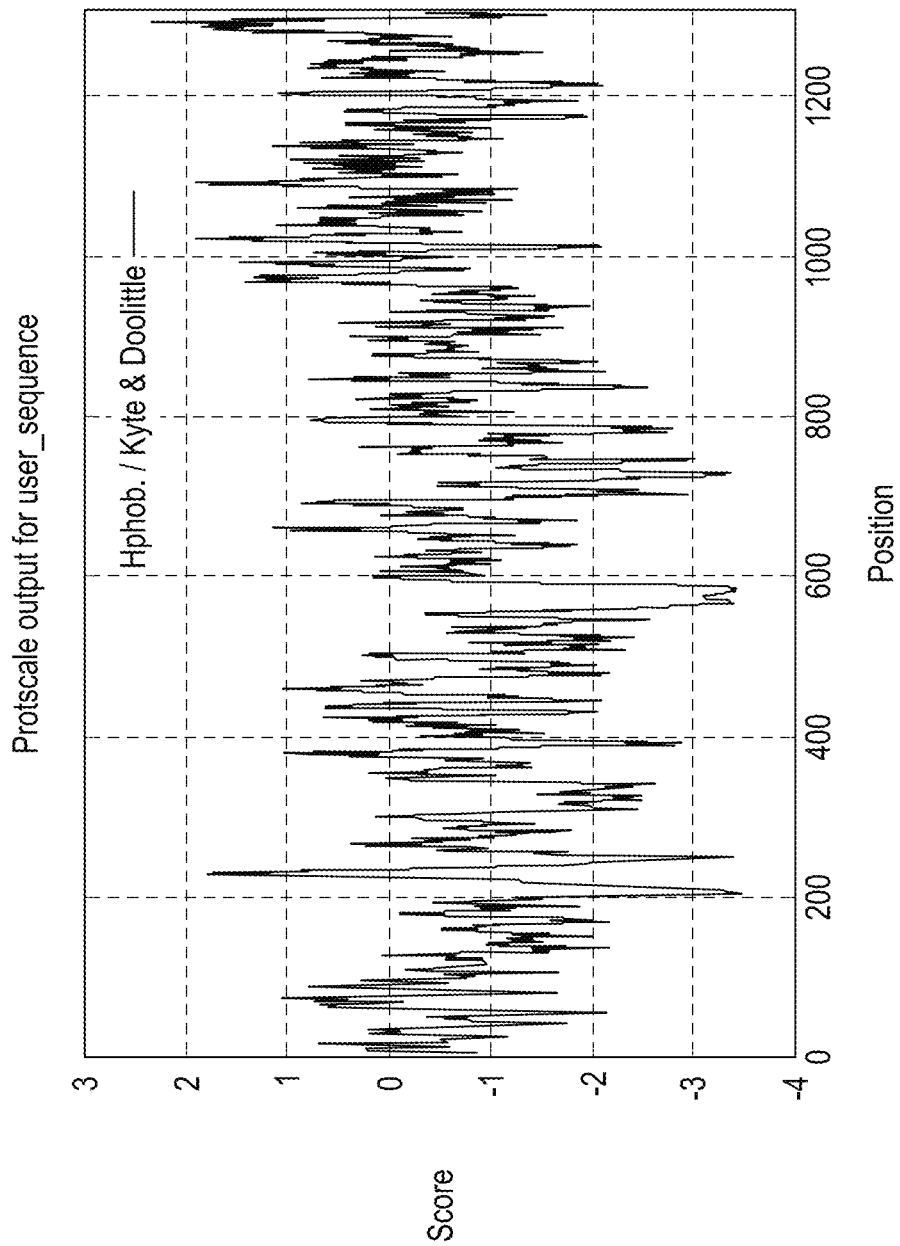
FIG. 8B shows a hydropathy plot of the native (full length) SSB7 protein comprising residue positions 1-1,308 of SEQ ID NO: 2 (per Kyte-Doolittle Hydropathy Index, 9-residue window, Kyte and Doolittle, 1982). For example.

For example, as shown in FIG. 7, the DO level in each bioreactor at a given level of agitation and the amount of agitation required to maintain a given DO level are indirect measures of fermentation broth viscosity, which measurements correlate with the observed fungal strain growth phenotypes described herein (e.g., see, FIG. 2). Although it would be ideal to vary only one variable (i.e., DO or agitation) and measure the other, it is desirable to prevent the DO from falling below 30%, to ensure the production of sufficient biomass in each bioreactor and achieve high productivity, thereby permitting a more meaningful comparison between the growth of the different fungal strains.

Thus, the two (2) measures of viscosity reduction described above were quantified from each bioreactor run, DO-limitation and Agitation-addition. Since strains differ in when they exhaust batched glucose and hence trigger feed-start, they also differ in when, during the fermentation, the DO becomes most limited. Therefore, these measurements were calculated using a window of the fermentation time spanning twenty (20) hours before and forty (40) hours after feed-start.

FIG. 7 shows this window, plus and minus ten (10) hours. The DO-limitation was defined as the ratio of sampling points where the DO level was lower than 20% above the minimum DO set point (i.e., DO below 36%). Agitation-addition was defined as the average of the additional agitation above the 800 RPM set point as triggered by the control loop. As the fermentation broth viscosity is a function of cell density, with viscosity increasing with cell density, comparison between mutant and parental strains is only valid at similar cell mass concentrations. Therefore, peak dry cell weight (DCW), during the window from which these indirect measures were calculated, are included in the examples.

Thus, viscosity evaluations were performed in bioreactors for parental TrGA 29-9 strain and ssb7 mutant (daughter) strains TrGA 29-9 ssb7(311) and TrGA 29-9 ssb7(TS1). At the end of the batch growth phase, when all the glucose had been consumed, all strains had achieved a similar biomass concentration (see, TABLE 3). Furthermore, both ssb7 alleles, ssb7(311) and ssb7(TS1), resulted in a reduction in bioreactor fermentation broth viscosity (i.e., relative to the TrGA 29-9 parent). In addition, DO was low for a shorter period of the fermentation. Thus, TABLE 3 provides quantified measures of the reduced amount of agitation required to maintain the DO above set point, and the reduced fraction of time during which the DO was at 20% above set point or lower. As shown in TABLE 3, the viscosity reduction was greater for the frame-shift allele ssb7(TS1) relative to the marker insertion ssb7(311).

TABLE 3

| Fermentation Broth Viscosity Measurements from Parental and Mutant TrGA 29-9 Strains | | | |
|---|---|---|---|
| Strain Name | Agitation Addition (RPM) | DO Limitation (ratio) | Dry Cell Weight (g/Kg) |
| TrGA 29-9 (Parental) | 244 | 0.86 | 50 |
| TrGA 29-9 ssb7(311) | 167 | 0.68 | 47 |
| TrGA 29-9 ssb7(TS1) | 84 | 0.44 | 55 |

Even without the viscosity quantification presented in TABLE 3, it is visually apparent in FIG. 7, that the agitation was reduced for the daughter strains comprising the mutant ssb7 alleles. One skilled in the art would recognize that the optimal set point values for minimal dissolved oxygen, initial agitation and maximal agitation may differ by filamentous fungus and fermentor vessel. It should be recognized that fermentation parameters should be set to ensure that the parental strain's dissolved oxygen limitation and agitation addition measurements are in a range to enable detection of broth viscosity changes during fermentation of mutant daughter cells. The parental profile in FIG. 7 illustrates such an informative profile.

Example 3

Targeted Mutation of ssb7 in Whole Cellulase Strain T4Abc

A. Overview

To further test the utility of ssb7 mutants, three (3) mutant alleles of ssb7 were also evaluated in a different *T. reesei* lineage named "T4abc", comprising a Nik1 (M743T) mutation (SEQ ID NO: 36) and expressing the native cocktail of cellulases. These mutants also demonstrated reduced viscosity phenotypes.

B. Alleles ssb7(311), ssb7(TS2) and ssb7(339fs) in Strain T4abc

The ssb7(311) allele was generated in strain T4abc pyr2 as described above in Example 2 to generate strain "T4abc ssb7(311)". The ssb7(TS2) allele was generated in strain T4abc, as was ssb7(TS1) in Example 2, except using the plasmid containing target sequence 2 (TS2). Thus, it contained the Morph 77B7 frame shift mutation at Scaffold 13, 167404, as well as a two additional G to C mutations at Scaffold 13, 167436 and Scaffold 13, 167466 to inactivate the TS1 and TS2 recognition sequences, respectively (FIG. 1). This strain was named "T4abc ssb7(TS2)".

The ssb7(339fs) allele was generated with plasmid pRATT339 which was prepared using standard molecular biology procedures, such that one skilled in the art may readily recreate this plasmid from the relevant DNA parts disclosed. This plasmid included a DNA sequence having a 3.4 Kb homology box homologous to the DNA sequence corresponding to Scaffold 13, 165839 to 169218 (Left Flank). Within this flank was a single G deletion causing a frame-shift mutation in exon 2. Also included within the plasmid was a DNA sequence having a 2.2 Kb homology box homologous to the DNA sequence corresponding to Scaffold 13, 169273 to 171458 (Right Flank). These sequences were designed to target the ssb7 gene and replace the regions of the genome between the Left and Right Flanks (Scaffold 13, 169219 to 169272) with the intervening cassette sequences.

These intervening cassette sequences included a pyr2 selection marker from *Trichoderma atroviride* intended to minimize homology to the endogenous *T. reesei* pyr2 in the genome of the strain to be transformed. Immediately upstream of the pyr2 selection marker was a directly repeated duplication of the 3'-end of the marker (Repeat), which facilitates the subsequent loss of the marker and isolation of useful pyr2 mutant derivatives of the transformants/disruptants. In a subset of transformants with the correctly targeted intervening cassette sequence, the frameshift mutation in the Left Flank would also be incorporated into the genome deleting a single G nucleotide in exon 2 (Scaffold 13, 167404). The ssb7(339fs) allele disclosed here contains both the nucleotide deletion at Scaffold 13, 167404 and the insertion of the repeat-flanked pyr2 marker between Scaffold 13, 169219 to 169272 (FIG. 1).

Thus, strain T4abc pyr2 was transformed with the ssb7 disruption cassette from pRATT339 using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the ssb7 disruption cassette integrated at the ssb7 locus by homologous recombination as described above in Example 2-B. Following spore purification, further PCR analysis was done to ensure integration occurred correctly and that the transformants were homokaryotic. Then a portion of the ssb7 gene spanning the frame-shift mutation was PCR amplified and sequenced to determine whether this mutation in the Left Flank was incorporated during the integration event. The generated strain with confirmed homologous integration of the ssb7 disruption cassette in exon 3 and frame-shift mutation in exon 2 was named "T4abc ssb7(339fs)".

C. Viscosity Reduction in Bioreactors

Viscosity evaluation was performed in bioreactors for T4abc and ssb7 mutant strains as described in Example 2. As shown in TABLE 4, at the end of the batch growth phase, when all the glucose had been consumed, all strains had achieved a similar biomass concentration (Dry Cell Weight). All three (3) ssb7 alleles resulted in a reduction in bioreactor broth viscosity relative to the T4abc parent, as evidenced by the reduced amount of agitation required to maintain the DO above set point (Agitation Addition) and the reduced fraction of time during which the DO was at 20% above set point or lower (DO Limitation).

TABLE 4

Broth Viscosity in T4abc (Parental) and T4abc (Daughter) Strains Comprising Mutant Alleles ssb7(311), ssb7(339fs) and ssb7(TS2)

| Strain Name | Agitation Addition | DO Limitation | Dry Cell Weight |
|---|---|---|---|
| T4abc (parental) | 36 +/− 5 | 0.15 +/− 0.2 | 40 +/− 1 |
| T4abc ssb 7(311) | 24 | 0.10 | 42 |
| T4abc ssb7(339fs) | 0 | 0.04 | 44 |
| T4abc ssb7(TS2) | 2 | 0.08 | 43 |

REFERENCES

PCT Application No. PCT/US2015/65693
PCT Publication No. WO2012/027580
PCT Publication No. WO2012/145584
PCT Publication No. WO2012/145592
PCT Publication No. WO2012/145595
PCT Publication No. WO2012/145596
PCT Publication No. WO2016/100272
PCT Publication No. WO2016/100568
PCT Publication No. WO2016/100571
PCT Publication No. WO2016/130523
PCT Publication No. WO20161/00562
U.S. Pat. No. 9,725,727
Altschul et al., *J. Mol. Biol.* 215:403-10, 1990.
Altschul et al., *Meth. Enzymol.* 266:460-80, 1996.
Ausubel et al., "Current Protocols in Molecular Biology", Eds., John Wiley & Sons, Inc., 1995, sections 2, 4 and 6.
Botstein and Shortie, *Science* 229: 4719, 1985.
Devereux et al., *Nucleic Acids Res.* 12:387-95, 1984.
Henikoff and Henikoff, *Proc. Natl. Acad. Sci. USA* 89:10915, 1989.
Higgins and Sharp, *CABIOS* 5:151-53, 1989.
Higgins et al., *Gene* 73:237-244, 1998.
Higuchi et al., *Nucleic Acids Research* 16: 7351, 1988.
Ho et al., *Gene* 77: 61, 1989.
Hopwood, The Isolation of Mutants in Methods in Microbiology (J. R. Norris and D. W Ribbons, eds.) pp 363-433, Academic Press, New York, 1970.
Horton et al., *Gene* 77: 61, 1989.
Iglesias and Trautner, *Molecular General Genetics* 189: 73-76, 1983.
Jourdier et al., "Proximity ligation scaffolding and comparison of two *Trichoderma reesei* strains genomes", *Biotechnology for Biofuels*, 10:151; 2017.
Karlin et al., *Proc. Natl. Acad. Sci. USA* 90:5873-87, 1993.
Kyte and Doolittle, "A simple method for displaying the hydropathic character of a protein", *J. Mol. Biol.* 157, 105-132, 1982.
Lo et al., *Proceedings of the National Academy of Sciences USA* 81: 2285, 1985.
Majoros et al., "TigrScan and GlimmerHMM: two opensource ab initio eukaryotic gene-finders", *Bioinformatics*, 2878-2879, 2004.
Needleman and Wunsch, *J. Mol. Biol.*, 48:443, 1970.
Parish and Stoker, *FEMS Microbiology Letters* 154: 151-157, 1997.
Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.

Sambrook et al., "*Molecular Cloning: A Laboratory Manual*", Cold Spring Harbor Press, Cold Spring Harbor, N.Y. (1989), chapters 7, 9 and 11.
Sarkar and Sommer, *BioTechniques* 8: 404, 1990.
Shimada, *Meth. Mol. Biol.* 57: 157; 1996.
Smith and Waterman, *Adv. Appl. Math.* 2:482, 1981.
Stanke et al., "AUGUSTUS: a web server for gene prediction in eukaryotes that allows user-defined constraints" *Nucleic acids research, Vol.* 33, Web Server issue: W465-7, 2005.

*The Genome Portal of the Department of Energy Joint Genome Institute*, I. V. Grigoriev, H. Nordberg, I. Shabalov, A. Aerts, M. Cantor, D. Goodstein, A. Kuo, S. Minovitsky, R. Nikitin, R. A. Ohm, R. Otillar, A. Poliakov, I. Ratnere, R. Riley, T. Smirnova, D. Rokhsar, and I. Dubchak, *Nucleic Acids Res.*, 2011, 0: gkr94 7v 1-gkr947; (genome.jgi-psf.org).

Youngman et al., *Proc. Natl. Acad. Sci. USA* 80: 2305-2309, 1983.

The invention claimed is:

1. A variant Ascomycota filamentous fungal strain derived from a parental Ascomycota strain, the variant strain comprising a disruption, partial deletion or complete deletion of a gene encoding a SSB7 protein comprising at least 80% sequence identity to SEQ ID NO: 2, SEQ ID NO: 8, SEQ ID NO: 9, SEQ ID NO: 10, SEQ ID NO: 11, SEQ ID NO: 12, SEQ ID NO: 13, SEQ ID NO: 31, SEQ ID NO: 33 or SEQ ID NO: 35, wherein the cells of the variant strain comprise a reduced viscosity phenotype relative to the cells of the parental strain.

2. The variant strain of claim 1, wherein the variant strain during aerobic fermentation in submerged culture (i) produces a cell broth that requires a reduced amount of agitation to maintain a preselected dissolved oxygen content, relative to the cells of the parental strain and/or (ii) produces a cell broth that maintains an increased dissolved oxygen content at a preselected amount of agitation, relative to the cells of the parental strain.

3. The variant strain of claim 1, further comprising a gene encoding a protein of interest.

4. The variant strain of claim 1, further comprising a genetic modification of one or more genes encoding a MPG1 protein, a SFB3 protein, a SEB1 protein, a CRZ1 protein and/or a GAS1 protein.

5. The variant strain of claim 1, wherein the Ascomycota filamentous fungal strain is selected from the group consisting of a Trichoderma sp. fungal strain, a Fusarium sp. fungal strain, a Neurospora sp. fungal strain, a Myceliophthora sp. fungal strain, a Talaromyces sp. fungal strain, an Aspergillus sp. fungal strain and a Penicillium sp. fungal strain.

6. A method for constructing a reduced viscosity strain of an Ascomycota filamentous fungus comprising:
(a) obtaining a parental Ascomycota filamentous fungal strain comprising a gene encoding a SSB7 protein having at least 80% sequence identity to SEQ ID NO: 2, SEQ ID NO: 8, SEQ ID NO: 9, SEQ ID NO: 10, SEQ ID NO: 11, SEQ ID NO: 12, SEQ ID NO: 13, SEQ ID NO: 31, SEQ ID NO: 33 or SEQ ID NO: 35, and modifying the strain by disrupting, partially deleting or completely deleting the gene encoding SSB7 protein, and
(b) isolating the modified strain,
wherein the cells of the variant modified strain comprise a reduced viscosity phenotype relative to the cells of the parental strain.

7. The method of claim 6, wherein the modified strain during aerobic fermentation in submerged culture (a) produces a cell broth that requires a reduced amount of agitation to maintain a preselected dissolved oxygen content, relative to the parental strain and/or (b) produces a cell broth maintains an increased dissolved oxygen content at a preselected amount of agitation, relative to the parental strain.

8. The method of claim 6, wherein the Ascomycota filamentous fungal strain is selected from the group consisting of a *Trichoderma* sp. fungal strain, a *Fusarium* sp. fungal strain, a *Neurospora* sp. fungal strain, a *Myceliophthora* sp. fungal strain, a *Talaromyces* sp. fungal strain, an *Aspergillus* sp. fungal strain and a *Penicillium* sp. fungal strain.

9. The method of claim 6, wherein the parental strain comprises a gene encoding a protein of interest.

\* \* \* \* \*